United States Patent
Plewe et al.

(10) Patent No.: US 11,352,328 B2
(45) Date of Patent: Jun. 7, 2022

(54) HETEROCYCLIC COMPOUNDS FOR THE TREATMENT OF ARENAVIRUS

(71) Applicant: ARISAN THERAPEUTICS INC., San Diego, CA (US)

(72) Inventors: Michael Plewe, San Diego, CA (US); Eric Brown, Santee, CA (US); Vidyasagar Gantla, San Diego, CA (US); Gregory Henkel, Carlsbad, CA (US); Kenneth McCormack, Oceanside, CA (US); Nadzeda V. Sokolova, San Diego, CA (US); Young-Jun Shin, San Diego, CA (US)

(73) Assignee: Arisan Therapeutics Inc., Carlsbad, CA (US)

( * ) Notice: Subject to any disclaimer, the term of this patent is extended or adjusted under 35 U.S.C. 154(b) by 0 days.

(21) Appl. No.: 16/309,858

(22) PCT Filed: Jul. 7, 2017

(86) PCT No.: PCT/US2017/041218
§ 371 (c)(1),
(2) Date: Dec. 13, 2018

(87) PCT Pub. No.: WO2018/013430
PCT Pub. Date: Jan. 18, 2018

(65) Prior Publication Data
US 2019/0308938 A1 Oct. 10, 2019

Related U.S. Application Data

(60) Provisional application No. 62/361,423, filed on Jul. 12, 2016, provisional application No. 62/378,177, filed on Aug. 22, 2016.

(51) Int. Cl.
| | | |
|---|---|---|
| *C07D 235/06* | (2006.01) | |
| *A61K 31/4184* | (2006.01) | |
| *A61P 31/14* | (2006.01) | |
| *A61K 31/4192* | (2006.01) | |
| *A61K 31/439* | (2006.01) | |

(Continued)

(52) U.S. Cl.
CPC .......... *C07D 235/06* (2013.01); *A61K 31/416* (2013.01); *A61K 31/4184* (2013.01);
(Continued)

(58) Field of Classification Search
CPC .......................... C07D 235/06; C07D 235/20
See application file for complete search history.

(56) References Cited

U.S. PATENT DOCUMENTS

| | | |
|---|---|---|
| 4,143,152 A | 3/1979 | Hammar |
| 4,153,721 A | 5/1979 | Hammar |

(Continued)

FOREIGN PATENT DOCUMENTS

| | | |
|---|---|---|
| CN | 102675286 A | 9/2012 |
| CN | 104672231 A | 6/2015 |

(Continued)

OTHER PUBLICATIONS

Lapierre et al., Discovery of 3-(3-(4-(1-Aminocyclobutyl)phenyl)-5-phenyl-3H-imidazo[4,5-b]pyridin-2-yl)pyridin-2-amine (ARQ 092): An Orally Bioavailable, Selective, and Potent Allosteric AKT Inhibitor, J. Med. Chem., 2016, pp. 6455-6469, vol. 59, American Chemical Society, USA.

(Continued)

*Primary Examiner* — Barbara P Badio
(74) *Attorney, Agent, or Firm* — Karl Neidert

(57) ABSTRACT

The invention relates to compounds of structural formula I

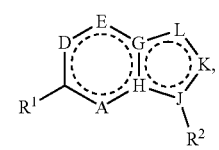

wherein A, D, and E are independently N or C—$R^3$, G, H, and J are independently N or C, K is N or C—H, L is N, N—$R^3$ or C—$R^3$, and A, D, E, G, H, J, K, and L together cannot have more than 4 N, $R^1$ is selected from ($C_6$ to $C_{10}$) aryl, ($C_2$ to $C_9$) heteroaryl, and 5-indolyl, wherein each of the said ($C_6$ to $C_{10}$) aryl and ($C_2$ to $C_9$) heteroaryl is substituted with at least one $R^{4a}$ group, and wherein said ($C_2$ to $C_9$) heteroaryl is C-attached, and $R^2$ is selected from the group consisting of

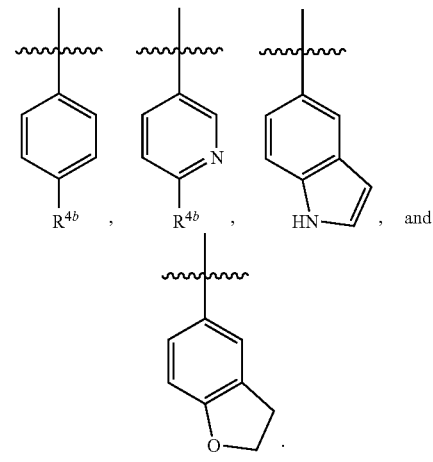

29 Claims, No Drawings

(51) Int. Cl.

| | |
|---|---|
| A61K 31/4439 | (2006.01) |
| A61K 31/454 | (2006.01) |
| A61K 31/519 | (2006.01) |
| A61K 31/53 | (2006.01) |
| A61K 31/5377 | (2006.01) |
| A61K 31/7056 | (2006.01) |
| A61K 31/7105 | (2006.01) |
| C07D 235/20 | (2006.01) |
| C07D 249/18 | (2006.01) |
| C07D 471/04 | (2006.01) |
| C07D 471/08 | (2006.01) |
| C07D 473/00 | (2006.01) |
| A61K 31/416 | (2006.01) |
| A61K 31/423 | (2006.01) |
| C07D 413/00 | (2006.01) |
| A61K 31/52 | (2006.01) |
| A61K 31/713 | (2006.01) |
| A61K 45/06 | (2006.01) |
| A61K 31/4985 | (2006.01) |
| A61K 31/437 | (2006.01) |
| A61K 31/5025 | (2006.01) |

(52) U.S. Cl.
CPC ........ *A61K 31/4192* (2013.01); *A61K 31/423* (2013.01); *A61K 31/437* (2013.01); *A61K 31/439* (2013.01); *A61K 31/4439* (2013.01); *A61K 31/454* (2013.01); *A61K 31/4985* (2013.01); *A61K 31/5025* (2013.01); *A61K 31/519* (2013.01); *A61K 31/52* (2013.01); *A61K 31/53* (2013.01); *A61K 31/5377* (2013.01); *A61K 31/7056* (2013.01); *A61K 31/713* (2013.01); *A61K 31/7105* (2013.01); *A61K 45/06* (2013.01); *A61P 31/14* (2018.01); *C07D 235/20* (2013.01); *C07D 249/18* (2013.01); *C07D 413/00* (2013.01); *C07D 471/04* (2013.01); *C07D 471/08* (2013.01); *C07D 473/00* (2013.01)

(56) References Cited

U.S. PATENT DOCUMENTS

| | | | |
|---|---|---|---|
| 4,526,896 A | 7/1985 | Scherrer | |
| 5,369,086 A | 11/1994 | James | |
| 5,496,954 A | 3/1996 | Condon | |
| 5,523,277 A | 6/1996 | Condon | |
| 6,498,165 B1 | 12/2002 | Armstrong | |
| 6,855,719 B1 | 2/2005 | Thomas | |
| 7,074,801 B1 | 7/2006 | Yoshida | |
| 7,405,299 B2 | 7/2008 | Beight | |
| 8,097,617 B2 | 1/2012 | Baeschlin | |
| 8,367,662 B2 | 2/2013 | Shaw | |
| 8,461,177 B2 | 6/2013 | Dai | |
| 8,629,170 B2 | 1/2014 | Hruby | |
| 8,729,074 B2 | 5/2014 | Bo | |
| 8,975,265 B2 | 3/2015 | Ince | |
| 9,085,560 B2 | 7/2015 | Ren | |
| 9,139,589 B2 | 9/2015 | Hirose | |
| 9,295,673 B2 | 3/2016 | Ren | |
| 9,388,140 B2 | 7/2016 | Klar | |
| 9,573,939 B2 | 2/2017 | Mccomas | |
| 9,682,141 B2 | 6/2017 | Jessen | |
| 2002/0161022 A1 | 10/2002 | Reich | |
| 2003/0109550 A1 | 6/2003 | Clare | |
| 2004/0009996 A1 | 1/2004 | Moon | |
| 2004/0067953 A1 | 4/2004 | Stein | |
| 2004/0097506 A1 | 5/2004 | Thomas | |
| 2004/0186115 A1 | 9/2004 | Ledeboer | |
| 2005/0026960 A1 | 2/2005 | Kephart | |
| 2005/0107386 A1 | 5/2005 | Narla | |
| 2006/0058295 A1 | 3/2006 | Beight | |
| 2006/0122179 A1 | 6/2006 | Zeldis | |
| 2006/0154105 A1 | 7/2006 | Yamamoto | |
| 2006/0154961 A1 | 7/2006 | Zeng | |
| 2006/0199809 A1 | 9/2006 | Lu | |
| 2007/0004777 A1 | 1/2007 | Bhagwat | |
| 2007/0021443 A1 | 1/2007 | Ohlmeyer | |
| 2007/0072879 A1 | 3/2007 | McArthur | |
| 2007/0099935 A1 | 5/2007 | Burns | |
| 2007/0161635 A1 | 7/2007 | Burns | |
| 2007/0254913 A1 | 11/2007 | Dunn | |
| 2007/0293491 A1 | 12/2007 | Shafer | |
| 2008/0004257 A1 | 1/2008 | Chan | |
| 2008/0161341 A1 | 7/2008 | Calderwood | |
| 2008/0200445 A1 | 8/2008 | Zhu | |
| 2008/0269200 A1 | 10/2008 | Baldwin | |
| 2008/0269227 A1 | 10/2008 | Rueckle | |
| 2008/0287468 A1 | 11/2008 | Ohlmeyer | |
| 2008/0300265 A1 | 12/2008 | Hruby | |
| 2009/0176778 A1 | 7/2009 | Schmitz | |
| 2009/0247517 A1 | 10/2009 | Liu | |
| 2009/0253689 A1 | 10/2009 | Baeschlin | |
| 2009/0318410 A1 | 12/2009 | Capraro | |
| 2010/0029733 A1 | 2/2010 | Atobe | |
| 2010/0056494 A1 | 3/2010 | Winzeler | |
| 2010/0056521 A1 | 3/2010 | Shimizu | |
| 2010/0069381 A1 | 3/2010 | Itoh | |
| 2010/0075965 A1 | 3/2010 | Ni | |
| 2010/0081658 A1 | 4/2010 | Chin | |
| 2010/0120761 A1 | 5/2010 | Berdini | |
| 2010/0183564 A1 | 7/2010 | Boitano | |
| 2010/0210641 A1 | 8/2010 | Shaw | |
| 2010/0216798 A1 | 8/2010 | Nakai | |
| 2010/0249122 A1 | 9/2010 | Kalman | |
| 2010/0305113 A1 | 12/2010 | Capraro | |
| 2010/0311729 A1 | 12/2010 | Capraro | |
| 2010/0311736 A1 | 12/2010 | Adams | |
| 2011/0003806 A1 | 1/2011 | Hirose | |
| 2011/0021521 A1 | 1/2011 | Corkey | |
| 2011/0028414 A1 | 2/2011 | Tsaklakidis | |
| 2011/0064693 A1 | 3/2011 | Dai | |
| 2011/0130384 A1 | 6/2011 | Setoh | |
| 2011/0172203 A1 | 7/2011 | Ashwell | |
| 2011/0263559 A1 | 10/2011 | Zhang | |
| 2012/0004222 A1 | 1/2012 | Wu | |
| 2012/0035409 A1 | 2/2012 | Michels | |
| 2012/0058997 A1 | 3/2012 | Xu | |
| 2012/0059162 A1 | 3/2012 | Kusakabe | |
| 2012/0071474 A1 | 3/2012 | Bo | |
| 2012/0077787 A1 | 3/2012 | Baeschlin | |
| 2012/0077810 A1 | 3/2012 | Chen | |
| 2012/0190666 A1 | 7/2012 | Bode | |
| 2012/0294930 A1 | 11/2012 | Ren | |
| 2012/0329791 A1 | 12/2012 | Ashwell | |
| 2012/0329793 A1 | 12/2012 | Ashwell | |
| 2013/0029964 A1 | 1/2013 | Aoki | |
| 2013/0035324 A1 | 2/2013 | Ren | |
| 2013/0065883 A1 | 3/2013 | Pastor Fernández | |
| 2013/0102613 A1 | 4/2013 | Xu | |
| 2013/0184273 A1 | 7/2013 | Ince | |
| 2013/0190332 A1 | 7/2013 | Ince | |
| 2013/0210768 A1 | 8/2013 | Arrington | |
| 2013/0210825 A1 | 8/2013 | Rehwinkel | |
| 2013/0216498 A1 | 8/2013 | Eastwood | |
| 2013/0280245 A1 | 10/2013 | Cai | |
| 2013/0338133 A1 | 12/2013 | Klar | |
| 2014/0023623 A1 | 1/2014 | Peled | |
| 2014/0031360 A1 | 1/2014 | Wang | |
| 2014/0080834 A1 | 3/2014 | Lanthorn | |
| 2014/0179675 A1 | 6/2014 | Abudusaimi | |
| 2014/0187553 A1 | 7/2014 | Wang | |
| 2014/0243367 A1 | 8/2014 | Dai | |
| 2014/0255392 A1 | 9/2014 | Koppitz | |
| 2014/0256717 A1 | 9/2014 | Fernández | |
| 2014/0256733 A1 | 9/2014 | Goodfellow | |
| 2014/0302010 A1 | 10/2014 | Klar | |
| 2014/0371199 A1 | 12/2014 | Nacro | |
| 2015/0023916 A1 | 1/2015 | Dai | |
| 2015/0030588 A1 | 1/2015 | Jessen | |
| 2015/0038506 A1 | 2/2015 | Nacro | |

(56) References Cited

U.S. PATENT DOCUMENTS

| | | |
|---|---|---|
| 2015/0051203 A1 | 2/2015 | Chimmanamada |
| 2015/0065482 A1 | 3/2015 | Blaquiere |
| 2015/0079108 A1 | 3/2015 | Falcenberg |
| 2015/0158859 A1 | 6/2015 | Ren |
| 2015/0183791 A1 | 7/2015 | Bi |
| 2015/0203472 A1 | 7/2015 | Ceccarelli |
| 2015/0246902 A1 | 9/2015 | Mccomas |
| 2015/0259334 A1 | 9/2015 | Ceccarelli |
| 2015/0259341 A1 | 9/2015 | Ceccarelli |
| 2015/0266876 A1 | 9/2015 | Bates |
| 2015/0272959 A1 | 10/2015 | Smith |
| 2015/0284383 A1 | 10/2015 | Lynch |
| 2016/0052909 A1 | 2/2016 | Bhamidipati |
| 2016/0067260 A1 | 3/2016 | Dransfield |
| 2016/0089371 A1 | 3/2016 | Liu |
| 2016/0168140 A1 | 6/2016 | Jones |
| 2016/0229816 A1 | 8/2016 | Sato |
| 2016/0235758 A1 | 8/2016 | Ren |
| 2016/0296528 A1 | 10/2016 | Pastor Fernández |
| 2016/0326162 A1 | 11/2016 | Lin |
| 2017/0050939 A1 | 2/2017 | Stewart |
| 2017/0096409 A1 | 4/2017 | Singh |
| 2017/0204093 A1 | 7/2017 | Chan |
| 2018/0228776 A1 | 8/2018 | Saitoh |
| 2018/0230152 A1 | 8/2018 | Dai |
| 2018/0240984 A1 | 8/2018 | Choi |
| 2018/0250297 A1 | 9/2018 | Lau |
| 2018/0297948 A1 | 10/2018 | Kim |

FOREIGN PATENT DOCUMENTS

| | | |
|---|---|---|
| CN | 104672240 A | 6/2015 |
| EP | 2818472 A1 | 12/2014 |
| JP | 200143978 A | 2/2001 |
| KR | 20130013264 A | 2/2013 |
| WO | 0058307 A2 | 10/2000 |
| WO | 0183481 A1 | 11/2001 |
| WO | 03099811 A1 | 12/2003 |
| WO | 2007096764 A2 | 8/2007 |
| WO | 2009071577 A1 | 6/2009 |
| WO | 2009133127 A1 | 11/2009 |
| WO | 2010012745 A2 | 2/2010 |
| WO | 2011041713 A2 | 4/2011 |
| WO | 2011050245 A1 | 4/2011 |
| WO | 2011055911 A1 | 5/2011 |
| WO | 2011106168 A1 | 9/2011 |
| WO | 2012131501 A1 | 10/2012 |
| WO | 2012174312 A2 | 12/2012 |
| WO | 2013078254 A1 | 5/2013 |
| WO | 2013147711 A1 | 10/2013 |
| WO | 2014020041 A1 | 2/2014 |
| WO | 2014055955 A1 | 4/2014 |
| WO | 2014080241 A1 | 5/2014 |
| WO | 2014157687 A1 | 10/2014 |
| WO | 2016044585 A1 | 3/2016 |
| WO | 2016064958 A1 | 4/2016 |
| WO | 2016089977 A1 | 6/2016 |
| WO | 2016143508 A1 | 9/2016 |
| WO | 2017026516 A1 | 2/2017 |
| WO | 2017040993 A1 | 3/2017 |
| WO | 2017044623 A1 | 3/2017 |

OTHER PUBLICATIONS

Lee et al., 7-Fluoroindazoles as Potent and Selective Inhibitors of Factor Xa, J. Med. Chem., 2008, p. 282-297, vol. 51, American Chemical Society, USA.

Nishiguchi et al., Discovery of novel 3,5-disubstituted indole derivatives as potent inhibitors of Pim-1, Pim-2, and Pim-3 protein kinases, Bioorganic & Medicinal Chemistry Letters, 2011, pp. 6366-6369, vol. 21, Elsevier, Netherlands.

Wurz et al., The discovery and optimization of aminooxadiazoles as potent Pim kinase inhibitors, Bioorganic & Medicinal Chemistry Letters, 2015, pp. 847-855, vol. 25, Elsevier, Netherlands.

Wu et al., Discovery of 5-(1 H-indol-5-yl)-1,3,4-thiadiazol-2-amines as potent PIM inhibitors, Bioorganic & Medicinal Chemistry Letters , 2015, pp. 775-780, vol. 25, Elsevier, Netherlands.

Penoni et al., Regioselective Synthesis of Indoles via Reductive Annulation of Nitrosoaromatics with Alkynes, Org. Lett., 2002, pp. 699-701, vol. 4, American Chemical Society, USA.

Sessions et al., Discovery and optimization of indole and 7-azaindoles as Rho kinase (ROCK) inhibitors (Part-II), Bioorganic & Medicinal Chemistry Letters, 2011, pp. 7113-7118, vol. 21, Elsevier, Netherlands.

Youn et al., Palladium-Catalyzed Regioselective Synthesis of 3-Arylindoles from NTs-Anilines and Styrenes, Angew. Chem. Int. Ed., 2017, pp. 6636-6640, vol. 56, Wiley-VCH, Germany.

Shashi Nayana et al., CoMFA and docking studies on triazolopyridine oxazole derivatives as p38 MAP kinase inhibitors, European Journal of Medicinal Chemistry, 2008, pp. 1261-1269, vol. 43, Elsevier, Netherlands.

PCT International Search Report for PCT International Application No. PCT/US2017/041218.

Search History for PCT Application No. PCT/US2017/041218.

Noji et al., Concise SAR Exploration Based on the "Head-to-Tail" Approach: Discovery of PI4KIIIα Inhibitors Bearing Diverse Scaffolds, ACS Med. Chem. Lett., 2016, pp. 919-923, vol. 7, American Chemical Society, USA.

Gunda et al., In Silico Analysis of Structural Requirements for Thiophene Derivatives Against Polo Like KINASE-1 (PLK1), International Journal of Pharmacy and Pharmaceutical Sciences, 2015, pp. 203-213, vol. 7, Innovare Academic Sciences, India.

Hay et al., The design and synthesis of 5- and 6-isoxazolylbenzimidazoles as selective inhibitors of the BET bromodomains, Med. Chem. Commun., 2013, pp. 140-144, vol. 4, The Royal Society of Chemistry, UK.

Bisignano et al., In Silico Deconstruction of ATP-Competitive Inhibitors of Glycogen Synthase Kinase-3β, J. Chem. Inf. Model., 2012, pp. 3233-3244, vol. 52, American Chemical Society, USA.

Osolodkin et al., Structure-Based Virtual Screening of Glycogen Synthase Kinase 3b Inhibitors: Analysis of Scoring Functions Applied to Large True Actives and Decoy Sets, Chemical Biology & Drug Design, 2011, pp. 378-390, vol. 78, John Wiley & Sons, USA.

Rheault et al., Heteroaryl-linked 5-(1H-benzimidazol-1-yl)-2-thiophenecarboxamides: Potent inhibitors of polo-like kinase 1 (PLK1) with improved drug-like properties, Bioorganic & Medicinal Chemistry Letters, 2010, pp. 4587-4592, vol. 20, Elsevier, Netherlands.

Saitoh et al., 2-{3-[4-(Alkylsulfinyl)phenyl]-1-benzofuran-5-yl}-5-methyl-1,3,4-oxadiazole Derivatives as Novel Inhibitors of Glycogen Synthase Kinase-3β with Good Brain Permeability, J. Med. Chem., 2009, pp. 6270-6286, vol. 52, American Chemical Society, USA.

Saitoh et al., Design, synthesis and structure-activity relationships of 1,3,4-oxadiazole derivatives as novel inhibitors of glycogen synthase kinase-3b, Bioorganic & Medicinal Chemistry, 2009, pp. 2017-2029, vol. 17, Elsevier, Netherlands.

Comelli et al., QSAR models for thiophene and imidazopyridine derivatives inhibitors of the Polo-Like Kinase 1, European Journal of Pharmaceutical Sciences, 2014, pp. 171-179, vol. 62, Elsevier, Netherlands.

Le Manach et al., A Novel Pyrazolopyridine with in Vivo Activity in Plasmodium berghei- and Plasmodium falciparum-infected Mouse Models from Structure-Activity Relationship Studies around the Core of Recently Identified Antimalarial Imidazopyridazines, J. Med. Chem., 2015, pp. 8713-8722, vol. 58, American Chemical Society, USA.

Iaroshenko et al., 3-Formylchromones, Acylpyruvates, and Chalcone as Valuable Substrates for the Syntheses of Fused Pyridines, Synthesis, 2010, pp. 2749-2758, Thieme, Germany.

Kannan et al., Probing the Binding Mechanism of Mnk Inhibitors by Docking and Molecular Dynamics Simulations, Biochemistry, 2015, pp. 32-46, vol. 54, American Chemical Society, USA.

(56) References Cited

OTHER PUBLICATIONS

Moine et al., A small-molecule cell-based screen led to the identification of biphenylimidazoazines with highly potent and broad-spectrum antiapicomplexan activity, European Journal of Medicinal Chemistry, 2015, 386-400, vol. 89, Elsevier, Netherlands.
Enguehard-Gueiffier et al., 3-Biphenylimidazo[1,2-a]pyridines or [1,2-b]pyridazines and analogues, novel Flaviviridae inhibitors, European Journal of Medicinal Chemistry, 2013, pp. 448-463, vol. 64, Elsevier, Netherlands.
Liu et al., Regioselective synthesis of 2- and 3-substituted imidazo[1,2-a]pyridines, Journal of Chemical Research, 2012, pp. 687-690, SAGE Publishing, USA.
Peterson et al., Discovery and optimization of potent and selective imidazopyridine and imidazopyridazine mTOR inhibitors, Bioorganic & Medicinal Chemistry Letters, 2012, pp. 4967-4974, vol. 22, Elsevier, Netherlands.
Jeong et al., Selectivity Enhancement Arising from Interactions at the PI3K Unique Pocket, ChemMedChem, 2012, 1379-1383, vol. 7, Wiley-VCH, Germany.
Yun et al., Induction of apoptosis and suppression of angiogenesis of hepatocellular carcinoma by HS-159, a novel phosphatidylinositol 3-kinase inhibitor, International Journal of Oncology, 2013, pp. 201-209, vol. 43, Spandidos Publications, Greece.
El Akkaoui et al., Pd-catalyzed regiocontrolled Sonogashira and Suzuki cross-coupling reaction of 3,6-dihalogenoimidazo[1,2-a]pyridines: one-pot double-coupling approach, Tetrahedron, 2011, pp. 7128-7138, vol. 67, Elsevier, Netherlands.
Kim et al., Design and Synthesis of Imidazopyridine Analogues as Inhibitors of Phosphoinositide 3-Kinase Signaling and Angiogenesis, J. Med. Chem., 2011, pp. 2455-2466, vol. 54, American Chemical Society, USA.
Ashwell et al., Discovery and Optimization of a Series of 3-(3-Phenyl-3Himidazo[ 4,5-b]pyridin-2-yl)pyridin-2-amines: Orally Bioavailable, Selective, and Potent ATP-lndependent Akt Inhibitors, J. Med. Chem., 2012, pp. 5291-5310, vol. 55, American Chemical Society, USA.
Buckley et al., IRAK-4 inhibitors. Part III: A series of imidazo[1,2-a]pyridines, Bioorganic & Medicinal Chemistry Letters, 2008, pp. 3656-3660, vol. 18, Elsevier, Netherlands.
Koubachi et al., Synthesis of Polysubstituted Imidazo[1,2-a]pyridines via Microwave-Assisted One-Pot Cyclization/Suzuki Coupling/ Palladium-Catalyzed Heteroarylation, J. Org. Chem., 2007, pp. 7650-7655, vol. 72, American Chemical Society, USA.
Jung et al., Suppression of tumor proliferation and angiogenesis of hepatocellular carcinoma by HS-104, a novel phosphoinositide 3-kinase inhibitor, Cancer Letters, 2013, pp. 176-187, vol. 328, Elsevier, Netherlands.
Iaroshenko et al., Facile Synthesis of Fluorinated 1-Desazapurines, Synthesis, 2009, pp. 1865-1875, Thieme, Germany.
Zaki et al., The synthesis of imidazo[4,5-d]pyridines from a substituted imidazole and acyl or sulfonyl acetonitrile, Tetrahedron, 2007, pp. 3745-3753, vol. 63, Elsevier, Netherlands.
Fang et al., Discovery of Inter-Domain Stabilizers—A Novel Assay System for Allosteric Akt Inhibitors, ACS Chem. Biol., 2015, pp. 279-288, vol. 10, American Chemical Society, USA.
Lv et al., Copper-Catalyzed Cascade Addition/Cyclization: An Efficient and Versatile Synthesis of N-Substituted 2-Heterobenzimidazoles, J. Org. Chem., 2009, pp. 5618-5621, vol. 74, American Chemical Society, USA.
Kumata et al., Radiosynthesis and preliminary PET evaluation of glycogen synthase kinase 3b (GSK-3b) inhibitors containing [11C]methylsulfanyl, [11C]methylsulfinyl or [11C]methylsulfonyl groups, Bioorganic & Medicinal Chemistry Letters, 2015, pp. 3230-3233, vol. 25, Elsevier, Netherlands.
Saitoh et al., Enantioselective Synthesis of the Novel Chiral Sulfoxide Derivative as a Glycogen Synthase Kinase 3b Inhibitor, Chem. Pharm. Bull., 2010, pp. 1252-1254, vol. 58, Pharmaceutical Society of Japan, Japan.

Giovannini et al., Photolyse des 3-Phenyl-2,I-benzisoxazolusn d einiger seiner Derivate in Salzsaure bzw. Schwefelsaure, Helvetica Chimica Acta, 1979, pp. 185-197, vol. 62, John Wiley & Sons, Switzerland.
Harrington et al., Pim Kinase Inhibitors Evaluated with a Single-Molecule Engineered Nanopore Sensor, Angew. Chem. Int. Ed., 2015, pp. 8154-8159, vol. 54, Wiley-VCH, Germany.
Lukasik et al., 2-(Arylamino)aryliminophosphoranes as Easily Available and Convenient Starting Materials in the Synthesis of 1,2,3-Benzotriazoles, SYNLETT, 2014, pp. 1987-1990, Thieme, Germany.
Ramachary et al., Organocatalytic Triazole Formation, Followed by Oxidative Aromatization: Regioselective Metal-Free Synthesis of Benzotriazoles, Chem. Eur. J., 2013, pp. 13175 -13181, vol. 19, Wiley-VCH, Germany.
Mukhopadhyay et al., A ligand-free copper (1) catalysed intramolecular N-arylation of diazoaminobenzenes in PEG-water: an expeditious protocol towards regiospecific 1-aryl benzotriazoles, Org. Biomol. Chem., 2010, pp. 4720-4729, vol. 8, The Royal Society of Chemistry, UK.
Kusakabe et al., Discovery of lmidazo[1,2-b]pyridazine Derivatives: Selective and Orally Available Mps1 (TTK) Kinase Inhibitors Exhibiting Remarkable Antiproliferative Activity, J. Med. Chem., 2015, pp. 1760-1775, vol. 58, American Chemical Society, USA.
Barsanti et al., Structure-Based Drug Design of Novel Potent and Selective Tetrahydropyrazolo[1,5-a]pyrazines as ATR Inhibitors, ACS Med. Chem. Lett., 2015, pp. 37-41, vol. 6, American Chemical Society, USA.
Le Manach et al., Medicinal Chemistry Optimization of Antiplasmodial Imidazopyridazine Hits from High Throughput Screening of a SoftFocus Kinase Library: Part 1, J. Med. Chem., 2014, pp. 2789-2798, vol. 57, American Chemical Society, USA.
Senhoraes et al., One-Pot Regioselective Synthesis of 2,6,9-Trisubstituted Adenines, SYNLETT, 2011, pp. 0181-0186, Thieme, Germany.
Correia et al., General Synthetic Approach to 2-Phenolic Adenine Derivatives, SYNLETT, 2012, pp. 1923-1926, Thieme, Germany.
Correia et al., Synthesis and in vitro activity of 6-amino-2,9-diarylpurines for *Mycobacterium tuberculosis*, Tetrahedron, 2009, pp. 6903-6911, vol. 65, Elsevier, Netherlands.
Areias et al., In silico directed chemical probing of the adenosine receptor family, Bioorganic & Medicinal Chemistry, 2010, pp. 3043-3052, vol. 18, Elsevier, Netherlands.
Garzon et al., A Direct Route into Fused Imidazo-diazines and Imidazo-pyridines Using Nucleophilic Nitrenoids in a Gold-Catalyzed Formal [3+2]-Dipolar Cycloaddition, Org. Lett., 2014, pp. 4850-4853, vol. 16, American Chemical Society, USA.
Zhou et al., Structural Optimization and Pharmacological Evaluation of Inhibitors Targeting Dual-Specificity Tyrosine Phosphorylation-Regulated Kinases (DYRK) and CDC-like kinases (CLK) in Glioblastoma, J. Med. Chem., 2017, pp. 2052-2070, vol. 60, American Chemical Society, USA.
Wang et al., Discovery of 5-Azaindole (GNE-955) as a Potent Pan-Pim Inhibitor with Optimized Bioavailability, J. Med. Chem., 2017, pp. 4458-4473, vol. 60, American Chemical Society, USA.
McCoull et al., lndazole-6-phenylcyclopropylcarboxylic Acids as Selective GPR120 Agonists with in Vivo Efficacy, J. Med. Chem., 2017, pp. 3187-3197, vol. 60, American Chemical Society, USA.
Zeng et al., 2-Aminothiadiazole inhibitors of AKT1 as potential cancer therapeutics, Bioorganic & Medicinal Chemistry Letters, 2010, pp. 1652-1656, vol. 20, Elsevier, Netherlands.
Laufer et al., Discovery of inhibitors of the mitotic kinase TTK based on N-(3-(3-sulfamoylphenyl)-1H-indazol-5-yl)-acetamides and carboxamides, Bioorganic & Medicinal Chemistry, 2014, pp. 4968-4997, vol. 22, Elsevier, Netherlands.
PCT International Search Report and Written Opinion of the International Searching Authority for PCT International Application No. PCT/US19/64223.
Search History for PCT Application No. PCT/US19/64223.
Pubchem. CID 117737344. Feb. 23, 2016, pp. 1-10. Retrieved from the Internet: <URL: https://pubchem.ncbi.nlm.nih.gov/compound/117737344>.

HETEROCYCLIC COMPOUNDS FOR THE TREATMENT OF ARENAVIRUS

CROSS REFERENCES TO RELATED APPLICATIONS

This patent application is a continuation in part of and claims the benefit of priority to PCT/US2017/041218 filed, Jul. 7, 2017, which is a continuation in part of and claims the benefit of priority to U.S. Provisional Patent Application Ser. Nos. 62/361,423, filed Jul. 12, 2016 and 62/378,177, filed Aug. 22, 2016, all applications are herein incorporated by reference for all purposes.

STATEMENT AS TO RIGHTS TO INVENTIONS MADE UNDER FEDERALLY SPONSORED RESEARCH AND DEVELOPMENT

This invention was made with government support under R44 AI112097 awarded by U.S. National Institutes of Health. The government has certain rights in the invention.

REFERENCE TO A "SEQUENCE LISTING, A TABLE, OR A COMPUTER PROGRAM LISTING APPENDIX SUBMITTED ON A COMPACT DISK

NOT APPLICABLE

FIELD OF THE INVENTION

The present invention relates to the use of heterocyclic compounds for inhibiting arenavirus infection in humans, other mammals, or in cell culture, to methods of treating arenavirus infection such as Lassa, Bolivian, Argentine, Venezuelan, Brazilian, Chapare and Lujo hemorrhagic fevers, to methods of inhibiting the replication of arenaviruses, to methods of reducing the amount of arenaviruses, and to compositions that can be employed for such methods.

BACKGROUND OF THE INVENTION

Arenaviridae comprise a diverse family of 29 (and growing) negative stranded enveloped RNA viruses. Arenaviruses are divided into two groups, Old and New World complex, based on serological, genetic and geographical data. Old World viruses are found primarily throughout South and West Africa and include the prototypic lymphocytic choriomeningitis virus (LCMV), along with Lassa (LASV), Lujo (LUJV), Mopeia (MOPV), Ippy and Mobala (MOBV) viruses. Both LASV and LUJV can cause lethal hemorrhagic fever (HF), while LCMV infection is associated with aseptic meningitis. Lassa (LASV) alone is estimated to cause over 300,000 disease cases each year in West Africa of which 15-20% of hospitalized patients die and survivors often suffer sequelae, including permanent bilateral hearing damage. The larger New World complex primarily located in the South American continent, is divided into 3 clades, A, B, and C, with clade B being important as many of the viruses in this group can cause lethal HF. Clade B HF viruses include, Junin (JUNV), Machupo (MACV), Guanarito (GTOV), Sabia (SABV) and Chapare, along with non-HF viruses such as Tacaribe (TCRV) and Amapari (AMPV). Human infection occurs through contact with the excretions of an infected rodent or by inhalation of tiny particles soiled with rodent urine or saliva (aerosol transmission). There is also evidence of human-to-human spread primarily in nosocomial settings (e.g. hospitals). Incubation period of virus is 1-2 weeks followed by fever, general malaise, weakness, sore throat, headache, cough, diarrhea, and vomiting. These general symptoms make it difficult to differentially diagnose arenavirus infection. Poor prognosis is indicated as symptoms worsen to include pleural effusions, facial edema, neurological complications and bleeding from mucosal surfaces. Current arenavirus treatment is limited to the use of ribavirin, which is only partially effective if given early and associated with significant side effects. Although a vaccine has been developed for Junin virus its usage is primarily restricted to the most at risk populations of farm workers in Argentina and there are no approved vaccines for any other arenaviruses. Although highly desirable, prophylactic vaccines may not always be effective countermeasures against rapidly emerging, antigenically distinct new virus strains and the existing vaccine development and production strategies cannot adequately respond to the diverse family of current or emergent arenaviruses. Novel broad-spectrum antiviral drugs could therefore provide a first line therapy and/or prophylactic, not only for endemic regions of arenavirus infection but also as a safeguard against potential biological warfare agents.

Arenaviruses consist of a nucleocapsid (NP) surrounded by an envelope membrane, and the NP contains two ambisense RNA genome segments L and S that direct the synthesis of two polypeptides. The L segment encodes the RNA-dependent-RNA polymerase (RdRp) and a small Ring Finger protein Z. The S segment encodes for nucleoprotein and a glycoprotein precursor GPC that is cleaved by host proteases and undergoes post-translational modification into a mature complex composed of glycoproteins GP1 (binds host protein at the cell surface), GP2 (directs pH dependent membrane fusion and release of genomic material in the cytoplasm) and a stable signal peptide (SSP1). The mature glycoprotein complex (GP) is formed in the viral envelope and is responsible for mediating viral entry. The Old World arenaviruses bind to host α-dystroglycan while New World arenaviruses bind to transferrin receptor 1 for entry/endocytosis into cells. Upon binding to cell surface receptors, the virus is endocytosed and directed to acidic late endosomes whereby GP2 mediates pH dependent membrane fusion and release of genomic material into the cytoplasm for viral replication and transcription. Therefore, viral entry inhibitors (e.g. small molecules) that target virus GP complex or host factors are a potential therapeutic/prophylactic approach in treating patients infected with arenavirus infection. Because the HF arenavirus species are classified as BSL-4, alternative approaches are needed to identify viral entry inhibitors. To facilitate the identification of arenavirus entry inhibitors one may express arenavirus GP complex in nonpathogenic BSL-2 envelope viruses, to produce single round infectious pseudoviruses whose viral entry functions are determined by the heterogeneous glycoprotein of interest. One viral expression system that may be utilized is the vesicular stomatitis virus (VSV) system, whereby the envelope protein of VSV is substituted with an envelope glycoprotein from another virus, e.g., LASV, to mediate entry of the pseudotype virion. The cell entry and infectivity properties of GP pseudotype VSV viruses have been shown for multiple viruses including HIV, Hepatitis B and C, Ebola, Lassa, Hanta and others [Ogino, M., et al. *Use of vesicular stomatitis virus pseudotypes bearing hantaan or seoul virus envelope proteins in a rapid and safe neutralization test.* Clin. Diagn. Lab. Immunol. (2003) 10(1):154-60; Saha, M. N., et al. *Formation of vesicular stomatitis virus pseudotypes bearing surface proteins of hepatitis B virus.* J. Virol.

(2005) 79(19):12566-74; Takada, A., et al. *A system for functional analysis of Ebola virus glycoprotein*, Proc. Natl. Acad. Sci. (1997) 94:14764-69; Garbutt, M., et al. *Properties of replication-competent vesicular stomatitis virus vectors expressing glycoproteins of filoviruses and arenaviruses*. J. Virol. (2004) 78(10):5458-65]. To monitor pseudovirus infection, a reporter gene such as green fluorescent protein (GFP) or luciferase can be engineered into the pseudovirus genome, and virus infectivity in mammalian cell lines (e.g. Vero or Hek293) can be monitored using optical detection methods (e.g. plate reader) [Cote, M.; Misasi, J.; Ren, T.; Bruchez, A., Lee, K., Filone, C. M.; Hensley, L.; Li, Q.; Ory, D.; Chandran, K.; Cunningham, J., *Small molecule inhibitors reveal Niemann-Pick C1 is essential for Ebola virus infection*, Nature (2011) 477: 344-348, Elshabrawy, H. A., et al. *Identification of a broad-spectrum antiviral amall molecule against severe scute respiratory syndrome Coronavirus and Ebola, Hendra, and Nipah Viruses by using a novel high-throughput screening assay*. J. Virol. (2014) 88: 4353-4365]. The "pseudoviruses" may therefore be used to screen chemical compound libraries to identify inhibitors of arenavirus cell entry while avoiding the complications of working with highly pathogenic BSL-4 agents. In the present invention, entry inhibitors described were identified using an arenavirus GP pseudovirus screen and selected compounds were tested against native non-HF virus TCRV to confirm activity against replicative arenavirus. Selected top compounds were then tested agaist native HF viruses including LASV and JUNV to confirm activity against the native highly pathogenic human (HF) arenaviruses.

BRIEF SUMMARY OF THE INVENTION

The present invention relates to the use of heterocyclic compounds for inhibiting arenavirus infection in humans, other mammals, or in cell culture, to methods of treating arenavirus infection such as Lassa, Bolivian, Argentine, Venezuelan, Brazilian, Chapare and Lujo hemorrhagic fevers, to methods of inhibiting the replication of arenaviruses, to methods of reducing the amount of arenaviruses, and to compositions that can be employed for such methods.

In one embodiment, the method comprises administering to humans, other mammals, cell culture, or biological sample an effective amount of a compound represented by Structural Formula I or a pharmaceutically acceptable salt, and a pharmaceutically acceptable carrier, diluent, or vehicle thereof, wherein:

A, D, and E are independently N or C—$R^3$;
G, H, and J are independently N or C;
K and L are independently N, O, S, N—$R^3$, or C—$R^3$;
and A, D, E, G, H, J, K, and L together cannot have more than 4 N;

$R^1$ is selected from ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^4$ group;

$R^2$ is selected from ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^4$ group;

each of the $R^3$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)NR$^{6a}$R$^{6b}$, —NR$^{6a}$R$^{6b}$, —S(O)$_m$R$^5$, —S(O)$_m$NR$^{6a}$R$^{6b}$, —NR$^{6a}$S(O)$_m$R$^5$, —(CH$_2$)$_n$C(O)OR$^5$, —(CH$_2$)$_n$C(O)NR$^{6a}$R$^{6b}$, —OC(O)R$^5$, —NR$^{6a}$C(O)R$^5$, and —NR$^{6c}$C(O)NR$^{5a}$R$^{5b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^4$ group;

$R^4$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)NR$^{6a}$R$^{6b}$, —NR$^{6a}$R$^{6b}$, —S(O)$_m$R$^5$, —S(O)$_m$NR$^{6a}$R$^{6b}$, —NR$^{6a}$S(O)$_m$R$^5$, —(CH$_2$)$_n$C(O)OR$^5$, —(CH$_2$)$_n$C(O)NR$^{6a}$R$^{6b}$, —OC(O)R$^5$, —NR$^{6a}$C(O)R$^5$, and —NR$^{6c}$C(O)NR$^{6a}$R$^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, or $R^{6a}$ and $R^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)N$R^{9a}R^{9b}$, —N$R^{9a}R^{9b}$, —S(O)$_m R^8$, —S(O)$_m$N$R^{9a}R^{9b}$, —N$R^{9a}$S(O)$_m R^8$, —(CH$_2$)$_n$C(O)O$R^8$, —(CH$_2$)$_n$C(O)N($R^{9a}R^{9b}$), —OC(O)$R^8$, —N$R^{9a}$C(O)$R^8$, and —N$R^{9a}$C(O)N($R^{9a}R^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;

each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;

each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted.

DETAILED DESCRIPTION OF THE INVENTION

The present invention relates to the use of heterocyclic compounds for inhibiting arenavirus infection in humans, other mammals, or in cell culture, to methods of treating arenavirus infection such as Lassa, Bolivian, Argentine, Venezuelan, Brazilian, Chapare, and Lujo hemorrhagic fevers, to methods of inhibiting the replication of arenaviruses, to methods of reducing the amount of arenaviruses, and to compositions that can be employed for such methods.

In one embodiment, the method comprises administering to humans, other mammals, cell culture, or biological sample an effective amount of a compound represented by Structural Formula I

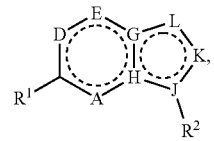

or a pharmaceutically acceptable salt, and a pharmaceutically acceptable carrier, diluent, or vehicle thereof, wherein:

A, D, and E are independently N or C—$R^3$;
G, H, and J are independently N or C;
K and L are independently N, O, S, N—$R^3$, or C—$R^3$;
and A, D, E, G, H, J, K, and L together cannot have more than 4 N;

$R^1$ is selected from ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^4$ group;

$R^2$ is selected from ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^4$ group;

each of the $R^3$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)N$R^{6a}R^{6b}$, —N$R^{6a}R^{6b}$, —S(O)$_m R^5$, —S(O)$_m$N$R^{6a}R^{6b}$, —N$R^{6a}$S(O)$_m R^5$, —(CH$_2$)$_n$C(O)O$R^5$, —(CH$_2$)$_n$C(O)N$R^{6a}R^{6b}$, —OC(O)$R^5$, —N$R^{6a}$C(O)$R^5$, and —N$R^{6c}$C(O)N$R^{5a}R^{5b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^4$ group;

$R^4$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)N$R^{6a}R^{6b}$, —N$R^{6a}R^{6b}$, —S(O)$_m R^5$, —S(O)$_m$N$R^{6a}R^{6b}$, —N$R^{6a}$S(O)$_m R^5$, —(CH$_2$)$_n$C(O)O$R^5$, —(CH$_2$)$_n$C(O)N$R^{6a}R^{6b}$, —OC(O)$R^5$, —N$R^{6a}$C(O)$R^5$, and —N$R^{6c}$C(O)N$R^{6a}R^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, or $R^{6a}$ and $R^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)N$R^{9a}R^{9b}$, —N$R^{9a}R^{9b}$, —S(O)$_m R^8$, —S(O)$_m$ N$R^{9a}R^{9b}$, —N$R^{9a}$S(O)$_m R^8$, —(CH$_2$)$_n$C(O)O$R^8$, —(CH$_2$)$_n$C(O)N($R^{9a}R^{9b}$), —OC(O)$R^8$, —N$R^{9a}$C(O)$R^8$, and —N$R^{9a}$C(O)N($R^{9a}R^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;

each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;

each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted;

m is 0, 1, or 2;

n is 0, 1, 2, 3, 4, 5, or 6.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, and E are independently N or C—$R^3$;

G, H, and J are independently N or C;

K and L are independently N, O, S, N—$R^3$, or C—$R^3$;

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

$R^2$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, wherein $R^3$ and $R^4$ are defined as above, or a pharmaceutically acceptable salt, and a pharmaceutically acceptable carrier, diluent, or vehicle thereof, wherein:

A, D, E, and K are independently N or C—$R^3$;

G, H, and J are independently N or C;

L is N, N—$R^3$, or C—$R^3$;

and A, D, E, G, H, J, K, and L together cannot have more than 4 N;

$R^1$ is selected from ($C_6$ to $C_{10}$) aryl and ($C_2$ to $C_9$) heteroaryl, wherein each of the said ($C_6$ to $C_{10}$) aryl, and ($C_2$ to $C_9$) heteroaryl is optionally substituted with at least one $R^4$ group, and wherein said ($C_2$ to $C_9$) heteroaryl is C-attached;

$R^2$ is selected from ($C_6$ to $C_{10}$) aryl and ($C_2$ to 09) heteroaryl, wherein each of the said ($C_6$ to $C_{10}$) aryl, and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, wherein A, D, E, G, H, J, K, L, $R^1$, and $R^3$ are defined as above, or a pharmaceutically acceptable salt, and a pharmaceutically acceptable carrier, diluent, or vehicle thereof, wherein:

$R^2$ is selected from the group consisting of

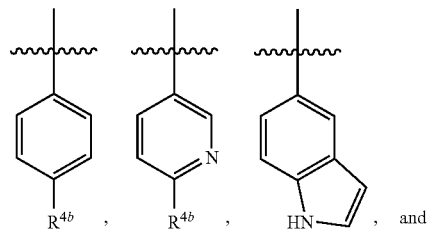

-continued wherein
$R^{4b}$ is selected from $(C_1$ to $C_6)$ alkyl, $(C_1$ to $C_6)$ alkenyl, $(C_1$ to $C_6)$ alkynyl, $(C_1$ to $C_6)$ alkoxy, aryloxy, $(C_3$ to $C_{10})$ cycloalkyl, $(C_5$ to $C_{10})$ cycloalkenyl, $(C_2$ to $C_9)$ cycloheteroalkyl, $(C_6$ to $C_{10})$ aryl, $(C_2$ to $C_9)$ heteroaryl, and —C(O)$R^5$, wherein
each of the said $(C_1$ to $C_6)$ alkyl, $(C_1$ to $C_6)$ alkenyl, $(C_1$ to $C_6)$ alkynyl, $(C_1$ to $C_6)$ alkoxy, aryloxy, $(C_3$ to $C_{10})$ cycloalkyl, $(C_5$ to $C_{10})$ cycloalkenyl, $(C_2$ to $C_9)$ cycloheteroalkyl, $(C_6$ to $C_{10})$ aryl, and $(C_2$ to $C_9)$ heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, $R^2$, and $R^3$ are defined as above, or a pharmaceutically acceptable salt, and a pharmaceutically acceptable carrier, diluent, or vehicle thereof, wherein $R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, $R^2$, and $R^3$ are defined as above, or a pharmaceutically acceptable salt, and a pharmaceutically acceptable carrier, diluent, or vehicle thereof, wherein:

$R^{4b}$ is isopropoxy, surprisingly providing improved metabolic stability in multi-species microsomal assays.

In another embodiment, the method comprises administering to humans, other mammals, cell culture, or biological sample an effective amount of a compound represented by Structural Formula I, wherein $R^3$ is defined as above, or a pharmaceutically acceptable salt, and a pharmaceutically acceptable carrier, diluent, or vehicle thereof, wherein:

A, D, and E are independently N or C—$R^3$;
G and H are C;
J and L are N;
K is C—$R^3$;
$R^1$ is selected from $(C_6$ to $C_{10})$ aryl and $(C_2$ to $C_9)$ heteroaryl, wherein
each of the said $(C_6$ to $C_{10})$ aryl and $(C_2$ to $C_9)$ heteroaryl is optionally substituted with at least one $R^4$ group, and wherein said $(C_2$ to $C_9)$ heteroaryl is C-attached;

$R^2$ is selected from $(C_6$ to $C_{10})$ aryl and $(C_2$ to $C_9)$ heteroaryl, wherein
each of the said $(C_6$ to $C_{10})$ aryl and $(C_2$ to $C_9)$ heteroaryl is optionally substituted with at least one $R^4$ group.

In another embodiment, the method comprises administering to humans, other mammals, cell culture, or biological sample an effective amount of a compound represented by Structural Formula I, wherein A, D, E, G, H, J, K, L, $R^1$, and $R^3$ are defined as above, or a pharmaceutically acceptable salt, and a pharmaceutically acceptable carrier, diluent, or vehicle thereof, wherein:

$R^2$ is selected from the group consisting of wherein
$R^{4b}$ is selected from $(C_1$ to $C_6)$ alkyl, $(C_1$ to $C_6)$ alkenyl, $(C_1$ to $C_6)$ alkynyl, $(C_1$ to $C_6)$ alkoxy, aryloxy, $(C_3$ to $C_{10})$ cycloalkyl, $(C_5$ to $C_{10})$ cycloalkenyl, $(C_2$ to $C_9)$ cycloheteroalkyl, $(C_6$ to $C_{10})$ aryl, $(C_2$ to $C_9)$ heteroaryl, and —C(O)$R^5$, wherein
each of the said $(C_1$ to $C_6)$ alkyl, $(C_1$ to $C_6)$ alkenyl, $(C_1$ to $C_6)$ alkynyl, $(C_1$ to $C_6)$ alkoxy, aryloxy, $(C_3$ to $C_{10})$ cycloalkyl, $(C_5$ to $C_{10})$ cycloalkenyl, $(C_2$ to $C_9)$ cycloheteroalkyl, $(C_6$ to $C_{10})$ aryl, and $(C_2$ to $C_9)$ heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, $R^2$, and $R^3$ are defined as above, or a pharmaceutically acceptable salt, and a pharmaceutically acceptable carrier, diluent, or vehicle thereof, wherein:

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen;
$R^{4b}$ is isopropoxy.

In another embodiment, the method comprises administering to humans, other mammals, cell culture, or biological sample an effective amount of a compound represented by Structural Formula I, wherein G and H are C, J and L are N, A, D, E, and K are independently C—$R^3$, and $R^1$ is defined as above, or a pharmaceutically acceptable salt, and a pharmaceutically acceptable carrier, diluent, or vehicle thereof, wherein:

$R^2$ is selected from the group consisting of

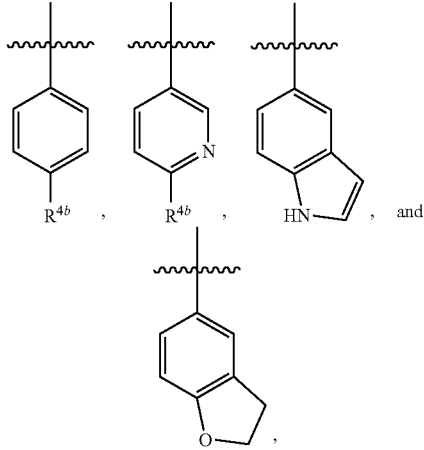

wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of
n-propyloxy, n-butyloxy, isobutyloxy, sec-butyloxy, cyclob wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, wherein G and H are C, D, J and L are N, and A, E, and K are independently C—$R^3$, or a pharmaceutically acceptable salt, and a pharmaceutically acceptable carrier, diluent, or vehicle thereof, wherein:

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group, and wherein said ($C_2$ to $C_9$) heteroaryl is C-attached;

$R^2$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, wherein A, D, E, G, H, J, K, L, and $R^1$ are defined as above, or a pharmaceutically acceptable salt, and a pharmaceutically acceptable carrier, diluent, or vehicle thereof, wherein:

$R^2$ is selected from the group consisting of wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, wherein G and H are C, A, D, J, and L are N, and E and K are independently C—$R^3$, or a pharmaceutically acceptable salt, and a pharmaceutically acceptable carrier, diluent, or vehicle thereof, wherein:

$R^1$ is selected from ($C_6$ to $C_{10}$) aryl and ($C_2$ to $C_9$) heteroaryl, wherein each of the said ($C_6$ to $C_{10}$) aryl, and ($C_2$ to $C_9$) heteroaryl is optionally substituted with at least one $R^4$ group, and wherein said ($C_2$ to $C_9$) heteroaryl is C-attached;

$R^2$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, wherein A, D, E, G, H, J, K, L, and $R^1$ are defined as above, or a pharmaceutically acceptable salt, and a pharmaceutically acceptable carrier, diluent, or vehicle thereof, wherein:

$R^2$ is selected from the group consisting of

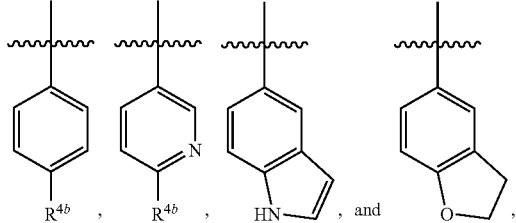

wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, and E are independently N or C—$R^3$, G and H are C, J and K are N, and L is $CR^3$, or a pharmaceutically acceptable salt, and a pharmaceutically acceptable carrier, diluent, or vehicle thereof, wherein:

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group, and wherein said ($C_2$ to $C_9$) heteroaryl is C-attached;

$R^2$ is selected from the group consisting of

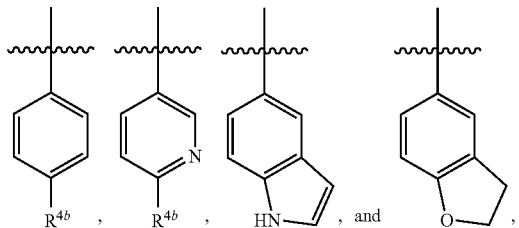

wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, and E are independently N or C—$R^3$, G, H and J are C, K and L are independently N or $NR^3$, or a pharmaceutically acceptable salt, and a pharmaceutically acceptable carrier, diluent, or vehicle thereof, wherein:

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group;

$R^2$ is selected from the group consisting of

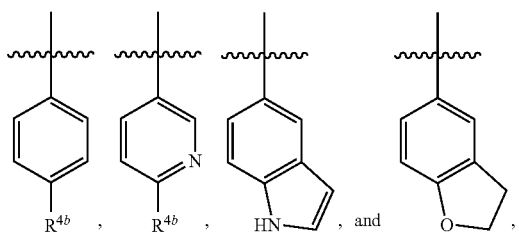

wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, and E are independently N or C—$R^3$;
G and J are C;
H and L are N;
K is C—$R^3$;
$R^1$ is selected from ($C_6$ to $C_{10}$) aryl and ($C_2$ to 09) heteroaryl, wherein each of the said ($C_6$ to $C_{10}$) aryl and ($C_2$ to $C_9$) heteroaryl is optionally substituted with at least one $R^4$ group, and wherein said ($C_2$ to $C_9$) heteroaryl is C-attached;

$R^2$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, wherein A, D, E, G, H, J, K, L, and $R^1$ are defined as above, or a pharmaceutically acceptable salt, and a pharmaceutically acceptable carrier, diluent, or vehicle thereof, wherein:

$R^2$ is selected from the group consisting of

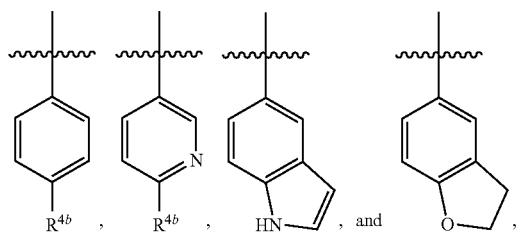

wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above or a pharmaceutically acceptable salt, and a pharmaceutically acceptable carrier, diluent, or vehicle thereof, wherein:

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen;
$R^{4b}$ is isopropoxy.

In another embodiment, the method comprises administering to humans, other mammals, cell culture, or biological sample an effective amount of a compound represented by Structural Formula I, wherein A, D, and E are independently C—$R^3$, G and J are C, H and L are N, K is C—$R^3$, and $R^1$ is define as above, or a pharmaceutically acceptable salt, and a pharmaceutically acceptable carrier, diluent, or vehicle thereof, wherein:

$R^2$ is selected from the group consisting of wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O) $R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, wherein D and E are independently C—$R^3$, G and J are C, A, H, and L are N, K is C—$R^3$, and $R^1$ is defined as above, or a pharmaceutically acceptable salt, and a pharmaceutically acceptable carrier, diluent, or vehicle thereof, wherein:

$R^2$ is selected from the group consisting of wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein D and E are independently C—$R^3$, G and J are C, A, H, and L are N, K is C—$R^3$, and $R^1$ and $R^2$ are defined as above, or a pharmaceutically acceptable salt, and a pharmaceutically acceptable carrier, diluent, or vehicle thereof, wherein:

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, wherein A and D are independently C—$R^3$, G and J are C, E, H, and L are N, and K is C—$R^3$, or a pharmaceutically acceptable salt, and a pharmaceutically acceptable carrier, diluent, or vehicle thereof, wherein:

$R^2$ is selected from the group consisting of wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, and E are independently N or C—$R^3$;
G and H are C;
J, K, and L are N;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^4$ group, wherein said ($C_2$ to $C_9$) heteroaryl is C-attached;
$R^2$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, wherein A, D, E, G, H, J, K, L, and $R^1$ are defined as above, or a pharmaceutically acceptable salt, and a pharmaceutically acceptable carrier, diluent, or vehicle thereof, wherein:

$R^2$ is selected from the group consisting of

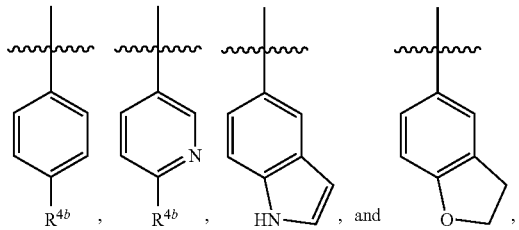

wherein
$R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein
each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of
n-propyloxy, n-butyloxy, is cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, and E are independently C—$R^3$;
G and J are C;
H, K, and L are N;
$R^1$ is selected from ($C_6$ to $C_{10}$) aryl and ($C_2$ to $C_9$) heteroaryl, wherein each of the said ($C_6$ to $C_{10}$) aryl, and ($C_2$ to $C_9$) heteroaryl is optionally substituted with at least one $R^4$ group, and wherein ($C_2$ to $C_9$) heteroaryl is C-attached;

$R^2$ is selected from ($C_6$ to $C_{10}$) aryl and ($C_2$ to $C_9$) heteroaryl, wherein each of the said ($C_6$ to $C_{10}$) aryl, and ($C_2$ to 09) heteroaryl is optionally substituted with at least one $R^4$ group.

In another embodiment, the method comprises administering to humans, other mammals, cell culture, or biological sample an effective amount of a compound represented by Structural Formula I, wherein A, D, E, G, H, J, K, L, and $R^1$ are defined as above, or a pharmaceutically acceptable salt, and a pharmaceutically acceptable carrier, diluent, or vehicle thereof, wherein:

$R^2$ is selected from the group consisting of wherein $R^{4b}$ is selected from ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, and —C(O)$R^5$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group.

In another embodiment, the method comprises administering to humans, other mammals, cell culture, or biological sample an effective amount of a compound represented by Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl.

In another embodiment, the method comprises administering to humans, other mammals, cell culture, or biological sample an effective amount of a compound represented by Structural Formula I, A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the method comprises administering to humans, other mammals, cell culture, or biological sample an effective amount of a compound represented by Structural Formula I, A, D, E, G, H, J, K, L, $R^1$ and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, and E are independently N or C—$R^3$;
G and H are C;
J and L are N;
K is C—$R^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, E, and K are independently C—$R^3$;
G and H are C;
J and L are N.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, E and K are independently C—$R^3$;
G and H are C;
J and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, E, and K are C—H;
G and H are C;
J and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, E, and K are independently C—$R^3$;
G and H are C;
J and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is 4-alkoxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, E, and K are C—H;
G and H are C;
J and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is 4-alkoxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, E and K are independently C—$R^3$;
G and H are C;
J and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is 4-isopropyloxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, E, and K are C—H;
G and H are C;
J and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is 4-isopropyloxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

D, E, and K are independently C—$R^3$;
G and H are C;
A, J and L are N.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

D, E, and K are independently C—$R^3$;
G and H are C;
A, J and L are N;

$R^1$ is selected from ($C_6$ to $C_{10}$) aryl and ($C_2$ to $C_9$) heteroaryl, wherein
  each of the said ($C_6$ to $C_{10}$) aryl, and ($C_2$ to $C_9$) heteroaryl is optionally substituted with at least one $R^4$ group;
$R^2$ is selected from ($C_6$ to $C_{10}$) aryl and ($C_2$ to $C_9$) heteroaryl, wherein
  each of the said ($C_6$ to $C_{10}$) aryl, and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  D, E, and K are C—H;
  G and H are C;
  A, J and L are N;
  $R^1$ is selected from ($C_6$ to $C_{10}$) aryl and ($C_2$ to $C_9$) heteroaryl, wherein
    each of the said ($C_6$ to $C_{10}$) aryl, and ($C_2$ to $C_9$) heteroaryl is optionally substituted with at least one $R^4$ group;
  $R^2$ is selected from ($C_6$ to $C_{10}$) aryl and ($C_2$ to $C_9$) heteroaryl, wherein
    each of the said ($C_6$ to $C_{10}$) aryl, and ($C_2$ to 09) heteroaryl is optionally substituted with at least one $R^4$ group.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  D, E, and K are independently C—$R^3$;
  G and H are C;
  A, J and L are N;
  $R^1$ is selected from ($C_6$ to $C_{10}$) aryl and ($C_2$ to 09) heteroaryl, wherein
    each of the said ($C_6$ to $C_{10}$) aryl, and ($C_2$ to $C_9$) heteroaryl is optionally substituted with at least one $R^4$ group;
  $R^2$ is 4-alkoxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  D, E, and K are C—H;
  G and H are C;
  A, J and L are N;
  $R^1$ is selected from ($C_6$ to $C_{10}$) aryl and ($C_2$ to $C_9$) heteroaryl, wherein
    each of the said ($C_6$ to $C_{10}$) aryl, and ($C_2$ to $C_9$) heteroaryl is optionally substituted with at least one $R^4$ group;
  $R^2$ is 4-alkoxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  D, E, and K are independently C—$R^3$;
  G and H are C;
  A, J and L are N;
  $R^1$ is selected from ($C_6$ to $C_{10}$) aryl and ($C_2$ to $C_9$) heteroaryl, wherein
    each of the said ($C_6$ to $C_{10}$) aryl, and ($C_2$ to $C_9$) heteroaryl is optionally substituted with at least one $R^4$ group;
  $R^2$ is 4-isopropyloxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  D, E, and K are C—H;
  G and H are C;
  A, J and L are N;
  $R^1$ is selected from ($C_6$ to $C_{10}$) aryl and ($C_2$ to $C_9$) heteroaryl, wherein
    each of the said ($C_6$ to $C_{10}$) aryl, and ($C_2$ to $C_9$) heteroaryl is optionally substituted with at least one $R^4$ group;
  $R^2$ is 4-isopropyloxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  A, D, and E are independently N or C—$R^3$;
  G and H are C;
  J is N;
  K and L are independently C—$R^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  A, D, and E are independently N or C—$R^3$;
  G, H, and J are C;
  K is C—$R^3$;
  L is N—$R^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  A, D, and E are independently N or C—$R^3$;
  G and H are C;
  J and K are N;
  L is C—$R^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  A, D, and E are independently N or C—$R^3$;
  G, H, and J are C;
  K is N;
  L is N—$R^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
  A, D, and E are independently N or C—$R^3$;
  G and J are C;
  H and L are N;
  K is C—$R^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, E and K are independently C—$R^3$;
G and J are C;
H and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to 09) heteroaryl is optionally substituted with at least one $R^4$ group; $R^2$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, E and K are C—H;
G and J are C;
H and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, E and K are independently C—$R^3$;
G and J are C;
H and L are N;
$R^1$ is selected from ($C_6$ to $C_{10}$) aryl and ($C_2$ to 09) heteroaryl, wherein
each of the said ($C_6$ to $C_{10}$) aryl, and ($C_2$ to 09) heteroaryl is optionally substituted with at least one $R^4$ group;
$R^2$ is 4-alkoxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, E and K are C—H;
G and J are C;
H and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is 4-alkoxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, E and K are independently C—$R^3$;
G and J are C;
H and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is 4-isopropyloxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, E and K are C—H;
G and J are C;
H and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^4$ group;
$R^2$ is 4-isopropyloxyphenyl.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, and E are independently N or C—$R^3$;
G and J are C;
H and K are N;
L is $CR^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, and E are independently N or C—$R^3$;
H and J are C;
G and K are N;
L is C—$R^3$.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, and E are independently N or C—$R^3$;
G and J are C;
H, K, and L are N.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, and E are independently N or C—$R^3$;
G and H are C;
J, K, and L are N.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:
A, D, and E are independently N or C—$R^3$;
G, H, and J are C;
K is C—$R^3$;
L is O.

In another embodiment, the method comprises administering to humans, other mammals, cell culture, or biological sample an effective amount of a compound represented by Structural Formula I, or a pharmaceutically acceptable salt, and a pharmaceutically acceptable carrier, diluent, or vehicle thereof, wherein:

A, D, and E are independently N or C—$R^3$;
G, H, and J are C;
K is O;
L is N.

In another embodiment, the invention relates to compounds of Structural Formula I or a pharmaceutically acceptable salt, and a pharmaceutically acceptable carrier, diluent, or vehicle thereof, wherein:

A, D, and E are independently N or C—$R^3$;
G, H, and J are independently N or C;
K is N or C—H;
L is N, N—$R^3$, or C—$R^3$;
and A, D, E, G, H, J, K, and L together cannot have more than 4 N;

$R^1$ is selected from ($C_6$ to $C_{10}$) aryl and ($C_2$ to $C_9$) heteroaryl, and 5-indolyl, wherein each of the said ($C_6$ to $C_{10}$) aryl and ($C_2$ to $C_9$) heteroaryl is substituted with at least one $R^{4a}$ group, and wherein said ($C_2$ to $C_9$) heteroaryl is C-attached;

with the proviso that $R^1$ is not selected from the group consisting of substituted 3-carbamoyl-2-phenyl-1-benzofuran-5-yl, substituted 1,3,4-oxadiazolyl, substituted 1,3,4-triazolyl, substituted 1,3,4-thiadiazolyl, substituted oxazoyl, substituted thiazoyl, substituted 1H-pyrazol-4-yl, substituted 1H-pyrazol-5-yl, optionally substituted 1-phenyl-1H-imidazol-5-yl, 4-{[(2-aminoethyl)amino]methyl}phenyl, (2-amino-1,3-benzoxazol)-5-yl; (2-amino-1,3-benzoxazol)-4-yl, 2-chloropyridyl-3-yl, 2-methylpyridinyl-4-yl, 2-fluoropyridyl-4-yl, 6-aminopyridyl-3-yl, 6-methoxypyridyl-3-yl, pyridyl-4-yl-N-oxide, 3,4-difluorphenyl, and substituted 1H-pyrrol-3-yl;

$R^2$ is selected from the group consisting of each of the $R^3$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)NR$^{6a}$R$^{6b}$, —NR$^{6a}$R$^{6b}$, —S(O)$_m$$R^5$, —S(O)$_m$NR$^{6a}$R$^{6b}$, —NR$^{6a}$S(O)$_m$$R^5$, —(CH$_2$)$_n$C(O)OR$^5$, —(CH$_2$)$_n$C(O)NR$^{6a}$R$^{6b}$, —OC(O)$R^5$, —NR$^{6a}$C(O)$R^5$, and —NR$^{6c}$C(O)NR$^{5a}$R$^{5b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4a}$ is independently selected from halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —NR$^{6a}$R$^{6b}$, —S(O)$_m$$R^5$, —S(O)$_m$NR$^{6a}$R$^{6b}$, —NR$^{6a}$S(O)$_m$$R^5$, —OC(O)$R^5$, —NR$^{6a}$C(O)$R^5$, and —NR$^{6c}$C(O)NR$^{6a}$R$^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, surprisingly providing broad spectrum activity against multiple arenavirus strains, and we believe that similar broad spectrum activity against multiple arenavirus strains can be observed when $R^{4b}$ is selected from the group consisting of
n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, tert-butyl, propanoyl, isobutanoyl, sec-butanoyl, tert-butanoyl, cyclopropanoyl, cyclobutanoyl, and cyclopentanoyl;

each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, or $R^{6a}$ and $R^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)NR$^{9a}$R$^{9b}$, —NR$^{9a}$R$^{9b}$, —S(O)$_m$$R^8$, —S(O)$_m$NR$^{9a}$R$^{9b}$, —NR$^{9a}$S(O)$_m$$R^8$, —(CH$_2$)$_n$C(O)OR$^8$, —(CH$_2$)$_n$ C(O)N($R^{9a}R^{9b}$), —OC(O)$R^8$, —N$R^{9a}$C(O)$R^8$, and —N$R^{9a}$C(O)N($R^{9a}R^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;

each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;

each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted;

m is 0, 1, or 2;

n is 1, 2, 3, 4, 5, or 6.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:

$R^3$ is hydrogen.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein $R^3$ is hydrogen;

$R^{4b}$ is isopropoxy.

In another embodiment, the invention relates to compounds of Structural Formula I, wherein $R^1$, and $R^2$ are defined as above, or a pharmaceutically acceptable salt, and a pharmaceutically acceptable carrier, diluent, or vehicle thereof, wherein:

A, D, and E are independently N or C—$R^3$;

G and H are C;

J and L are N;

K is C—H.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein $R^3$ is hydrogen.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein $R^{4b}$ is isopropoxy.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen;

$R^{4b}$ is isopropoxy.

In another embodiment, the invention relates to compounds of Structural Formula I, wherein G and H are C, J and L are N, K is C—H, and $R^1$ and $R^2$ are defined as above, or a pharmaceutically acceptable salt, and a pharmaceutically acceptable carrier, diluent, or vehicle thereof, wherein:

A, D, and E are independently C—$R^3$.

In another embodiment, the invention relates to compounds of Structural Formula I, wherein A, D, E, G, H, J, K, L, $R^1$ and $R^2$ are defined as above, or a pharmaceutically acceptable salt, and a pharmaceutically acceptable carrier, diluent, or vehicle thereof, wherein:

$R^3$ is hydrogen.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein: $R^{4b}$ is isopropoxy.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:

D and E are independently C—$R^3$;

G and H are C;

A, J, and L are N;

K is C—H.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^3$ is hydrogen.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:

$R^{4b}$ is isopropoxy.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:

A and E are independently C—$R^3$;

G and H are C;

D, J, and L are N;

K is C—H.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^3$ is hydrogen.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^{4b}$ is isopropoxy.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:
E is C—$R^3$;
G and H are C;
K is C—H;
A, D, J, and L are N.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^3$ is hydrogen.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein
$R^{4b}$ is isopropoxy.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:
A, D, and E are independently N or C—$R^3$;
G and H are C;
J is N;
K is C—H;
L is C—$R^3$.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:
A, D, and E are independently N or C—$R^3$;
G and H are C;
J and K are N;
L is C—$R^3$.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:
A, D, and E are independently N or C—$R^3$;
G, H, and J are C;
K is N;
L is N—$R^3$.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:
A, D, and E are independently N or C—$R^3$;
G and J are C;
H and L are N;
K is C—H.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^3$ is hydrogen.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^{4b}$ is isopropoxy.

In another embodiment, the invention relates to compounds of Structural Formula I, wherein G and J are C; H and L are N, K is C—H, and $R^1$ and $R^2$ are defined as above, or a pharmaceutically acceptable salt, and a pharmaceutically acceptable carrier, diluent, or vehicle thereof, wherein:
A, D, and E are independently C—$R^3$.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^3$ is hydrogen.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^{4b}$ is isopropoxy.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:
D and E are independently C—$R^3$;
A, H, and L are N;
K is C—H;
G and J are C.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^3$ is hydrogen.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^{4b}$ is isopropoxy.

In another embodiment, the invention relates to compounds of Structural Formula I, wherein $R^1$ and $R^2$ are defined as above, or a pharmaceutically acceptable salt, and a pharmaceutically acceptable carrier, diluent, or vehicle thereof, wherein:
A and D are independently C—$R^3$;
G and J are C;
K is C—H;
E, H, and L are N.

In another embodiment, the invention relates to compounds of Structural Formula I, wherein A, D, E, G, H, J, K, L, $R^1$, and $R^2$ are defined as above, or a pharmaceutically acceptable salt, and a pharmaceutically acceptable carrier, diluent, or vehicle thereof, wherein:
$R^3$ is hydrogen.

In another embodiment, the invention relates to compounds of Structural Formula I, wherein A, D, E, G, H, J, K, L, R¹ and R² are defined as above, or a pharmaceutically acceptable salt, and a pharmaceutically acceptable carrier, diluent, or vehicle thereof, wherein:

R$^{4b}$ is isopropoxy.

In another embodiment, the invention relates to compounds of Structural Formula I, wherein R¹ and R² are defined as above, or a pharmaceutically acceptable salt, and a pharmaceutically acceptable carrier, diluent, or vehicle thereof, wherein:

A, D, and E are independently N or C—R³;
G and J are C;
J, K, and L are N.

In another embodiment, the invention relates to compounds of Structural Formula I, wherein A, D, E, G, H, J, K, L, R¹, and R² are defined as above, or a pharmaceutically acceptable salt, and a pharmaceutically acceptable carrier, diluent, or vehicle thereof, wherein:

R³ is hydrogen.

In another embodiment, the invention relates to compounds of Structural Formula I, wherein A, D, E, G, H, J, K, L, R¹, and R² are defined as above, or a pharmaceutically acceptable salt, and a pharmaceutically acceptable carrier, diluent, or vehicle thereof, wherein:

R$^{4b}$ is isopropoxy.

In another embodiment, the invention relates to compounds of Structural Formula I, wherein G and H are C, J, K, and L are N, and R¹ and R² are defined as above, or a pharmaceutically acceptable salt, and a pharmaceutically acceptable carrier, diluent, or vehicle thereof, wherein:

A, D, and E are independently C—R³.

In another embodiment, the invention relates to compounds of Structural Formula I, wherein A, D, E, G, H, J, K, L, R¹, and R² are defined as above, or a pharmaceutically acceptable salt, and a pharmaceutically acceptable carrier, diluent, or vehicle thereof, wherein:

R³ is hydrogen.

In another embodiment, the invention relates to compounds of Structural Formula I, wherein A, D, E, G, H, J, K, L, R¹, and R² are defined as above, or a pharmaceutically acceptable salt, and a pharmaceutically acceptable carrier, diluent, or vehicle thereof, wherein:

R$^{4b}$ is isopropoxy.

In another embodiment, the invention relates to compounds of Structural Formula I, wherein R¹ and R² are defined as above, or a pharmaceutically acceptable salt, and a pharmaceutically acceptable carrier, diluent, or vehicle thereof, wherein:

A, D, and E are independently C—R³,
G and J are C;
H, K, and L are N.

In another embodiment, the invention relates to compounds of Structural Formula I, wherein A, D, E, G, H, J, K, L, R¹, and R² are defined as above, or a pharmaceutically acceptable salt, and a pharmaceutically acceptable carrier, diluent, or vehicle thereof, wherein:

R³ is hydrogen.

In another embodiment, the invention relates to compounds of Structural Formula I, wherein A, D, E, G, H, J, K, L, R¹ and R² are defined as above, or a pharmaceutically acceptable salt, and a pharmaceutically acceptable carrier, diluent, or vehicle thereof, wherein:

R$^{4b}$ is isopropoxy.

In another embodiment, the invention relates to compounds of Structural Formula I, wherein R¹ and R² are defined as above, or a pharmaceutically acceptable salt, and a pharmaceutically acceptable carrier, diluent, or vehicle thereof, wherein:

A, D, and E are independently N or C—R³;
H and J are C;
G and K are N;
L is C—R³.

In another embodiment, the invention relates to compounds of Structural Formula I, wherein R¹ and R² are defined as above, or a pharmaceutically acceptable salt, and a pharmaceutically acceptable carrier, diluent, or vehicle thereof, wherein A, D, and E are independently N or C—R³;
G, H, and J are C;
K is C—H;
L is O.

In another embodiment, the invention relates to compounds of Structural Formula I, wherein R¹ and R² are defined as above, or a pharmaceutically acceptable salt, and a pharmaceutically acceptable carrier, diluent, or vehicle thereof, wherein A, D, and E are independently N or C—R³;
G, H, and J are C;
K is N;
L is O.

In another embodiment, the invention relates to compounds of Structural Formula I

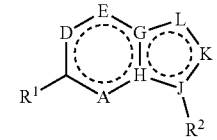

or a pharmaceutically acceptable salt, and a pharmaceutically acceptable carrier, diluent, or vehicle thereof, wherein A, D, E, and K are C—H;
G and H are C;
J and L are N;
R¹ is selected from (C$_6$ to C$_{10}$) aryl and (C$_2$ to C$_9$) heteroaryl, wherein each of the said (C$_6$ to C$_{10}$) aryl, and (C$_2$ to C$_9$) heteroaryl is optionally substituted with at least one R$^{4a}$ group, with the proviso that R¹ is not selected from the group consisting of optionally substituted 3-carbamoyl-2-phenyl-1-benzofuran-5-yl, optionally substituted 1,3,4-oxadiazolyl, optionally substituted 1H-pyrazol-4-yl, optionally substituted 1-phenyl-1H-pyrazol-5-yl, optionally substituted 1-phenyl-1H-imidazol-5-yl, 4-{[(2-aminoethyl)amino]methyl}phenyl, and (2-amino-1,3-benzoxazol)-5-yl;

R² is

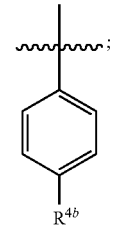

R$^{4a}$ is independently selected from hydrogen, halogen, cyano, OH, CF$_3$, (C$_1$ to C$_6$) alkyl, (C$_1$ to C$_6$) alkenyl, (C$_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)R$^5$, —NR$^{6a}$R$^{6b}$, —S(O)$_m$R$^5$, —S(O)$_m$NR$^{6a}$R$^{6b}$, —NR$^{6a}$S(O)$_m$R$^5$, —OC(O)R$^5$, —NR$^{6a}$C(O)R$^5$, and —NR$^{6c}$C(O)NR$^{6a}$R$^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one R$^7$ group;

R$^{4b}$ is selected from halogen, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)R$^5$, —C(O)NR$^{6a}$R$^{6b}$, —NR$^{6a}$R$^{6b}$, —S(O)$_m$R$^5$, —S(O)$_m$NR$^{6a}$R$^{6b}$, —NR$^{6a}$S(O)$_m$R$^5$, —(CH$_2$)$_n$C(O)OR$^5$, —(CH$_2$)$_n$C(O)NR$^{6a}$R$^{6b}$, —OC(O)R$^5$, —NR$^{6a}$C(O)R$^5$, and —NR$^{6c}$C(O)NR$^{6a}$R$^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one R$^7$ group;

each of the R$^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one R$^7$ group;

each of the R$^{6a}$, R$^{6b}$, and R$^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, or R$^{6a}$ and R$^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one R$^7$ group;

R$^7$ is independently selected from hydrogen, halogen, OH, CF$_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)R$^8$, —C(O)NR$^{9a}$R$^{9b}$, —NR$^{9a}$R$^{9b}$, —S(O)$_m$R$^8$, —S(O)$_m$NR$^{9a}$R$^{9b}$, —NR$^{9a}$S(O)$_m$R$^8$, —(CH$_2$)$_n$C(O)OR$^8$, —(CH$_2$)$_n$C(O)N(R$^{9a}$R$^{9b}$), —OC(O)R$^8$, —NR$^{9a}$C(O)R$^8$, and —NR$^{9a}$C(O)N(R$^{9a}$R$^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one R$^{10}$ group;

each of the R$^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one R$^{10}$ group;

each of the R$^{9a}$, R$^{9b}$, and R$^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or R$^{9a}$ and R$^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

R$^{10}$ is independently selected from hydrogen, halogen, cyano, OH, CF$_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted;

m is 0, 1, or 2;

n is 1, 2, 3, 4, 5, or 6;

with the proviso that the following compound is excluded: 2-(cyclopentyloxy)-5-{4-[6-(5-oxo-2,5-dihydro-1,2,4-oxadiazol-3-yl)-1H-1,3-benzodiazol-1-yl]phenyl}benzonitrile

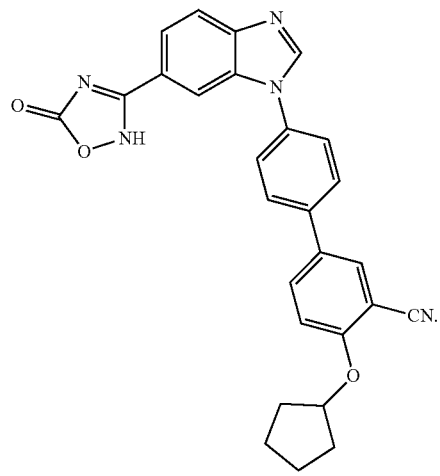 [SMILES: N#Cc1cc(-c2ccc(-n3cnc4ccc(-c5nc(=O)o[nH]5)cc43)cc2)ccc1OC1CCCC1]

In another embodiment, the invention relates to compounds of Structural Formula I

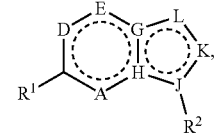

or a pharmaceutically acceptable salt, and a pharmaceutically acceptable carrier, diluent, or vehicle thereof, wherein D, E, and K are C—H;
G and H are C;
A, J and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^{4a}$ group,
with the proviso that $R^1$ is not selected from the group consisting of optionally substituted 3-carbamoyl-2-phenyl-1-benzofuran-5-yl, optionally substituted 1,3,4-oxadiazolyl, optionally substituted 1H-pyrazol-4-yl; optionally substituted 1-phenyl-1H-pyrazol-5-yl, optionally substituted 1-phenyl-1H-imidazol-5-yl, and (2-amino-1,3-benzoxazol)-5-yl;
$R^2$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^{4b}$ group,
$R^{4a}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —NR$^{6a}$R$^{6b}$, —S(O)$_m$R$^5$, —S(O)$_m$NR$^{6a}$R$^{6b}$, —NR$^{6a}$S(O)$_m$R$^5$, —OC(O)R$^5$, —NR$^{6a}$C(O)R$^5$, and —NR$^{6c}$C(O)NR$^{6a}$R$^{6b}$, wherein
each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;
$R^{4b}$ is independently selected from halogen, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)NR$^{6a}$R$^{6b}$, —NR$^{6a}$R$^{6b}$, —S(O)$_m$R$^5$, —S(O)$_m$NR$^{6a}$R$^{6b}$, —NR$^{6a}$S(O)$_m$R$^5$, —(CH$_2$)$_n$C(O)OR$^5$, —(CH$_2$)$_n$C(O)NR$^{6a}$R$^{6b}$, —OC(O)R$^5$, —NR$^{6a}$C(O)R$^5$, and —NR$^{6c}$C(O)NR$^{6a}$R$^{6b}$, wherein
each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;
each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein
each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;
each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl,
or $R^{6a}$ and $R^{6b}$ may be taken together with the nitrogen atom to which they are attached to form a 4 to 8 membered cycloheteroalkyl ring, wherein
said 4 to 8 membered cycloheteroalkyl ring has 1 to 3 ring heteroatoms selected from the group consisting of N, O, and S, and wherein
the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)NR$^{9a}$R$^{9b}$, —NR$^{9a}$R$^{9b}$, —S(O)$_m$R$^8$, —S(O)$_m$NR$^{9a}$R$^{9b}$, —NR$^{9a}$S(O)$_m$R$^8$, —(CH$_2$)$_n$C(O)OR$^8$, —(CH$_2$)$_n$C(O)N(R$^{9a}$R$^{9b}$), —OC(O)R$^8$, —NR$^{9a}$C(O)R$^8$, and —NR$^{9a}$C(O)N(R$^{9a}$R$^{9b}$), wherein
each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;
each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein
each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;
each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl,
or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;
$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein
each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted;
m is 0, 1, or 2;
n is 1, 2, 3, 4, 5, or 6;
with the proviso that the following compound is excluded:
3,5-dipyridin-2-yl-3H-imidazo[4,5-b]pyridine

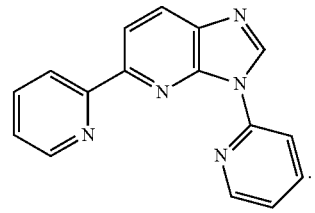 [SMILES: c1ccc(-c2ccc3ncn(-c4ccccn4)c3n2)nc1]

In another embodiment, the invention relates to compounds of Structural Formula I

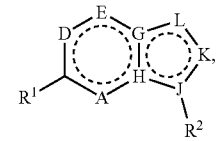

I or a pharmaceutically acceptable salt, and a pharmaceutically acceptable carrier, diluent, or vehicle thereof, wherein A, D, E, and K are CH;
G and J are C;
H and L are N;
$R^1$ is selected from ($C_6$ to $C_{10}$) aryl and ($C_2$ to $C_9$) heteroaryl, wherein
each of the said ($C_6$ to $C_{10}$) aryl, and ($C_2$ to $C_9$) heteroaryl is optionally substituted with at least one $R^{4a}$ group with the proviso that
$R^1$ is not selected from the group consisting of optionally substituted 3-carbamoyl-2-phenyl-1-benzofuran-5-yl, optionally substituted optionally 1,3,4-oxadiazolyl, optionally substituted 1H-pyrazol-4-yl, optionally substituted 1-phenyl-1H-pyrrol-2-yl, optionally substituted 1-phenyl-1H-pyrazol-5-yl, optionally substituted 1-phenyl-1H-imidazol-5-yl, 2-(4-fluoro-3-methylphenyl)pyridin-3-yl, and (2-amino-1,3-benzoxazol)-5-yl;
$R^2$ is

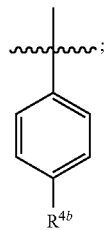

$R^{4a}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —N$R^{6a}R^{6b}$, —S(O)$_m R^5$, —S(O)$_m$N$R^{6a}R^{6b}$, —N$R^{6a}$S(O)$_m$$R^5$, —OC(O)$R^5$, —N$R^{6a}$C(O)$R^5$, and —N$R^{6c}$C(O)N$R^{6a}R^{6b}$, wherein
each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;
$R^{4b}$ is selected from the group consisting of
$CF_3$, (C to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, —C(O)$R^5$, —C(O)N$R^{6a}R^{6b}$, —N$R^{6a}R^{6b}$, —S$R^5$, —S(O)$_m$N$R^{6a}R^{6b}$, —N$R^{6a}$S(O)$_m$$R^5$, —(CH$_2$)$_n$C(O)O$R^5$, —(CH$_2$)$_n$C(O)N$R^{6a}R^{6b}$, —OC(O)$R^5$, —N$R^{6a}$C(O)$R^5$, and —N$R^{6c}$C(O)N$R^{6a}R^{6b}$, wherein
each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group,
with the proviso when
$R^{4b}$ is selected from the group consisting of isopropylthio, morpholin-4-yl, thiomorpholine-1,1-dione-4-yl, and amino,
then $R^1$ is not selected from the group consisting of

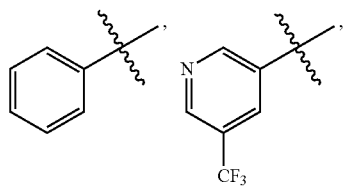

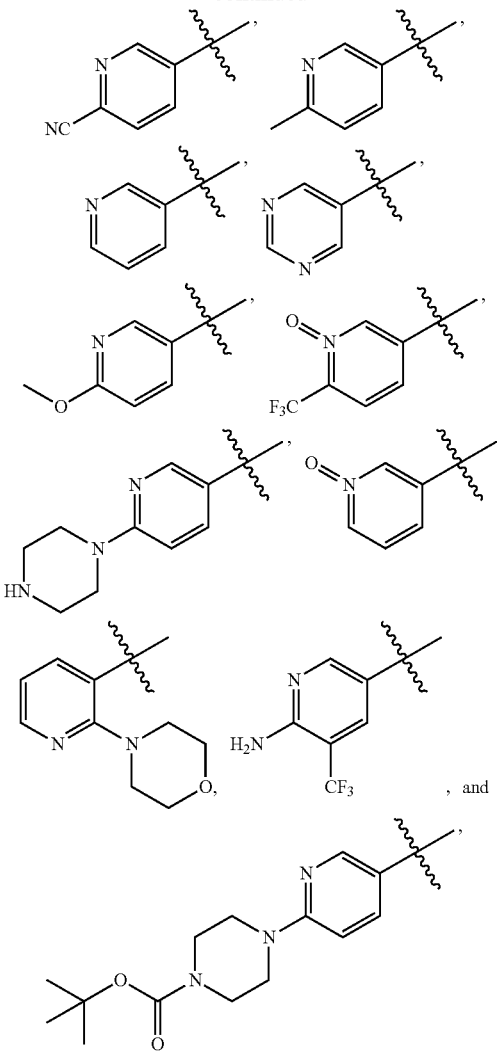

and with the proviso when
$R^{4b}$ is selected from the group consisting of 2-hydroxyethoxy, 2-(oxan-2-yloxy)ethoxy, 2-(oxan-4-yloxy)ethoxy, and 2-(oxan-4-yloxy)ethylamino,
then $R^1$ is not selected from the group consisting of 1H-pyrrol-3-yl, 1H-pyrazol-lyl, 1H-imidazol-1-yl, 4-pyridin-1-yl, 1-methyl-1H-methyl-pyrazol-4-yl, and 1,3-oxazol-2-yl;
each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein
each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;
each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl,
or $R^{6a}$ and $R^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)N$R^{9a}R^{9b}$, —N$R^{9a}R^{9b}$, —S(O)$_m R^8$, —S(O)$_m$N$R^{9a}R^{9b}$, —N$R^{9a}$S(O)$_m R^8$, —(CH$_2$)$_n$C(O)O$R^8$, —(CH$_2$)$_n$C(O)N($R^{9a}R^{9b}$), —OC(O)$R^8$, —N$R^{9a}$C(O)$R^8$, and —N$R^{9a}$C(O)N($R^{9a}R^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;

each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;

each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted.

m is 0, 1, or 2;

n is 1, 2, 3, 4, 5, or 6.

In another embodiment, the invention relates to compounds, or a pharmaceutically acceptable salt, and a pharmaceutically acceptable carrier, diluent, or vehicle thereof, selected from the group consisting of the compounds described as examples A1 to A31, B1 to B15, C1 to C51, and D1 to D23 in the method of preparation section.

One can treat Arenavirus infection by administering a pharmaceutically effective amount of a pharmaceutical composition comprising a compound selected of Structural Formula I or a compound as shown above with a pharmaceutically acceptable carrier, dilutant, or vehicle. Additionally a therapeutically effective amount of a therapeutic agent selected from the group consisting of Ribaviron, polymerase inhibitors, T-705 (favipiravir), Triazavirin, small interfering RNAs (siRNAs), vaccines, and immunomodulators can be administered with the compound of the invention.

Definitions

As used herein, the terms "comprising" and "including" are used in their open, non-limiting sense.

The terms "halo" and/or "halogen" refer to fluorine, chlorine, bromine or iodine.

The term "($C_1$ to $C_6$)" alkyl refers to a saturated aliphatic hydrocarbon radical including straight chain and branched chain groups of 1 to 6 carbon atoms. Examples of ($C_1$ to $C_6$) alkyl groups include methyl, ethyl, propyl, 2-propyl, n-butyl, iso-butyl, tert-butyl, pentyl, and the like. The terms "Me" and "methyl," as used herein, mean a —$CH_3$ group. The terms "Et" and "ethyl," as used herein, mean a —$C_2H_5$ group.

The term "($C_2$ to $C_8$) alkenyl", as used herein, means an alkyl moiety comprising 2 to 8 carbons having at least one carbon-carbon double bond. The carbon-carbon double bond in such a group may be anywhere along the 2 to 8 carbon chain that will result in a stable compound. Such groups include both the E and Z isomers of said alkenyl moiety. Examples of such groups include, but are not limited to, ethenyl, propenyl, butenyl, allyl, and pentenyl. The term "allyl," as used herein, means a —$CH_2CH=CH_2$ group. The term, "C(R)=C(R)," as used herein, represents a carbon-carbon double bond in which each carbon is substituted by an R group, and includes E and Z isomers.

As used herein, the term "($C_2$ to $C_8$) alkynyl" means an alkyl moiety comprising from 2 to 8 carbon atoms and having at least one carbon-carbon triple bond. The carbon-carbon triple bond in such a group may be anywhere along the 2 to 8 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

The term "($C_1$ to $C_8$) alkoxy", as used herein, means an O-alkyl group wherein said alkyl group contains from 1 to 8 carbon atoms and is straight, branched, or cyclic. Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The term "($C_6$ to $C_{10}$) aryl", as used herein, means a group derived from an aromatic hydrocarbon containing from 6 to 10 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

"($C_2$ to $C_9$) heteroaryl", as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The ($C_2$ to $C_9$) heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

"($C_2$ to $C_9$) cycloheteroalkyl", as used herein, means a non-aromatic, monocyclic, bicyclic, tricyclic, spirocyclic, or tetracyclic group having a total of from 4 to 13 atoms in its ring system, and containing from 5 to 9 carbon atoms and from 1 to 4 heteroatoms each independently selected from O, S and N, and with the proviso that the ring of said group does not contain two adjacent O atoms or two adjacent S atoms. Furthermore, such $C_2$ to $C_9$ cycloheteroalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a $C_2$ to $C_9$ cycloheteroalkyl group contains a sulfur atom, said sulfur atom may be oxidized with one or two oxygen atoms to afford either a sulfoxide or sulfone. An example of a 4 membered cycloheteroalkyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such $C_2$ to $C_9$ cycloheteroalkyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl quinolizinyl, 3-oxopiperazinyl, 4-methylpiperazinyl, 4-ethylpiperazinyl, and 1-oxo-2,8,diazaspiro[4.5]dec-8-yl.

The term "($C_3$ to $C_{10}$) cycloalkyl group" means a saturated, monocyclic, fused, spirocyclic, or polycyclic ring structure having a total of from 3 to 10 carbon ring atoms. Examples of such groups include, but are not limited to, cyclopropyl, cyclobutyl, cyclopentyl, cyclopentenyl, cyclohexyl, cycloheptyl, and adamantyl.

The term "spirocyclic" as used herein has its conventional meaning, that is, any compound containing two or more rings wherein two of the rings have one ring carbon in common. The rings of a spirocyclic compound, as herein defined, independently have 3 to 20 ring atoms. Preferably, they have 3 to 10 ring atoms. Non-limiting examples of a spirocyclic compound include spiro[3.3]heptane, spiro[3.4]octane, and spiro[4.5]decane.

The term "($C_5$ to $C_8$) cycloalkenyl" means an unsaturated, monocyclic, fused, spirocyclic ring structures having a total of from 5 to 8 carbon ring atoms. Examples of such groups include, but are not limited to, cyclopentenyl, cyclohexenyl.

The term cyano" refers to a —C≡N group.

An "aldehyde" group refers to a carbonyl group where R is hydrogen.

An "alkoxy" group refers to both an —O-alkyl and an —O-cycloalkyl group, as defined herein.

An "alkoxycarbonyl" refers to a —C(O)OR.

An "alkylaminoalkyl" group refers to an -alkyl-NR-alkyl group.

An "alkylsulfonyl" group refer to a —$SO_2$ alkyl.

An "amino" group refers to an —$NH_2$ or an —NRR' group.

An "aminoalkyl" group refers to an -alkyl-NRR' group.

An "aminocarbonyl" refers to a —C(O)NRR'.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)Oaryl.

An "arylsulfonyl" group refers to a —$SO_2$ aryl.

A "C-amido" group refers to a —C(O)NRR' group.

A "carbonyl" group refers to a —C(O)R.

A "C-carboxyl" group refers to a —C(O)OR groups.

A "carboxylic acid" group refers to a C-carboxyl group in which R is hydrogen.

A "dialkylaminoalkyl" group refers to an -(alkyl)N(alkyl)$_2$ group.

A "halo" or "halogen" group refers to fluorine, chlorine, bromine or iodine.

A "haloalkyl" group refers to an alkyl group substituted with one or more halogen atoms.

A "heteroalicycloxy" group refers to a heteroalicyclic-O group with heteroalicyclic as defined herein.

A "heteroaryloxyl" group refers to a heteroaryl-O group with heteroaryl as defined herein.

A "hydroxy" group refers to an —OH group.

An "N-amido" group refers to a —R'C(O)NR group.

An "N-carbamyl" group refers to a —ROC(O)NR-group.

A "nitro" group refers to a —$NO_2$ group.

An "N-Sulfonamido" group refers to a —NR—S(O)$_2$R group.

An "N-thiocarbamyl" group refers to a ROC(S)NR' group.

An "O-carbamyl" group refers to a —OC(O)NRR' group.

An "O-carboxyl" group refers to a RC(O)O group.

An "O-thiocarbamyl" group refers to a —OC(S)NRR' group.

An "oxo" group refers to a carbonyl moiety such that alkyl substituted by oxo refers to a ketone group.

A "perfluoroalkyl group" refers to an alkyl group where all of the hydrogen atoms have been replaced with fluorine atoms.

A "phosphonyl" group refers to a —P(O)(OR)$_2$ group.

A "silyl" group refers to a —$SiR_3$ group.

An "S-sulfonamido" group refers to a —S(O)$_2$NR-group.

A "sulfinyl" group refers to a —S(O)R group.

A "sulfonyl" group refers to a —S(O)$_2$R group.

A "thiocarbonyl" group refers to a —C(=S)—R group.

A "trihalomethanecarbonyl" group refers to a $Z_3$CC(O) group, where Z is halogen.

A "trihalomethanesulfonamido" group refers to a $Z_3$CS(O)$_2$NR-group.

A "trihalomethanesulfonyl" group refers to a $Z_3$CS(O)$_2$ group.

A "trihalomethyl" group refers to a —$CZ_3$ group.

A "C-carboxyl" group refers to a —C(O)OR groups.

The term "substituted," means that the specified group or moiety bears one or more substituents.

The term "unsubstituted," means that the specified group bears no substituents. The term "optionally substituted" means that the specified group is unsubstituted or substituted by one or more substituents. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

The term "solvate," is used to describe a molecular complex between compounds of the present invention and solvent molecules. Examples of solvates include, but are not limited to, compounds of the invention in combination water, isopropanol, ethanol, methanol, dimethylsulfoxide (DMSO), ethyl acetate, acetic acid, ethanolamine, or mixtures thereof. The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The term "pharmaceutically acceptable formulation," as used herein, means a combination of a compound of the invention, or a salt or solvate thereof, and a carrier, diluent, and/or excipient(s) that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional agents that reduce abnormal cell growth.

The term "Arenavirus GP-inhibiting amount" as used herein, refers to the amount of a compound of the present invention, or a salt or solvate thereof, required to inhibit the cell entry of Arenaviruses in vivo, such as in a mammal, birds or in vitro. The amount of such compounds required to cause such inhibition can be determined without undue experimentation using methods described herein and those known to those of ordinary skill in the art.

The term "therapeutically effective amount," as used herein, means an amount of a compound of the present invention, or a salt thereof, that, when administered to a mammal in need of such treatment, is sufficient to effect treatment, as defined herein. Thus, a therapeutically effective amount of a compound of the present invention, or a salt thereof, is a quantity sufficient to modulate or inhibit the activity of the Arenavirus GP protein such that cell entry and replication of arenaviruses that is mediated by activity of the Arenavirus GP protein is reduced or alleviated.

The terms "treat", "treating", and "treatment" with reference to arenavirus infection, in mammals, particularly a human, include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition.

Unless indicated otherwise, all references herein to the inventive compounds include references to salts, solvates, and complexes thereof, including polymorphs, stereoisomers, tautomers, and isotopically labeled versions thereof. For example, compounds of the present invention can be pharmaceutically acceptable salts and/or pharmaceutically acceptable solvates.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. A pure enantiomer can be contaminated with up to 2% of the opposite enantiomer.

The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another. In accordance with a convention used in the art, the symbol is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g., represents a methyl group,

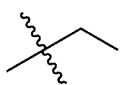

represents an ethyl group,

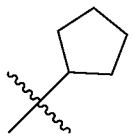 [SMILES: *C1CCCC1]

represents a cyclopentyl group, etc.

The compounds of the present invention may have asymmetric carbon atoms. The carbon carbon bonds of the compounds of the present invention may be depicted herein using a solid line ( —— ) a solid wedge ( ▬ ), or a dotted wedge ( ⋯ ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid ordotted wedge to depict bonds to other asymmetric carbon atoms in the same compound is meant to indicate that a mixture of diastereomers is present.

Unless otherwise defined, a substituent "R" may reside on any atom of the ring system, assuming replacement of a depicted, implied, or expressly defined hydrogen from one of the ring atoms, so long as a stable structure is formed.

Conventional techniques for the preparation/isolation of individual enantiomers include chiral synthesis from a suitable optically pure precursor or resolution of the reaceamate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenyl ethyl amine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E L Eliel (Wiley, New York, 1994), the disclosure of which is incorporated herein by reference in its entirety.

Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. Examples of tautomerism include keto and enol tautomers. A single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof. Cis/trans isomers may be separated by conventional techniques well known to those skilled in the art, for example, chromatography and fractional crystallization.

The compounds of the present invention may be administered as prodrugs. Thus certain derivatives of compounds of Formula I, which may have little or no pharmacological activity themselves can, when administered to a mammal, be converted into a compound of Formula (I) having the desired activity, for example, by hydrolytic cleavage. Such derivatives are referred to as "prodrugs". Prodrugs can, for example, be produced by replacing appropriate functionalities present in the compounds of Formula I with certain moieties known to those skilled in the art. See, e.g. "Prodrugs as Novel Delivery Systems", Vol. 14, ACS Symposium Series (T Higuchi and W Stella) and "Bioreversible Carriers in Drug Design", Pergamon Press, 1987 (ed. E B Roche, American Pharmaceutical Association), the disclosures of which are incorporated herein by reference in their entireties. Some examples of such prodrugs include: an ester moiety in the place of a carboxylic acid functional group; an ether moiety or an amide moiety in place of an alcohol functional group; and an amide moiety in place of a primary or secondary amino functional group. Further examples of replacement groups are known to those of skill in the art. See, e.g. "Design of Prodrugs" by H Bundgaard (Elsevier, 1985), the disclosure of which is incorporated herein by reference in its entirety. It is also possible that certain compounds of Formula I may themselves act as prodrugs of other compounds of Formula I.

Salts of the present invention can be prepared according to methods known to those of skill in the art. Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, dihydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methanesulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalicacid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The invention also includes isotopically-labeled compounds of the invention, wherein one or moreatoms is replaced by an atom having the same atomic number, but an atomic mass or mass number different from the atomic mass or mass number usually found in nature. Examples of isotopes suitable forinclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labeled compounds of the invention, for example, those incorporating a radioactive isotope, are useful in drug and/or substrate tissue distribution studies. The radioactive isotopes tritium, ($^3$H) and carbon-14, ($^{14}$C) are particularly useful for this purpose in view of their ease of incorporation and ready means of detection. Substitution with heavier isotopes such as deuterium, $^2$H, may afford certain therapeutic advantages resulting from greater metabolic stability, for example, $^{35}$S increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

To treat or prevent diseases or conditions mediated in part or whole by arenavirus infection, a pharmaceutical composition of the invention is administered in a suitable formulation prepared by combining a therapeutically effective amount (i.e., an arenavirus GP modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer.

For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterizedifferent combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a cosolvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol 300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a cosolvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol® Transcutol® and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal, such as a human, suffering from a condition or disease mediated by arenavirus, either alone or as part of a pharmaceutically acceptable formulation, once a day, twice a day, three times a day, four times a day, or even more frequently.

The compounds of the present invention, or salts or solvates thereof, may be administered to a mammal, such as a human, suffering from a condition or disease mediated by arenavirus in combination with at least one other agent used for treatment of arenavirus selected from the group consisting of Ribavirin, viral RNA-dependent-RNA-polymerase inhibitors as shown by Ng K K, Arnold J J and Cameron C E, *Structure-Function Relationships Among RNA-Dependent RNA Polymerases*, Curr Top Microbiol Immunol, 2008; 320: 137-156, incorporated herein by reference in its entirety, Favipiravir, a broad-spectrum inhibitor of viral RNA-Dependent RNA Polymerases, Triazavirin, a broad-spectrum inhibitor of viral RNA-Dependent RNA Polymerases, small interfering RNAs (siRNAs) and microRNAs as shown by Carthew R W and Sontheimer E J, *Origins and Mechanisms of miRNAs and siRNAs*, Nature, 2009; 136: 642-655, incorporated herein by reference in its entirety, vaccines as shown by Nablel G J, *Designing Tomorrow's Vaccines*, NEJM, 2013; 368: 551-560, incorporated herein by reference in its entirety, and immunomodulators as shown by Patil U S, Jaydeokar A V and Bandawane D D, *Immunomodulators: A Pharmacological Review*, Internatl J Pharmacy and Pharmaceutical Sci, 2012; 4: 30-36, incorporated herein by reference in its entirety], alone or as part of a pharmaceutically acceptable formulation, once a day, twice a day, three times a day, four times a day, or even more frequently.

Those of ordinary skill in the art will understand that with respect to the compounds of the present invention, the particular pharmaceutical formulation, the dosage, and the number of doses given per day to a mammal requiring such treatment, are all choices within the knowledge of one of ordinary skill in the art and can be determined without undue experimentation.

The compounds of the present invention are useful for modulating or inhibiting arenavirus GP.

Accordingly, these compounds are useful for the prevention and/or treatment of disease states associated with arenavirus infection.

This invention also relates to a method for the treatment of arenavirus infection including a human comprising administering to said mammal an amount of a compound of the Formula I, as defined above, or a salt or solvate thereof, that is effective in treating disease states associated with Arenavirus infection.

In the following Preparations and Examples, "Ac" means acetyl, "Me" means methyl, "Et" means ethyl, "Ph" means phenyl, "Py" means pyridine, "BOC", "Boc" or "boc" means N-tert-butoxycarbonyl, "Ns" means 2-Nitrophenylsulfonyl, "DCM" ($CH_2Cl_2$) means dichloromethane or methylene chloride, "dba" means dibenzylideneacetone, "DCE" means dichloroethane or ethylene chloride, "DIAD" means diisopropylazadicarboxylate, "DIPEA" or "DIEA" means diisopropyl ethyl amine, "DMA" means N,N-dimethylacetamide, "DMF" means N—N-dimethyl formamide, "DMSO" means dimethylsulfoxide, "DPPP" means 1,3-bis(diphenylphosphino)propane, "HOAc" means acetic acid, "IPA" means isopropyl alcohol, "NMP" means 1-methyl 2-pyrrolidinone, "TEA" means triethyl amine, "TFA" means trifluoroacetic acid, "DCM" means dichloromethane, "EtOAc" means ethyl acetate, "$MgSO_4$" means magnesium sulphate, "$Na_2SO_4$" means sodium sulphate, "MeOH" means methanol, "$Et_2O$" means diethyl ether, "EtOH" means ethanol, "$H_2O$" means water, "HCl" means hydrochloric acid, "$POCl_3$" means phosphorus oxychloride, "$SOCl_2$" means thionylchloride, "$K_2CO_3$" means potassium carbonate, "THF" means tetrahydrofuran, "DBU" means 1,8-diazabicyclo[5.4.0]undec-7-ene, "LiHMDS" or "LHMDS" means lithium hexamethyldisilazide, "TBME" or "MTBE" means tert-butyl methyl ether, "LDA" means lithium diisopropylamide, "NBS" means N-bromosuccinimide, "NIS" means N-iodosuccinimide, "Xanthphos" means 4,5-bis(diphenylphosphino)-9,9-dimethylxanthene; "$P(Ph_3)$" means triphenylphosphine, "N" means Normal, "M" means molar, "mL" means millilitre, "mmol" means millimoles, "pmol" means micromoles, "eq." means equivalent, "° C." means degrees Celsius, "Pa" means pascals, "Xanthphos" means 4,5-bis(diphenylphosphino)-9,9-dimethylxanthene, "rt" means room temperature.

Methods of Preparation.

Compounds of the present invention may be prepared using the reaction routes and synthetic schemes described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

Scheme 1 shows a method useful for the synthesis of compounds of structural Formula I wherein G and H are C, J and L are N, and K is C—$R^3$. Compound 1-1 (X=Cl, Br, or I, and Y is F, Cl, Br, or I) can be reacted with amine $R_2NH_2$ in the presence of a base such as NaH or $Cs_2CO_3$ in a solvent such as THF or DMF to form compound 1-2. Reduction of the nitro group using a reducing agent such as Fe or $SnCl_2$ in a solvent such as THF or methanol can provide aniline 1-3 which can be reacted with ester $R_3CO_2R$ or orthoester $R_3C(OR)_3$ to form 1-4. Coupling of 1-4 with a boronic acid or boronic ester $R^1B(OR)_2$ using a catalyst such as [1,1'-bis(diphenylphosphino)ferrocene]palladium(II) dichloride in the presence of a base such as $K_2CO_3$ in a solvent such as dimethoxyethane can provide compound of structural Formula I.

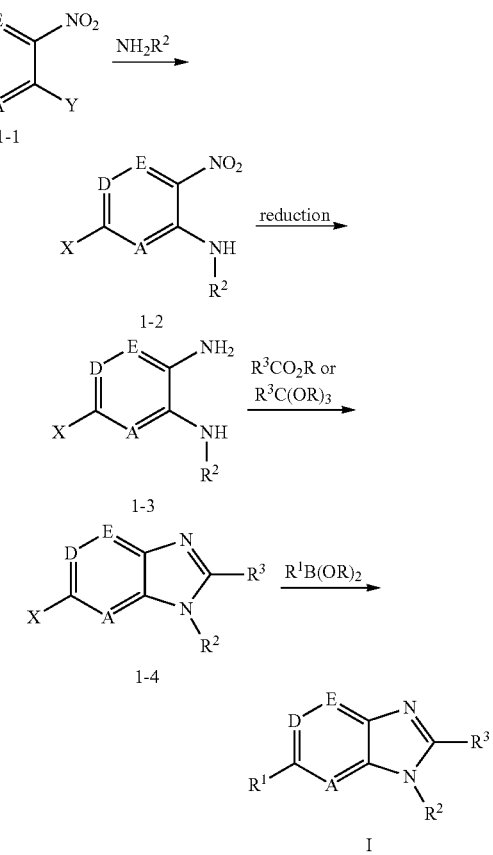

Scheme 1

Scheme 2 shows a method useful for the synthesis of compounds of structural Formula I wherein G and H are C, E, J and L are N, and K is C—$R^3$. Compound 2-1 (X=Cl, Br, or I, and Y is F, Cl, Br, or I) can be reacted with amine $R_2NH_2$ in the presence of a base such as NaH or $Cs_2CO_3$ in a solvent such as THF or DMF to form compound 2-4 which can be reacted with ester $R_3CO_2R$ or orthoester $R_3C(OR)_3$ to form 2-5. Alternatively, 2-5 can be formed by reaction of compound 2-2 (X=Cl, Br, or I, and Y is F, $C_1$, Br, or I) on treatment with primary amide 2-3 in a presence of a palladium catalyst such as $Pd(dba)_3$ [A. Rosenberg, J. Zhao, D. A. Clark, Org. Lett. 14, 2012, 1764-1767]. Coupling of 2-5 with a boronic acid or boronic ester $R^1B(OR)_2$ using a catalyst such as [1,1'-bis(diphenylphosphino)ferrocene]palladium (11) dichloride in the presence of a base such as $K_2CO_3$ in a solvent such as dimethoxyethane can provide compound of structural Formula I.

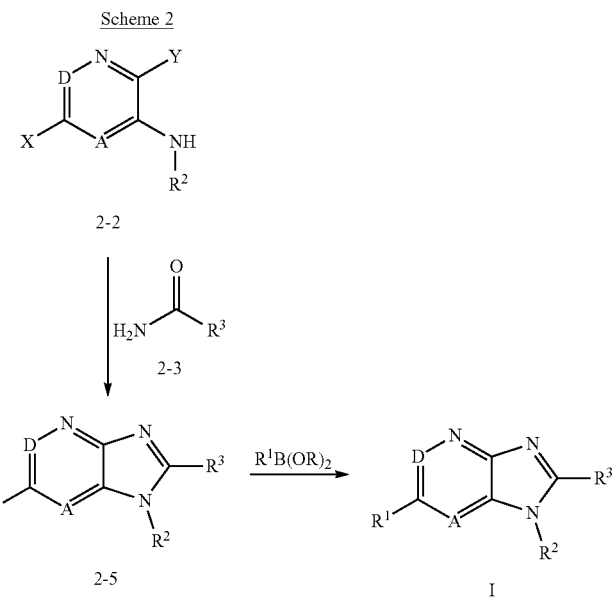

Scheme 3 depicts an alternative method useful for the synthesis of compounds of structural Formula I wherein G, and H are C, J and L are N, and K is C—$R^3$. Compound 3-1 (X=Cl, Br, or I) can be reacted with an alkyl halide $R^2Z$ (Z=Cl, Br, or I) in the presence of a base such as NaH or $Cs_2CO_3$ in a solvent such as THF or DMF, or with an aryl halide $R^2Z$ (Z=I) in the presence of CuI, a ligand such as 1,10-phenanthroline, and a base such as $K_2CO_3$ in a solvent such as DMF [C. Baumgartner et al. Helv. Chim. Acta 90, 2007, 1043-1068] to form a mixture of isomers 3-2 and 3-3 which can be separated by column chromatography or other methods know to whose skilled in the arts. Coupling of 3-3 with a boronic acid or boronic ester $R^1B(OR)_2$ using a catalyst such as [1,1'-bis(diphenylphosphino)ferrocene] palladium(II)dichloride in the presence of a base such as $K_2CO_3$ in a solvent such as dimethoxyethane can provide compound of structural Formula I.

Scheme 3

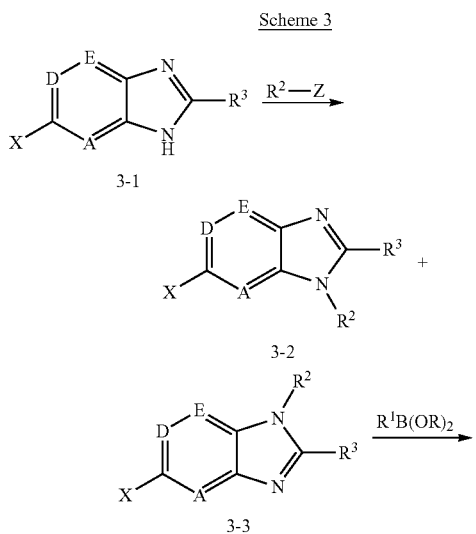

-continued

Scheme 4 displays a method useful for the synthesis of compounds of structural Formula I wherein G and H are C, J is N, and K and L are independently C—$R^3$. Compound 4-1 (X=Cl, Br, or I) can be reacted with an alkyl halide $R^2Z$ (Z=Cl, Br, or I) in the presence of a base such as NaH or $Cs_2CO_3$ in a solvent such as THF or DMF, or with an aryl halide $R^2Z$ (Z=I) in the presence of CuI, a ligand such as 1,10-phenanthroline, and a base such as $K_2CO_3$ in a solvent such as DMF to form compound 4-2. Coupling of 4-2 with a boronic acid or boronic ester $R^1B(OR)_2$ using a catalyst such as [1,1'-bis(diphenylphosphino)ferrocene]palladium (II) dichloride in the presence of a base such as $K_2CO_3$ in a solvent such as dimethoxyethane can provide compound of structural Formula I.

Scheme 4

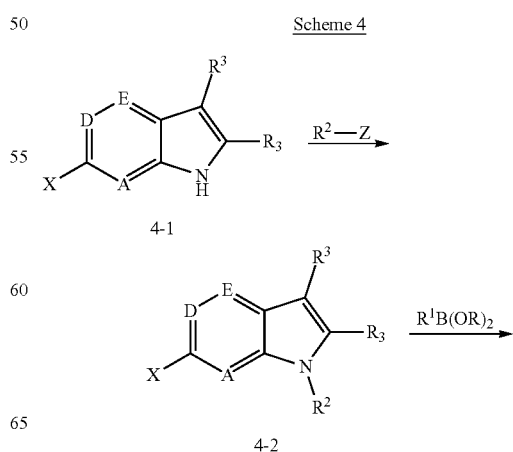

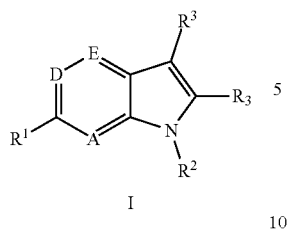

Scheme 5 shows a method useful for the synthesis of compounds of structural Formula I wherein G, H, and J are C, K is C—$R^3$, and L is N—$R^3$. Compound 5-1 (X=Br) can be reacted with an aryl bromide $R^2Br$ in the presence a catalyst such as Pd(OAc)$_2$ and a base such as K$_2$CO$_3$ in a solvent such as toluene [F. Bellina, F. Benelli, R. Rossi J. Org. Chem. 2008, 73, 5529-5535] to form compound 5-2. Coupling of 5-2 with a boronic acid or boronic ester $R^1B(OR)_2$ using a catalyst such as [1,1'-bis(diphenylphosphino)ferrocene]palladium(II) dichloride in the presence of a base such as K$_2$CO$_3$ in a solvent such as dimethoxyethane can provide compound of structural Formula I.

Scheme 5

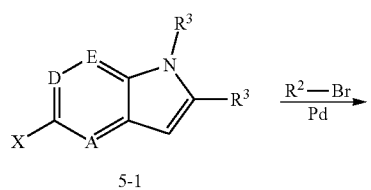

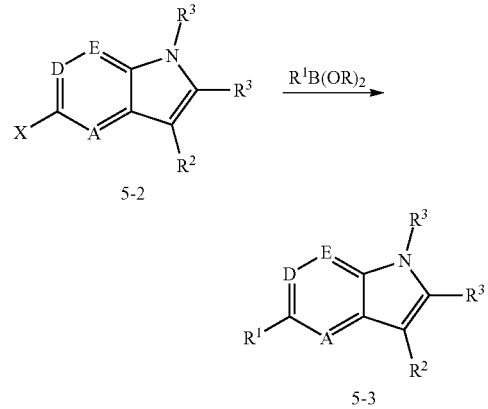

Scheme 6 shows a method useful for the synthesis of compounds of structural Formula I wherein G and H are C, J and K are N, and L is C—$R^3$. Compound 6-1 (X=Cl, Br, or I, and Y is F, Cl, Br, or I) can be reacted with hydrazine 6-2 in the presence of a base such as DIEA in a solvent such as THF or DMF to form hydrazone 6-3 which can cyclize to 6-5 on treatment with a base such as sodium t-butoxide with or without a catalyst such as Pd(dba)$_3$. Alternatively, compound 6-4 can be reacted with an alkyl halide $R^2Z$ (Z=Cl, Br, or I) in the presence of a base such as NaH or Cs$_2$CO$_3$ in a solvent such as THF or DMF, or with an aryl halide $R^2Z$ (Z=I) in the presence of CuI, a ligand such as 1,10-phenanthroline, and a base such as K$_2$CO$_3$ in a solvent such as DMF to form compound 6-5.

Coupling of 6-5 with a boronic acid or boronic ester $R^1B(OR)_2$ using a palladium catalyst such as [1,1'-bis(diphenylphosphino)ferrocene] palladium(II)dichloride in the presence of a base such as K$_2$CO$_3$ in a solvent such as dimethoxyethane can provide compound of structural Formula I.

Scheme 6

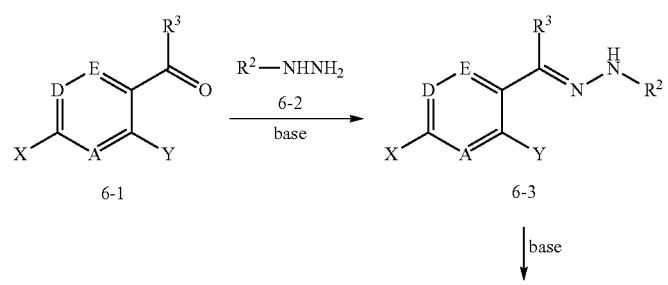

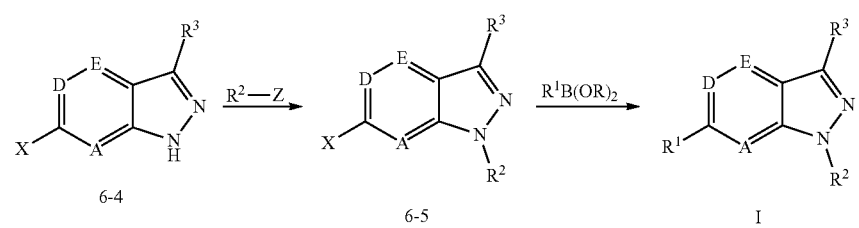

Scheme 7 depicts a method useful for the synthesis of compounds of structural Formula I wherein G, H, and J are C, K is N, and L is NR³. Compound 7-1 (X=Cl, Br) can be coupled with a boronic acid or boronic ester R²B(OR)₂ using a catalyst such as tetrakis(triphenylphosphine)palladium in the presence of a base such as K₂CO₃ in a solvent such as dioxane to form 7-2 which can react with a second boronic acid or boronic ester R¹B(OR)₂ using a catalyst such as [1,1'-bis(diphenylphosphino) ferrocene]palladium(II)dichloride in the presence of a base such as K₂CO₃ in a solvent such as dimethoxyethane to provide a compound of structural Formula I.

Scheme 7

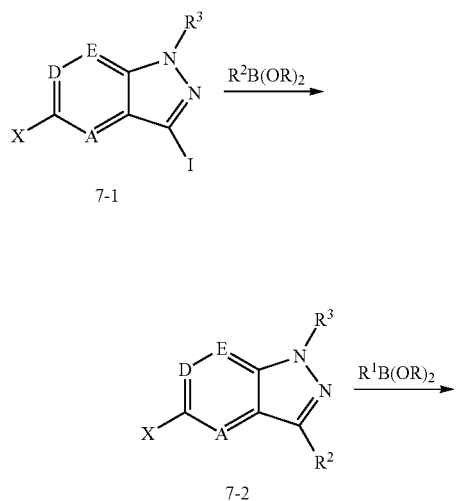

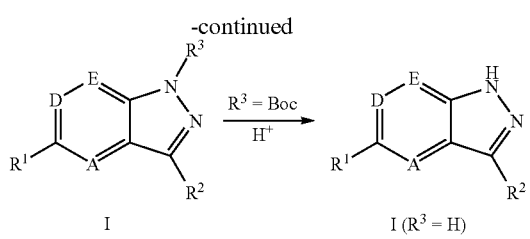

Scheme 8 depicts a method useful for the synthesis of compounds of structural Formula I wherein G, and J are C, H and L are N, and K is C—R³. Compound 8-1 (X=Cl, Br) can be coupled with a boronic acid or boronic ester R¹B(OR)₂ using a catalyst such as [1,1'-bis(diphenylphosphino) ferrocene] palladium(II) dichloride in the presence of a base such as K₂CO₃ in a solvent such as dimethoxyethane to form 8-2 which can be treated with a halogenation reagent such as bromine or N-bromosuccinimide (NBS), or iodine or N-iodosuccinimide (NIS) to form compound 8-3 (Y=Br, I). Treatment of 8-3 with a boronic acid or boronic ester R²B(OR)₂ using a catalyst such as tetrakis(triphenylphosphine)palladium in the presence of a base such as K₂CO₃ in a solvent such as dioxane can provide a compound of Structural Formula I. Alternatively, compound 8-4 (X=Cl, Br) can react with boronic acid or boronic ester R²B(OR)₂ using a catalyst such as tetrakis(triphenylphosphine) palladium in the presence of a base such as K₂CO₃ in a solvent such as dioxane to provide compound 8-5 which can react with a second boronic acid or boronic ester R¹B(OR)₂ using a catalyst such as [1,1'-bis(diphenylphosphino)ferrocene] palladium(II) dichloride in the presence of a base such as K₂CO₃ in a solvent such as dimethoxyethane to provide a compound of structural Formula I.

Scheme 8

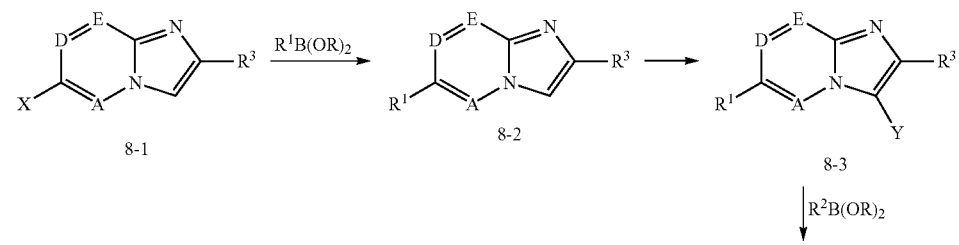

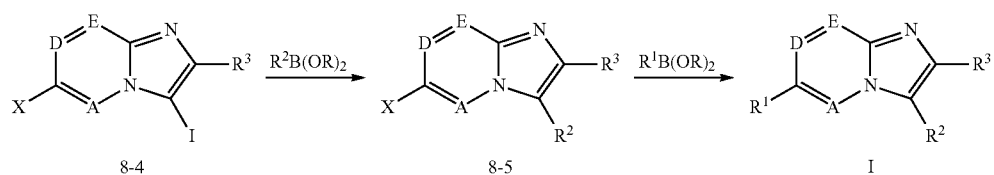

Scheme 9 shows a method useful for the synthesis of compounds of structural Formula I wherein G and J are C, H and K are N, and L is C—$R^3$. Amine 9-1 (X=Cl, Br) can be reacted with an acyl halide $R^2COZ$ (Z=Cl, Br) in the presence of a base such as DIEA to form amide 9-2 which on treatment with $POCl_3$ can cyclize to 9-3. Treatment of 9-3 with a boronic acid or boronic ester $R^1B(OR)_2$ using a catalyst such as [1,1'-bis(diphenylphosphino)ferrocene]palladium(II) dichloride in the presence of a base such as $K_2CO_3$ in a solvent such as dimethoxyethane can provide a compound of structural Formula I. Alternatively, compound 9-4 can react with a boronic acid or boronic ester $R^1B(OR)_2$ using a palladium catalyst such as [1,1'-bis(diphenylphosphino)ferrocene]palladium(II) dichloride in the presence of a base such as $K_2CO_3$ in a solvent such as dimethoxyethane to form 9-5 which then can undergo a cross-coupling reaction with an aryl halide $R^2Z$ (Z=Br, I) in a presence of a catalyst such as $Pd(OAc)_2$ in a presence of a base such as tetrabutylammmonium acetate in a solvent such as toluene [C. Huang, A. Giokaris, V. Gevorgyan, Chem. Lett. 40, 2011, 1053-1054] to provide a compound of structural Formula I.

Scheme 9

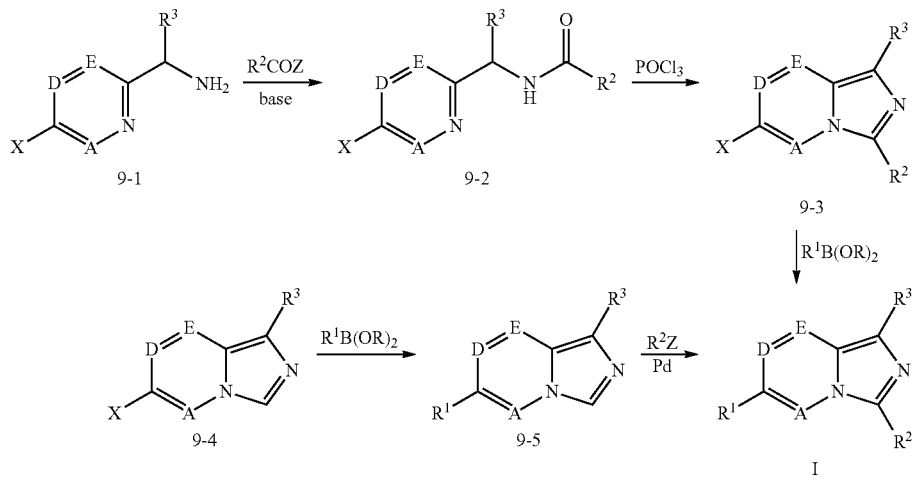

Scheme 10 depicts a method useful for the synthesis of compounds of structural Formula I wherein H and J are C, G and K are N, and L is C—$R^3$. Compound 10-1 (X=Cl, Br) can be coupled with a boronic acid or boronic ester $R^1B(OR)_2$ using a catalyst such as [1,1'-bis(diphenylphosphino)ferrocene] palladium(II) dichloride in the presence of a base such as $K_2CO_3$ in a solvent such as dimethoxyethane to form 10-2 which can be treated with a halogenation reagent such as bromine or N-bromosuccinimide (NBS), or iodine or N-iodosuccinimide (NIS) to form compound 10-3 (Y=Br, I). Treatment of 10-3 with a boronic acid or boronic ester $R^2B(OR)_2$ using a catalyst such as tetrakis(triphenylphosphine)palladium in the presence of a base such as $K_2CO_3$ in a solvent such as dioxane can provide a compound of structural Formula I. Alternatively, compound 10-4 (X=Cl, Br) can react with boronic acid or boronic ester $R^2B(OR)_2$ using a catalyst such as tetrakis (triphenylphosphine)palladium in the presence of a base such as $K_2CO_3$ in a solvent such as dioxane to provide compound 10-5 which can react with a second boronic acid or boronic ester $R^1B(OR)_2$ using a palladium catalyst such as [1,1'-bis(diphenylphosphino) ferrocene] palladium(II) dichloride in the presence of a base such as $K_2CO_3$ in a solvent such as dimethoxyethane to provide a compound of structural Formula I.

Scheme 10

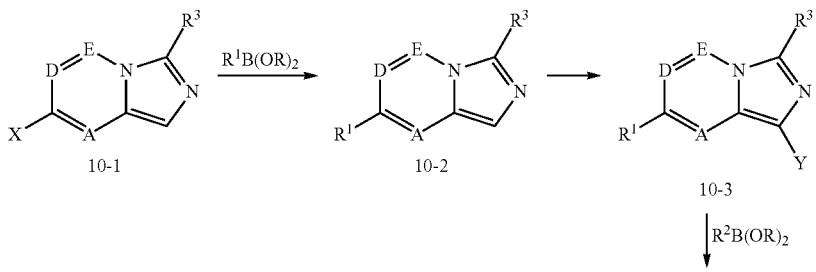

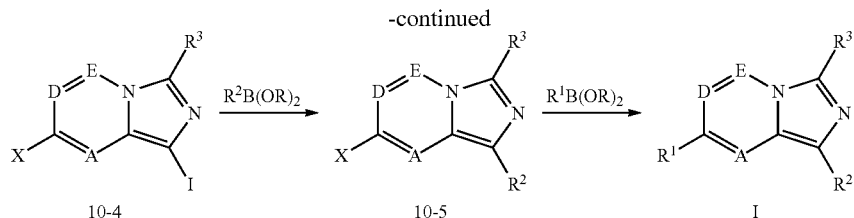

Scheme 11 depicts a method useful for the synthesis of compounds of structural Formula I wherein G and J are C, and H, K, and L are N. Compound 10-1 (X=Cl, Br) can react with hydrazine to form 11-2 which upon treatment with an acyl halide or ester R²COZ (Z=Cl, Br, OR) can form acyl hydrazide 11-3. Under acidic conditions (e g. acetic acid) 11-3 can cyclize to form 11-4 which then can be coupled with a boronic acid or boronic ester R¹B(OR)₂ using a catalyst such as [1,1'-bis(diphenylphosphino)ferrocene]palladium(II) dichloride in the presence of a base such as K₂CO₃ in a solvent such as dimethoxyethane to provide a compound of structural Formula I.

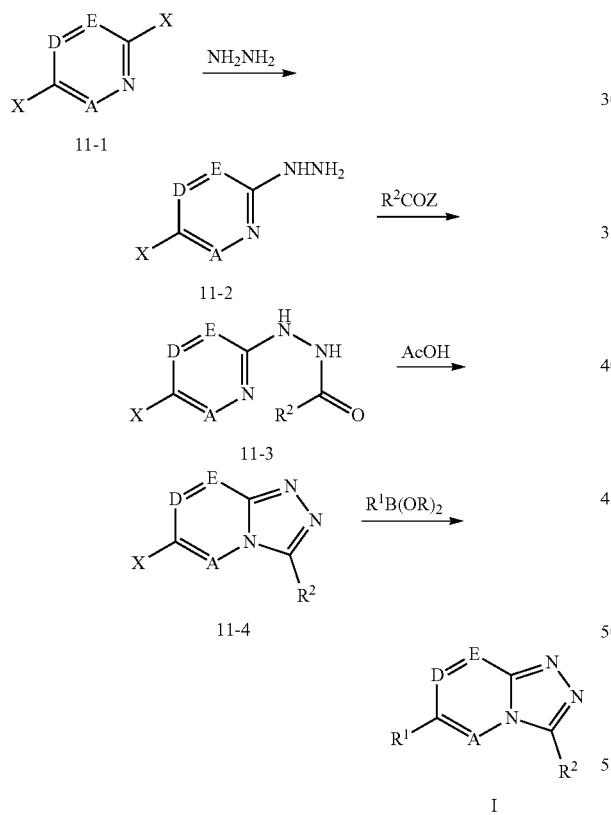

Scheme 12 depicts a method useful for the synthesis of compounds of structural Formula I wherein G and H are C, and J, K, and L are N. Compound 12-1 (X=Cl, Br, or I, and Y is F, C₁, Br, or I) can be reacted with amine R₂NH₂ in the presence of a base such as NaH or K₂CO₃ in a solvent such as THF or DMF to form compound 12-2. Reduction of the nitro groups using a reducing agent such as Fe or SnCl₂ in a solvent such as THF or methanol can provide aniline 12-3 which can be reacted with nitric acid to form 12-4. Coupling of 12-4 with a boronic acid or boronic ester R¹B(OR)₂ using a catalyst such as [1,1'-bis(diphenylphosphino)ferrocene] palladium(II) dichloride in the presence of a base such as K₂CO₃ in a solvent such as dimethoxyethane can provide compound of structural Formula I.

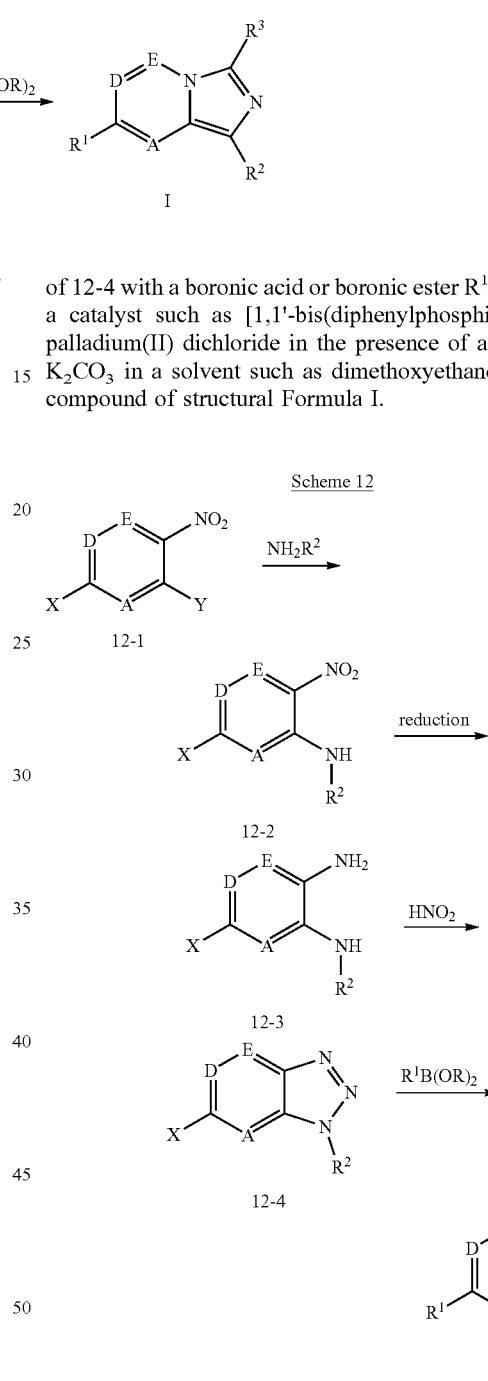

Scheme 13 depicts a method useful for the synthesis of compounds of structural Formula I wherein G, H, and J are C, K is C—R³, and L is O. Compound 13-1 (X=Cl, Br) can react with haloketone 13-2 (Z=Cl, Br) in a presence of a base such as Cs₂CO₃ in a solvent such as DMF to form 13-3 which under acidic conditions using an acid such as para toluene sulfonic acid can undergo cyclodehydration to form 13-4. Coupling of 13-4 with a boronic acid or boronic ester R¹B(OR)₂ using a catalyst such as [1,1'-bis(diphenylphosphino)ferrocene]palladium(II) dichloride in the presence of a base such as K₂CO₃ in a solvent such as dimethoxyethane can provide a compound of structural Formula I.

Scheme 13

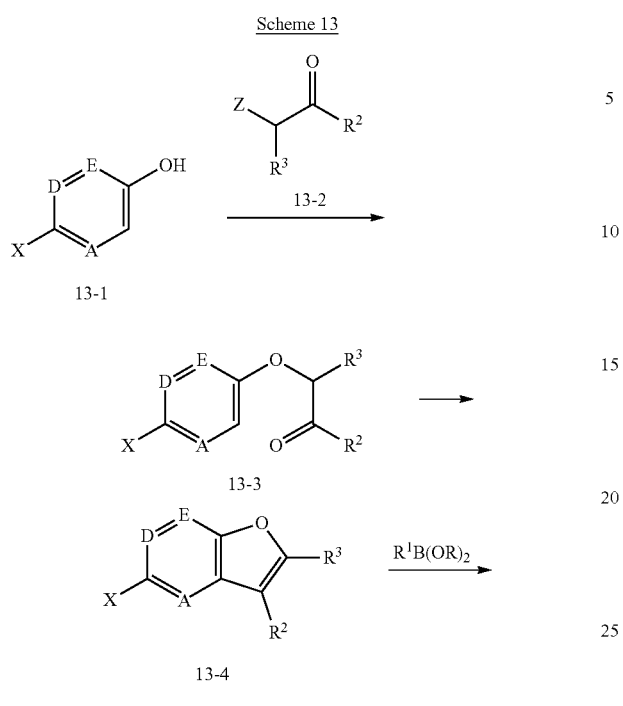

Scheme 14 shows a method useful for the synthesis of compounds of structural Formula I wherein G, H, and J are C, K is O, and L is N. Compound 14-1 (X=Cl, Br) can react with nitrile 14-2 using as base such as KOH in solvent such as methanol to form 14-3 which can react with a boronic acid or boronic ester R¹B(OR)₂ using a catalyst such as [1,1'-bis(diphenylphosphino)ferrocene]palladium(II) dichloride in the presence of a base such as K₂CO₃ in a solvent such as dimethoxyethane to provide a compound of structural Formula I.

Scheme 14

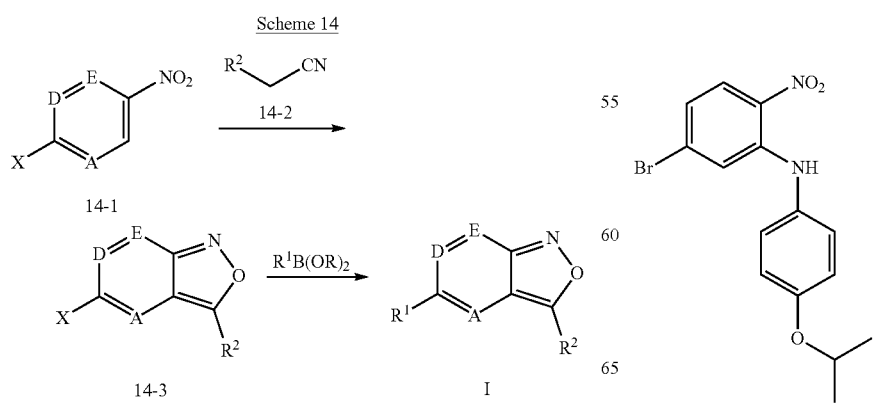

EXAMPLES

Preparation of Intermediates for Examples A1 to A31

6-Bromo-1-[4-(propan-2-yloxy)phenyl]-1H-1,3-benzodiazole

Step 1: 5-Bromo-2-nitro-N-[4-(propan-2-yloxy)phenyl]aniline

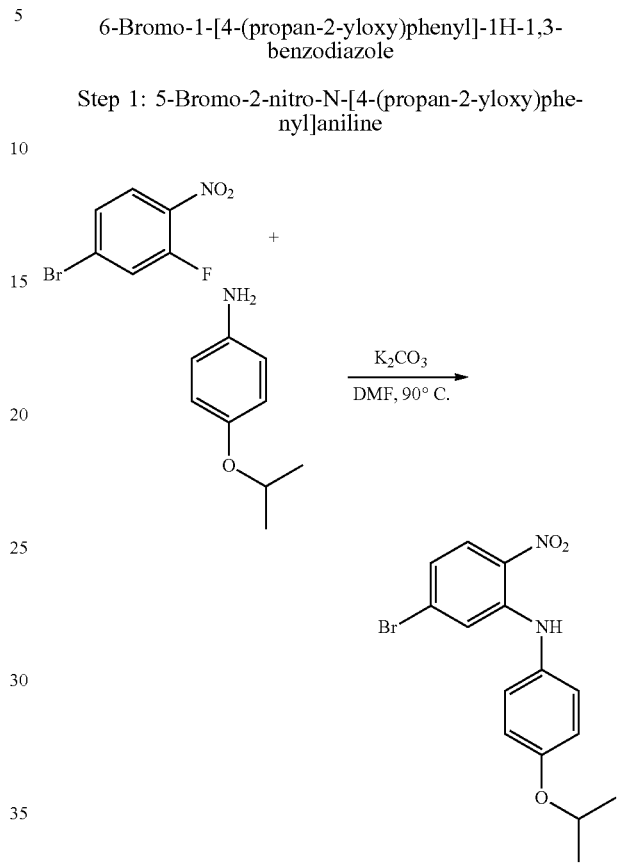

A mixture of 4-bromo-2-fluoro-1-nitrobenzene (0.3 g, 1.36 mmol), 4-(propan-2-yloxy)aniline (0.22 g, 1.43 mmol) and K₂CO₃ (0.38 g, 2.73 mmol) in DMF (3 mL) was stirred at 90° C. for 5 h. Then the reaction mixture was diluted with EtOAc and washed with 5% aq. LiCl solution. The organic phase was dried over Na₂SO₄, filtered, and concentrated in vacuo. The residue was purified by SiO₂ column chromatography (hexanes/EtOAc from 30:1 to 20:1) to give 0.43 g (90%) of the product as orange solid. ¹H NMR (500 MHz, CDCl₃) δ 9.37 (s, 1H), 8.04 (d, 1H), 7.12-7.17 (m, 3H), 6.93-6.97 (m, 2H), 6.81 (dd, 1H), 4.56 (sep, 1H), 1.36 (d, 6H).

Step 2: 6-Bromo-1-[4-(propan-2-yloxy)phenyl]-1H-1,3-benzodiazole

-continued

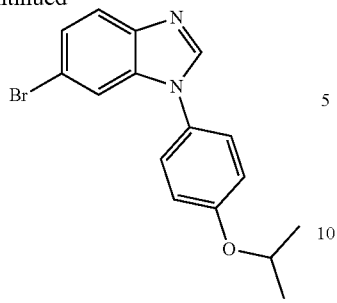

To a solution of 5-bromo-2-nitro-N-[4-(propan-2-yloxy)phenyl]aniline (0.156 g, 0.44 mmol) in 2-propanol (2.2 mL) were added iron powder (0.248 g, 4.4 mmol), NH₄Cl (0.237 g, 4.4 mmol) and formic acid (2.2 mL) (E. J. Hanan, B. K. Chan, A. A. Estrada, D. G. Shore and J. P. Lyssikatos, Synlett 2010, 2759-2764). The resulting reaction mixture was stirred at 80° C. for 5 h. Then the reaction mixture was diluted with 2-propanol, filtered through Celite, and the filtrate was concentrated. The resulting residue was diluted with dichloromethane and washed with saturated aq. NaHCO₃ solution. The organic phase was dried over Na₂SO₄, filtered, and concentrated in vacuo. The residue was purified by SiO₂ column chromatography (hexanes/EtOAc from 7:3 to 1:2) to give 0.1 g (68%) of the product as pale pink solid. LC/MS m/z: 331.06 (⁷⁹Br, M+H)⁺, 332.9 (⁸¹Br, M+H)⁺.

5-Bromo-N-(4-methoxyphenyl)-2-nitroaniline

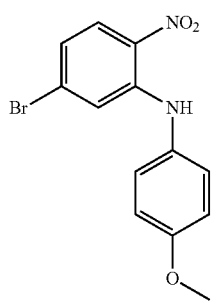 [SMILES: COc1ccc(Nc2cc(Br)ccc2[N+](=O)[O-])cc1]

The title compound was prepared from 4-bromo-2-fluoro-1-nitrobenzene and 4-methoxyaniline in the same manner as described for 5-bromo-2-nitro-N-[4-(propan-2-yloxy)phenyl]aniline.

6-Bromo-1-(4-methoxyphenyl)-1H-1,3-benzodiazole

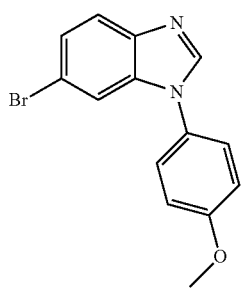 [SMILES: COc1ccc(-n2cnc3ccc(Br)cc32)cc1]

The title compound was prepared from 5-bromo-N-(4-methoxyphenyl)-2-nitroaniline in the same manner as described for 6-bromo-1-[4-(propan-2-yloxy)phenyl]-1H-1,3-benzodiazole. LC/MS m/z: 303.15 (⁷⁹Br, M+H)⁺, 305.12 (⁸¹Br, M+H)⁺.

3-Bromo-N-(4-methoxyphenyl)-2-nitroaniline

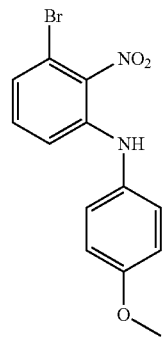 [SMILES: COc1ccc(Nc2cccc(Br)c2[N+](=O)[O-])cc1]

The title compound was prepared from 1-bromo-3-fluoro-2-nitrobenzene and 4-methoxyaniline in the same manner as described for 5-bromo-2-nitro-N-[4-(propan-2-yloxy)phenyl]aniline.

4-Bromo-1-(4-methoxyphenyl)-1H-1,3-benzodiazole

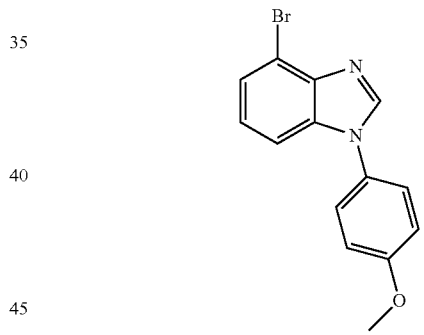

The title compound was prepared from 3-bromo-N-(4-methoxyphenyl)-2-nitroaniline in the same manner as described for 6-bromo-1-[4-(propan-2-yloxy)phenyl]-1H-1,3-benzodiazole. LC/MS m/z: 303.09 (⁷⁹Br, M+H)⁺, 305.15 (⁸¹Br, M+H)⁺.

5-Bromo-N-(2-methoxyphenyl)-2-nitroaniline

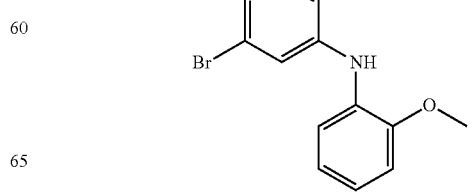

The title compound was prepared from 4-bromo-2-fluoro-1-nitrobenzene and 2-methoxyaniline in the same manner as described for 5-bromo-2-nitro-N-[4-(propan-2-yloxy)phenyl]aniline.

6-Bromo-1-(2-methoxyphenyl)-1H-1,3-benzodiazole

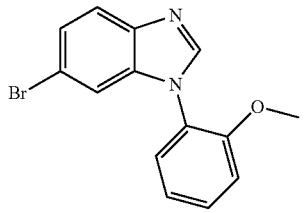 [SMILES: COc1ccccc1-n1cnc2ccc(Br)cc21]

The title compound was prepared from 5-bromo-N-(2-methoxyphenyl)-2-nitroaniline in the same manner as described for 6-bromo-1-[4-(propan-2-yloxy)phenyl]-1H-1,3-benzodiazole. LC/MS m/z: 302.99 ($^{79}$Br, M+H)$^+$, 304.98 ($^{81}$Br, M+H)$^+$.

5-Bromo-N-(3-methoxyphenyl)-2-nitroaniline

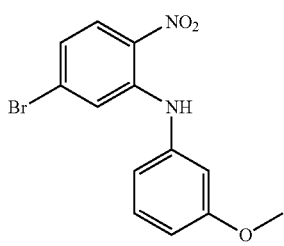 [SMILES: COc1cccc(Nc2cc(Br)ccc2[N+](=O)[O-])c1]

The title compound was prepared from 4-bromo-2-fluoro-1-nitrobenzene and 3-methoxyaniline in the same manner as described for 5-Bromo-2-nitro-N-[4-(propan-2-yloxy)phenyl]aniline.

6-Bromo-1-(3-methoxyphenyl)-1H-1,3-benzodiazole

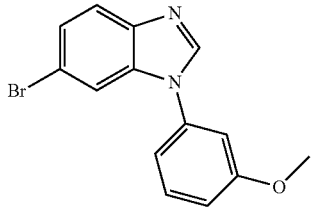 [SMILES: COc1cccc(-n2cnc3ccc(Br)cc32)c1]

The title compound was prepared from 5-bromo-N-(3-methoxyphenyl)-2-nitroaniline in the same manner as described for 6-bromo-1-[4-(propan-2-yloxy)phenyl]-1H-1,3-benzodiazole. LC/MS m/z: 303.08 ($^{79}$Br, M+H)$^+$, 304.93 ($^{81}$Br, M+H)$^+$.

5-Bromo-N-(4-isopropoxyphenyl)-4-methylbenzene-1,2-diamine

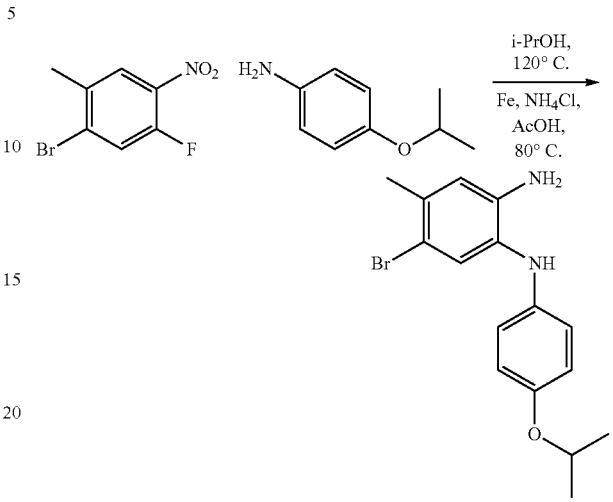

To a solution of 1-bromo-5-fluoro-2-methyl-4-nitrobenzene (200 mg, 0.85 mmol) in i-propanol (2 mL), was added 4-isopropoxyaniline (129 mg, 0.85 mmol). The resulting mixture was stirred at 120° C. for 30 min under microwave irradiation. After cooling to room temperature, the reaction was concentrated under reduced pressure and the residue was dissolved in ethanol (0.6 mL), dioxane (0.6 mL), and water (0.3 mL). To the solution was added iron (476 mg, 8.5 mmol) and NH$_4$Cl (457 mg, 8.5 mmol). The reaction was stirred at 80° C. for 2 hr. After cooling to room temperature, the reaction was filtered through a celite pad. The filtrate was concentrated under reduced pressure and the residue was poured into water and extracted with ethyl acetate. The organic phase was dried over Na$_2$SO$_4$, filtered, and concentrated in vacuo. The residue was purified by SiO$_2$ column chromatography (hexane/EtOAc=3:1) to give 198 mg (69.2%) of the product as a white solid. LC/MS m/z: 335.13 ($^{79}$Br, M+H)$^+$, 337.19 ($^{81}$Br, M+H)$^+$, 376.28 ($^{79}$Br, M+H+CH$_3$CN)$^+$, 378.25 ($^{81}$Br, M+H+CH$_3$CN)$^+$.

6-Bromo-5-methyl-1-[4-(propan-2-yloxy)phenyl]-1H-1,3-benzodiazole

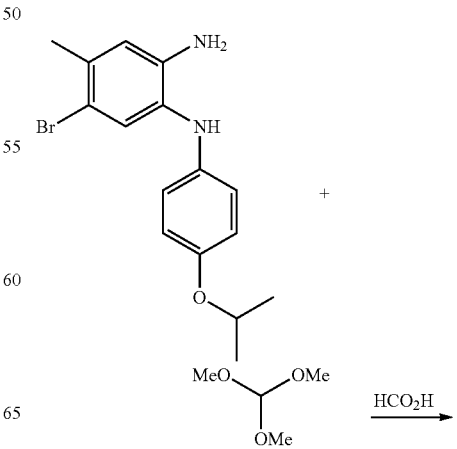

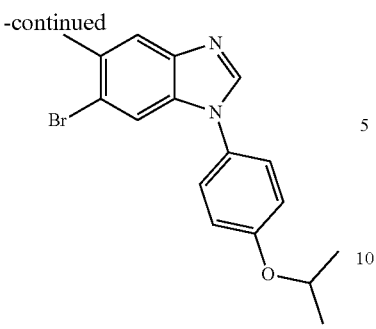

To a solution of 5-bromo-N-(4-isopropoxyphenyl)-4-methylbenzene-1,2-diamine (50.1 mg, 0.15 mmol) in THF (1 mL), was added trimethoxymethane (18.9 mg, 0.18 mmol) followed by formic acid (100 uL). The resulting mixture was stirred at 80° C. for 2 hr. After cooling to room temperature, the reaction was poured into water and extracted with ethyl acetate. The organic phase was dried over $Na_2SO_4$, filtered, and concentrated in vacuo. The residue was purified by $SiO_2$ column chromatography (hexane/EtOAc=1:1) to give 42.1 mg (81.7%) of the product as a white solid.

LC/MS m/z: 345.15 ($^{79}$Br, M+H)$^+$, 347.21 ($^{81}$Br, M+H)$^+$, 386.28 ($^{79}$Br, M+H+CH$_3$CN)$^+$, 388.20 ($^{81}$Br, M+H+CH$_3$CN)$^+$.

5-Bromo-N-(1H-indol-5-yl)benzene-1,2-diamine

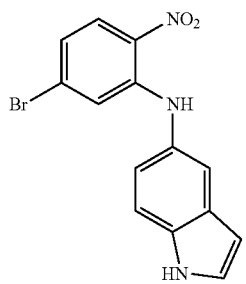 [SMILES: O=[N+]([O-])c1ccc(Br)cc1Nc1ccc2[nH]ccc2c1]

The title compound was prepared from 4-bromo-2-fluoro-1-nitrobenzene and 1H-indol-5-amine in the same manner as described for 5-bromo-N-(4-isopropoxyphenyl)-4-methylbenzene-1,2-diamine. LCMS m/z: 302.12 ($^{79}$Br, M+H)$^+$, 344.13 ($^{81}$Br, M+H)$^+$, 343.18 ($^{79}$Br, M+H+CH$_3$CN)$^+$, 345.22 ($^{81}$Br, M+H+CH$_3$CN)$^+$.

6-Bromo-1-(1H-indol-5-yl)-1H-1,3-benzodiazole

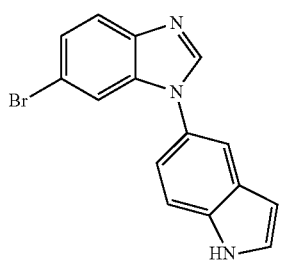 [SMILES: Brc1ccc2ncn(-c3ccc4[nH]ccc4c3)c2c1]

The title compound was prepared from 5-bromo-N-(1H-indol-5-yl)benzene-1,2-diamine in the same manner as described for 6-bromo-5-methyl-1-[4-(propan-2-yloxy)phenyl]-1H-1,3-benzodiazole. LC/MSm/z: 312.04 ($^{79}$Br, M+H)$^+$, 314.03 ($^{81}$Br, M+H)$^+$, 353.09 ($^{79}$Br, M+H+CH$_3$CN)$^+$, 355.12 ($^{81}$Br, M+H+CH$_3$CN)$^+$.

5-Bromo-4-methoxy-2-nitro-N-[4-(propan-2-yloxy)phenyl]aniline

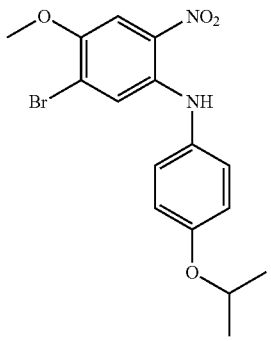 [SMILES: COc1cc([N+](=O)[O-])c(Nc2ccc(OC(C)C)cc2)cc1Br]

The title compound was prepared from 1-bromo-5-fluoro-2-methoxy-4-nitrobenzene and 4-(propan-2-yloxy)aniline in the same manner as described for 5-Bromo-2-nitro-N-[4-(propan-2-yloxy)phenyl]aniline.

6-Bromo-5-methoxy-1-[4-(propan-2-yloxy)phenyl]-1H-1,3-benzodiazole

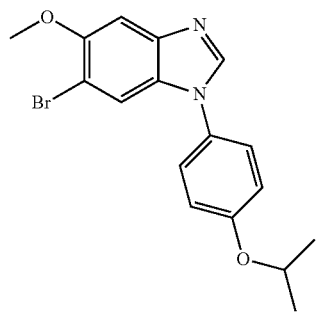 [SMILES: COc1cc2ncn(-c3ccc(OC(C)C)cc3)c2cc1Br]

The title compound was prepared from 5-bromo-4-methoxy-2-nitro-N-[4-(propan-2-yloxy)phenyl]aniline in the same manner as described for 6-Bromo-1-[4-(propan-2-yloxy)phenyl]-1H-1,3-benzodiazole. LC/MS m/z: 402.12 (M+H)+.

Example A1: 1-(4-Methoxyphenyl)-6-[3-(propan-2-yl)phenyl]-1H-1,3-benzodiazole

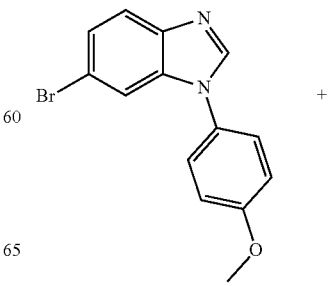

-continued

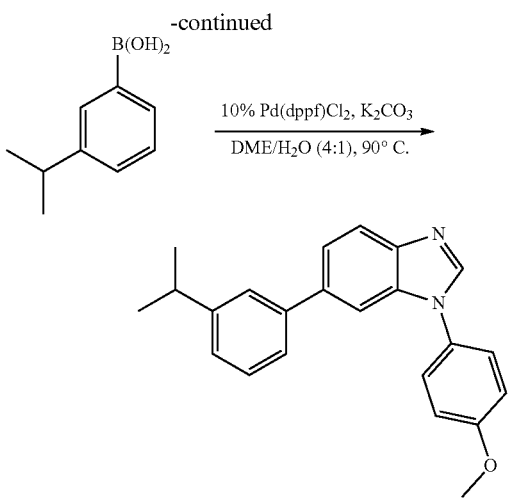

To a solution of 6-bromo-1-(4-methoxyphenyl)-1H-1,3-benzodiazole (30 mg, 0.1 mmol) in 1,2-dimethoxyethane (1 mL) were added [3-(propan-2-yl)phenyl]boronic acid (32 mg, 0.2 mmol), [1,1'-bis(diphenylphosphino)ferrocene]palladium(II) dichloride (7 mg, 0.01 mmol), potassium carbonate (40 mg, 0.3 mmol) and water (0.25 mL). The resulting reaction mixture was degassed with nitrogen for 10 min, then heated to 90° C. for 5 h. Then the reaction mixture was diluted with ethyl acetate and washed with water. The organic phase was dried over $Na_2SO_4$, filtered, and concentrated in vacuo. The residue was purified by $SiO_2$ column chromatography (hexanes/EtOAc from 7:3 to 1:4) to give 21 mg (62%) of the product as a colorless oil. LC/MS m/z: 343.34 $(M+H)^+$, 384.30 $(M+H+CH_3CN)^+$.

Examples A2 to A31 were prepared in the same manner as described above for 1-(4-methoxyphenyl)-6-[3-(propan-2-yl)phenyl]-1H-1,3-benzodiazole using the appropriate bromide and commercial boronic acid or boronic acid pinacol ester performing the reaction either under conventional heating or in a microwave reactor.

| Ex. | Starting materials | Product/Name | Analytical Data |
|---|---|---|---|
| A2 | 6-bromo-1-(4-methoxyphenyl)-1H-1,3-benzodiazol [4-(propan-2-yl)phenyl] boronic acid | 1-(4-methoxyphenyl)-6-[4-(propan-2-yl)phenyl]-1H-1,3-benzodiazole | LC/MS m/z: 343.26 $(M + H)^+$ |
| A3 | 6-bromo-1-(4-methoxyphenyl)-1H-1,3-benzodiazole (4-methoxyphenyl) boronic acid | 1,6-bis(4-methoxyphenyl)-1H-1,3-benzodiazole | LC/MS m/z: 331.25 $(M + H)^+$, 661.42 $(2M + H)^+$ |
| A4 | 6-bromo-1-(4-methoxyphenyl)-1H-1,3-benzodiazole (4-cyanophenyl) boronic acid | 4-[1-(4-methoxyphenyl)-1H-1,3-benzodiazol-6-yl] benzonitrile | LC/MS m/z: 326.22 $(M + H)^+$, 367.25 $(M + H + CH_3CN)^+$ |

-continued

| Ex. | Starting materials | Product/Name | Analytical Data |
|---|---|---|---|
| A5 | 6-bromo-1-(4-methoxy phenyl)-1H-1,3-benzodiazole (2-methoxyphenyl) boronic acid | 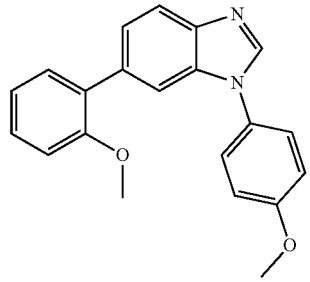<br>6-(2-methoxyphenyl)-1-(4-methoxyphenyl)-1H-1,3-benzodiazole | LC/MS m/z: 331.22 (M + H)+ |
| A6 | 6-bromo-1-(4-methoxy phenyl)-1H-1,3-benzodiazole (3-methoxyphenyl) boronic acid | 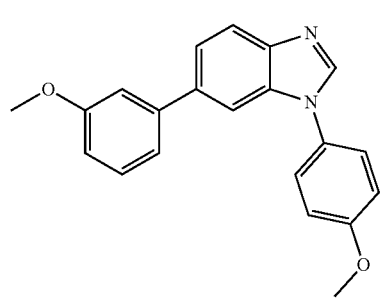<br>6-(3-methoxyphenyl)-1-(4-methoxyphenyl)-1H-1,3-benzodiazole | LC/MS m/z: 331.22 (M + H)+ |
| A7 | 6-bromo-1-(4-methoxy phenyl)-1H-1,3-benzodiazole [4-(dimethylamino)phenyl] boronic acid | 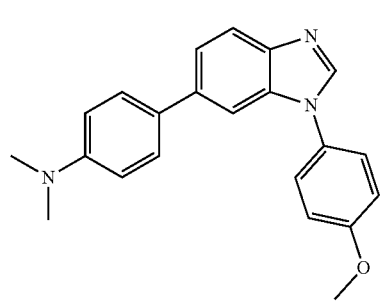<br>4-[1-(4-methoxyphenyl)-1H-1,3-benzodiazol-6-yl]-N,N-dimethylaniline | LC/MS m/z: 344.32 (M + H)+ |
| A8 | 6-bromo-1-(4-methoxyphenyl)-1H-1,3-benzodiazole [4-(2-hydroxypropan-2-yl)phenyl]boronic acid | 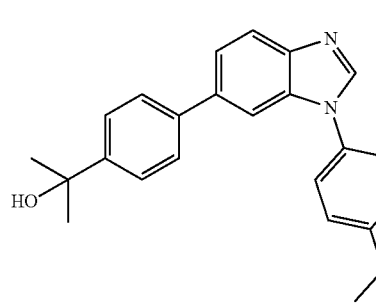<br>2-{4-[1-(4-methoxyphenyl)-1H-1,3-benzodiazol-6-yl]phenyl}propan-2-ol | LC/MS m/z: 359.27 (M + H)+, 400.30 (M + H + CH3CN)+ |

-continued

| Ex. | Starting materials | Product/Name | Analytical Data |
|---|---|---|---|
| A9 | 6-bromo-1-(4-methoxyphenyl)-1H-1,3-benzodiazole 4,4,5,5-tetramethyl-2-[(4-methylphenyl)methyl]-1,3,2-dioxaborolane | 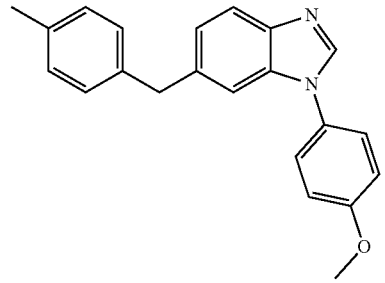<br>1-(4-methoxyphenyl)-6-[(4-methylphenyl)methyl]-1H-1,3-benzodiazole | LC/MS m/z: 329.23 (M + H)+, 370.27 (M + H + CH$_3$CN)+ |
| A10 | 6-bromo-1-(4-methoxyphenyl)--1,3-benzodiazole [4-(hydroxymethyl)phenyl] boronic acid | 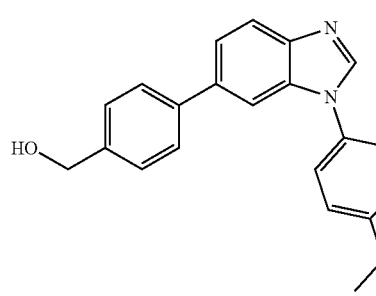<br>{4-[1-(4-methoxyphenyl)-1H-1,3-benzodiazol-6-yl] phenyl} methanol | LC/MS m/z: 331.27 (M + H)+ |
| A11 | 6-bromo-1-(4-methoxyphenyl)-1H-1,3-benzodiazole (4-methanesulfonyl phenyl)boronic acid | 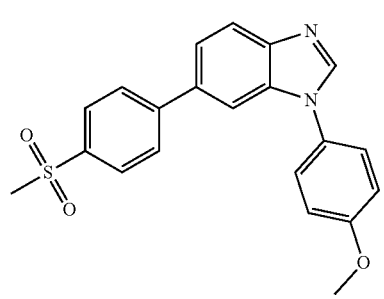<br>6-(4-methanesulfonyl phenyl)-1-(4-methoxy phenyl)-1H-1,3-benzodiazole | LC/MS m/z: 379.19 (M + H)+, 420.16 (M + H + CH$_3$CN)+ |
| A12 | 6-bromo-1-(4-methoxy phenyl)-1H-1,3-benzodiazole 1H-indol-5-ylboronic acid | 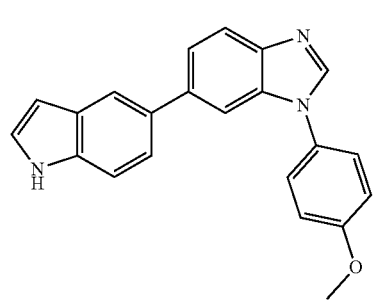<br>6-(1H-indol-5-yl)-1-(4-methoxyphenyl)-1H-1,3-benzodiazole | LC/MS m/z: 340.27 (M + H)+, 679.38 (2M + H)+ |

-continued

| Ex. | Starting materials | Product/Name | Analytical Data |
|---|---|---|---|
| A13 | 6-bromo-1-(4-methoxyphenyl)-1H-1,3-benzodiazole (4-hydroxyphenyl)boronic acid | 4-[1-(4-methoxyphenyl)-1H-1,3-benzodiazol-6-yl]phenol | LC/MS m/z: 317.23 (M + H)+ |
| A14 | 6-bromo-1-(4-methoxyphenyl)-1H-1,3-benzodiazole (4-acetylphenyl)boronic acid | 1-{4-[1-(4-methoxyphenyl)-1H-1,3-benzodiazol-6-yl]phenyl}ethan-1-one | LC/MS m/z: 343.13 (M + H)+ |
| A15 | 6-bromo-1-(4-methoxyphenyl)-1H-1,3-benzodiazole [4-(piperidin-1-yl)phenyl]boronic acid | 1-(4-methoxyphenyl)-6-[4-(piperidin-1-yl)phenyl]-1H-1,3-benzodiazole | LC/MS m/z: 384.34 (M + H)+ |
| A16 | 6-bromo-1-(4-methoxyphenyl)-1H-1,3-benzodiazole [4-(morpholin-4-yl)phenyl]boronic acid | 1-(4-methoxyphenyl)-6-[4-(morpholin-4-yl)phenyl]-1H-1,3-benzodiazole | LC/MS m/z: 386.29 (M + H)+ |

-continued

| Ex. | Starting materials | Product/Name | Analytical Data |
|---|---|---|---|
| A17 | 6-bromo-1-[4-(propan-2-yloxy)phenyl]-1H-1,3-benzodiazole [4-(2-hydroxypropan-2-yl)phenyl]boronic acid | 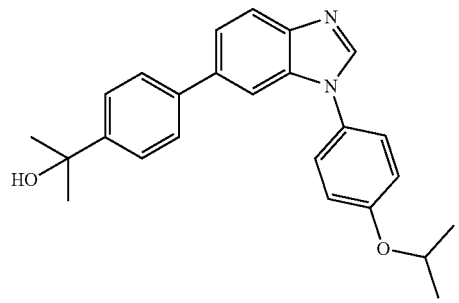<br>2-(4-{1-[4-(propan-2-yloxy)phenyl]-1H-1,3-benzodiazol-6-yl}phenyl) propan-2-ol | $^1$H NMR (300 MHz, CDCl$_3$) δ 8.67 (br. s, 1H), 8.07 (d, 1H), 7.71 (d, H), 7.64 (s, 1H), 7.58-7.40 (m, 6H), 7.12-7.04 (m, 2H), 4.69-4.59 (m, 1H), 3.35 (br. s, 1H), 1.61 (s, 6H), 1.40 (d, 6H). LC/MS m/z: 387.32 (M + H)$^+$ |
| A18 | 6-bromo-1-[4-(propan-2-yloxy)phenyl]-1H-1,3-benzodiazole [4-(dimethylamino)phenyl]boronic acid | 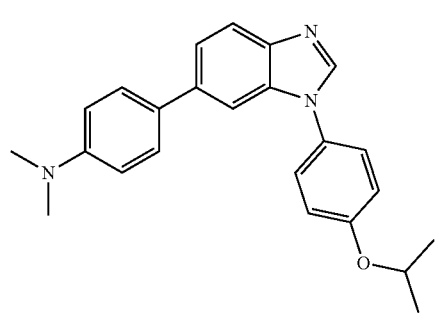<br>N,N-dimethyl-4-{1-[4-(propan-2-yloxy)phenyl]-1H-1,3-benzodiazol-6-yl}aniline | $^1$H NMR (300 MHz, CDCl$_3$) δ 8.10 (s, 1H), 7.88 (d, 1H), 7.59-7.48 (m, 4H), 7.42 (d, 2H), 7.05 (d, 2H), 6.84 (d, 2H), 4.62 (sep, 1H), 2.99 (s, 6H), 1.40 (d, 6H). LC/MS m/z: 372.24 (M + H)$^+$ |
| A19 | 4-bromo-1-(4-methoxyphenyl)-1H-1,3-benzodiazole [4-(propan-2-yl)phenyl]boronic acid | 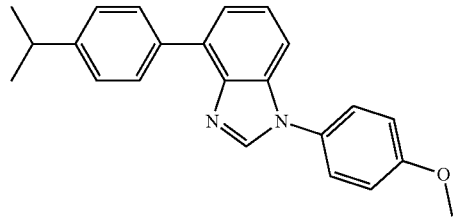<br>1-(4-methoxyphenyl)-4-[4-(propan-2-yl)phenyl]-1H-1,3-benzodiazole | LC/MS m/z: 343.21 (M + H)$^+$ |
| A20 | 4-bromo-1-(4-methoxyphenyl)-1H-1,3-benzodiazole [3-(propan-2-yl)phenyl]boronic acid | 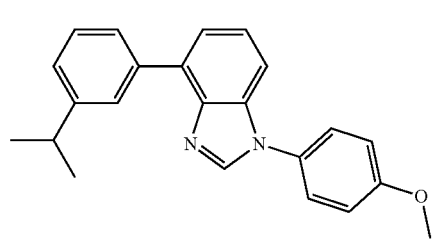<br>1-(4-methoxyphenyl)-4-[3-(propan-2-yl)phenyl]-1H-1,3-benzodiazole | LC/MS m/z: 343.3 (M + H)$^+$, 685.45 (2M + H)$^+$ |

-continued

| Ex. | Starting materials | Product/Name | Analytical Data |
|---|---|---|---|
| A21 | 6-bromo-1-[4-(propan-2-yloxy)phenyl]-1H-1,3-benzodiazole [4-(morpholin-4-yl)phenyl]boronic acid | 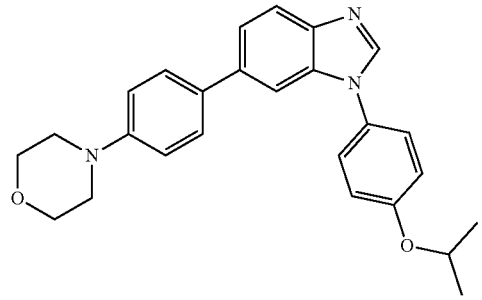<br>6-[4-(morpholin-4-yl)phenyl]-1-[4-(propan-2-yloxy)phenyl]-1H-1,3-benzodiazole | LC/MS m/z: 414.28 (M + H)+ |
| A22 | 6-bromo-1-(2-methoxyphenyl)-1H-1,3-benzodiazole [4-(2-hydroxypropan-2-yl)phenyl]boronic acid | 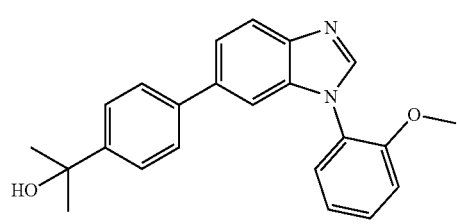<br>2-{4-[1-(2-methoxyphenyl)-1H-1,3-benzodiazol-6-yl]phenyl}propan-2-ol | LC/MS m/z: 359.22 (M + H)+ |
| A23 | 6-bromo-1-(3-methoxyphenyl)-1H-1,3-benzodiazole [4-(2-hydroxypropan-2-yl)phenyl]boronic acid | 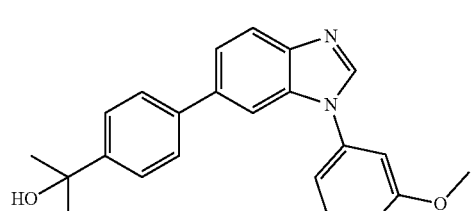<br>2-{4-[1-(3-methoxyphenyl)-1H-1,3-benzodiazol-6-yl]phenyl}propan-2-ol | LC/MS m/z: 359.23 (M + H)+ |
| A24 | 6-bromo-1-[4-(propan-2-yloxy)phenyl]-1H-1,3-benzodiazole 1H-indol-5-ylboronic acid | 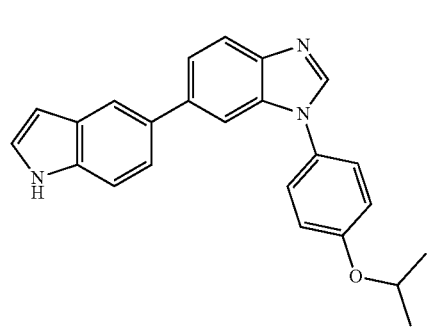<br>6-(1H-indol-5-yl)-1-[4-(propan-2-yloxy)phenyl]-1H-1,3-benzodiazole | 1H NMR (300 MHz, CDCl3) δ 8.44 (br. s, 1H), 8.33 (s, 1H), 7.96 (d, 1H), 7.83 (s, 1H), 7.73-7.64 (m, 2H), 7.47-7.39 (m, 4H), 7.06 (d, 2H), 6.60-6.56 (m, 1H), 4.62 (sep, 1H), 3.66 (br. s, 1H), 1.39 (d, 6H). LC/MS m/z: 368.22 (M + H)+ |

-continued

| Ex. | Starting materials | Product/Name | Analytical Data |
|---|---|---|---|
| A25 | 6-bromo-1-[4-(propan-2-yloxy)phenyl]-1H-1,3-benzodiazole (4-isopropoxyphenyl) boronic acid | 1,6-bis[4-(propan-2-yloxy)phenyl]-1H-1,3-benzodiazole | $^1$H NMR (300 MHz, CDCl$_3$) δ 8.27 (br, 1H), 7.97 (br, 1H), 7.61 (br, 2H), 7.53 (d, 2H), 7.45 (d, 2H), 7.11 (d, 2H), 6.97 (d, 2H), 4.70-4.5 (m, 2H), 1.43 (d, 6H), 1.38 (d, 6H). LC/MS m/z: 387.35 (M + H)$^+$ |
| A26 | 6-bromo-1-[4-(propan-2-yloxy)phenyl]-1H-1,3-benzodiazole (4-acetylphenyl)boronic acid | 1-(4-{1-[4-(propan-2-yloxy)phenyl]-1H-1,3-benzodiazol-6-yl}phenyl) ethan-1-one | LC/MS m/z: 371.32 (M + H)$^+$, 412.21 (M + H + CH$_3$CN)$^+$ |
| A27 | 6-bromo-1-(1H-indol-5-yl)-1H-1,3-benzodiazole (4-isopropoxyphenyl) boronic acid | 1-(1H-indol-5-yl)-6-[4-(propan-2-yloxy)phenyl]-1H-1,3-benzodiazole | LC/MS m/z: 368.28 (M + H)$^+$ |
| A28 | 6-bromo-1-(1H-indol-5-yl)-1H-1,3-benzodiazole (4-acetylphenyl)boronic acid | 1-{4-[1-(1H-indol-5-yl)-1H-1,3-benzodiazol-6-yl]phenyl} ethan-1-one | LC/MS m/z: 352.25 (M + H)$^+$ |

| Ex. | Starting materials | Product/Name | Analytical Data |
|---|---|---|---|
| A29 | 6-bromo-1-(1H-indol-5-yl)-1H-1,3-benzodiazole<br>1H-indol-5-ylboronic acid | 1,6-bis(1H-indol-5-yl)-1H-1,3-benzodiazole | LC/MS m/z: 349.22 (M + H)$^+$ |
| A30 | 6-bromo-5-methyl-1-[4-(propan-2-yloxy)phenyl]-1H-1,3-benzodiazole<br>(4-isopropoxyphenyl)boronic acid | 5-methyl-1,6-bis[4-(propan-2-yloxy)phenyl]-1H-1,3-benzodiazole | $^1$H NMR (300 MHz, CDCl$_3$) δ 8.44 (br, 1H), 8.04 (d, 1H), 7.92 (s, 1H), 7.43 (d, 2H), 7.23 (d, 2H), 7.03 (d, 2H), 6.94 (d, 2H), 4.53-4.78 (m, 2H), 2.41 (s, 3H), 1.40 (d, 6H), 1.38 (d, 6H). LC/MS m/z: 401.29 (M + H)$^+$ |
| A31 | 6-bromo-5-methoxy-1-[4-(propan-2-yloxy)phenyl]-1H-1,3-benzodiazole<br>(4-isopropoxyphenyl)boronic acid | 5-methoxy-1,6-bis[4-(propan-2-yloxy)phenyl]-1H-1,3-benzodiazole | LC/MS m/z: 417.28 (M + H)$^+$ |

Preparation of Intermediates for Examples B1 to B15

6-Bromo-3-nitro-N-[4-(propan-2-yloxy) phenyl] pyridin-2-amine

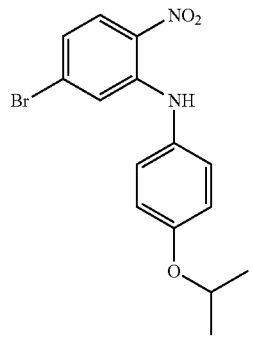 [SMILES: CC(C)Oc1ccc(Nc2cc(Br)ccc2[N+](=O)[O-])cc1]

The title compound was prepared from 2,6-dibromo-3-nitropyridine and 4-(propan-2-yloxy)aniline in the same manner as described for 5-bromo-2-nitro-N-[4-(propan-2-yloxy)phenyl]aniline.

5-Bromo-3-[4-(propan-2-yloxy)phenyl]-3H-imidazo[4,5-b]pyridine

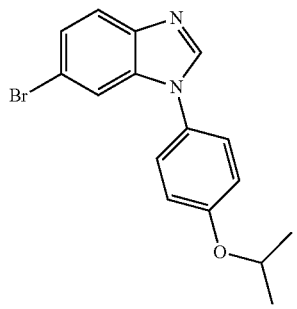 [SMILES: CC(C)Oc1ccc(-n2cnc3ccc(Br)cc32)cc1]

The title compound was prepared from 6-Bromo-3-nitro-N-[4-(propan-2-yloxy)phenyl]pyridin-2-amine in the same manner as described for 6-Bromo-1-[4-(propan-2-yloxy)phenyl]-1H-1,3-benzodiazole.

LC/MS m/z: 332.19 ($^{79}$Br, M+H)$^+$, 334.11 ($^{81}$Br, M+H)$^+$.

6-bromo-1-[4-(propan-2-yloxy)phenyl]-1H-imidazo[4,5-c]pyridine

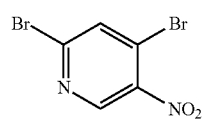 +

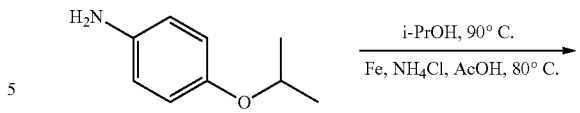

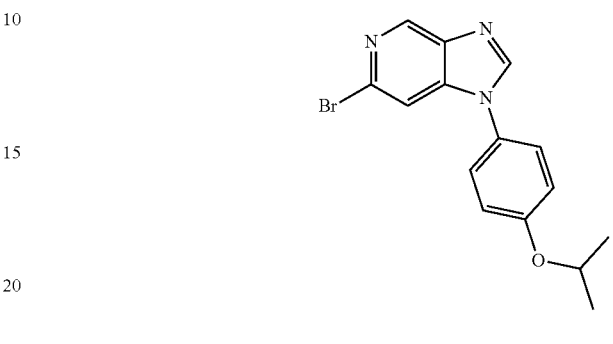

To a solution of 2,4-dibromo-5-nitropyridine (200 mg, 0.71 mmol) in i-propanol (3 mL) was added 4-isopropoxyaniline (128 mg, 0.85 mmol) at room temperature. The resulting mixture was heated to 90° C. for 1 hr. After cooling to room temperature, iron was added (391 mg, 7.1 mmol), followed by NH$_4$Cl (377 mg, 7.1 mmol), and acetic acid (3 mL). The reaction was stirred at 80° C. for 8 hr. After cooling to room temperature, the reaction was filtered through a celite pad. The filtrate was concentrated under reduced pressure and the residue was poured into water and extracted with ethyl acetate. The organic phase was dried over Na$_2$SO$_4$, filtered, and concentrated in vacuo. The residue was purified by SiO$_2$ column chromatography (hexane/EtOAc=1:1) to give 215 mg (87%) of the product as a white solid. LC/MS m/z: 332.29 ($^{79}$Br, M+H)$^+$, 334.19 ($^{81}$Br, M+H)$^+$, 373.22 ($^{79}$Br, M+H+CH$_3$CN)$^+$, 375.19 ($^{81}$Br, M+H+CH$_3$CN)$^+$.

2-chloro-9-[4-(propan-2-yloxy)phenyl]-9H-purine

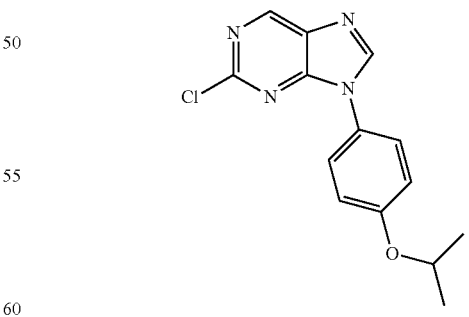

The title compound was prepared from 2,4-dichloro-5-nitropyrimidine and 4-sopropoxyaniline in the same manner as described for 6-bromo-1-[4-(propan-2-yloxy)phenyl]-1H-imidazo[4,5-c]pyridine. LC/MS m/z: 289.24 (M+H)$^+$, 330.24 (M+H+CH$_3$CN)$^+$.

99

5-bromo-N-(4-isopropoxyphenyl)benzene-1,2-diamine

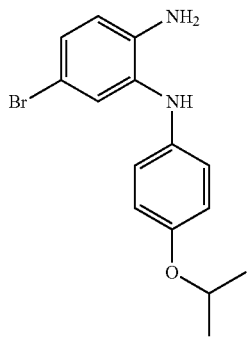

The title compound was prepared from 4-bromo-2-fluoro-1-nitrobenzene and 4-isopropoxyaniline in the same manner as described for 5-bromo-N-(4-isopropoxyphenyl)-4-methylbenzene-1,2-diamine. LCMS m/z 321.20 ($^{79}$Br, M+H)$^+$, 323.19 ($^{81}$Br, M+H)$^+$, 362.20 ($^{79}$Br, M+H+CH$_3$CN)$^+$, 364.24 ($^{81}$Br, M+H+CH$_3$CN)$^+$.

6-bromo-1-[4-(propan-2-yloxy)phenyl]-1H-1,2,3-benzotriazole

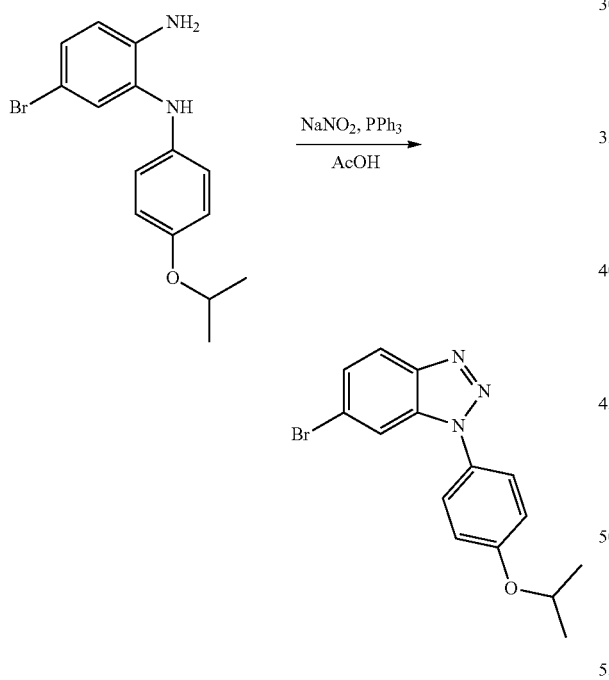

To a solution of 5-bromo-N'-(4-isopropoxyphenyl)benzene-1,2-diamine (100 mg, 0.3 mmol) in acetic acid (3 mL), was added PPh$_3$ (81.6 mg, 0.3 mmol) followed by addition of sodium nitrite (25.8 mg, 0.36 mmol) at 0° C. The reaction was warmed to room temperature and stirred for 1 h. The reaction was poured into water and extracted with ethyl acetate. The organic phase was dried over Na$_2$SO$_4$, filtered, and concentrated in vacuo. The residue was purified by SiO$_2$ column chromatography (hexane/EtOAc=2:1) to give 98.0 mg (95%) of the product as a white solid. LC/MS m/z: 332.07 ($^{79}$Br, M+H)$^+$, 334.08 ($^{81}$Br, M+H)$^+$, 373.15 ($^{79}$Br, M+H+CH$_3$CN)$^+$, 375.14 ($^{81}$Br, M+H+CH$_3$CN)$^+$.

100

6-bromo-1-(4-isopropoxyphenyl)-5-methyl-1H-benzo[d][1,2,3]triazole

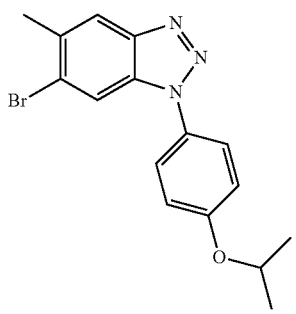 [SMILES: Cc1cc2nnn(-c3ccc(OC(C)C)cc3)c2cc1Br]

The title compound was prepared from 5-bromo-N-(4-isopropoxyphenyl)-4-methylbenzene-1,2-diamine in the same manner as described for 6-bromo-1-[4-(propan-2-yloxy)phenyl]-1H-1,2,3-benzotriazole. LC/MS m/z: 345.89 ($^{79}$Br, M+H)$^+$, 347.94 ($^{81}$Br, M+H)$^+$, 387.15 ($^{79}$Br, M+H+CH$_3$CN)+, 389.10 ($^{81}$Br, M+H+CH$_3$CN)$^+$.

Example B1: 2-(4-{3-[4-(propan-2-yloxy)phenyl]-3H-imidazo[4,5-b]pyridin-5-yl}phenyl)propan-2-ol

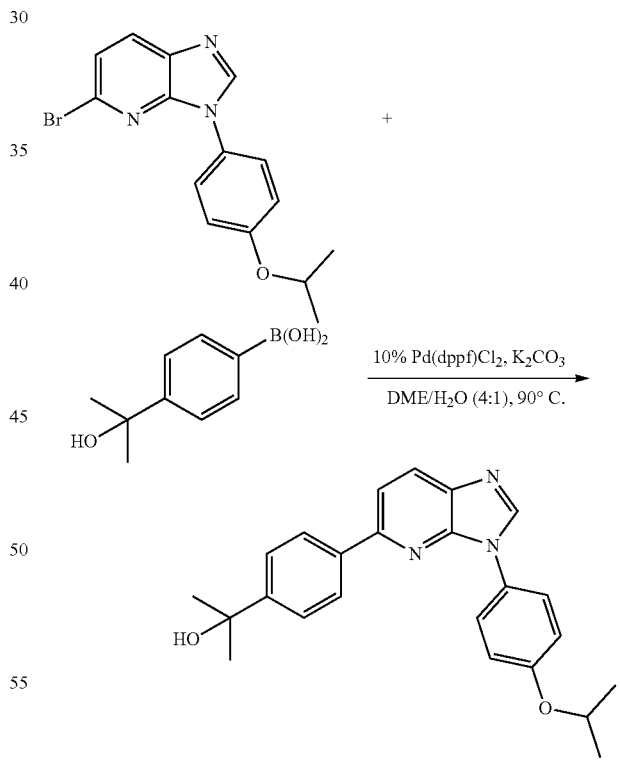

To a solution of 5-bromo-3-[4-(propan-2-yloxy)phenyl]-3H-imidazo[4,5-b]pyridine (11 mg, 0.033 mmol) in 1,2-dimethoxyethane (0.4 mL) were added [4-(2-hydroxypropan-2-yl)phenyl]boronic acid (12 mg, 0.066 mmol), [1,1'-bis(diphenylphosphino)ferrocene]palladium(II) dichloride (2.4 mg, 0.0033 mmol), potassium carbonate (14 mg, 0.1 mmol) and water (0.1 mL). The resulting reaction mixture was degassed with nitrogen for 10 min, then heated to 90°

C. for 5 h. Then the reaction mixture was diluted with ethyl acetate and washed with water. The organic phase was dried over Na$_2$SO$_4$, filtered, and concentrated in vacuo. The residue was purified by SiO$_2$ column chromatography (hexanes/EtOAc from 1:1 to 1:8) to give 6 mg (47%) of the product as a colorless oil. 1H NMR (500 MHz, CDCl$_3$) δ 8.49 (br. s, 1H), 8.24 (d, 1H), 8.03 (d, 2H), 7.84 (d, 1H), 7.72 (d, 2H), 7.59 (d, 2H), 7.08 (d, 2H), 4.63 (sep, 1H), 2.24 (br. s, 1H), 1.62 (s, 6H), 1.40 (d, 6H). LC/MS m/z: 388.25 (M+H)$^+$, 429.28 (M+H+CH$_3$CN)$^+$.

Examples B2 to B15 were prepared in the same manner as described above for example B1, 2-(4-{3-[4-(propan-2-yloxy)phenyl]-3H-imidazo[4,5-b]pyridin-5-yl}phenyl)propan-2-ol using the appropriate starting materials performing the reaction either under conventional heating or in a microwave reactor.

| Ex. | Starting materials | Product/Name | Analytical Data |
|---|---|---|---|
| B2 | 5-bromo-3-[4-(propan-2-yloxy)phenyl]-3H-imidazo[4,5-b]pyridine (4-isopropoxyphenyl) boronic acid | 3,5-bis[4-(propan-2-yloxy)phenyl]-3H-imidazo[4,5-b]pyridine | $^1$H NMR (300 MHz, CDCl$_3$) δ 8.61 (s, 1H), 8.30 (d, 1H), 8.08 (d, 1H), 8.02 (d, 2H), 7.73 (d, 2H), 7.13 (d, 2H), 7.01 (d, 2H), 4.70-4.61 (m, 2H), 1.44 (d, 6H), 1.39 (d, 6H). LC/MS m/z: 388.33 (M + H)$^+$, 429.25 (M + H + CH$_3$CN)$^+$. |
| B3 | 5-bromo-3-[4-(propan-2-yloxy)phenyl]-3H-imidazo[4,5-b]pyridine 1H-indol-5-ylboronic acid | 5-{3-[4-(propan-2-yloxy)phenyl]-3H-imidazo[4,5-b]pyridin-5-yl}-1H-indole | LC/MS m/z: 369.26 (M + H)$^+$. |
| B4 | 5-bromo-3-[4-(propan-2-yloxy)phenyl]-3H-imidazo[4,5-b]pyridine (4-acetylphenyl) boronic acid | 1-(4-{3-[4-(propan-2-yloxy)phenyl]-3H-imidazo[4,5-b]pyridin-5-yl}phenyl)ethan-1-one | LC/MS m/z: 372.24 (M + H)$^+$, 413.24 (M + H + CH$_3$CN)$^+$ |

| Ex. | Starting materials | Product/Name | Analytical Data |
|---|---|---|---|
| B5 | 6-bromo-1-[4-(propan-2-yloxy)phenyl]-1H-imidazo[4,5-c]pyridine [4-(2-hydroxypropan-2-yl)phenyl]boronic acid | 2-(4-{1-[4-(propan-2-yloxy)phenyl]-1H-imidazo[4,5-c]pyridin-6-yl}phenyl)propan-2-ol | LC/MS m/z: 388.32 (M + H)+ |
| B6 | 6-bromo-1-[4-(propan-2-yloxy)phenyl]-1H-imidazo[4,5-c]pyridine (4-isopropoxyphenyl)boronic acid | 1,6-bis[4-(propan-2-yloxy)phenyl]-1H-imidazo[4,5-c]pyridine | LC/MS m/z: 388.27 (M + H)+ |
| B7 | 6-bromo-1-[4-(propan-2-yloxy)phenyl]-1H-imidazo[4,5-c]pyridine 1H-indol-5-ylboronic acid | 5-{1-[4-(propan-2-yloxy)phenyl]-1H-imidazo[4,5-c]pyridin-6-yl}-1H-indole | LC/MS m/z: 369.39 (M + H)+ |
| B8 | 6-bromo-1-[4-(propan-2-yloxy)phenyl]-1H-imidazo[4,5-c]pyridine (4-acetylphenyl)boronic acid | 1-(4-{1-[4-(propan-2-yloxy)phenyl]-1H-imidazo[4,5-c]pyridin-6-yl}phenyl)ethan-1-one | LC/MS m/z: 372.29 (M + H)+ |

-continued

| Ex. | Starting materials | Product/Name | Analytical Data |
|---|---|---|---|
| B9 | 2-chloro-9-[4-(propan-2-yloxy)phenyl]-9H-purine [4-(2-hydroxypropan-2-yl)phenyl]boronic acid | 2-(4-{9-[4-(propan-2-yloxy)phenyl]-9H-purin-2-yl}phenyl)propan-2-ol | LC/MS m/z: 389.14 (M + H)+ |
| B10 | 2-chloro-9-[4-(propan-2-yloxy)phenyl]-9H-purine (4-isopropoxyphenyl)boronic acid | 2,9-bis[4-(propan-2-yloxy)phenyl]-9H-purine | LC/MS m/z: 389.31 (M + H)+ |
| B11 | 2-chloro-9-[4-(propan-2-yloxy)phenyl]-9H-purine 1H-indol-5-ylboronic acid | 2-(1H-indol-5-yl)-9-[4-(propan-2-yloxy)phenyl]-9H-purine | LC/MS m/z: 370.32 (M + H)+ |
| B12 | 6-bromo-1-[4-(propan-2-yloxy)phenyl]-1H-1,2,3-benzotriazole (4-isopropoxyphenyl)boronic acid | 1,6-bis[4-(propan-2-yloxy)phenyl]-1H-1,2,3-benzotriazole | $^1$H NMR (300 MHz, CDCl$_3$) δ 8.17 (s, 1H), 7.77 (s, 1H), 7.66 (s, 1H), 7.68 (d, 2H), 7.58 (d, 2H), 7.13 (d, 2H), 7.01 (d, 2H), 4.65-4.62 (m, 2H), 1.43 (d, 6H), 1.40 (d, 6H). LC/MS m/z: 388.22 (M + H)+, 429.27 (M + H + CH$_3$CN)+ |

| Ex. | Starting materials | Product/Name | Analytical Data |
|---|---|---|---|
| B13 | 6-bromo-1-[4-(propan-2-yloxy)phenyl]-1H-1,2,3-benzotriazole 1H-indol-5-ylboronic acid | 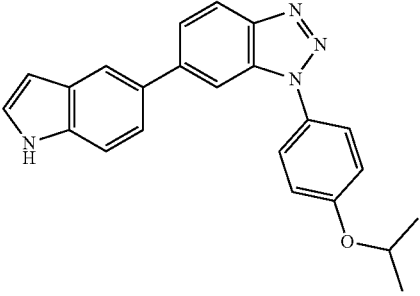<br>6-(1H-indol-5-yl)-1-[4-(propan-2-yloxy)phenyl]-1H-1,2,3-benzotriazole | $^1$H NMR (300 MHz, CDCl$_3$) δ 8.35 (br, 1H), 8.20 (d, 1H), 7.93 (s, 1H), 7.87 (s, 1H), 7.79 (d, 1H), 7.72 (d, 2H), 7.52 (s, 1H), 7.29 (s, 1H), 7.13 (d, 2H), 6.66 (s, 1H), 4.63-4.80 (m, 2H), 1.45 (d, 6H). LC/MS m/z: 369.17 (M + H)$^+$. |
| B14 | 6-bromo-1-[4-(propan-2-yloxy)phenyl]-1H-1,2,3-benzotriazole (4-acetylphenyl)boronic acid | 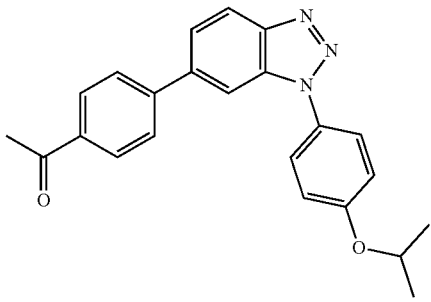<br>1-(4-{1-[4-(propan-2-yloxy)phenyl]-1H-1,2,3-benzotriazol-6-yl}phenyl)ethan-1-one | $^1$H NMR (300 MHz, CDCl$_3$) δ 8.18 (s, 1H), 7.77 (s, 1H), 7.70 (d, 2H), 7.68 (s, 1H), 7.59 (d, 2H), 7.14 (d, 2H), 7.02 (d, 2H), 4.65-4.82 (m, 2H), 1.44 (d, 6H), 1.41 (d, 6H). LC/MS m/z: 372.26 (M + H)$^+$, 413.31 (M + H + CH$_3$CN)$^+$. |
| B15 | 6-bromo-5-methyl-1-[4-(propan-2-yloxy)phenyl]-1H-1,2,3-benzotriazole (4-isopropoxyphenyl)boronic acid | 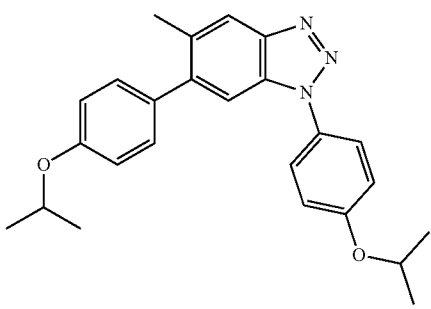<br>5-methyl-1,6-bis[4-(propan-2-yloxy)phenyl]-1H-1,2,3-benzotriazole | $^1$H NMR (300 MHz, CDCl$_3$) δ 8.03 (br, 1H), 7.67 (d, 2H), 7.54 (s, 1H), 7.28 (d, 2H), 7.06 (d, 2H), 6.97 (d, 2H), 4.57-4.68 (m, 2H), 2.43 (s, 3H), 1.41 (d, 6H), 1.39 (d, 6H). LC/MS m/z: 401.29 (M + H)$^+$. |

Example C1: 2-(4-{3-[4-(propan-2-yloxy)phenyl]imidazo[1,2-a]pyridin-6-yl}phenyl)propan-2-ol

Step 1: 6-bromo-3-[4-(propan-2-yloxy)phenyl]imidazo[1,2-a]pyridine

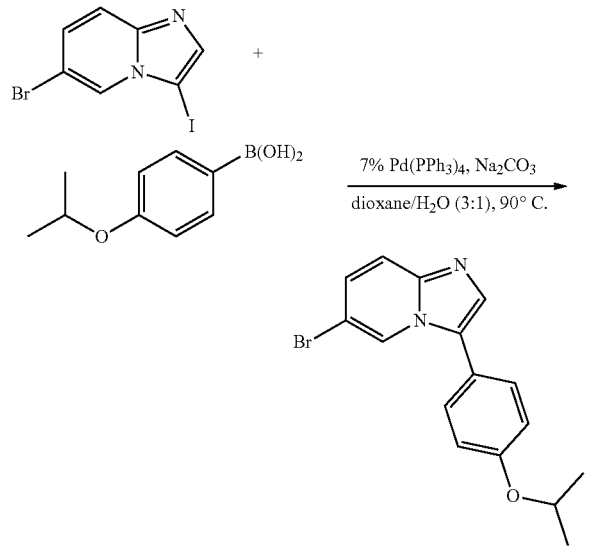

To a solution of 6-bromo-3-iodoimidazo[1,2-a]pyridine (0.3 g, 0.93 mmol) in dioxane (9 mL) were added (4-isopropoxyphenyl)boronic acid (0.167 g, 0.93 mmol), tetrakis(triphenylphosphine) palladium(0) (0.075 g, 0.065 mmol), sodium carbonate (0.3 g, 2.8 mmol) and water (3 mL). The resulting reaction mixture was degassed with nitrogen for 10 min, then heated to 90° C. for 5 h. Then the reaction mixture was diluted with ethyl acetate and washed with water. The organic phase was dried over $Na_2SO_4$, filtered, and concentrated in vacuo. The residue was purified by $SiO_2$ column chromatography (hexanes/EtOAc from 4:1 to 1:2) to give 0.26 g (84%) of the product as a white solid. $^1$H NMR (500 MHz, CDCl$_3$) δ 8.36 (s, 1H), 7.62 (s, 1H), 7.57 (d, 1H), 7.42 (d, 2H), 7.23 (d, 1H), 7.03 (d, 2H), 4.62 (sep, 1H), 1.39 (d, 6H). LC/MS m/z: 331.07 ($^{79}$Br, M+H)$^+$, 333.14 ($^{81}$Br, M+H)+.

Step 2: 2-(4-{3-[4-(propan-2-yloxy)phenyl]imidazo[1,2-a]pyridin-6-yl}phenyl)propan-2-ol

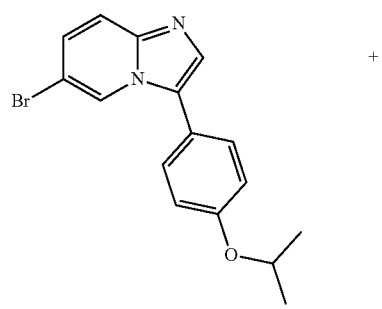

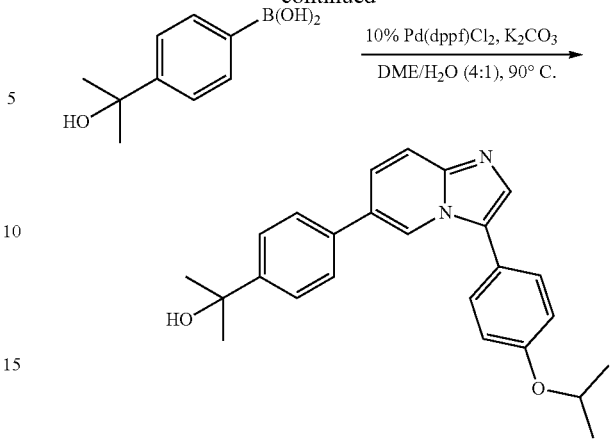

To a solution of 6-bromo-3-[4-(propan-2-yloxy)phenyl]imidazo[1,2-a]pyridine (20 mg, 0.06 mmol) in 1,2-dimethoxyethane (0.8 mL) were added [4-(2-hydroxypropan-2-yl)phenyl]boronic acid (22 mg, 0.12 mmol), [1,1'-bis(diphenylphosphino)ferrocene]palladium(II) dichloride (4.4 mg, 0.006 mmol), potassium carbonate (25 mg, 0.18 mmol) and water (0.2 mL). The resulting reaction mixture was degassed with nitrogen for 10 min, then heated to 90° C. for 5 h. Then the reaction mixture was diluted with ethyl acetate and washed with water. The organic phase was dried over $Na_2SO_4$, filtered, and concentrated in vacuo. The residue was purified by $SiO_2$ column chromatography (hexanes/EtOAc from 1:1 to 1:10, then pure EtOAc) to give 12 mg (52%) of the product as a colorless oil. 1H NMR (300 MHz, CDCl$_3$) δ8.42 (s, 1H), 7.82 (d, 1H), 7.66 (s, 1H), 7.59 (d, 2H), 7.48-7.51 (m, 3H), 7.46 (d, 2H), 7.05 (d, 2H), 4.62-4.64 (m, 1H), 2.20-2.45 (br s, 1H), 1.62 (s, 6H), 1.40 (d, 6H). LC/MS m/z: 387.27 (M+H)$^+$.

Example C2: 3,6-bis[4-(propan-2-yloxy)phenyl]imidazo[1,2-a]pyridine

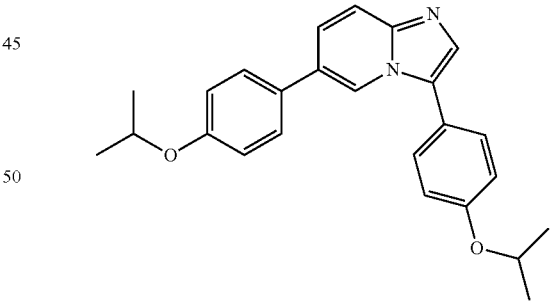

To a solution of 6-bromo-3-iodoimidazo[1,2-a]pyridine (0.3 g, 0.93 mmol) in dioxane (9 mL) and water (3 mL) was added (4-isopropoxyphenyl)boronic acid (0.334 g, 1.86 mmol) and sodium carbonate (0.6 g, 5.6 mmol). The reaction mixture was purged with nitrogen, then Pd(dppf)Cl$_2$ (0.05 g, 0.06 mmol) was added. The resulting reaction mixture was heated to 90° C. for 12 h, brought to room temperature and was extracted with ethyl acetate. Dried over $Na_2SO_4$, filtered, and concentrated in vacuo. The residue was purified by $SiO_2$ column chromatography (hexanes/EtOAc from 4:1 to 1:2) to give 0.24 g (62%) of the title compound as a beige solid. $^1$H NMR (300 MHz, CDCl$_3$) δ 8.37 (s, 1H), 7.70 (d, 1H), 7.64 (s, 1H), 7.49 (d, 2H), 7.44 (d, 2H), 7.41 (d, 1H), 7.05 (d, 2H), 6.97 (d, 2H), 4.56-4.67 (m, 2H), 1.40 (d, 6H), 1.37 (d, 6H). LC/MS m/z: 387.28 (M+H)+.

Examples C3 to C26 were prepared in the same manner as described above for example C1, 2-(4-{3-[4-(propan-2-yloxy)phenyl]imidazo[1,2-a]pyridin-6-yl}phenyl)propan-2-ol using 6-bromo-3-[4-(propan-2-yloxy)phenyl]imidazo[1,2-a]pyridine and appropriate commercial boronic acid or boronic acid pinacol ester performing the reaction either under conventional heating or in a microwave reactor.

| Ex. | Starting materials | Product/Name | Analytical Data |
|---|---|---|---|
| C3 | 4-(cyclopropoxy) phenylboronic acid | 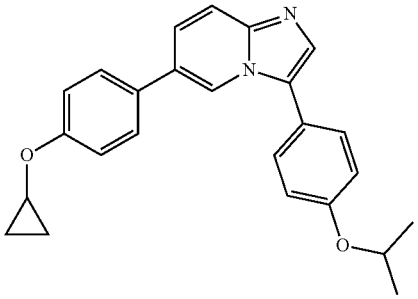<br>6-(4-cyclopropoxyphenyl)-3-[4-(propan-2-yloxy)phenyl] imidazo[1,2-a]pyridine | LC/MS m/z: 385.31 (M + H)+ |
| C4 | 4-(difluoromethoxy) phenyl boronic acid | 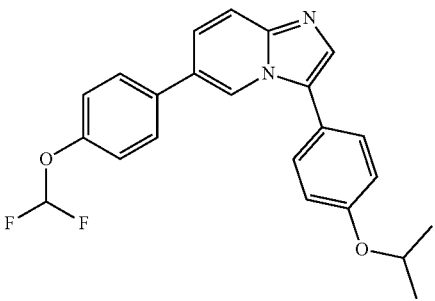<br>6-[4-(difluoromethoxy) phenyl]-3-[4-(propan-2-yloxy) phenyl] imidazo[1,2-a]pyridine | LC/MS m/z: 395.22 (M + H)+ |
| C5 | 4-(difluoromethyl) phenyl boronic acid | 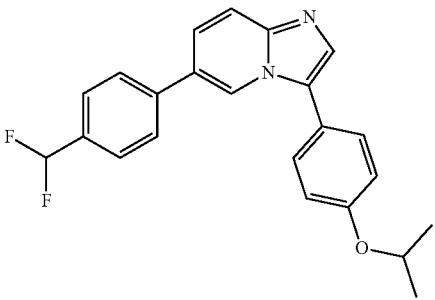<br>6-[4-(difluoromethyl)phenyl]-3-[4-(propan-2-yloxy)phenyl] imidazo[1,2-a]pyridine | LC/MS m/z: 379.23 (M + H)+ |

-continued

| Ex. | Starting materials | Product/Name | Analytical Data |
|---|---|---|---|
| C6 | 4-hydroxyphenyl boronic acid | 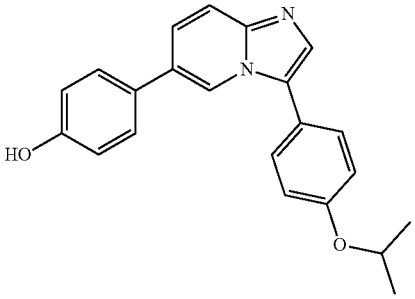<br>4-{3-[4-(propan-2-yloxy) phenyl]imidazo[1,2-a]pyridin-6-yl}phenol | LC/MS m/z: 345.27 (M + H)+ |
| C7 | 4-fluorophenyl boronic acid | 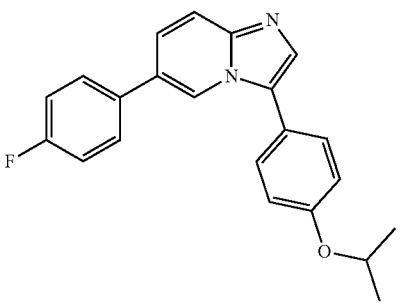<br>6-(4-fluorophenyl)-3-[4-(propan-2-yloxy)phenyl] imidazo[1,2-a]pyridine | LC/MS m/z: 347.30 (M + H)+ |
| C8 | 1H-indol-5-ylboronic acid | 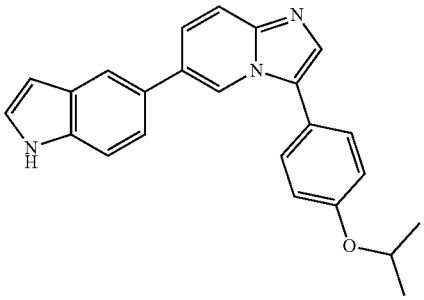<br>5-{3-[4-(propan-2-yloxy) phenyl]imidazo[1,2-a]pyridin-6-yl}-1H-indole | LC/MS m/z: 368.28 (M + H)+ |
| C9 | 4-(1-hydroxycyclo butyl)phenyl boronic acid | 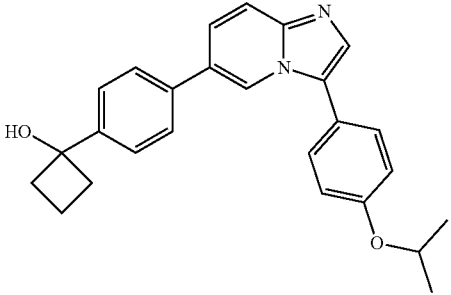<br>1-(4-{3-[4-(propan-2-yloxy) phenyl]imidazo[1,2-a] pyridin-6-yl}phenyl) cyclobutan-1-ol | LC/MS m/z: 399.28 (M + H)+ |

-continued

| Ex. | Starting materials | Product/Name | Analytical Data |
|---|---|---|---|
| C10 | 1H-indazol-5-ylboronic acid | 5-{3-[4-(propan-2-yloxy)phenyl]imidazo[1,2-a]pyridin-6-yl}-1H-indazole | LC/MS m/z: 369.33 (M + H)+ |
| C11 | 1H-indol-6-boronic acid | 6-{3-[4-(propan-2-yloxy)phenyl]imidazo[1,2-a]pyridin-6-yl}-1H-indole | LC/MS m/z: 368.36 (M + H)+ |
| C12 | 2-isopropoxypyridine-5-boronic acid | 2-(propan-2-yloxy)-5-{3-[4-(propan-2-yloxy)phenyl]imidazo[1,2-a]pyridin-6-yl}pyridine | LC/MS m/z: 388.28 (M + H)+ |
| C13 | (4-acetylphenyl)boronic acid | 1-(4-{3-[4-(propan-2-yloxy)phenyl]imidazo[1,2-a]pyridin-6-yl}phenyl)ethan-1-one | $^1$H NMR (300 MHz, CDCl$_3$) δ 8.48 (s, 1H), 8.06 (d, 2H), 7.93 (d, 1H), 7.70 (s, 1H), 7.66-7.58 (m, 3H), 7.49 (d, 2H), 7.08 (d, 2H), 4.69-4.61 (m, 1H), 2.65 (s, 3H), 1.41 (d, 6H)., LC/MS m/z: 371.33 (M + H)+ |

-continued

| Ex. | Starting materials | Product/Name | Analytical Data |
|---|---|---|---|
| C14 | 5-(4,4,5,5-tetramethyl-1,3,2-dioxaborolan-2-yl)pyridin-2-amine | 5-{3-[4-(propan-2-yloxy)phenyl]imidazo[1,2-a]pyridin-6-yl}pyridin-2-amine | LC/MS m/z: 345.32 (M + H)+ |
| C15 | 4-(1-aminocyclopropyl)phenyl boronic acid | 1-(4-{3-[4-(propan-2-yloxy)phenyl]imidazo[1,2-a]pyridin-6-yl}phenyl) cyclopropan-1-amine | LC/MS m/z: 384.35 (M + H)+ |
| C16 | (4-carbamoylphenyl) boronic acid | 4-{3-[4-(propan-2-yloxy)phenyl]imidazo[1,2-a]pyridin-6-yl}benzamide | LC/MS m/z: 372.23 (M + H)+ |
| C17 | 1-cyclopropyl-4-(4,4,5,5-tetramethyl-1,3,2-dioxaborolan-2-yl)pyrazole | 1-cyclopropyl-4-{3-[4-(propan-2-yloxy)phenyl]imidazo[1,2-a]pyridin-6-yl}-1H-pyrazole | LC/MS m/z: 359.26 (M + H)+ |

-continued

| Ex. | Starting materials | Product/Name | Analytical Data |
|---|---|---|---|
| C18 | 4-isopropoxy-2-methylphenyl boronic acid | 6-[2-methyl-4-(propan-2-yloxy)phenyl]-3-[4-(propan-2-yloxy)phenyl]imidazo[1,2-a]pyridine | LC/MS m/z: 401.39 (M + H)$^+$ |
| C19 | 4-isopropoxy-3-methylphenyl boronic acid | 6-[3-methyl-4-(propan-2-yloxy)phenyl]-3-[4-(propan-2-yloxy)phenyl]imidazo[1,2-a]pyridine | $^1$H NMR (300 MHz, CDCl$_3$) δ 8.36 (s, 1H), 8.13 (d, 1H), 7.76 (d, 1H), 7.69 (s, 1H), 7.48 (d, 2H), 7.29 (s, 1H), 7.26 (d, 1H), 7.09 (d, 2H), 6.92 (d, 1H), 4.51-4.73 (m, 2H), 2.27 (s, 3H), 1.41 (d, 6H), 1.38 (d, 6H)., LC/MS m/z: 401.34 (M + H)$^+$ |
| C20 | {4-[(propan-2-yloxy)carbonyl]phenyl}boronic acid | propan-2-yl 4-{3-[4-(propan-2-yloxy)phenyl]imidazo[1,2-a]pyridin-6-yl}benzoate | LC/MS m/z: 415.30 (M + H)$^+$ |
| C21 | [4-(tert-butoxy)phenyl]boronic acid | 6-[4-(tert-butoxy)phenyl]-3-[4-(propan-2-yloxy)phenyl]imidazo[1,2-a]pyridine | $^1$H NMR (300 MHz, CDCl$_3$) δ 8.39 (s, 1H), 7.94 (d, 1H), 7.68 (s, 1H), 7.62 (d, 1H), 7.49 (d, 2H), 7.43 (d, 2H), 7.09 (d, 2H), 7.06 (d, 2H), 4.60-4.71 (m, 1H), 1.42 (d, 6H), 1.39 (s, 9H)., LC/MS m/z: 401.30 (M + H)$^+$ |

-continued

| Ex. | Starting materials | Product/Name | Analytical Data |
|---|---|---|---|
| C22 | 1-methylindole-5-boronic acid | 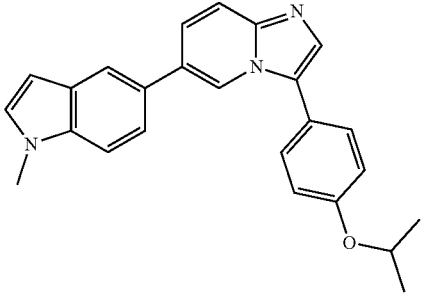<br>1-methyl-5-{3-[4-(propan-2-yloxy)phenyl]imidazo[1,2-a]pyridin-6-yl}-1H-indole | $^1$H NMR (300 MHz, CDCl$_3$) δ 8.45 (s, 1H), 7.85 (d, 1H), 7.77 (s, 1H), 7.66 (s, 1H), 7.64 (d, 1H), 7.51 (d, 2H), 7.40 (br s, 2H), 7.12 (d, 1H), 7.06 (d, 2H), 6.55 (d, 1H), 4.61-4.69 (m, 1H), 3.84 (s, 3H), 1.41 (d, 6H)., LC/MS m/z: 382.35 (M + H)$^+$ |
| C23 | [2-fluoro-4-(propan-2-yloxy)phenyl]boronic acid | 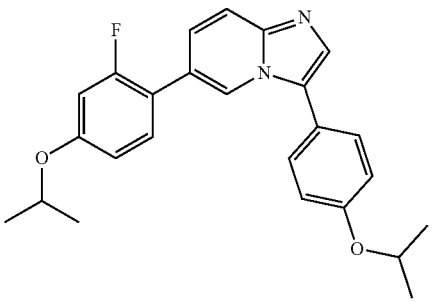<br>6-[2-fluoro-4-(propan-2-yloxy)phenyl]-3-[4-(propan-2-yloxy)phenyl]imidazo[1,2-a]pyridine | LC/MS m/z: 405.30 (M + H)$^+$ |
| C24 | [3-fluoro-4-(propan-2-yloxy)phenyl]boronic acid | 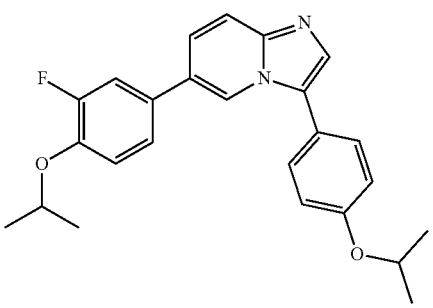<br>6-[3-fluoro-4-(propan-2-yloxy phenyl]-3-[4-(propan-2-yloxy)phenyl]imidazo[1,2-a]pyridine | $^1$H NMR (300 MHz, CDCl$_3$) δ 8.36 (s, 1H), 7.99 (d, 1H), 7.69 (s, 1H), 7.59 (d, 1H), 7.48 (d, 2H), 7.28 (s, 1H), 7.23 (d, 1H), 7.08 (d, 2H), 7.05 (d, 1H), 4.53-4.72 (m, 2H), 1.41 (d, 6H), 1.39 (d, 6H)., LC/MS m/z: 405.26 (M + H)$^+$ |
| C25 | 4-(2-morpholino ethoxy) phenyl boronic acid | 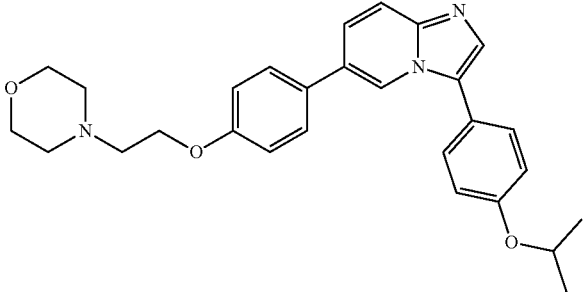<br>4-[2-(4-{3-[4-(propan-2-yloxy)phenyl]imidazo[1,2-a]pyridin-6-yl}phenoxy)ethyl]morpholine | LC/MS m/z: 458.32 (M + H)$^+$ |

| Ex. | Starting materials | Product/Name | Analytical Data |
|---|---|---|---|
| C26 | N-(propan-2-yl)-4-(4,4,5,5-tetramethyl-1,3,2-dioxaborolan-2-yl) aniline | 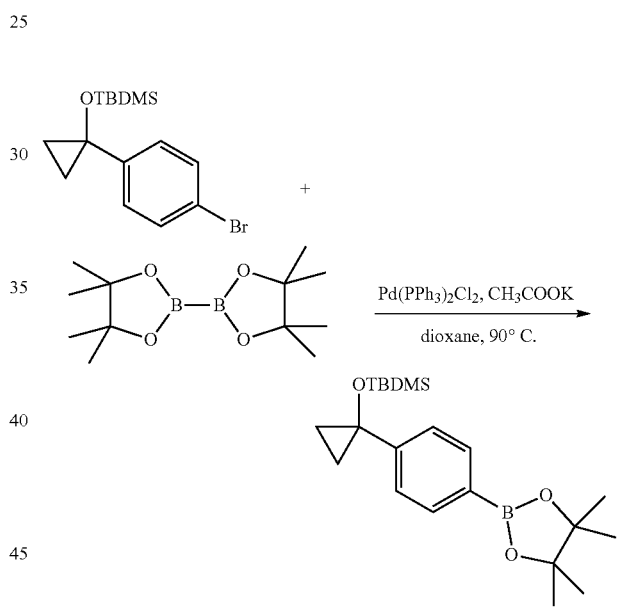<br>N-(propan-2-yl)-4-{3-[4-(propan-2-yloxy)phenyl]imidazo[1,2-a]pyridin-6-yl} aniline | $^1$H NMR (300 MHz, CDCl$_3$) δ 8.32 (s, 1H), 8.19 (d, 1H), 7.82 (dd, 1H), 7.66 (s, 1H), 7.45 (d, 2H), 7.31 (d, 2H), 7.07 (d, 2H), 6.65 (d, 2H), 4.69-4.59 (m, 1H), 3.73-3.60 (m, 1H), 1.40 (d, 6H), 1.23 (d, 6H). LC/MS m/z: 386.32 (M + H)$^+$ |

Preparation of Boronic Acid Pinacol Esters for Examples C27-C29 tert-butyldimethyl{1-[4-(4,4,5,5-tetramethyl-1,3,2-dioxaborolan-2-yl)phenyl]cyclopropoxy}silane

Step 1: [1-(4-bromophenyl)cyclopropoxy](tert-butyl)dimethylsilane

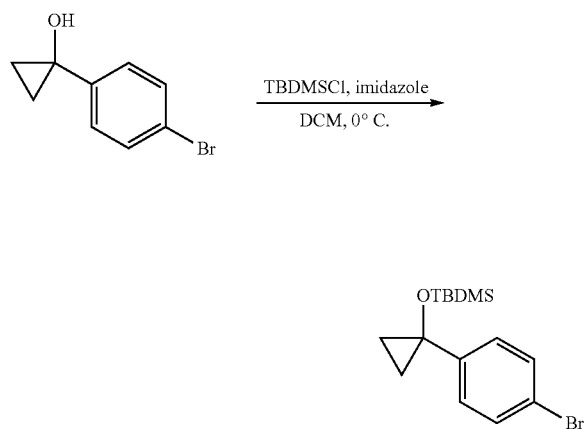

To a solution of 1-(4-bromophenyl)cyclopropan-1-ol (90 mg, 0.42 mmol) in DCM (1.5 mL) cooled to 0° C. was added imidazole (57 mg, 0.84 mmol), followed by TBDMSCl (76 mg, 0.5 mmol). The reaction mixture was brought to r.t. gradually and stirred for 2 h. Then DCM (10 mL) was added and the reaction mixture was washed with water. The organic layer was dried over Na$_2$SO$_4$, filtered, and concentrated in vacuo. The residue was dissolved in DCM and passed through a short pad of silica gel eluting with DCM. Then volatiles were removed in vacuo to give 0.14 g (quantitative yield) of the product as a colorless oil, which was used in the next step.

Step 2: tert-butyldimethyl{1-[4-(4,4,5,5-tetramethyl-1,3,2-dioxaborolan-2-yl)phenyl]cyclopropoxy}silane To a degassed mixture of [1-(4-bromophenyl)cyclopropoxy](tert-butyl)dimethylsilane (0.14 g, 0.42 mmol), bis(pinacolato)diboron (0.16 g, 0.63 mmol) and potassium acetate (0.13 g, 1.3 mmol) in anhydrous dioxane (1.6 mL) was added bis(triphenylphosphine)palladium(II) dichloride (0.03 g, 0.042 mmol). The resulting reaction mixture was stirred under N$_2$ atmosphere at 90° C. for 3 h. Then the reaction mixture was diluted with ethyl acetate and washed with water. The organic phase was dried over Na$_2$SO$_4$, filtered, and concentrated in vacuo. The residue was purified by flash chromatography on SiO$_2$ (hexanes/EtOAc 8:1) to give 0.11 g (69%) of the product as a colorless oil which solidified upon standing. 1H NMR (300 MHz, CDCl$_3$) b 7.75 (d, 2H), 7.31 (d, 2H), 1.35 (s, 12H), 1.23-1.17 (m, 2H), 1.04-0.99 (m, 2H), 0.89 (s, 9H), 0.00 (s, 6H).

125

{[3-(4-Bromophenyl)oxetan-3-yl]oxy}(tert-butyl)dimethylsilane

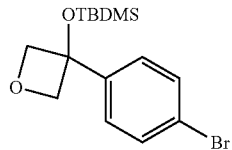

The title compound was prepared from 3-(4-bromophenyl)oxetan-3-ol in the same manner as described above for [1-(4-bromophenyl)cyclopropoxy](tert-butyl)dimethylsilane.

tert-Butyldimethyl({3-[4-(4,4,5,5-tetramethyl-1,3,2-dioxaborolan-2-yl)phenyl]oxetan-3-yl}oxy)silane

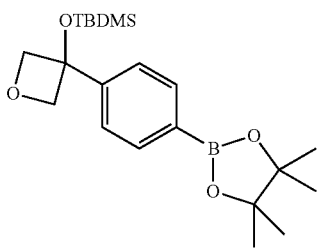 [SMILES: CC1(C)OB(c2ccc(C3(O[Si](C)(C)C(C)(C)C)COC3)cc2)OC1(C)C]

The title compound was prepared from {[3-(4-bromophenyl)oxetan-3-yl]oxy}(tert-butyl)dimethylsilane in the same manner as described above for tert-butyldimethyl{1-[4-(4,4,5,5-tetramethyl-1,3,2-dioxaborolan-2-yl)phenyl]cyclopropoxy}silane. $^1$H NMR (300 MHz, CDCl$_3$) δ 7.87 (d, 2H), 7.62 (d, 2H), 5.00 (d, 2H), 4.84 (d, 2H), 1.37 (s, 12H), 0.96 (s, 9H), 0.00 (s, 6H).

tert-Butyl 3-(4-bromophenyl)-3-[(tert-butyldimethylsilyl)oxy]azetidine-1-carboxylate

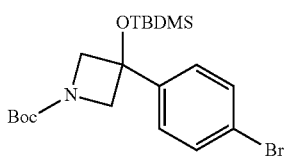 [SMILES: CC(C)(C)OC(=O)N1CC(O[Si](C)(C)C(C)(C)C)(c2ccc(Br)cc2)C1]

The title compound was prepared from tert-butyl 3-(4-bromophenyl)-3-hydroxyazetidine-1-carboxylate in the same manner as described above for [1-(4-bromophenyl)cyclopropoxy](tert-butyl)dimethylsilane.

126 tert-Butyl 3-[(tert-butyldimethylsilyl)oxy]-3-[4-(4,4,5,5-tetramethyl-1,3,2-dioxaborolan-2-yl)phenyl]azetidine-1-carboxylate

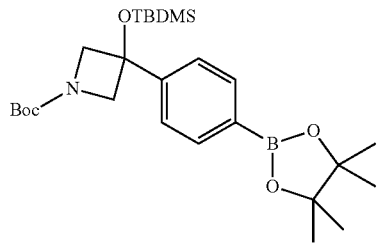 [SMILES: CC(C)(C)OC(=O)N1CC(O[Si](C)(C)C(C)(C)C)(c2ccc(B3OC(C)(C)C(C)(C)O3)cc2)C1]

The title compound was prepared from tert-butyl 3-(4-bromophenyl)-3-[(tert-butyldimethylsilyl)oxy]azetidine-1-carboxylate in the same manner as described above for tert-butyldimethyl{1-[4-(4,4,5,5-tetramethyl-1,3,2-dioxaborolan-2-yl) phenyl]cyclopropoxy}silane.

Example C27: 1-(4-{3-[4-(propan-2-yloxy)phenyl]imidazo[1,2-a]pyridin-6-yl}phenyl)cyclopropan-1-ol Step 1: 6-(4-{1-[(tert-butyldimethylsilyl)oxy]cyclopropyl}phenyl)-3-[4-(propan-2-yloxy)phenyl]imidazo[1,2-a]pyridine

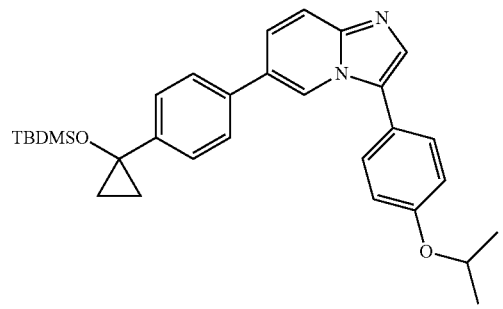 [SMILES: CC(C)Oc1ccc(-c2cnc3ccc(-c4ccc(C5(O[Si](C)(C)C(C)(C)C)CC5)cc4)cn23)cc1]

The title compound was prepared from 6-bromo-3-[4-(propan-2-yloxy)phenyl]imidazo[1,2-a]pyridine and tert-butyldimethyl{1-[4-(4,4,5,5-tetramethyl-1,3,2-dioxaborolan-2-yl)phenyl]cyclopropoxy}silane in the same manner as described above for 2-(4-{3-[4-(propan-2-yloxy)phenyl]imidazo[1,2-a]pyridin-6-yl}phenyl)propan-2-ol (Example C1). LC/MS m/z: 499.36 (M+H)$^+$.

Step 2: 1-(4-{3-[4-(propan-2-yloxy)phenyl]imidazo[1,2-a]pyridin-6-yl}phenyl)cyclopropan-1-ol

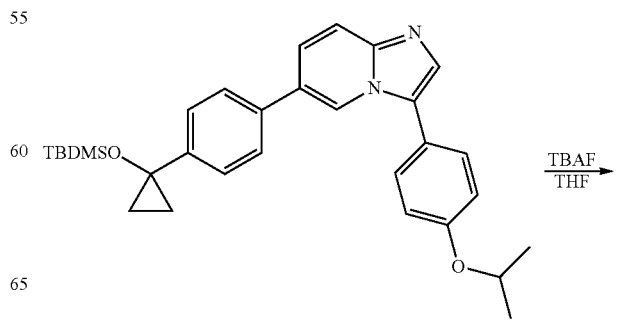

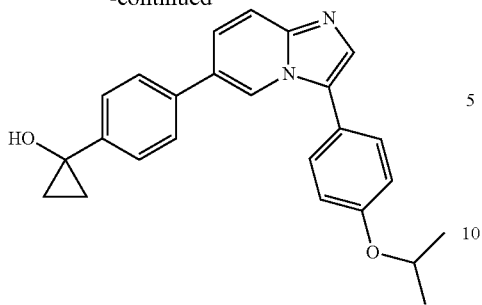

To a solution of 6-(4-{1-[(tert-butyldimethylsilyl)oxy]cyclopropyl}phenyl)-3-[4-(propan-2-yloxy)phenyl]imidazo[1,2-a]pyridine (12 mg, 0.024 mmol) in THF (0.5 mL) was added TBAF·3H$_2$O (20 mg, 0.063 mmol). The reaction mixture was stirred at r.t. for 2 h, then concentrated in vacuo. The residue was dissolved in EtOAc and washed with water. The organic layer was dried over Na$_2$SO$_4$, filtered, and concentrated in vacuo. The residue was purified by SiO$_2$ column chromatography (hexanes/EtOAc from 1:1 to 1:10, then pure EtOAc) to give 5.6 mg (60%) of the title compound as a white solid. $^1$H NMR (300 MHz, CDCl$_3$) δ 8.39 (s, 1H), 8.02 (d, 1H), 7.69-7.63 (m, 2H), 7.46-7.36 (m, 6H), 7.06 (d, 2H), 4.63 (sep, 1H), 3.31 (br. s, 1H), 1.39 (d, 6H), 1.37-1.33 (m, 2H), 1.09-1.05 (m, 2H). LC/MS m/z: 385.29 (M+H)+.

Example C28: 3-(4-{3-[4-(propan-2-yloxy)phenyl]imidazo[1,2-a]pyridin-6-yl}phenyl)oxetan-3-ol Step 1: 6-(4-{3-[(tert-butyldimethylsilyl)oxy]oxetan-3-yl}phenyl)-3-[4-(propan-2-yloxy)phenyl]imidazo [1,2-a]pyridine

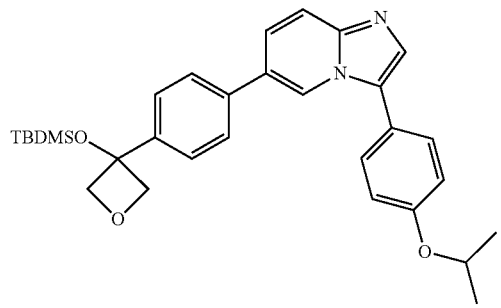 [SMILES: CC(C)Oc1ccc(-c2cnc3ccc(-c4ccc(C5(O[Si](C)(C)C(C)(C)C)COC5)cc4)cn23)cc1]

The title compound was prepared from 6-bromo-3-[4-(propan-2-yloxy)phenyl]imidazo[1,2-a]pyridine and tert-butyldimethyl({3-[4-(4,4,5,5-tetramethyl-1,3,2-dioxaborolan-2-yl)phenyl]oxetan-3-yl}oxy)silane in the same manner as described above for 2-(4-{3-[4-(propan-2-yloxy)phenyl]imidazo[1,2-a]pyridin-6-yl}phenyl)propan-2-ol (Example C1). LC/MS m/z: 515.38 (M+H)+.

Step 2: 3-(4-{3-[4-(propan-2-yloxy)phenyl]imidazo[1,2-a]pyridin-6-yl}phenyl)oxetan-3-ol

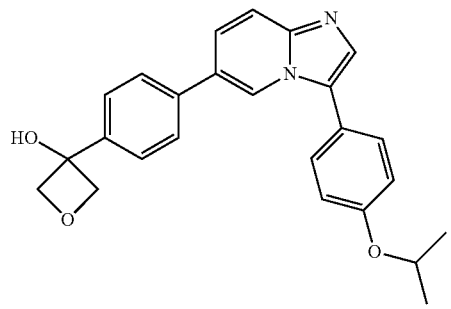 [SMILES: CC(C)Oc1ccc(-c2cnc3ccc(-c4ccc(C5(O)COC5)cc4)cn23)cc1]

The title compound was prepared from 6-(4-{3-[(tert-butyldimethylsilyl)oxy]oxetan-3-yl}phenyl)-3-[4-(propan-2-yloxy)phenyl]imidazo[1,2-a]pyridine in the same manner as described above for 1-(4-{3-[4-(propan-2-yloxy)phenyl]imidazo[1,2-a]pyridin-6-yl}phenyl)cyclopropan-1-ol. LC/MS m/z: 401.31 (M+H)$^+$.

Example C29: 3-(4-{3-[4-(propan-2-yloxy)phenyl]imidazo[1,2-a]pyridin-6-yl}phenyl)azetidin-3-ol Step 1: tert-butyl 3-[(tert-butyldimethylsilyl)oxy]-3-(4-{3-[4-(propan-2-yloxy)phenyl]imidazo[1,2-a]pyridin-6-yl}phenyl)azetidine-1-carboxylate

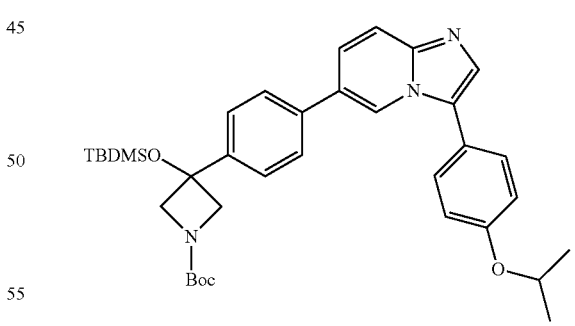

The title compound was prepared from 6-bromo-3-[4-(propan-2-yloxy)phenyl]imidazo[1,2-a]pyridine and tert-butyl 3-[(tert-butyldimethylsilyl)oxy]-3-[4-(4,4,5,5-tetramethyl-1,3,2-dioxaborolan-2-yl)phenyl]azetidine-1-carboxylate in the same manner as described above for 2-(4-{3-[4-(propan-2-yloxy)phenyl]imidazo[1,2-a]pyridin-6-yl}phenyl)propan-2-ol (Example C1). LC/MS m/z: 614.42 (M+H)$^+$.

129

Step 2: 3-[(tert-butyldimethylsilyl)oxy]-3-(4-{3-[4-(propan-2-yloxy)phenyl]imidazo[1,2-a]pyridin-6-yl}phenyl)azetidine

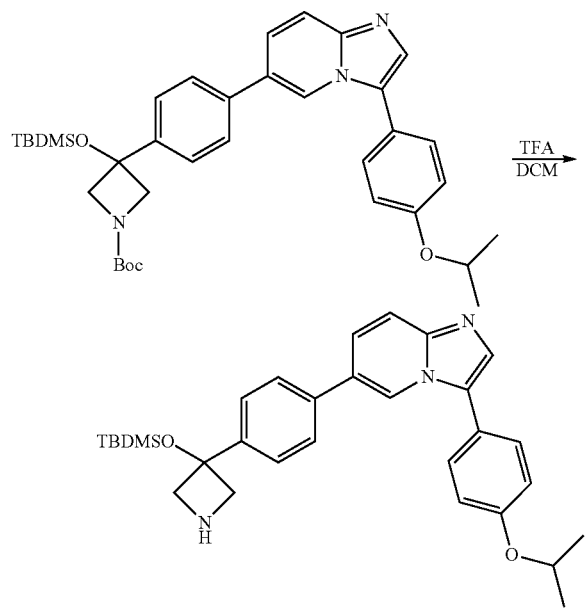

To a solution of tert-butyl 3-[(tert-butyldimethylsilyl)oxy]-3-(4-{3-[4-(propan-2-yloxy)phenyl]imidazo[1,2-a]pyridin-6-yl}phenyl)azetidine-1-carboxylate(29 mg, 0.047 mmol) in DCM (1 mL) was added trifluoroacetic acid (0.25 mL). The reaction mixture was stirred at r.t. overnight. Then, solvent was evaporated, and the residue was dissolved in DCM and washed with saturated aq. NaHCO₃ solution. The organic phase was dried over Na₂SO₄, filtered, and concentrated in vacuo to give 20 mg (83%) of the product as a colorless oil, which was used in the next step without further purification. LC/MS m/z: 514.44 (M+H)⁺.

Step 3: 3-(4-{3-[4-(propan-2-yloxy)phenyl]imidazo[1,2-a]pyridin-6-yl}phenyl)azetidin-3-ol

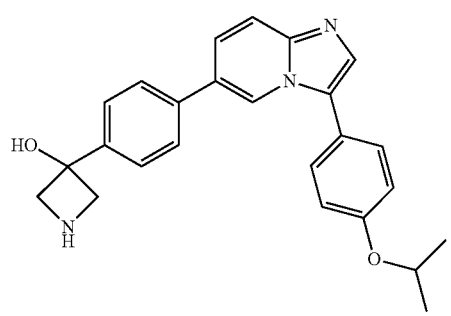 [SMILES: CC(C)Oc1ccc(-c2cnc3ccc(-c4ccc(C5(O)CNC5)cc4)cn23)cc1]

The title compound was prepared from 3-[(tert-butyldimethylsilyl)oxy]-3-(4-{3-[4-(propan-2-yloxy)phenyl]imidazo[1,2-a]pyridin-6-yl}phenyl)azetidine in the same manner as described above for 1-(4-{3-[4-(propan-2-yloxy)phenyl]imidazo[1,2-a]pyridin-6-yl}phenyl)cyclopropan-1-ol. LC/MS m/z: 400.41 (M+H)⁺.

130

Example C30: 3-(4-cyclopropylphenyl)-6-[4-(propan-2-yloxy)phenyl]imidazo[1,2-a]pyridine Step 1: 3-bromo-6-[4-(propan-2-yloxy)phenyl]imidazo[1,2-a]pyridine

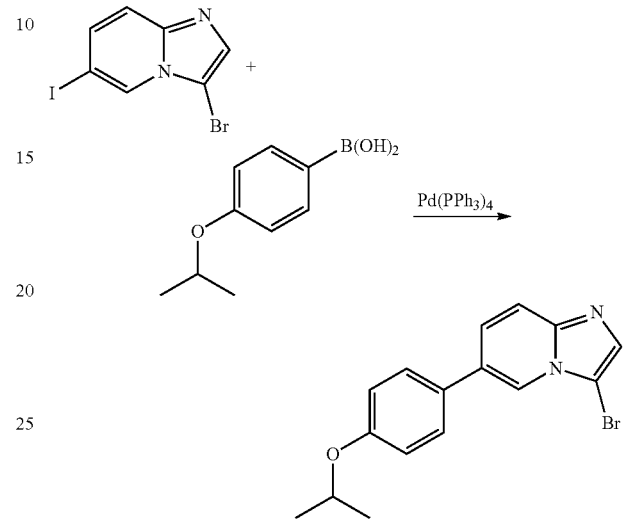

3-bromo-6-iodoimidazo[1,2-a]pyridine (100 mg, 0.3 mmol) was added to a microwave reactor vial followed by 4-isopropoxyphenyl boronic acid (62 mg, 0.34 mmol), tetrakis(triphenylphosphine) palladium(0) (34 mg, 0.03 mmol), sodium carbonate (94 mg, 0.9 mmol), 3 mL of 1,4-dioxane, and 1 mL of water. The mixture was capped tightly and degassed by bubbling nitrogen through the septum for 5 minutes. The resulting solution was heated to 90° C. for 15 minutes in a microwave reactor and allowed to cool. The mixture was then diluted with ethyl acetate, washed with water (2×) and brine (1×), dried over sodium sulfate, and evaporated. The crude oil was purified by flash chromatography on silica (1:1 hexanes:ethyl acetate, isocratic) to provide the title compound (82 mg) as a light yellow oil that slowly solidified. LC/MS m/z: 331.24 (⁷⁹Br, M+H)⁺, 333.28 (⁸¹Br, M+H)⁺.

Step 2: 3-(4-cyclopropylphenyl)-6-[4-(propan-2-yloxy)phenyl]imidazo[1,2-a]pyridine

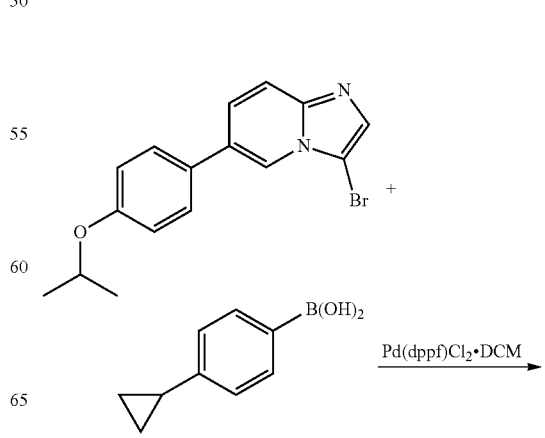

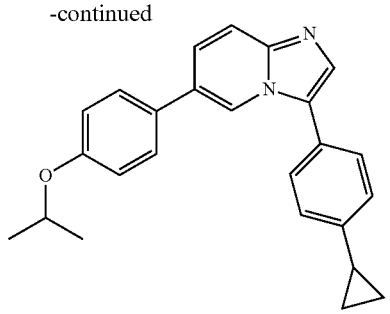

To a solution of 3-bromo-6-[4-(propan-2-yloxy)phenyl] imidazo[1,2-a]pyridine (20 mg, 0.06 mmol) in 2 mL THF: Water 3:1 was added 4-cyclopropylboronic acid (12 mg, 0.072 mmol), potassium carbonate (5 mg, 0.18 mmol), and Pd(dppf)Cl$_2$ dichloromethane complex (5 mg, 0.006 mmol). The mixture was capped tightly and degassed by bubbling nitrogen through the septum for 5 minutes. The resulting solution was heated to 100° C. for 15 minutes in a microwave reactor and allowed to cool. The mixture was then diluted with ethyl acetate, washed with water (2×) and brine (1×), dried over sodium sulfate, and evaporated. The crude oil was purified by flash chromatography on silica (3:7 hexanes:ethyl acetate, isocratic) to provide 13 mg of the title compound as a light yellow oil. LC/MS m/z: 369.26 (M+H)$^+$ Examples C31 to C43 were prepared in the same manner as described above for example C30, 3-(4-cyclopropylphenyl)-6-[4-(propan-2-yloxy)phenyl]imidazo[1,2-a]pyridine, using 3-bromo-6-[4-(propan-2-yloxy)phenyl]imidazo[1,2-a] pyridine, the appropriate commercial boronic acid or boronic acid pinacol ester, and the appropriate catalyst (Method A: Pd(PPh$_3$)$_4$; Method B: Pd(dppf)Cl$_2$.DCM; Method C: Pd(dba)$_2$ (0.1 eq.)/PCy$_3$ (0.15 eq.))

| Ex. | Method | Starting materials | Product/Name | Analytical Data |
|---|---|---|---|---|
| C31 | A | (4-cyclopropoxy phenyl)boronic acid | 3-(4-cyclopropoxyphenyl)-6-[4-(propan-2-yloxy)phenyl] imidazo[1,2-a]pyridine | $^1$H NMR (300 MHz, CDCl$_3$) δ ppm 8.39 (s, 1H), 8.08 (d, 1H), 7.72 (d, 2H), 7.56-7.39 (m, 5H), 7.25 (s, 1H), 7.00 (d, 2H), 4.62 (sep, 1H), 3.88-3.80 (m, 1H), 1.38 (d, 6H), 0.87 (br:s, 4H)., LC/MS m/z: 385.31 (M + H)$^+$ |
| C32 | A | (4-(tert-butoxy) phenyl) boronic acid | 3-[4-(tert-butoxy)phenyl]-6-[4-(propan-2-yloxy)phenyl] imidazo[1,2-a]pyridine | $^1$H NMR (300 MHz, CDCl$_3$) δ ppm 8.41 (s, 1H), 8.02 (d, 1H), 7.72 (s, 1H), 7.66 (d, 1H), 7.47 (dd, 4H), 7.19 (d, 2H), 7.00 (d, 2H), 4.62 (sept, 1H), 1.46 (s, 9H), 1.39 (d, 6H)., LC/MS m/z: 401.35 (M + H)$^+$ |
| C33 | A | (4-(cyclopropyl methoxy)phenyl) boronic acid | 3-[4-(cyclopropylmethoxy) phenyl]-6-[4-(propan-2-yloxy) phenyl]imidazo[1,2a]pyridine | $^1$H NMR (300 MHz, CDCl$_3$) δ ppm 8.37 (s, 1H), 8.05 (d, 1H), 7.73-7.66 (m, 2H), 7.47 (dd, 4H), 7.11 (d, 2H), 6.99 (d, 2H), 4.62 (sept, 1H), 3.91 (d, 2H), 1.39 (d, 6H), 0.77-0.66 (m, 2H), 0.46-0.37 (m, 2H)., LC/MS m/z: 399.31 (M + H)$^+$ |

| Ex. | Method | Starting materials | Product/Name | Analytical Data |
|---|---|---|---|---|
| C34 | A | (2,3-dihydro benzofuran-5-yl) boronic acid | 3-(2,3-dihydro-1-benzofuran-5-yl)-6-[4-(propan-2-yloxy) phenyl]imidazo[1,2-a]pyridine | LC/MS m/z: 371.35 (M + H)+ |
| C35 | A | (3-isopropoxy phenyl)boronic acid | 3-[3-(propan-2-yloxy)phenyl]-6-[4-(propan-2-yloxy)phenyl] imidazo[1,2-a]pyridine | LC/MS m/z: 387.34 (M + H)+, 428.47 (M + H + CH$_3$CN)+ |
| C36 | B | (4-(difluoromethyl) phenyl)boronic acid | 3-[4-(difluoromethyl)phenyl]-6-[4-(propan-2-yloxy)phenyl] imidazo[1,2-a]pyridine | LC/MS m/z: 379.31 (M + H)+, 420.51 (M + H + CH$_3$CN)+ |
| C37 | A | (6-isopropoxy pyridin-3-yl)boronic acid | 2-(propan-2-yloxy)-5-{6-[4-(propan-2-yloxy)phenyl] imidazo[1,2-a]pyridin-3-yl}pyridine | LC/MS m/z: 388.32 (M + H)+, 429.34 (M + H + CH$_3$CN)+ |

-continued

| Ex. | Method | Starting materials | Product/Name | Analytical Data |
|---|---|---|---|---|
| C38 | B | (4-(2-hydroxy propan-2-yl phenyl) boronic acid | 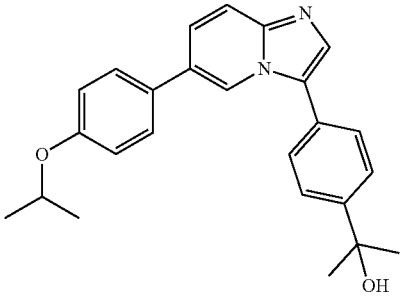<br>2-(4-{6-[4-(propan-2-yloxy) phenyl]imidazo[1,2-a]pyridin-3-yl}phenyl)propan-2-ol | LC/MS m/z: 387.28 (M + H)+, 428.55 (M + H + CH$_3$CN)+ |
| C39 | B | 1H-indol-5-ylboronic acid | 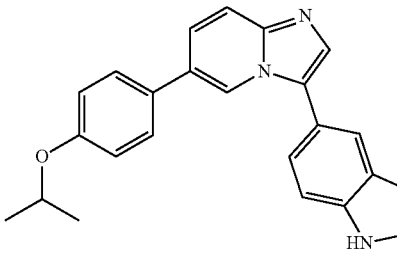<br>5-{6-[4-(propan-2yloxy)phenyl]imidazo[1,2-a]pyridin-3-yl}-1H-indole | LC/MS m/z: 368.24 (M + H)+ |
| C40 | C | (4-(difluoro methoxy)phenyl) boronic acid | 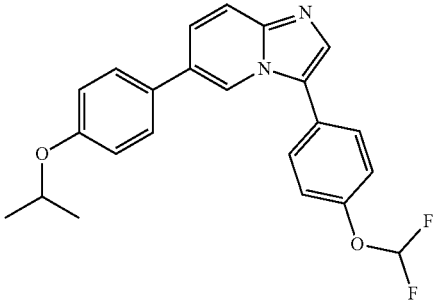<br>3-[4-(difluoromethoxy) phenyl]-6-[4-(propan-2-yloxy)phenyl] imidazo[1,2a]pyridine | LC/MS m/z: 395.26 (M + H)+, 436.22 (M + H + CH$_3$CN)+ |
| C41 | A | (4-acetylphenyl) boronic acid | 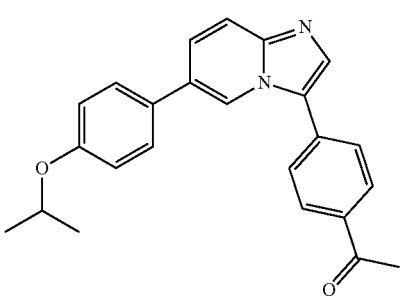<br>1-(4-{6-[4-(propan-2-yloxy) phenyl]imidazo[1,2-a]pyridin-3-yl}phenyl)ethan-1-one | LC/MS m/z: 371.28 (M + H)+ |

| Ex. | Method | Starting materials | Product/Name | Analytical Data |
|---|---|---|---|---|
| C42 | B | [4-(2-methoxy ethoxy) phenyl] boronic acid | 3-[4-(2-methoxyethoxy) phenyl]-6-[4-(propan-2-yloxy)phenyl]imidazo[1,2-a]pyridine | LC/MS m/z: 403.31 (M + H)+ |
| C43 | B | 4-(2-morpholino ethoxy)phenyl boronic acid | 4-[2-(4-{6-[4-(propan-2-yloxy)phenyl]imidazo[1,2-a]pyridin-3-yl}phenoxy) ethyl]morpholine | LC/MS m/z: 458.10 (M + H)+ |

Example C44: 1-(4-{6-[4-(propan-2-yloxy)phenyl] imidazo[1,2-a]pyridin-3-yl}phenyl)cyclopropan-1-ol Step 1: 3-(4-{1-[(tert-butyldimethylsilyl)oxy] cyclopropyl}phenyl)-6-[4-(propan-2-yloxy)phenyl] imidazo[1,2-a]pyridine

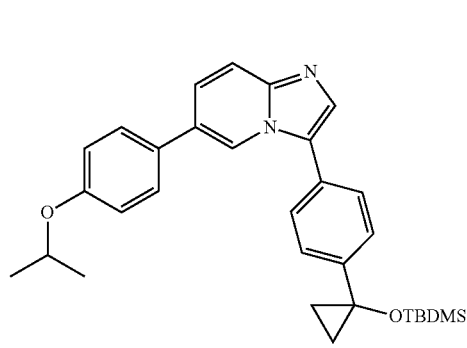 [SMILES: CC(C)Oc1ccc(-c2ccc3ncc(-c4ccc(C5(O[Si](C)(C)C(C)(C)C)CC5)cc4)n3c2)cc1]

The title compound was prepared from 3-bromo-6-[4-(propan-2-yloxy)phenyl]imidazo[1,2-a]pyridine and tert-butyldimethyl{1-[4-(4,4,5,5-tetramethyl-1,3,2-dioxaborolan-2-yl)phenyl]cyclopropoxy}silane in the same manner as described above for 3-(4-cyclopropylphenyl)-6-[4-(propan-2-yloxy)phenyl]imidazo[1,2-a]pyridine (Example C30). LC/MS m/z: 499.33 (M+H)+.

Step 2: 1-(4-{6-[4-(propan-2-yloxy)phenyl]imidazo [1,2-a]pyridin-3-yl}phenyl)cyclopropan-1-ol

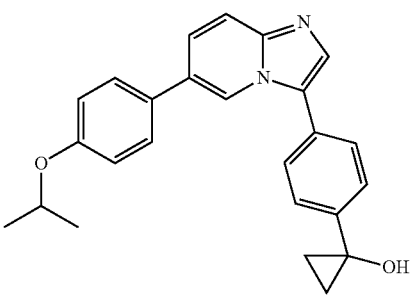 [SMILES: CC(C)Oc1ccc(-c2ccc3ncc(-c4ccc(C5(O)CC5)cc4)n3c2)cc1]

The title compound was prepared from 3-(4-{1-[(tert-butyldimethylsilyl)oxy]cyclopropyl}phenyl)-6-[4-(propan-2-yloxy)phenyl]imidazo[1,2-a]pyridine in the same manner as described above for 1-(4-{3-[4-(propan-2-yloxy)phenyl] imidazo[1,2-a]pyridin-6-yl}phenyl)cyclopropan-1-ol. 1H NMR (300 MHz, CDCl$_3$) δ 8.43-8.37 (m, 2H), 7.97 (d, 1H), 7.63 (s, 1H), 7.55-7.48 (m, 4H), 7.41 (d, 2H), 6.99 (d, 2H), 4.60 (sep, 1H), 1.96 (br. s, 1H), 1.47-1.42 (m, 2H), 1.36 (d, 6H), 1.17-1.13 (m, 2H). LC/MS m/z: 385.35 (M+H)+.

Example C45: 4-{6-[4-(propan-2-yloxy)phenyl]imidazo[1,2-a]pyridin-3-yl}benzoic Acid Step 1: ethyl 4-{6-[4-(propan-2-yloxy)phenyl]imidazo[1,2-a]pyridin-3-yl}benzoate

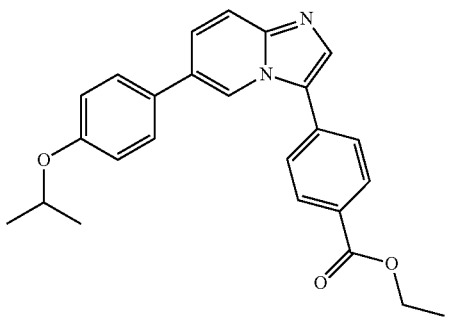 [SMILES: CCOC(=O)c1ccc(-c2cnc3ccc(-c4ccc(OC(C)C)cc4)cn23)cc1]

The title compound was prepared from 3-bromo-6-[4-(propan-2-yloxy)phenyl]imidazo[1,2-a]pyridine and [4-(ethoxycarbonyl)phenyl]boronic acid in the same manner as described above for 3-(4-cyclopropylphenyl)-6-[4-(propan-2-yloxy)phenyl]imidazo[1,2-a]pyridine (Example C30). LC/MS m/z: 401.31 (M+H)+.

Step 2: 4-{6-[4-(propan-2-yloxy)phenyl]imidazo[1,2-a]pyridin-3-yl}benzoic Acid

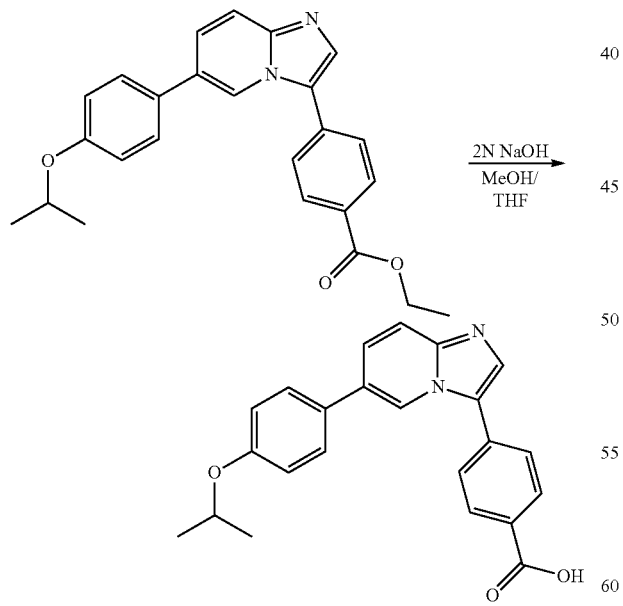

To a solution of ethyl 4-{6-[4-(propan-2-yloxy)phenyl]imidazo[1,2-a]pyridin-3-yl}benzoate (9.7 mg, 0.024 mmol) in a mixture of MeOH/THF (1:1) (0.5 mL) was added 2N NaOH (0.25 mL). The reaction mixture was stirred at r.t. for 4 h, then concentrated in vacuo. The residue was acidified with 1N HCl, and then purified by preparative HPLC to afford 2 mg (22%) of the product as a white solid. LC/MS m/z: 373.20 (M+H)+.

Example C46: 3,6-bis(4-cyclopropoxyphenyl)imidazo[1,2-a]pyridine

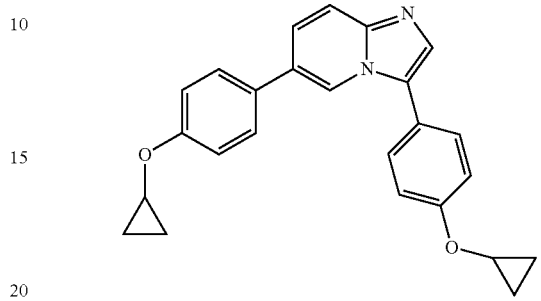

The title compound was prepared from 6-bromo-3-iodo-imidazo[1,2-a]pyridine and 4-(cyclopropoxy)phenylboronic acid in the same manner as described above for 3,6-bis[4-(propan-2-yloxy)phenyl]imidazo[1,2-a]pyridine (Example C2). LC/MS m/z: 383.33 (M+H)+.

Example C47: 1-(4-{3-[4-(1-hydroxycyclobutyl)phenyl]imidazo[1,2-a]pyridin-6-yl}phenyl)cyclobutan-1-ol

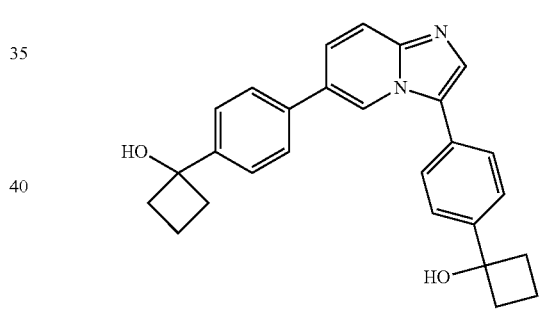

The title compound was prepared from 6-bromo-3-iodo-imidazo[1,2-a]pyridine and 4-(1-hydroxycyclobutyl)phenylboronic acid in the same manner as described above for 3,6-bis[4-(propan-2-yloxy)phenyl]imidazo[1,2-a]pyridine (Example C2). LC/MS m/z: 411.34 (M+H)+.

Example C48: 7-methyl-3,6-bis[4-(propan-2-yloxy)phenyl]imidazo[1,2-a]pyridine

Step 1: 6-bromo-3-iodo-7-methylimidazo[1,2-a]pyridine

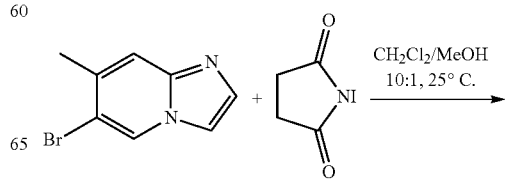

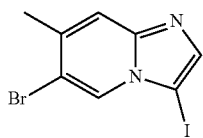

To a solution of 6-bromo-7-methylimidazo[1,2-a]pyridine (100 mg, 0.47 mmol) in CH$_2$C$_{12}$ (1 mL), was added 1-Iodopyrrolidine-2,5-dione (84 mg, 0.47 mmol) and MeOH (0.1 mL). The resulting mixture was stirred at room temperature for 2 h. The reaction was poured into water and extracted with ethyl acetate. The organic phase was dried over Na$_2$SO$_4$, filtered, and concentrated in vacuo. The residue was purified by SiO$_2$ column chromatography (hexane/EtOAc=1:1) to give 122 mg (77%) of the product as a white solid. LC/MS m/z: 337.00 (M+H)$^+$.

Step 2: 7-methyl-3,6-bis[4-(propan-2-yloxy)phenyl]imidazo[1,2-a]pyridine

The title compound was prepared from 6-bromo-3-iodo-7-methylimidazo[1,2-a]pyridine and [4-(propan-2-yloxy)phenyl]boronic acid in the same manner as described above for 3,6-bis[4-(propan-2-yloxy)phenyl]imidazo[1,2-a]pyridine (Example C2). LC/MS m/z: 401.33 (M+H)$^+$.

Example C49: 7-methoxy-3,6-bis[4-(propan-2-yloxy)phenyl]imidazo[1,2-a]pyridine

Step 1: 6-bromo-3-iodo-7-methoxyimidazo[1,2-a]pyridine

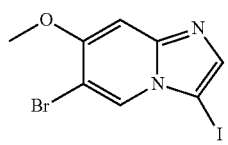

The title compound was prepared from 6-bromo-7-methoxyimidazo[1,2-a]pyridine in the same manner as described above for 6-bromo-3-iodo-7-methylimidazo[1,2-a]pyridine (Example C48, step 1). LC/MS m/z: 394.01 (M+H+CH$_3$CN)$^+$.

Step 2: 7-methoxy-3,6-bis[4-(propan-2-yloxy)phenyl]imidazo[1,2-a]pyridine

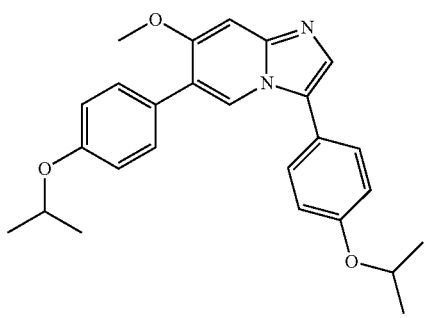 [SMILES: COc1cc2ncc(-c3ccc(OC(C)C)cc3)n2cc1-c1ccc(OC(C)C)cc1]

The title compound was prepared from 6-bromo-3-iodo-7-methoxyimidazo[1,2-a]pyridine and [4-(propan-2-yloxy)phenyl]boronic acid in the manner as described above for 3,6-bis[4-(propan-2-yloxy)phenyl]imidazo[1,2-a]pyridine (Example C2). $^1$H NMR (300 MHz, CDCl$_3$) δ 8.06 (s, 1H), 7.68 (s, 1H), 7.53 (s, 1H), 7.41 (d, 2H), 7.34 (d, 2H), 7.06 (d, 2H), 6.96 (d, 2H), 4.54-4.68 (m, 2H), 4.05 (s, 3H), 1.39 (d, 6H), 1.37 (d, 6H)., LC/MS m/z: 417.27 (M+H)$^+$.

Example C50: 8-methyl-3,6-bis[4-(propan-2-yloxy)phenyl]imidazo[1,2-a]pyridine

Step 1: 6-bromo-3-iodo-8-methylimidazo[1,2-a]pyridine

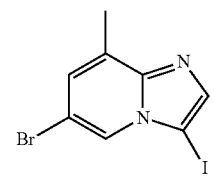

The title compound was prepared from 6-bromo-8-methylimidazo[1,2-a]pyridine in the same manner as described above for 6-bromo-3-iodo-7-methylimidazo[1,2-a]pyridine (Example C48, step 1). LC/MS m/z: 337.05 ($^{79}$Br, M+H)$^+$, 339.04 ($^{81}$Br, M+H)$^+$, 378.22 ($^{79}$Br, M+H+CH$_3$CN)$^+$, 380.00 ($^{81}$Br, M+H+CH$_3$CN)$^+$.

Step 2: 8-methyl-3,6-bis[4-(propan-2-yloxy)phenyl]imidazo[1,2-a]pyridine

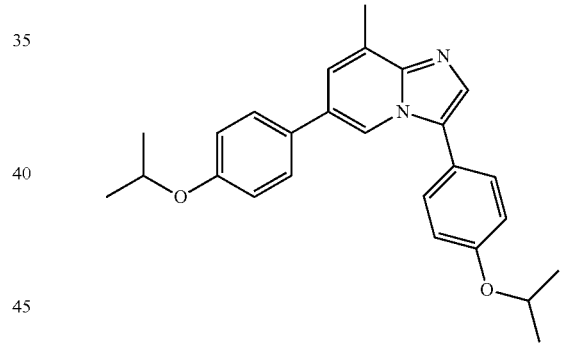

The title compound was prepared from 6-bromo-3-iodo-8-methylimidazo[1,2-a]pyridine and [4-(propan-2-yloxy)phenyl]boronic acid in the same manner as described above for 3,6-bis[4-(propan-2-yloxy)phenyl]imidazo[1,2-a]pyridine (Example C2). LC/MS m/z: 401.33 (M+H)$^+$.

Example C51: 5-methyl-3,6-bis[4-(propan-2-yloxy)phenyl]imidazo[1,2-a]pyridine

Step 1: 6-bromo-3-iodo-5-methylimidazo[1,2-a]pyridine

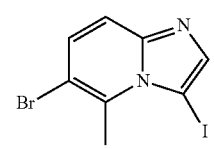

The title compound was prepared from 6-bromo-7-methylimidazo[1,2-a]pyridine in the same manner as described above for 6-bromo-3-iodo-8-methylimidazo[1,2-a]pyridine (Example C50, step 1). LC/MS m/z: 337.00 (M+H)⁺.

Step 2: 5-methyl-3,6-bis[4-(propan-2-yloxy)phenyl]imidazo[1,2-a]pyridine

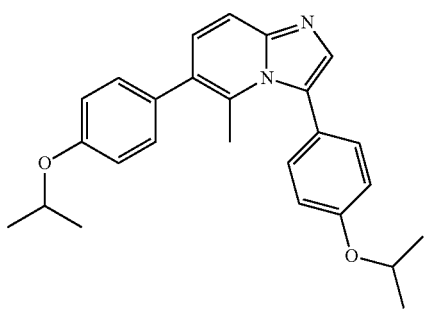 [SMILES: Cc1c(-c2ccc(OC(C)C)cc2)ccc2ncc(-c3ccc(OC(C)C)cc3)n12]

The title compound was prepared from 6-bromo-3-iodo-7-methoxyimidazo[1,2-a]pyridine and [4-(propan-2-yloxy)phenyl]boronic acid in the same manner as described above for 3,6-bis[4-(propan-2-yloxy)phenyl]imidazo[1,2-a]pyridine (Example C2). ¹H NMR (300 MHz, CDCl₃) δ8.14 (d, 1H), 7.63 (s, 1H), 7.56 (d, 1H), 7.37 (d, 2H), 7.18 (d, 2H), 6.97 (d, 2H), 6.94 (d, 2H), 4.53-4.69 (m, 2H), 2.19 (s, 3H), 1.39 (d, 6H), 1.37 (d, 6H)., LC/MS m/z: 401.29 (M+H)⁺.

Example D1: 1,6-bis[4-(propan-2-yloxy)phenyl]-1H-indazole

Step 1: 6-bromo-1-(4-isopropoxyphenyl)-1H-indazole

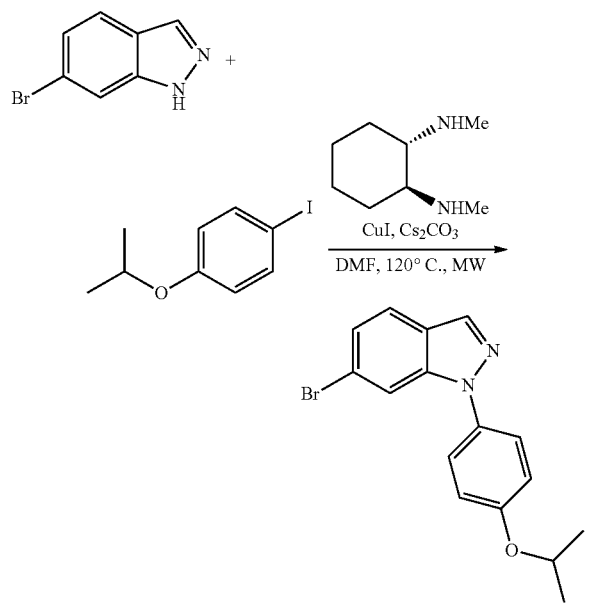

To a solution of 6-bromo-1H-indazole (10 mg, 0.04 mmol) in DMF (1 mL), were added 1-iodo-4-isopropoxybenzene (10 mg, 0.06 mmol), (1S,2S)—N¹,N²-dimethylcyclohexane-1,2-diamine (0.8 mg, 0.084 mmol), copper(I) iodide (0.25 mg, 0.042 mmol), and Cs₂CO₃ (32.5 mg, 0.10 mmol). The resulting mixture was stirred at 120° C. for 2 hr under microwave irradiation. After cooling to room temperature, the reaction was filtered through a celite pad. The filtrate was concentrated under reduced pressure and the residue was poured into water and extracted with ethyl acetate. The organic phase was dried over Na₂SO₄, filtered, and concentrated in vacuo. The residue was purified by SiO₂ column chromatography (hexane/EtOAc=1:1) to give 7.5 mg (45.2%) of the product as a colorless oil. LC/MS m/z: 331.13 (⁷⁹Br, M+H)⁺, 333.14 (⁸¹Br, M+H)⁺, 374.23 (⁷⁹Br, M+H+CH₃CN)⁺, 376.22 (⁸¹Br, M+H+CH₃CN)⁺.

Step 2: 1,6-bis[4-(propan-2-yloxy)phenyl]-1H-indazole

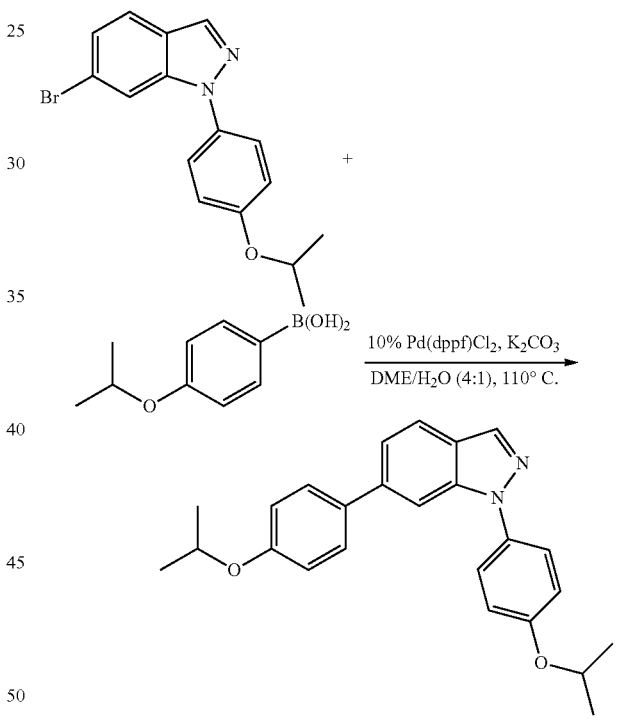

To a solution of 6-bromo-1-(4-isopropoxyphenyl)-1H-indazole (10 mg, 0.03 mmol) in dioxane (1.0 mL) and water (0.3 mL) was added (4-isopropoxyphenyl)boronic acid (6.5 mg, 1.2 eq.) and sodium carbonate (10.4 mg g, 2.5 eq.). The reaction mixture was purged with nitrogen, then Pd(dppf)Cl₂ (2.2 mg, 0.1 eq.) was added. The resulting reaction mixture was heated to 110° C. for 0.5 h under microwave irradiation. After cooling the reaction was poured into water and extracted with ethyl acetate. Dried over Na₂SO₄, filtered, and concentrated in vacuo. The residue was purified by SiO₂ column chromatography (hexanes/EtOAc=1:2) to give 7.2 mg (65%) of the title compound as an oil. LC/MS m/z: 387.34 (M+H)⁺.

Example D2: 6-(1H-indol-5-yl)-1-[4-(propan-2-yloxy)phenyl]-1H-indazole

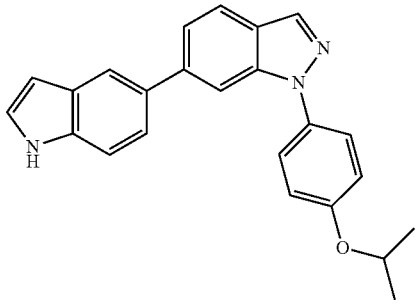

The title compound was prepared from 6-bromo-1-(4-isopropoxyphenyl)-1H-indazole and (1H-indol-5-yl)boronic acid in the same manner as described above for 1,6-bis[4-(propan-2-yloxy)phenyl]-1H-indazole. LC/MS m/z: 368.27 (M+H)$^+$.

Example D3: 1-(4-{1-[4-(propan-2-yloxy)phenyl]-1H-indazol-6-yl}phenyl)ethan-1-one

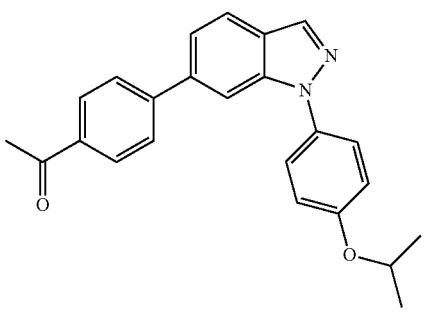 [SMILES: CC(=O)c1ccc(-c2ccc3cnn(-c4ccc(OC(C)C)cc4)c3c2)cc1]

The title compound was prepared from 6-bromo-1-(4-isopropoxyphenyl)-1H-indazole and (4-acetylphenyl)boronic acid in the same manner as described above for 1,6-bis[4-(propan-2-yloxy)phenyl]-1H-indazole. LC/MS m/z: 371.30 (M+H)$^+$, 413.24 (M+H+CH$_3$CN)$^+$.

Example D4: 1,6-bis[4-(propan-2-yloxy)phenyl]-1H-indole

Step 1: 6-bromo-1-(4-isopropoxyphenyl)-1H-indole

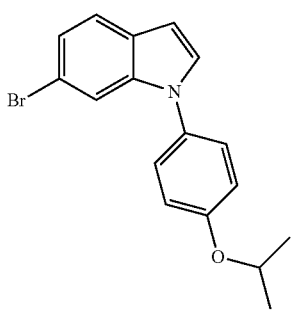

The title compound was prepared from 6-bromo-1H-indole and 1-iodo-4-isopropoxybenzene in the same manner as described above for 6-bromo-1-(4-isopropoxyphenyl)-1H-indazole (Example D1, Step 1). LC/MS m/z: 330.12 ($^{79}$Br, M+H)$^+$, 332.14 ($^{81}$Br, M+H)$^+$ Step 2: 1,6-bis[4-(propan-2-yloxy)phenyl]-1H-indole

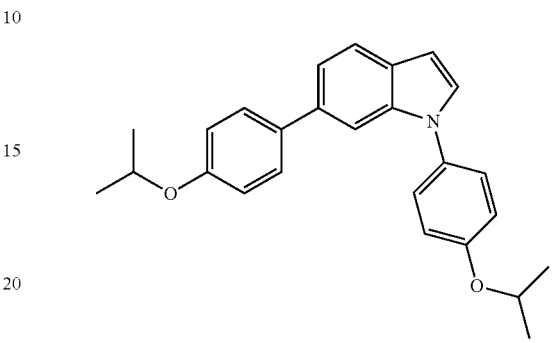

The title compound was prepared from 6-bromo-1-(4-isopropoxyphenyl)-1H-indole and (4-isopropoxyphenyl)boronic acid in the same manner as described above for 1,6-bis[4-(propan-2-yloxy)phenyl]-1H-indazole. LC/MS m/z: 386.33 (M+H)$^+$.

Example D5: 6-(1H-indol-5-yl)-1-[4-(propan-2-yloxy)phenyl]-1H-indole

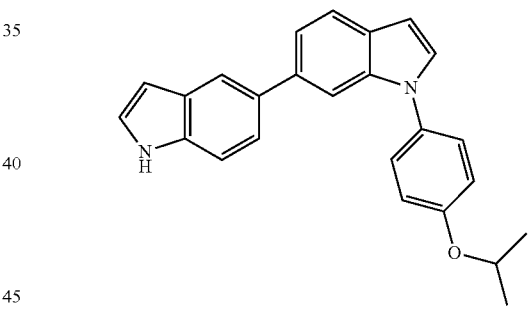

The title compound was prepared from 6-bromo-1-(4-isopropoxyphenyl)-1H-indole and (1H-indol-5-yl)boronic acid in the same manner as described above for 1,6-bis[4-(propan-2-yloxy)phenyl]-1H-indazole. LC/MS m/z: 386.33 (M+H)$^+$.

Example D6: 3,6-bis[4-(propan-2-yloxy)phenyl]-[1,2,4]triazolo[4,3-a]pyridine

Step 1: 3-bromo-6-(4-isopropoxyphenyl)-[1,2,4]triazolo[4,3-a]pyridine

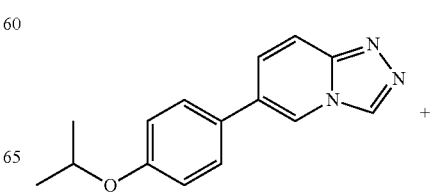

-continued

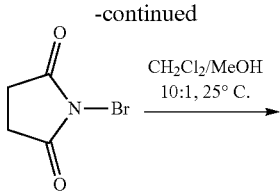

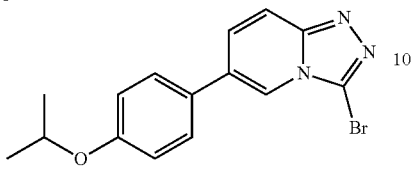

To a solution of 6-(4-isopropoxyphenyl)-[1,2,4]triazolo[4,3-a]pyridine (10 mg, 0.039 mmol) in $CH_2Cl_2$ (0.5 mL), was added 1-bromopyrrolidine-2,5-dione (14.1 mg, 0.80 mmol) and MeOH (0.05 mL). The resulting mixture was stirred at room temperature for 2 hr. The reaction was poured into water and extracted with ethyl acetate. The organic phase was dried over $Na_2SO_4$, filtered, and concentrated in vacuo. The residue was purified by $SiO_2$ column chromatography (EtOAc) to give 7.2 mg (56%) of the product as a white solid. LC/MS m/z: 342.08 ($^{79}Br$, M+H)$^+$, 344.14 ($^{81}Br$, M+H)$^+$, 373.13 ($^{79}Br$, M+H+$CH_3CN$)$^+$, 375.22 ($^{81}Br$, M+H+$CH_3CN$)$^+$.

Step 2: 3,6-bis[4-(propan-2-yloxy)phenyl]-[1,2,4]triazolo[4,3-a]pyridine

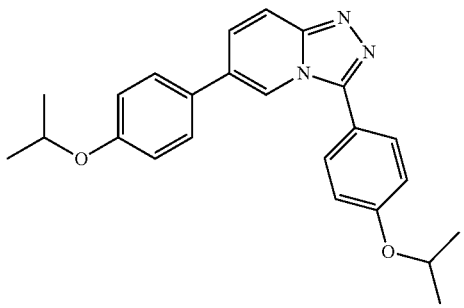

The title compound was prepared from 6-bromo-3-(4-isopropoxyphenyl)-[1,2,4]triazolo[4,3-a]pyridine and (4-isopropoxyphenyl)boronic acid in the same manner as described above for 1,6-bis[4-(propan-2-yloxy)phenyl]-1H-indazole. LC/MS m/z: 388.83 (M+H)$^+$.

Example D7: 5-{3-[4-(propan-2-yloxy)phenyl]-[1,2,4]triazolo[4,3-a]pyridin-6-yl}-1H-indole

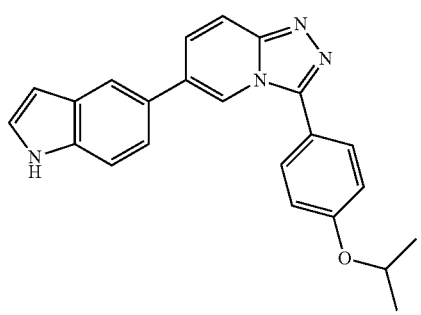 [SMILES: CC(C)Oc1ccc(-c2nnc3ccc(-c4ccc5[nH]ccc5c4)cn23)cc1]

The title compound was prepared from 3-bromo-6-(4-isopropoxyphenyl)-[1,2,4]triazolo[4,3-a]pyridine and (1H-indol-5-yl)boronic acid in the same manner as described above for 1,6-bis[4-(propan-2-yloxy)phenyl]-1H-indazole. LC/MS m/z: 369.27 (M+H)$^+$.

Example D8: 3,5-bis[4-(propan-2-yloxy)phenyl]-1-benzofuran

Step 1: 5-bromo-3-(4-isopropoxyphenyl)benzofuran

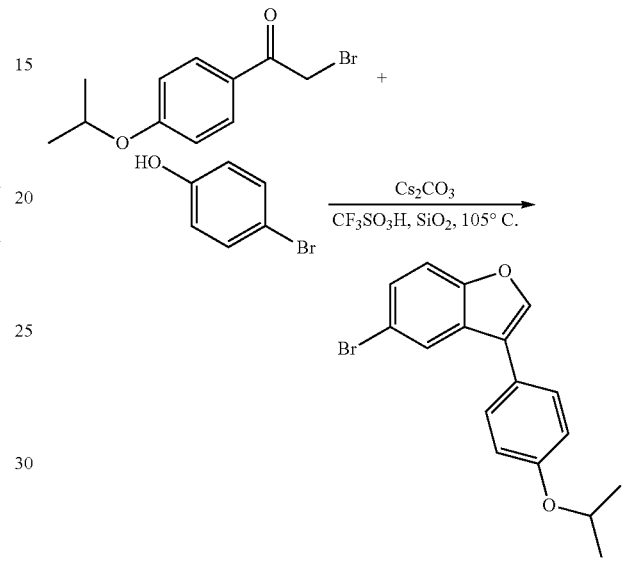

To a solution of 2-bromo-1-(4-isopropoxyphenyl)ethan-1-one (100 mg, 0.39 mmol) in DMF (5 mL), were added 4-bromophenol (67.2, 0.39 mmol) and $Cs_2CO_3$ (252 mg, 0.78 mmol) at room temperature. The resulting mixture was stirred at 40° C. for 1 hr. After cooling to room temperature, the reaction was filtered with a through pad. The filtrate was poured into water and extracted with ethyl acetate. The organic phase was dried over $Na_2SO_4$, filtered, and concentrated in vacuo. The residue was dissolved in toluene (5 mL) and then treated with trifluoromethylsulfonic acid (23.3 mg, 0.16 mmol) with 1 g of $SiO_2$. The resulting mixture was heated to 105° C. for 5 hr. After cooling, the reaction was filtered through a celite pad. The filtrate was washed with water and the organic phase was dried over $Na_2SO_4$, filtered, and concentrated in vacuo. The residue was purified by $SiO_2$ (hexane/EtOAc=5:1) to afford 102 mg of the title compound (82 mg, 63.4%) as a colorless oil.

Step 2: 3,5-bis[4-(propan-2-yloxy)phenyl]-1-benzofuran

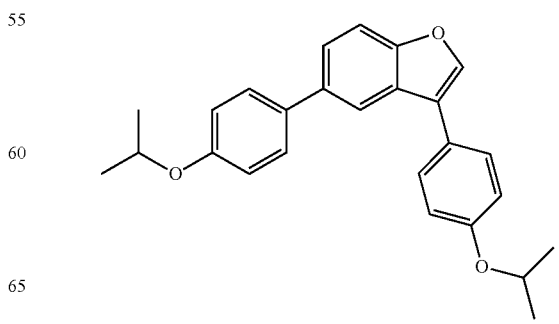

The title compound was prepared from 5-bromo-3-(4-isopropoxyphenyl)benzofuran and (4-isopropoxyphenyl)boronic acid in the same manner as described above for 1,6-bis[4-(propan-2-yloxy)phenyl]-1H-indazole.

Example D9: 5-{3-[4-(propan-2-yloxy)phenyl]-1-benzofuran-5-yl}-1H-indole

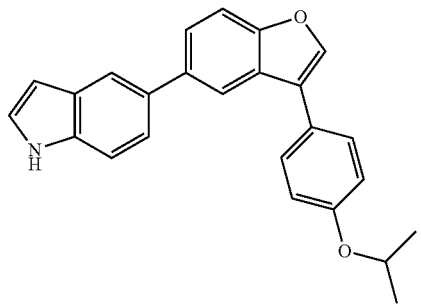 [SMILES: CC(C)Oc1ccc(-c2coc3ccc(-c4ccc5[nH]ccc5c4)cc23)cc1]

The title compound was prepared from 5-bromo-3-(4-isopropoxyphenyl)benzofuran and (1H-indol-5-yl)boronic acid in the same manner as described above for 1,6-bis[4-(propan-2-yloxy)phenyl]-1H-indazole.

Example D10: 3,6-bis[4-(propan-2-yloxy)phenyl]imidazo[1,2-b]pyridazine

Step 1: 6-chloro-3-[4-(propan-2-yloxy)phenyl]imidazo[1,2-b]pyridazine

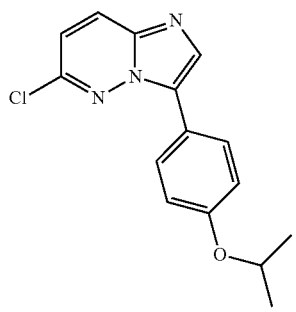 [SMILES: CC(C)Oc1ccc(-c2cnc3ccc(Cl)nn23)cc1]

The title compound was prepared from 6-chloro-3-iodo-imidazo[1,2-b]pyridazine and (4-isopropoxyphenyl)boronic acid in the same manner as described above for 6-bromo-3-[4-(propan-2-yloxy)phenyl]imidazo[1,2-a]pyridine. LC/MS m/z: 288.13 ($^{35}$Cl, M+H)$^+$, 290.15 ($^{37}$Cl, M+H)$^+$.

Step 2: 3,6-bis[4-(propan-2-yloxy)phenyl]imidazo[1,2-b]pyridazine

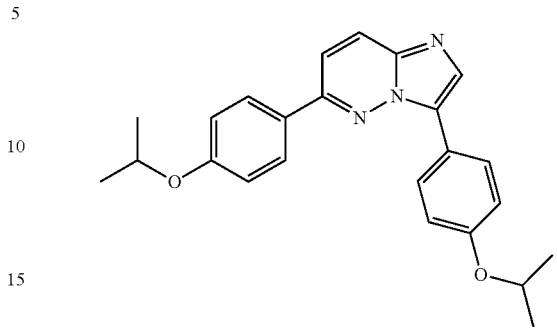

The title compound was prepared from 6-chloro-3-[4-(propan-2-yloxy)phenyl]imidazo[1,2-b]pyridazine and (4-isopropoxyphenyl)boronic acid in the same manner as described above for 1,6-bis[4-(propan-2-yloxy)phenyl]-1H-indazole. LC/MS m/z: 388.25 (M+H)$^+$.

Example D11: 3,5-bis[4-(propan-2-yloxy)phenyl]-1H-indazole

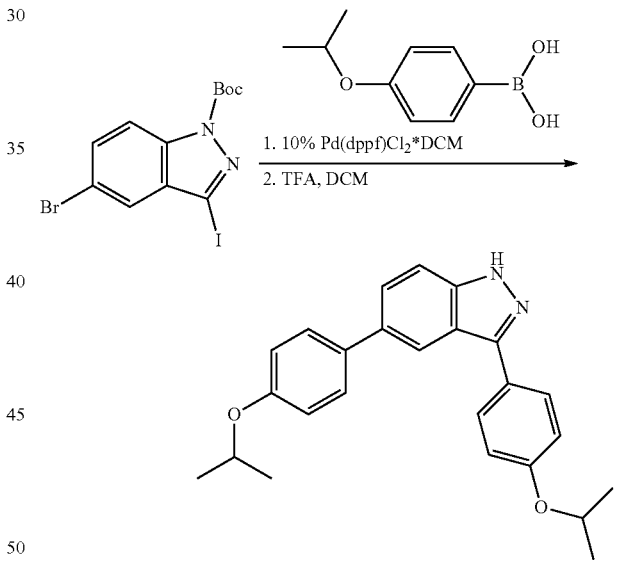

To a solution of tert-butyl 5-bromo-3-iodo-1H-indazole-1-carboxylate (30 mg, 0.071 mmol) in dioxane (0.5 mL) were added (4-isopropoxyphenyl)boronic acid (25 mg, 0.14 mmol), [1,1'-bis(diphenylphosphino) ferrocene]dichloropalladium(II) complex with dichloromethane (5.8 mg, 0.0071 mmol), potassium carbonate (30 mg, 0.22 mmol) and water (0.125 mL). The resulting reaction mixture was degassed with nitrogen for 10 min, heated to 100° C. for 10 min in a microwave reactor, then heated to 120° C. for additional 15 min. Then, the reaction mixture was diluted with ethyl acetate and washed with water. The organic phase was dried over Na$_2$SO$_4$, filtered, and concentrated in vacuo. The residue was dissolved in DCM (1 mL) and TFA (0.25 mL) was added dropwise. The reaction mixture was stirred at r.t. for 3 h, then concentrated in vacuo. The residue was purified by preparative HPLC to afford 7 mg (26%) of the product as a yellow solid. LC/MS m/z: 387.28 (M+H)⁺, 773.52 (2M+H)⁺.

Example D12: 3,6-bis[4-(propan-2-yloxy)phenyl] imidazo[1,2-a]pyrazine

Step 1: 6-(4-isopropoxyphenyl)imidazo[1,2-a]pyrimidine

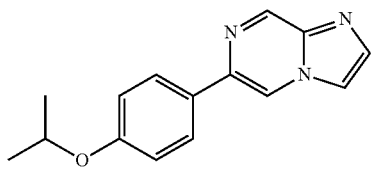 [SMILES: CC(C)Oc1ccc(-c2cn3ccnc3cn2)cc1]

The title compound was prepared from 6-bromoimidazo[1,2-a]pyrazine and (4-isopropoxyphenyl)boronic acid in the same manner as described above for 1,6-bis[4-(propan-2-yloxy)phenyl]-1H-indazole. LC/MS m/z: 254.54 (M+H)⁺.

Step 2: 3-bromo-6-(4-isopropoxyphenyl)imidazo[1,2-a]pyrazine

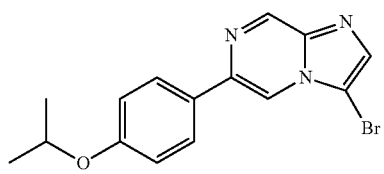 [SMILES: CC(C)Oc1ccc(-c2cn3c(Br)cnc3cn2)cc1]

The title compound was prepared from 6-(4-isopropoxyphenyl)imidazo[1,2-a]pyrazine in the same manner as described above for 3-bromo-6-(4-isopropoxyphenyl)-[1,2,4]triazolo[4,3-a]pyridine (Example D6, Step 1). LC/MS m/z: 342.19 (⁷⁹Br, M+H)⁺, 344.17 (⁸¹Br, M+H)⁺, 373.16 (⁷⁹Br, M+H+CH₃CN)⁺, 375.14 (⁸¹Br, M+H+CH₃CN)⁺.

Step 3: 3,6-bis[4-(propan-2-yloxy)phenyl]imidazo[1,2-a]pyrazine

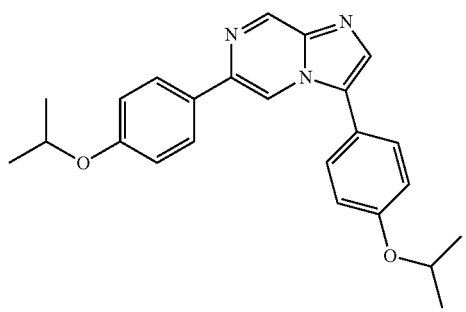 [SMILES: CC(C)Oc1ccc(-c2cn3c(-c4ccc(OC(C)C)cc4)cnc3cn2)cc1]

The title compound was prepared from 3-bromo-6-(4-isopropoxyphenyl)imidazo[1,2-a]pyrazine and (4-isopropoxyphenyl)boronic acid in the same manner as described above for 1,6-bis[4-(propan-2-yloxy)phenyl]-1H-indazole. LC/MS m/z: 388.26 (M+H)⁺, 429.31 (M+H+CH₃CN)⁺.

Example D13: 5-{6-[4-(propan-2-yloxy)phenyl] imidazo[1,2-a]pyrazin-3-yl}-1H-indole

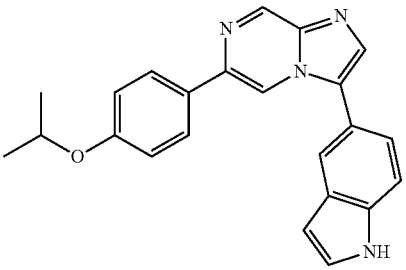 [SMILES: CC(C)Oc1ccc(-c2cn3c(-c4ccc5[nH]ccc5c4)cnc3cn2)cc1]

The title compound was prepared from 3-bromo-6-(4-isopropoxyphenyl)imidazo[1,2-a]pyrazine and (1H-indol-5-yl)boronic acid in the same manner as described above for 1,6-bis[4-(propan-2-yloxy)phenyl]-1H-indazole. LC/MS m/z: 369.27 (M+H)⁺.

Example D14: 1-(4-{6-[4-(propan-2-yloxy)phenyl] imidazo[1,2-a]pyrazin-3-yl}phenyl)ethan-1-one

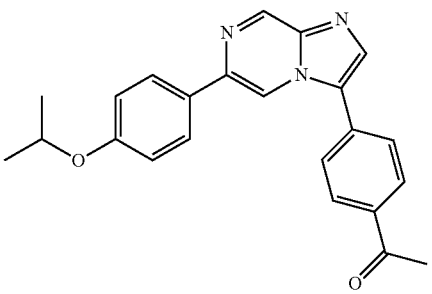 [SMILES: CC(=O)c1ccc(-c2cnc3cnc(-c4ccc(OC(C)C)cc4)cn23)cc1]

The title compound was prepared from 3-bromo-6-(4-isopropoxyphenyl)imidazo[1,2-a]pyrazine and (4-acetylphenyl)boronic acid in the same manner as described above for 1,6-bis[4-(propan-2-yloxy)phenyl]-1H-indazole. LC/MS m/z: 369.27 (M+H)⁺, 413.35 (M+H+CH₃CN)+.

Example D15: 3,6-bis[4-(propan-2-yloxy)phenyl] imidazo[1,2-a]pyrimidine

Step 1: 3-bromo-6-(4-isopropoxyphenyl)imidazo[1,2-a]pyrimidine

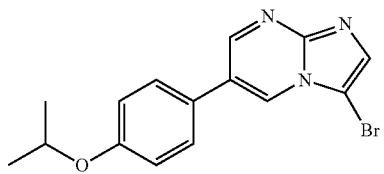 [SMILES: CC(C)Oc1ccc(-c2cnc3ncc(Br)n3c2)cc1]

The title compound was prepared from 6-(4-isopropoxyphenyl)imidazo[1,2-a]pyrimidine in the same manner as described above for 3-bromo-6-(4-isopropoxyphenyl)-[1,2,4]triazolo[4,3-a]pyridine (Example D6, Step 1). LC/MS m/z: 332.16 (⁷⁹Br, M+H)⁺, 334.15 (⁸¹Br, M+H)⁺.

Step 2: 3,6-bis[4-(propan-2-yloxy)phenyl]imidazo[1,2-a]pyrimidine

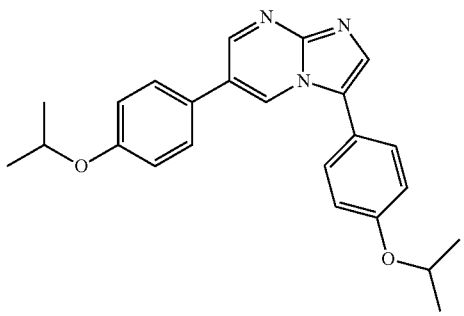 [SMILES: CC(C)Oc1ccc(-c2cnc3ncc(-c4ccc(OC(C)C)cc4)n3c2)cc1]

The title compound was prepared from 6-bromo-3-(4-isopropoxyphenyl)imidazo[1,2-a]pyrimidine and (4-isopropoxyphenyl)boronic acid in the same manner as described above for 1,6-bis[4-(propan-2-yloxy)phenyl]-1H-indazole. LC/MS m/z: 388.28 (M+H)⁺.

Example D16: 5-{6-[4-(propan-2-yloxy)phenyl]imidazo[1,2-a]pyrimidin-3-yl}-1H-indole

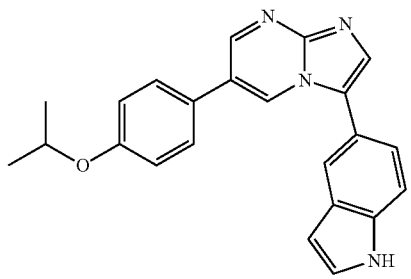 [SMILES: CC(C)Oc1ccc(-c2cnc3ncc(-c4ccc5[nH]ccc5c4)n3c2)cc1]

The title compound was prepared from 3-bromo-6-(4-isopropoxyphenyl)imidazo[1,2-a]pyrimidine and (1H-indol-5-yl)boronic acid in the same manner as described above for 1,6-bis[4-(propan-2-yloxy)phenyl]-1H-indazole as a colorless oil. LC/MS m/z: 369.31 (M+H)+.

Example D17: 3,6-bis[4-(propan-2-yloxy)phenyl]imidazo[1,5-a]pyridine

Step 1: 6-(4-isopropoxyphenyl)imidazo[1,5-a]pyridine

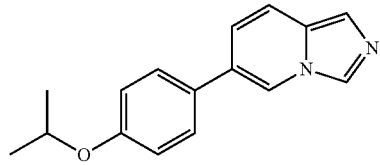 [SMILES: CC(C)Oc1ccc(-c2ccc3cncn3c2)cc1]

The title compound was prepared from 6-bromoimidazo[1,5-a]pyridine and (4-isopropoxyphenyl)boronic acid in the same manner as described above for 1,6-bis[4-(propan-2-yloxy)phenyl]-1H-indazole. LC/MS m/z: 253.22 (M+H)⁺.

Step 2: 3-iodo-6-(4-isopropoxyphenyl)imidazo[1,5-a]pyridine

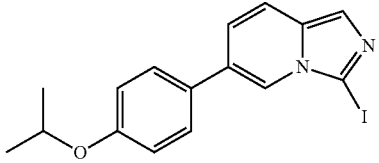 [SMILES: CC(C)Oc1ccc(-c2ccc3cnc(I)n3c2)cc1]

The title compound was prepared from 6-(4-isopropoxyphenyl)imidazo[1,5-a]pyridine in the same manner as described above for 6-bromo-3-iodo-7-methylimidazo[1,2-a]pyridine (Example C48, step 1). LC/MS m/z: 379.16 (M+H), 420.13 (M+H+CH₃CN)⁺.

Step 3: 3,6-bis[4-(propan-2-yloxy)phenyl]imidazo[1,5-a]pyridine

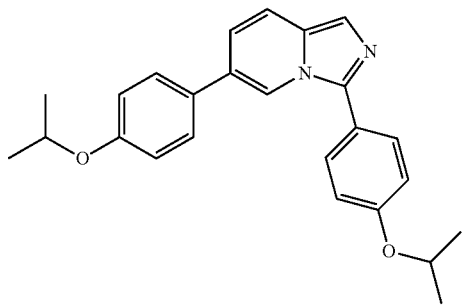 [SMILES: CC(C)Oc1ccc(-c2ccc3cnc(-c4ccc(OC(C)C)cc4)n3c2)cc1]

The title compound was prepared from 3-iodo-6-(4-isopropoxyphenyl)imidazo[1,5-a]pyridine and (4-isopropoxyphenyl)boronic acid in the same manner as described above for 1,6-bis[4-(propan-2-yloxy)phenyl]-1H-indazole as a colorless oil. LC/MS m/z: 387.39 (M+H)⁺.

Example D18: 3,5-bis[4-(propan-2-yloxy)phenyl]-2,1-benzoxazole

Step 1: 5-bromo-3-[4-(propan-2-yloxy)phenyl]-2,1-benzoxazole

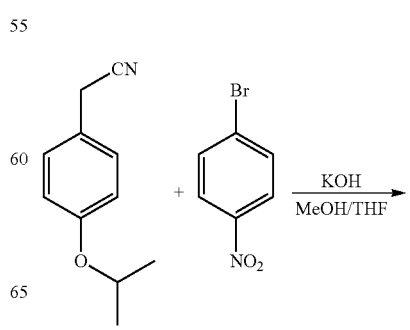

-continued

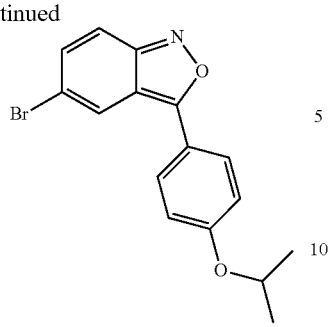

To a vigorously stirred solution of KOH (0.64 g, 11.4 mmol) in MeOH (1.3 mL) cooled to 0° C. was added 2-[4-(propan-2-yloxy)phenyl]acetonitrile (0.1 g, 0.57 mmol). After the solution was complete, a solution of 1-bromo-4-nitrobenzene (0.115 g, 0.57 mmol) in a mixture of THF (0.5 mL) and MeOH (1 mL) was added dropwise. The reaction mixture was brought to r.t. gradually and stirred overnight, then concentrated in vacuo. The residue was dissolved in EtOAc and washed with water. The organic layer was dried over $Na_2SO_4$, filtered, and concentrated in vacuo. The residue was purified by $SiO_2$ column chromatography (hexanes/EtOAc from 9:1 to 4:1) to give 36 mg (19%) of the product as yellow solid. LC/MS m/z: 331.92 ($^{79}Br$, M+H)$^+$, 333.97 ($^{81}Br$, M+H)+.

Step 2: 3,5-bis[4-(propan-2-yloxy)phenyl]-2,1-benzoxazole

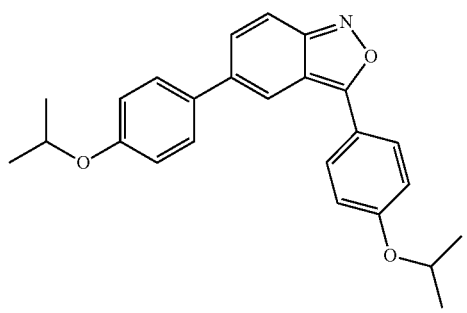 [SMILES: CC(C)Oc1ccc(-c2ccc3noc(-c4ccc(OC(C)C)cc4)c3c2)cc1]

The title compound was prepared from 5-bromo-3-[4-(propan-2-yloxy)phenyl]-2,1-benzoxazole and (4-isopropoxyphenyl)boronic acid in the same manner as described above for 1,6-bis[4-(propan-2-yloxy)phenyl]-1H-indazole. LC/MS m/z: 388.21 (M+H)$^+$, 775.52 (2M+H)+.

Example D19: 1,7-bis[4-(propan-2-yloxy)phenyl] imidazo[1,5-a]pyridine

Step 1: 7-bromo-1-iodoimidazo[1,5-a]pyridine

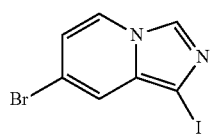 [SMILES: Brc1ccn2cnc(I)c2c1]

The title compound was prepared from 7-bromoimidazo[1,5-a]pyridine in the same manner as described above for 6-bromo-3-iodo-7-methylimidazo[1,2-a]pyridine (Example C48, step 1). LC/MS m/z: 322.56 ($^{79}Br$, M+H)$^+$, 324.93 ($^{81}Br$, M+H)$^+$, 364.01 ($^{79}Br$, M+H+$CH_3CN$)$^+$, 366.05 ($^{81}Br$, M+H+$CH_3CN$)$^+$.

Step 2: 1,7-bis[4-(propan-2-yloxy)phenyl]imidazo [1,5-a]pyridine

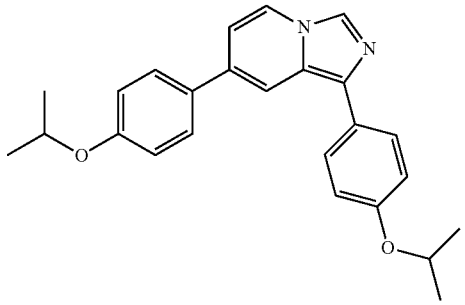 [SMILES: CC(C)Oc1ccc(-c2ccn3cnc(-c4ccc(OC(C)C)cc4)c3c2)cc1]

The title compound was prepared from 7-bromo-1-iodo-imidazo[1,5-a]pyridine and (4-isopropoxyphenyl)boronic acid in the same manner as described above for 3,6-bis[4-(propan-2-yloxy)phenyl]imidazo[1,2-a]pyridine (Example C2). LC/MS m/z: 387.30 (M+H)+.

Example D20: ethyl 3,6-bis[4-(propan-2-yloxy) phenyl]imidazo[1,2-a]pyridine-2-carboxylate Step 1: ethyl 3,6-dibromoimidazo[1,2-a]pyridine-2-carboxylate

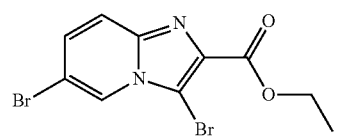 [SMILES: CCOC(=O)c1nc2ccc(Br)cn2c1Br]

The title compound was prepared from ethyl 6-bromo-imidazo[1,2-a]pyridine-2-carboxylate in the same manner as described above for 3-bromo-6-(4-isopropoxyphenyl)-[1,2,4]triazolo[4,3-a]pyridine (Example D6, Step 1). LC/MS m/z: 346.95 ($^{79}Br$, M+H)$^+$, 348.97 ($^{81}Br$, M+H)$^+$.

Step 2: ethyl 3,6-bis[4-(propan-2-yloxy)phenyl] imidazo[1,2-a]pyridine-2-carboxylate

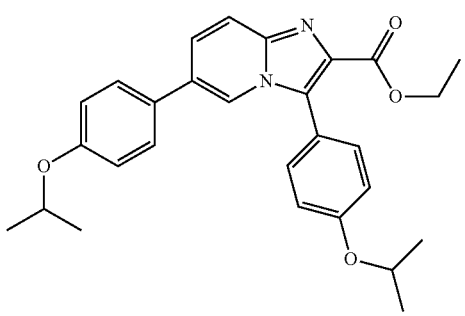 [SMILES: CCOC(=O)c1nc2ccc(-c3ccc(OC(C)C)cc3)cn2c1-c1ccc(OC(C)C)cc1]

The title compound was prepared from ethyl 3,6-dibromoimidazo[1,2-a]pyridine-2-carboxylate and (4-isopropoxyphenyl)boronic acid in the same manner as described above for 3,6-bis[4-(propan-2-yloxy)phenyl]imidazo[1,2-a]pyridine (Example C2). LC/MS m/z: 459.27 (M+H)⁺.

Example D21: 3,6-bis[4-(propan-2-yloxy)phenyl]imidazo[1,2-a]pyridine-2-carboxylic Acid

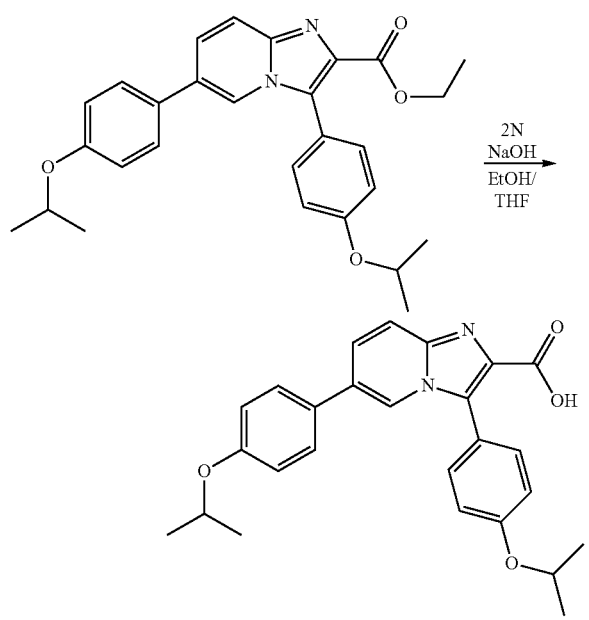

To a solution of ethyl 3,6-bis[4-(propan-2-yloxy)phenyl]imidazo[1,2-a]pyridine-2-carboxylate (30 mg, 0.065 mmol) in a mixture of EtOH/THF (1:1) (1 mL) was added 2N NaOH (0.5 mL). The reaction mixture was stirred at r.t. for 4 h, then concentrated in vacuo. The residue was acidified with 1N HCl, and then purified by preparative HPLC to afford 19.6 mg (70%) of the product as a white solid. LC/MS m/z: 431.25 (M+H)⁺.

Example D22: 3,6-bis[4-(propan-2-yloxy)phenyl]imidazo[1,2-a]pyridine-2-carboxamide

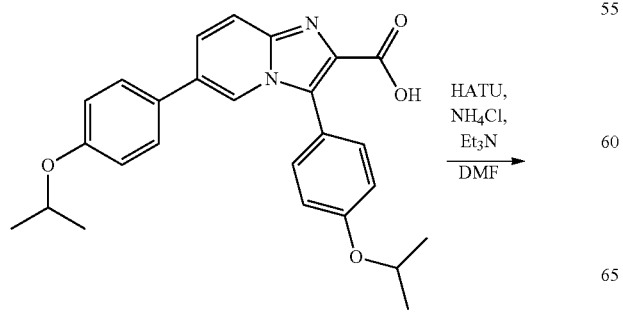

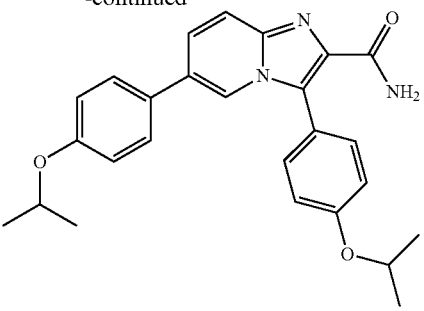

To a solution of 3,6-bis[4-(propan-2-yloxy)phenyl]imidazo[1,2-a]pyridine-2-carboxylic acid (16 mg, 0.037 mmol) in DMF (0.5 mL) cooled to 10° C. were added Et₃N (11 mg, 0.11 mmol) and HATU (21 mg, 0.055 mmol). The reaction mixture was stirred at r.t. for 0.5 h, and then NH₄Cl (8 mg, 0.15 mmol) was added. The reaction mixture was stirred at r.t. overnight, then diluted with DCM. The organic phase was washed with saturated NaHCO₃ solution and water. The organic layer was dried over Na₂SO₄, filtered, and concentrated in vacuo. The residue was purified by preparative HPLC to afford 6 mg (37%) of the product as a white solid. LC/MS m/z: 430.28 (M+H)⁺.

Example D23: 3,6-bis[4-(propan-2-yloxy)phenyl]imidazo[1,2-a]pyridine-2-carbonitrile Step 1: 6-bromoimidazo[1,2-a]pyridine-2-carbonitrile

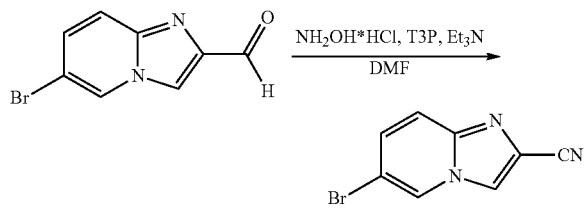

To a mixture of 6-bromoimidazo[1,2-a]pyridine-2-carbaldehyde (0.1 g, 0.44 mmol), hydroxylamine hydrochloride (34 mg, 0.49 mmol), and Et₃N (49 mg, 0.49 mmol) in DMF (0.5 mL) was added propylphosphonic anhydride solution in DMF (50 wt. %, 0.29 mL, 0.49 mmol). The reaction mixture was stirred at 100° C. for 3 h. Then, the reaction mixture was cooled to r.t., diluted with EtOAc and washed with saturated NaHCO₃ solution and water. The organic layer was dried over Na₂SO₄, filtered, and concentrated in vacuo. The residue was purified by SiO₂ column chromatography (hexanes/EtOAc from 7:3 to 1:1) to give 35 mg (35%) of the product as a white solid. LC/MS m/z: 222.08 (⁷⁹Br, M+H)⁺, 224.13 (⁸¹Br, M+H)⁺.

Step 2: 3,6-dibromoimidazo[1,2-a]pyridine-2-carbonitrile

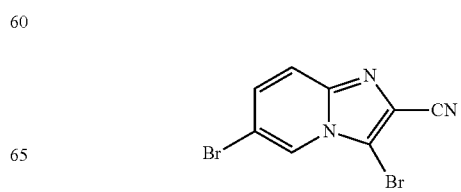

The title compound was prepared from 6-bromoimidazo[1,2-a]pyridine-2-carbonitrile in the same manner as described above for 3-bromo-6-(4-isopropoxyphenyl)-[1,2,4]triazolo[4,3-a]pyridine (Example D6, Step 1). LC/MS m/z: 340.92 ($^{79}$Br, M+CH$_3$CN+H)$^+$, 342.97 ($^{81}$Br, M+CH$_3$CN+H)$^+$.

Step 3: 3,6-bis[4-(propan-2-yloxy)phenyl]imidazo[1,2-a]pyridine-2-carbonitrile

The title compound was prepared from 3,6-dibromoimidazo[1,2-a]pyridine-2-carbonitrile and (4-isopropoxyphenyl)boronic acid in the same manner as described above for 3,6-bis[4-(propan-2-yloxy)phenyl]imidazo[1,2-a]pyridine (Example C2). LC/MS m/z: 412.21 (M+H)$^+$.

Arenavirus GP Pseudotype Assay.

Utilizing a VSV pseudotype system expressing arenavirus glycoproteins (pseudotyped viruses here to referred to as LASV-p, MACV-p, JUNV-p, GTOV-p and TCRV-p) and the *Renilla* luciferase reporter gene heterocyclic compounds were screened to identify individual compounds that inhibit infectivity of the pseudotyped viruses but not the native VSV virus expressing the VSV glycoprotein. VSV viruses expressing the VSV glycoprotein or pseudotyped with LASV, MACV, JUNV, GTOV and TCRV glycoproteins (LASV-p, MACV-p, JUNV-p, GTOV-p and TCRV-p) were generated in cultured HEK-293T cells (ATCC CRL-3216), which were grown in 10 cm dishes in DMEM supplemented with 10% FBS, 1× Pen-Strep, non-essential amino acids and L-glutamine. When cells reached approximately 80% confluency, they were transfected with a mixture of 15 pg of the pCAGGS plasmid encoding the desired glycoprotein and 45 μl of PEI (polyethylenimine) transfection reagent (PEI MAX, Polysciences Inc., #24765). The cells were incubated with the solution for 5 hours at 37° C. at 5% CO$_2$ then washed and the mixture replaced with supplemented DMEM and incubated at 37° C. at 5% CO$_2$ for approximately 16-18 hours. Subsequently cells were infected with approximately 50 μl of VSV reporter virus whereby the VSV glycoprotein was replaced with a luciferase reporter gene. The cells were infected for 1 hour, then washed 1× with PBS and incubated in supplemented media. 24 hours post-infection, supernatant was collected, clarified by centrifugation and filtration through a 0.45 um filter, aliquoted and stored at −80° C. Both VSV-Luciferase and arenavirus glycoprotein pseudotypes were titrated for luminescence activity in Vero cells as described in the Luciferase assay protocol (below). Vero cells (ATCC: CCL-81) were grown in clear 384 well plates (3000 cells/well) in supplemented DMEM media. After incubating overnight at 37° C. and 5% CO$_2$, cells were treated with compounds at desired concentrations and pseudotyped virus in assay media. Assay media consisted of 50% Opti-MEM, 50% DMEM, with 1% FBS, Pen-Strep, non-essential amino acids and L-glutamine. Each of the viral supernatants generated was diluted (from 1:100 to 1:2000) to give similar luminescence signal/background values of ≥200. Final DMSO concentration in the compound testing wells was kept ≤1% and control wells were treated with assay media and 1% DMSO. Cells were incubated for 24 hours at 37° C. and 5% CO$_2$. The compound-virus mixture was aspirated off the cells 24 hours post-infection and washed 1× with PBS. Cells were then lysed using 20 μl of lysis buffer from a Luciferase kit diluted according to manufacturer's instructions. After incubating for approximately 20 minutes, 5 μl of cell lysate was transferred to an opaque white plate, and mixed with 12.5 μl of Coelenterazine diluted in buffer. This mixture was incubated at room temperature for 10 minutes on a plate shaker and then the luminescence was read using a plate reader (Beckman Coulter DTX 880 multimode detector with an emission of 535 nm). Luminescence signals were obtained for compound containing and control wells to determine % activity (inhibition of luciferase signal) for each compound.

Surprisingly, it was found that certain R$^2$ groups such as $R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, and acetyl, can provide broad spectrum activity across multiple arenavirus strains.

Replicative Tacaribe Virus Testing

Selected compounds were tested against native replicating Tacaribe (TCRV) virus (TRVL-11573, BEI Resources) using an ELISA-based assay. Vero cells (ATCC: CCL-81) were grown in a 96-well format (5000 cells/well) in supplemented DMEM media. After overnight incubation, cells were treated with TCRV and compounds at desired concentrations, in MEM media with 1% FBS and supplements. Final DMSO concentration in the compound testing wells was kept ≤1% and control wells were treated with TCRV or media and 1% DMSO. After 5 days of incubation at 37° C. in 5% CO$_2$, cells were fixed with 2% paraformaldehyde for 45 minutes and then washed with PBS. Subsequently the cells were permeabilized with 0.25% triton-X, then TCRV was detected using ELISA with the following protocol. Monoclonal Anti-Junin Virus antibody (BEI #NR 41860), which cross reacts with TCRV nucleoprotein, was used to stain cells. After washing, cells were treated with biotin conjugated secondary antibody and subsequently, streptavidin conjugated horseradish peroxidase. TMB substrate was added to the wells, and the reaction was stopped using 2M sulfuric acid. The absorbance was read using a plate reader (Beckman Coulter DTX 880 multimode detector with an emission of 450 nm). OD readings were obtained for compound containing and control wells to determine % activity for each compound.

Cytotoxicity Screening

Active compounds in the pseudotype assays were also evaluated for cytotoxicity over a period of 3 days. Compounds were serially diluted and added to Vero cells (4000 cells/well) with final DMSO concentration maintained at 1% in growth media consisting of minimal essential media (MEM) with 1% FBS. The plates were incubated at 37° C. for 3 days, and then dead cells were removed by washing with Phosphate buffered saline (PBS). CPE was assessed by staining cells with neutral red dye for 1 hour and then de-staining with a solution of 50% ethanol/1% acetic acid solution. Absorbances were read at 540 nm and 690 nm on a Spectramax Plus 384 spectrophotometer. Data were analyzed as (540 nm-690 nm) and then compared to untreated controls to obtain % cell survival.

Replicative LASV and JUNV Inhibitory Activity Plaque Assays

Confluent or near-confluent cell culture monolayers in 12-well disposable cell culture plates were prepared. Cells were maintained in MEM or DMEM supplemented with 10% FBS. For antiviral assays the same medium was used but with FBS reduced to 2% or less and supplemented with 1% penicillin/streptomycin. The test compounds were prepared at seven half log 10 final concentrations, (01-10 μM) in 2×MEM or 2×DMEM. Test compounds and positive control compounds (favipiravir or ribavirin) were run in parallel in biological triplicates. The assay was initiated by first removing growth media from the 12-well plates of cells, which was challenged with compound at a given concentration and 0.01 MOI of virus or about 50 to 100 plaque forming units (pfu). Cells were incubated for 60 min: 100 μL inoculum/well, at 37° C., 5% $CO_2$ with constant gentle rocking. Virus inoculum was removed, cells washed and overlaid with either 1% agarose or 1% methylcellulose diluted 1:1 with 2×MEM and supplemented with 2% FBS and 1% penicillin/streptomycin and along with the corresponding drug concentration. Cells were incubated at 37° C. with 5% $CO_2$ for 5 days. The overlay was then removed and plates stained with 0.05% crystal violet in 10% buffered formalin for approximately twenty minutes at room temperature. The plates were washed, dried and the number of plaques counted. The number of plaques in each set of compound dilution was converted to a percentage relative to the untreated virus control. The 50% effective ($EC_{50}$, virus-inhibitory) concentrations were then calculated by linear regression analysis. The quotient of CCso divided by $EC_{50}$ gives the selectivity index (SI) value. Compounds showing SI values ≥10 were considered active.

LCMV CPE inhibitory assay

Confluent or near-confluent cell culture monolayers in 96-well disposable microplates were prepared and maintained in MEM or DMEM supplemented with FBS, which was reduced to 2% or less for antiviral testing supplemented with 50 pg/ml gentamicin. The test compound was prepared at four log 10 final concentrations. Four compounds were tested per microplate with five microwells per dilution: three for infected cultures and two for uninfected toxicity cultures. Controls for the experiment consist of six microwells that were infected (virus controls) and six that were untreated (cell controls). The virus control and cell control wells were on every microplate. In parallel, a known active drug ribavirin was tested as a positive control using the same method as applied for test compounds. The assay was initiated by first removing growth media from the 96-well plates of cells and the test compound was applied in 0.1 ml volume to wells at 2× concentration. Virus, normally at ≤100 50% cell culture infectious doses ($CCID_{50}$) in 0.1 ml volume, were placed in those wells designated for virus infection. Medium devoid of virus was placed in toxicity control wells and cell control wells. Virus control wells were treated similarly with virus. Plates were incubated at 37° C. with 5% $CO_2$ until maximum CPE (cytopathic effect or cell death) was observed in virus control wells. The plates were then stained with 0.011% neutral red for approximately two hours at 37° C. in a 5% $CO_2$ incubator. The neutral red medium was removed by complete aspiration, and the cells rinsed 1× with phosphate buffered solution (PBS) to remove residual dye. The PBS was removed and the incorporated neutral red was eluted with 50% Sorensen's citrate buffer/50% ethanol for 30 minutes. Neutral red dye penetrates into living cells, thus, the more intense the red color, the larger the number of viable cells present in the wells. The dye content in each well was quantified using a 96-well spectrophotometer at 540 nm wavelength. The dye content in each set of wells was converted to a percentage of dye present in untreated control wells using a Microsoft Excel computer-based spreadsheet. The 90% effective ($EC_{90}$, virus-inhibitory) concentrations and 50% cytotoxic ($CC_{50}$, cell-inhibitory) concentrations were calculated by linear regression analysis. The quotient of $CC_{50}$ divided by $EC_{90}$ gives the selectivity index ($SI_{90}$) value. Compounds showing SI values ≥10 were considered active.

Microsomal Assays

In addition to the ability of compounds to demonstrate broad inhibitory activity against arenaviruses in vitro, compounds must also have certain drug-like properties for them to be used to inhibit arenaviruses and provide methods of treatment for arenavirus infection in mammals in vivo. Such compounds may exhibit drug-like properties including but not limited to chemical stability against metabolic degradation by liver microsomal CYP p450 enzymes, cell permeability and oral bioavailability (if the drug is to delivered orally) and lack of inhibition of the hERG ion channel, which is associated with cardiac safety [Kerns, E. H. Li, D. *Drug-like Properties: Concepts, Structure Design and Methods from ADME to Toxicity Optimization*, (2008) Academic Press, Burlington Mass.]. To characterize drug-like properties of the chemical series example compounds were evaluated for metabolic stability in human, mouse, guinea pig, monkey, rat, mouse, and dog liver microsome assays (Table 3), and for inhibition of the hERG ion channel (Table 4). Compounds exhibiting >60% remaining of parent indicate attractive chemical stability. The demonstration of good microsomal stability in human and nonhuman species facilitates the ability to test and optimize compounds in preclinical animal studies.

A reaction premixture was set up, containing 1 uM compound of interest, 1 mg/mL liver microsomes of desired species, 2.1 mM $MgCl_2$ and 0.1 M sodium phosphate buffer, pH 7.4. This premixture was incubated at 37° C. for 30 minutes with gentle agitation to allow the compound to be completely dissolved in the mixture. Then freshly made NADPH solution in 0.1M sodium phosphate buffer was added at a concentration of 2 mM to start the reaction. A 'Time 0' sample (30 uL) was taken out immediately after addition of NADPH and added to 140 uL cold acetonitrile containing luM of pre-decided internal standard. The rest of the reaction mixture was incubated at 37° C. for the remaining time period. Test compounds were left in the reaction mixture for 60 minutes before 'Time 60' sample was added to acetonitrile with internal standard. The control compound (Verapamil for human, monkey and dog LM, Lidocaine for Guinea pig LM, and diphenhydramine for rat and mouse LM) was incubated in reaction mixture for 15 minutes before 'Time 15' samples were collected and added to cold acetonitrile with internal standard. The samples were then spun in a centrifuge for 10 minutes at 4000 rpm, supernatant was collected and mixed with equal parts distilled water. These were then analyzed on a Varian 500-MS. Surprisingly, when $R^{4b}$ was isopropoxy, better microsomal stability was observed across multiple species tested.

hERG Channel Assay

Drugs belonging to different classes have been shown to be associated with QT prolongation and in some cases serious ventricular arrhythmias. The most common mechanism for these adverse events is the inhibition of one or more cardiac potassium channels, in particular hERG. This channel is important for cardiac myocyte repolarization and is a common target for drugs that prolong the QT interval. Test articles in this study were therefore, characterized to determine their ability to inhibit the hERG channel. Ion channel activity was measured using a stably transfected Chinese Hamster Ovary (CHO) cell line expressing the hERG mRNA. The pharmacology of this cloned channel expressed in the CHO cell line is very similar to that observed in native tissue. Cells were cultured in DMEM/F12 containing 10% FBS, 1% penicillin/streptomycin and 500 pg/ml G418. Before testing, cells were harvested using Accumax (Innovative Cell Technologies). For electrophysiological recordings, the following solutions were used: External solution: 2 mM $CaCl_2$; 2 mM $MgCl_2$; 4 mM KCl; 150 mM NaCl; 10 mM Glucose; 10 mM HEPES; 305-315 mOsm; pH 7.4 (adjusted with 5M NaOH); Internal solution: 140 mM KCl; 10 mM MgCl2; 6 mM EGTA; 5 mM HEPES-Na; 5 mM ATP-Mg; 295-305 mOsm; pH 7.25 (adjusted with 1M KOH). Whole cell recordings were performed using PX 7000A (Axon Instruments) with AVIVA's SealChip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally, a step back to −50 mV for 5 s removed activation and the deactivating tail current was recorded. External solution containing 0.1% DMSO (vehicle) was applied to the cells to establish a baseline. After allowing the current to stabilize for 3 to 10 min, test articles were applied. Test article solutions were added to cells in 4 separate additions. Cells were kept in test solution until effect of the test article reached steady state, to a maximum of 12 min. Next, 1 µM cisapride (positive control) was added. Finally, washout with External Solution was performed until the recovery current reached steady state. Data analysis was performed using DataXpress (Axon Instruments), Clampfit (Axon Instruments) and Origin (OriginLab Corporation) software.

TABLE 1

Examples. Example compounds and their observed inhibitory activities against the indicated pseudotyped viruses (LASV-p, MACV-p, JUNV-p, TCRV-p, GTOV-p, VSV-p) or in cellular cytotoxicity assays; shown are $EC_{50}$ for LASV-p, MACV-p, JUNV-p, TCRV-p, and GTOV-p, and VSV-p $CC_{50}$ for cytotoxicity;

| Ex. | LASV-p $EC_{50}$ (nM) | MACV-p $EC_{50}$ (nM) | JUNV-p $EC_{50}$ (nM) | TCRV-p $EC_{50}$ (nM) | GTOV-p $EC_{50}$ (nM) | VSV-p $EC_{50}$ (nM) | $CC_{50}$ (nM) |
|---|---|---|---|---|---|---|---|
| A1 | 31.7 | >100 | >100 | >100 | nd | nd | 12,890 |
| A2 | 6.6 | >100 | >100 | >100 | nd | nd | 25,580 |
| A3 | 7.6 | >25 | >25 | >25 | nd | nd | <300 |
| A4 | >25 | >25 | >25 | >25 | nd | nd | <300 |
| A5 | >25 | >25 | >25 | >25 | nd | nd | <300 |
| A6 | >25 | >25 | >25 | >25 | nd | nd | 9,720 |
| A7 | 8.9 | 17.0 | 1.8 | >25 | nd | 980 | 3,960 |
| A8 | 6.4 | 22.3 | 3.98 | 21.7 | nd | >1,000 | 9,540 |
| A9 | >100 | nd | nd | nd | nd | nd | nd |
| A10 | 21.8 | >25 | >25 | >25 | nd | nd | 4,560 |
| A11 | >25 | >25 | >25 | >25 | nd | nd | nd |
| A12 | 0.81 | >25 | 19.3 | 21.4 | nd | 800 | 200 |
| A13 | 5.0 | >25 | >25 | >25 | nd | nd | 1,270 |
| A14 | 7.4 | >25 | >25 | >25 | nd | nd | 1,950 |
| A15 | 14.7 | 24.95 | 2.23 | 29.6 | nd | nd | 12,940 |
| A16 | 17.2 | >25 | 15.29 | >25 | nd | >1,000 | >100,000 |
| A17 | 1.1 | 0.2 | 0.2 | 0.6 | 0.52 | >1,000 | 5,810 |
| A18 | 1.08 | 2.27 | 1.55 | 12.50 | 0.07 | >1,000 | 14,000 |
| A19 | >100 | nd | nd | nd | nd | nd | nd |
| A20 | >100 | nd | nd | nd | nd | nd | nd |
| A21 | 3.07 | 14.4 | 3.5 | >25 | nd | nd | 5,220 |
| A22 | >25 | >25 | >25 | >25 | nd | nd | nd |
| A23 | >25 | >25 | >25 | >25 | nd | nd | nd |
| A24 | 0.91 | 3.7 | 1.7 | 15.9 | 0.3 | nd | 71,320 |
| A25 | 1.61 | 7.1 | 4.9 | 28.0 | 0.2 | nd | 12,190 |
| A26 | 0.59 | 0.70 | 0.81 | 1.45 | 0.73 | nd | 7,520 |
| A27 | 0.60 | 0.38 | 0.39 | 2.57 | nd | nd | 3,860 |
| A28 | 11.0 | >25 | 7.29 | >25 | nd | nd | nd |
| A29 | 0.53 | 11.07 | 6.96 | 15.23 | nd | nd | nd |
| A30 | 0.53 | 0.21 | 0.03 | 0.07 | 0.21 | 5.31 | 3,670 |
| A31 | 2.6 | 0.9 | 0.18 | 0.7 | nd | nd | 3,790 |
| B1 | 1.61 | 7.09 | 4.95 | 27.99 | 0.88 | >1,000 | 12,190 |
| B2 | 0.41 | 0.935 | 0.21 | 5.53 | 0.07 | >10,000 | 4,140 |
| B3 | 1.01 | 10.27 | 1.79 | 27.73 | nd | nd | >100,000 |
| B4 | 0.956 | 18.63 | 4.31 | 14.95 | nd | nd | 19,740 |
| B5 | >25 | >25 | 13.38 | >25 | nd | nd | nd |
| B6 | 17.76 | 14.28 | 3.35 | 18.83 | nd | nd | nd |
| B7 | 8.18 | 24.08 | 16.19 | >25 | nd | nd | 13,900 |
| B8 | >25 | >25 | >25 | >25 | nd | nd | nd |

TABLE 1-continued Examples. Example compounds and their observed inhibitory activities against the indicated pseudotyped viruses (LASV-p, MACV-p, JUNV-p, TCRV-p, GTOV-p, VSV-p) or in cellular cytotoxicity assays; shown are EC$_{50}$ for LASV-p, MACV-p, JUNV-p, TCRV-p, and GTOV-p, and VSV-p CC$_{50}$ for cytotoxicity;

| Ex. | LASV-p EC$_{50}$ (nM) | MACV-p EC$_{50}$ (nM) | JUNV-p EC$_{50}$ (nM) | TCRV-p EC$_{50}$ (nM) | GTOV-p EC$_{50}$ (nM) | VSV-p EC$_{50}$ (nM) | CC$_{50}$ (nM) |
|---|---|---|---|---|---|---|---|
| B9 | 19.72 | 29.7 | 11.88 | >25 | nd | nd | 27,700 |
| B10 | 11.0 | 19.6 | 3.1 | >25 | nd | nd | 4,680 |
| B11 | 6.4 | 25.0 | 25.0 | >25 | nd | nd | 24,200 |
| B12 | 0.88 | 1.04 | 0.26 | 5.21 | 0.04 | 5,490 | >100,000 |
| B13 | 1.53 | 5.58 | 1.805 | 20.38 | 1.24 | 5,360 | 6,620 |
| B14 | 1.055 | 15.43 | 1.36 | >25 | nd | nd | 7,390 |
| B15 | 0.95 | 0.25 | 0.02 | 0.37 | 0.18 | >10,000 | >100,000 |
| C1 | 0.59 | 0.7 | 0.82 | 1.45 | 0.08 | >1,000 | 7,520 |
| C2 | 0.6 | 0.38 | 0.4 | 2.57 | 0.14 | >1,000 | 3,860 |
| C3 | 7.25 | 2.7 | 1.17 | 10.57 | 0.31 | >10,000 | 6,160 |
| C4 | 4.35 | 23.94 | 4.62 | 29.88 | nd | nd | 4,560 |
| C5 | 4.1 | 31.4 | 9.09 | >25 | nd | nd | 4,690 |
| C6 | 2.7 | 18.59 | 7.02 | >25 | nd | nd | 10,510 |
| C7 | >25 | >25 | >25 | >25 | nd | nd | 4,810 |
| C8 | 2.03 | 1.7 | 1.08 | 9.44 | 0.21 | 8,120 | 31,130 |
| C9 | 1.15 | 0.71 | 0.45 | 1.7 | 0.27 | 5,810 | 3,970 |
| C10 | 4.61 | 28.93 | 19.04 | >25 | nd | nd | >100 |
| C11 | 2.83 | 10.04 | 3.21 | 18.44 | 0.86 | 3,090 | 25,240 |
| C12 | 6.07 | 3.12 | 1.32 | 7.76 | 0.44 | 5,060 | 4,020 |
| C13 | 0.3 | 1.22 | 0.62 | 2.95 | 0.29 | 1,880 | 5,090 |
| C14 | >25 | >25 | >25 | >25 | nd | nd | nd |
| C15 | 7.97 | 13.46 | 2.85 | 7.6 | 0.58 | 5,060 | nd |
| C16 | >25 | >25 | >25 | >25 | nd | nd | nd |
| C17 | 13.37 | 28.8 | 6.38 | >25 | nd | nd | 23,880 |
| C18 | 18.13 | 0.59 | 0.305 | 2.68 | nd | nd | 3,980 |
| C19 | 2.9 | 0.23 | 0.195 | 1.83 | 0.2 | 9.86 | 8,200 |
| C20 | 4.98 | 6.82 | 1.43 | 5.12 | 0.15 | >10,000 | 3,750 |
| C21 | 0.51 | 0.16 | 0.115 | >25 | 0.2 | >10,000 | 3,980 |
| C22 | 2.33 | 0.335 | 0.415 | 4.94 | 0.45 | nd | 24,390 |
| C23 | >25 | >25 | >25 | >25 | nd | nd | nd |
| C24 | 4.58 | 0.875 | 0.416 | 3.91 | 0.15 | 9,810 | 4,180 |
| C25 | >25 | >25 | 25 | >25 | nd | nd | nd |
| C26 | 0.56 | 0.2 | 0.1 | 0.2 | 0.27 | 4,530 | 3,540 |
| C27 | 0.66 | 0.68 | 0.51 | 0.58 | 0.24 | >10,000 | 5,280 |
| C28 | 17.27 | >25 | 14.86 | >25 | nd | nd | >100,000 |
| C29 | >25.0 | >25 | >25 | >25 | nd | nd | nd |
| C30 | 1.02 | 1.08 | 0.82 | 3.83 | 0.05 | 6,960 | 3,980 |
| C31 | 1.35 | 2.09 | 0.65 | 2.65 | 0.76 | >10,000 | >10,000 |
| C32 | 0.4 | 0.11 | 0.06 | 0.06 | 0.2 | 4,840 | 4,840 |
| C33 | 1.3 | 5.31 | 2.3 | 6.57 | 0.91 | 4,770 | 4,770 |
| C34 | 4.73 | 25.14 | 3.68 | 16.52 | nd | nd | nd |
| C35 | 14.46 | 28.2 | 13.05 | >25 | nd | nd | nd |
| C36 | 8.18 | >25 | 23.19 | >25 | nd | nd | nd |
| C37 | 3.34 | 2.36 | 0.38 | >25 | 0.25 | 9,950 | nd |
| C38 | 0.84 | 0.34 | 0.2 | 1.77 | 0.2 | 7,390 | 95,870 |
| C39 | 8.41 | 2.67 | 0.73 | 9.86 | nd | nd | >100,000 |
| C40 | 3.83 | 5.85 | 0.97 | 22.64 | 1.35 | 6,170 | 4,110 |
| C41 | 0.67 | 13.96 | 1.6 | >25 | nd | nd | 8,650 |
| C42 | 3.08 | 23.08 | 2.6 | 11.67 | nd | nd | 5,360 |
| C43 | >25 | >25 | >25 | >25 | nd | nd | nd |
| C44 | 0.23 | 0.32 | 0.07 | 0.135 | nd | nd | >100 |
| C45 | >25 | >25 | >25 | >25 | nd | nd | nd |
| C46 | 7.23 | 8.47 | 4.42 | 22.52 | 1.26 | 4,550 | 4,610 |
| C47 | 1.8 | 0.5 | 0.55 | 1.17 | 0.44 | 4,340 | 7,860 |
| C48 | 0.38 | 0.41 | 0.165 | 0.2 | nd | nd | 4,710 |
| C49 | 8.02 | 0.86 | 0.16 | 1.1 | nd | nd | 5,270 |
| C50 | 15.48 | 6.56 | 4.65 | >25 | nd | nd | 3,810 |
| C51 | 0.31 | 0.13 | 0.15 | 0.37 | 0.21 | nd | 4,190 |
| D1 | >25 | >25 | 13.98 | >25 | nd | nd | nd |
| D2 | 7.99 | 22.46 | 17.78 | >25 | nd | nd | 4,340 |
| D3 | 7.04 | 15.5 | 20.25 | >25 | nd | nd | 15,900 |
| D4 | >25 | 16.94 | 8.1 | >25 | nd | nd | nd |
| D5 | 12.47 | >25 | 27.81 | >25 | nd | nd | 5.870 |
| D6 | 9.6 | 2.56 | 1.005 | 15.45 | 0.53 | 6,420 | 4,410 |
| D7 | 4.1 | >25 | 18.04 | 26.33 | nd | nd | 1,870 |
| D8 | >25 | >25 | >25 | >25 | nd | nd | nd |
| D9 | >25 | >25 | >25 | >25 | nd | nd | nd |
| D10 | 1.5 | 14.755 | 0.95 | >25 | nd | 9,360 | 7,720 |
| D11 | 10.5 | >25 | 3.22 | >25 | nd | nd | 5,210 |
| D12 | 2.95 | 16.37 | 2.605 | 20.68 | 0.93 | 6,980 | 8,510 |
| D13 | 12.34 | 12.0 | 3.2911 | 10.35 | nd | nd | >100,000 |
| D14 | 6.77 | 25.0 | 13.53 | 20.25 | nd | nd | 13,030 |

TABLE 1-continued

Examples. Example compounds and their observed inhibitory activities against the indicated pseudotyped viruses (LASV-p, MACV-p, JUNV-p, TCRV-p, GTOV-p, VSV-p) or in cellular cytotoxicity assays; shown are $EC_{50}$ for LASV-p, MACV-p, JUNV-p, TCRV-p, and GTOV-p, and VSV-p $CC_{50}$ for cytotoxicity;

| Ex. | LASV-p $EC_{50}$ (nM) | MACV-p $EC_{50}$ (nM) | JUNV-p $EC_{50}$ (nM) | TCRV-p $EC_{50}$ (nM) | GTOV-p $EC_{50}$ (nM) | VSV-p $EC_{50}$ (nM) | $CC_{50}$ (nM) |
|---|---|---|---|---|---|---|---|
| D15 | 1.24 | 1.65 | 0.34 | 3.57 | 1.04 | >10,000 | 6,230 |
| D16 | 5.37 | 19.1 | 1.05 | 19.85 | 3.52 | nd | 7,530 |
| D17 | >25 | >25 | >25 | >25 | nd | nd | nd |
| D18 | >25 | >25 | 5.58 | >25 | Nd | nd | >100,000 |
| D19 | >25 | >25 | >25 | >25 | nd | nd | 7,540 |
| D20 | >25 | >25 | >25 | >25 | nd | nd | nd |
| D21 | >25 | >25 | >25 | >25 | nd | nd | nd |
| D22 | >25 | >25 | >25 | >25 | nd | nd | 49,520 |
| D23 | 27.35 | >25 | 3.78 | >25 | nd | nd | >100,000 | nd: not determined

TABLE 2

Inhibition of Native Arenaviruses. Example compounds and their observed inhibitory activities and selectivity index values (SI) in replicative LASV, JUNV, TCRV, and LCMV inhibitory activity assays

| Ex. | LASV $EC_{50}$ uM | SI | JUNV $EC_{50}$ uM | SI | TCRV $EC_{50}$ uM | $SI_{50}$ | LCMV $EC_{90}$ uM | $SI_{90}$ |
|---|---|---|---|---|---|---|---|---|
| A17 | 0.06 | 249 | 0.115 | 82 | 0.023 | 609 | 0.71 | 12 |
| A24 | 0.06 | 527 | 0.56 | 53 | 0.010 | 7100 | 0.56 | 18 |
| C1 | 0.025 | 921 | 0.055 | 352 | 0.003 | 2500 | 0.82 | 37 |
| C2 | 0.015 | 1200 | 0.035 | 509 | 0.002 | 1950 | 0.44 | 22 |

TABLE 3

Multi-species Microsomal Stability. Percent parent compound remaining at 60 minutes in liver microsomes

| Ex. | Human | Guinea | Monkey | Rat | Mouse | Dog |
|---|---|---|---|---|---|---|
| A17 | 69 | 62 | 7 | 86 | 44 | nd |
| A24 | 63 | 0 | nd | 32 | nd | nd |
| A30 | 95 | 99 | 20 | 100 | 100 | 100 |
| A31 | 93 | 100 | 40 | nd | nd | nd |
| B2 | 100 | 81 | 68 | 85 | 100 | 93 |
| B12 | 100 | 93 | 98 | 100 | 99 | 92 |
| B15 | 100 | 100 | 5 | 100 | 100 | 100 |
| C1 | 76 | 42 | 16 | 77 | 22 | nd |
| C2 | 82 | 77 | 53 | nd | 103 | nd |
| C51 | 100 | 95 | 21 | 75 | 92 | 82 |

TABLE 4 hERG Channel Assay

| Ex. | Dose (uM) | hERG % Inhibition |
|---|---|---|
| A30 | 3 | <10 |
| A31 | 3 | <10 |
| B2 | 3 | <10 |
| B12 | 3 | 17 |
| B15 | 3 | <10 |
| C1 | 3 | 55 |
| C2 | 3 | 89 |
| C51 | 3 | 49 |

To determine if the compound series demonstrates oral exposure, an oral pharmacokinetic (PK) study was done with example compounds (A17, C2) in guinea pigs. 3 guinea pigs per compound were dosed at 10 mg/kg via oral gavage and blood samples taken at times 0, 1, 2, 4, 8, 12 and 24 hr. Bioanalysis was done on a LC-MS/MS (Water Acquity-UPLC/API4000 mass spectrometer). Both compounds demonstrated oral exposure in guinea pigs with half-lives between 4 and 6 hours.

TABLE 5

Pharmacokinetic (PK) data in guinea pig

| Example | Cmax (ng/mL) | Tmax (hr) | $T^{1/2}$ (hr) |
|---|---|---|---|
| A17 | 639.3 | 1 | 4-6 |
| C2 | 156.0 | 1 | 4-6 |

What is claimed is:

1. A compound of Structural Formula I

I wherein:
G and H are C;
J and L are N;
K is C—H;
A, D, and E are independently C—$R^3$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is substituted with at least one $R^{4a}$ group, and wherein said ($C_2$ to $C_9$) heteroaryl is C-attached;
with the proviso that $R^1$ is not selected from the group consisting of substituted 3-carbamoyl-2-phenyl-1-benzofuran-5-yl, substituted 1,3,4-oxadiazolyl, substituted 1,3,4-triazolyl, substituted 1,3,4-thiadiazolyl, substituted oxazoyl, substituted thiazoyl, substituted 1H-pyrazol-4- yl, substituted 1H-pyrazol-5-yl, optionally substituted 1-phenyl-1H-imidazol-5-yl, 4-{[(2-aminoethyl) amino]methyl}phenyl, (2-amino-1,3-benzoxazol)-5-yl; (2-amino-1,3-benzoxazol)-4-yl, 2-chloropyridyl-3-yl, 2-methylpyridinyl-4-yl, 2-fluoropyridyl-4-yl, 6-aminopyridyl-3-yl, 6-methoxypyridyl-3-yl, pyridyl-4-yl-N-oxide, 3,4-difluorphenyl, and substituted 1H-pyrrol-3-yl;

$R^2$ is selected from the group consisting of

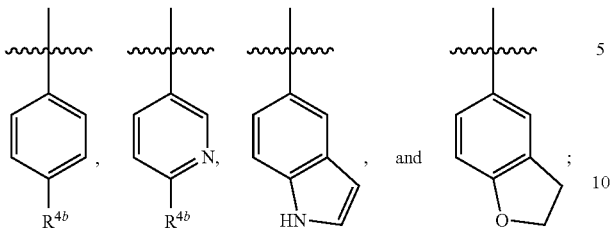

each of the $R^3$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)N$R^{6a}R^{6b}$, —N$R^{6a}R^{6b}$, —S(O)$_m R^5$, —S(O)$_m$N$R^{6a}R^{6b}$, —N$R^{6a}$S(O)$_m R^5$, —(CH$_2$)$_n$C(O)O$R^5$, —(CH$_2$)$_n$C(O)N$R^{6a}R^{6b}$, —OC(O)$R^5$, —N$R^{6a}$C(O)$R^5$, and —N$R^{6c}$C(O)N$R^{5a}R^{5b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4a}$ is independently selected from halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —N$R^{6a}R^{6b}$, —N$R^{6a}$S(O)$_m R^5$, —OC(O)$R^5$, —N$R^{6a}$C(O)$R^5$, and —N$R^{6c}$C(O)N$R^{6a}R^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, acetyl, n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, propanoyl, isobutanoyl, sec-butanoyl, tert-butanoyl, cyclopropanoyl, cyclobutanoyl, and cyclopentanoyl;

each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, or $R^{6a}$ and $R^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)N$R^{9a}R^{9b}$, —N$R^{9a}R^{9b}$, —N$R^{9a}$S(O)$_m R^8$, —(CH$_2$)$_n$C(O)O$R^8$, —(CH$_2$)$_n$C(O)N($R^{9a}R^{9b}$), —OC(O)$R^8$, —N$R^{9a}$C(O)$R^8$, and —N$R^{9a}$C(O)N($R^{9a}R^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;

each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;

each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted;

m is 0, 1, or 2;

n is 1, 2, 3, 4, 5, or 6.

2. The compound of claim 1, wherein $R^{4b}$ is isopropoxy.

3. The compound of claim 1, wherein:

A, D, and E are independently C—$R^3$ and $R^3$ is H, $CH_3$, —CN, $CF_3$, —C(O)O$C_2H_5$, —$OCH_3$, —COOH, —C(O)$NH_2$, and halogen.

4. The compound of claim 2, wherein:

A, D, and E are independently C—$R^3$ and $R^3$ is H, $CH_3$, —CN, $CF_3$, —C(O)O$C_2H_5$, —$OCH_3$, —COON, —C(O)$NH_2$, and halogen.

5. The compound of claim 1, wherein:
D is C—R³ and R³ is CH₃.
6. The compound of claim 5, wherein:
A and E are CH, and D is C CH₃.
7. A compound selected from the group consisting of
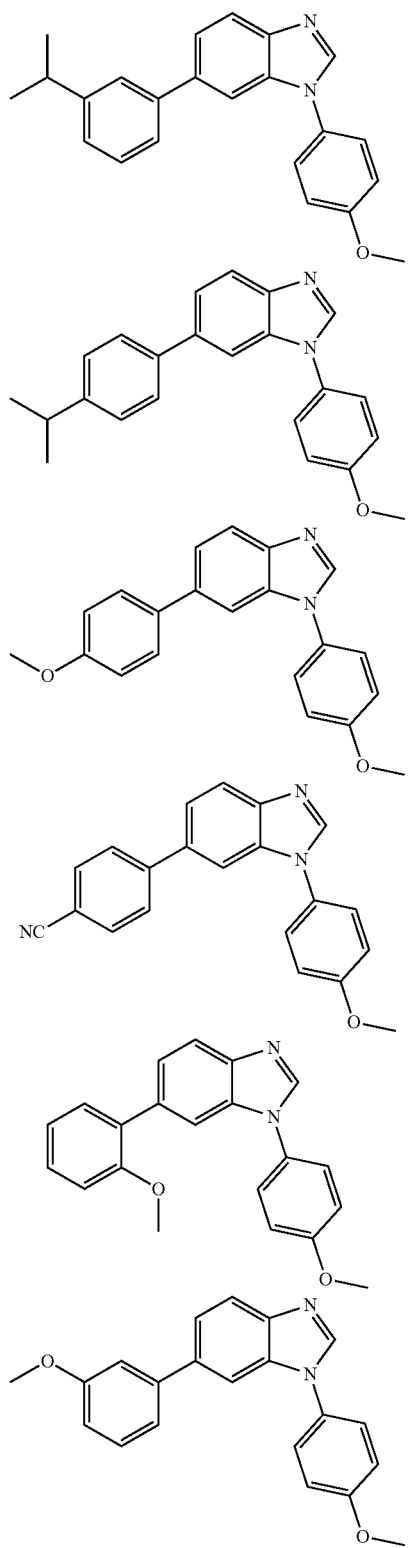
-continued
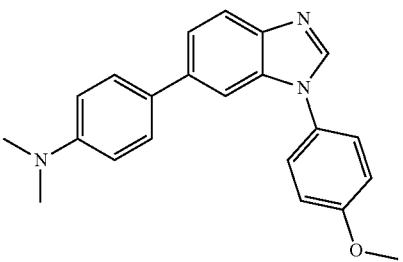
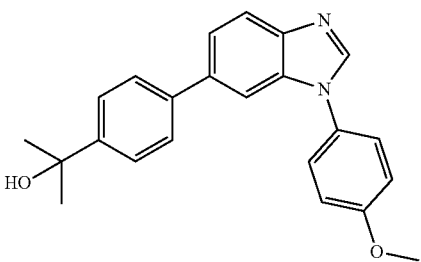
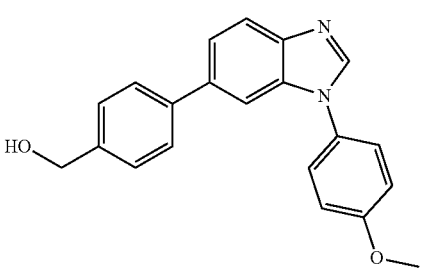
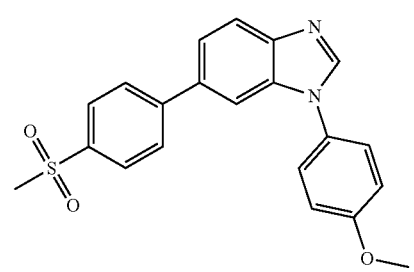
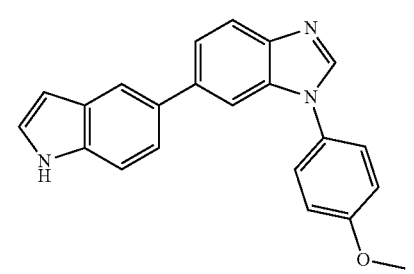
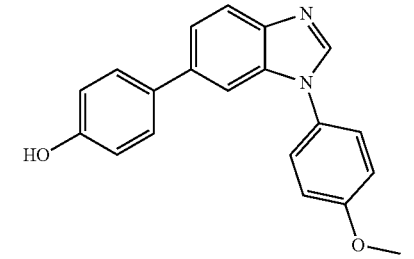

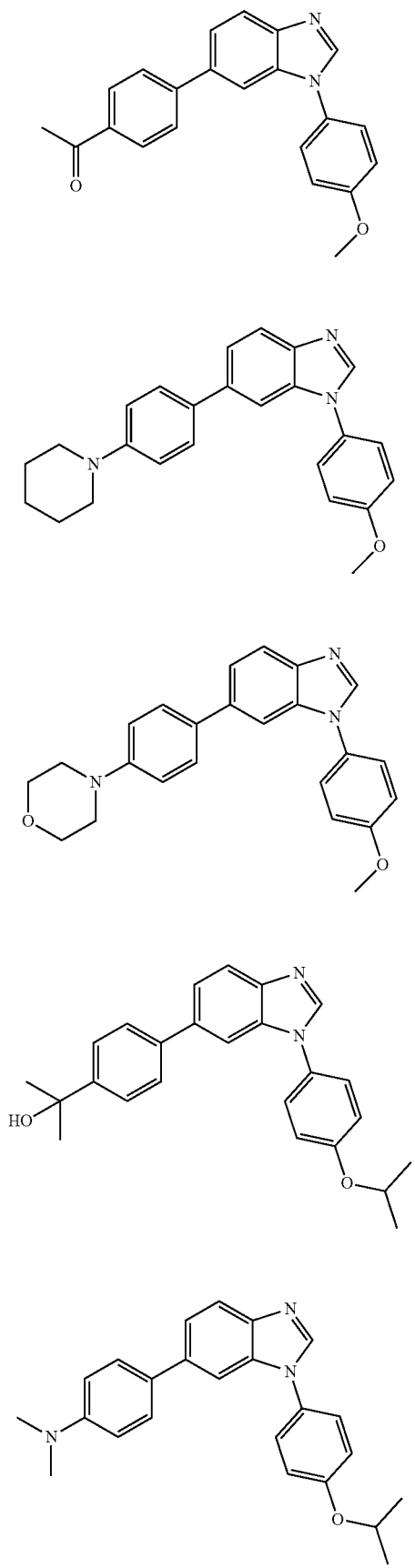

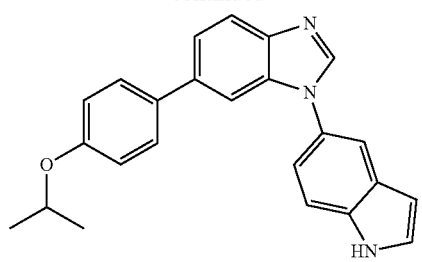
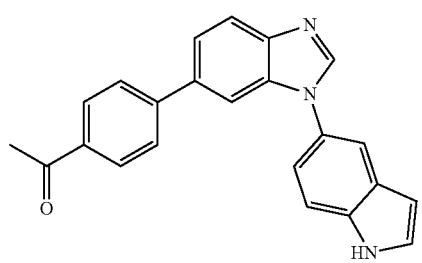
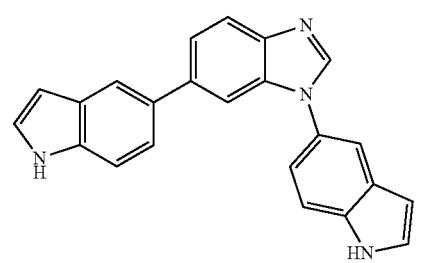
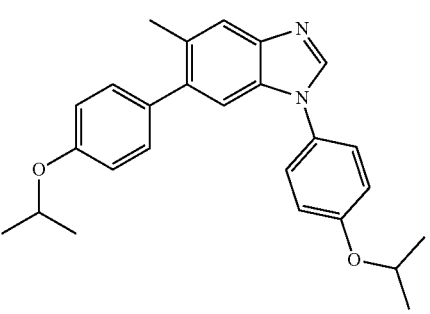
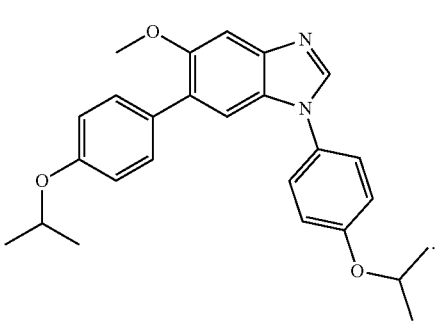
8. The compound of claim 7, wherein the compound is selected from the group consisting of
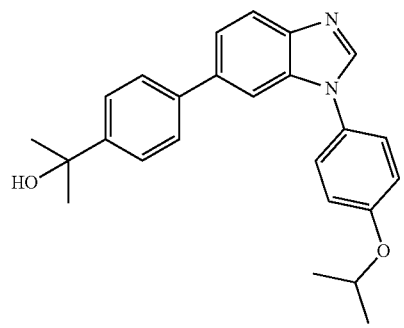
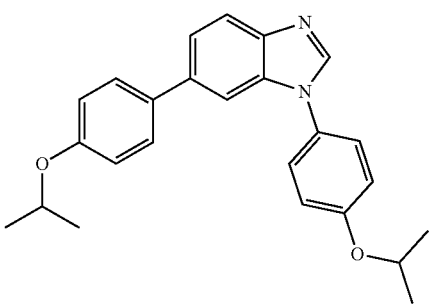
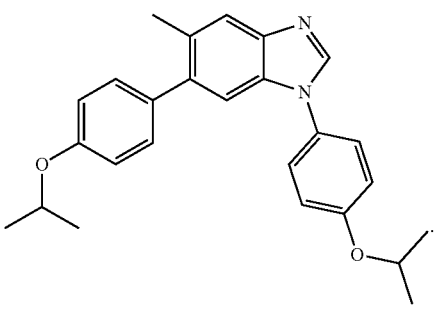
9. A pharmaceutical composition comprising a therapeutically effective amount of a compound, selected from:
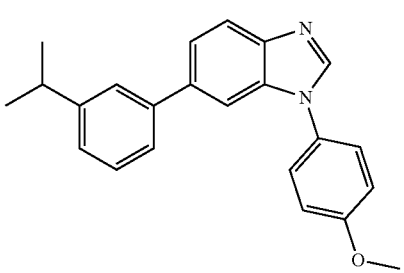
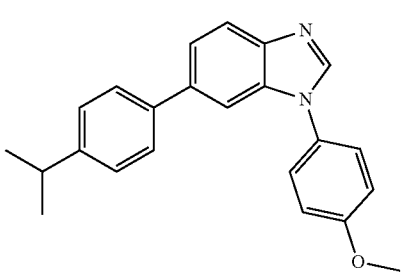

177 178
-continued -continued
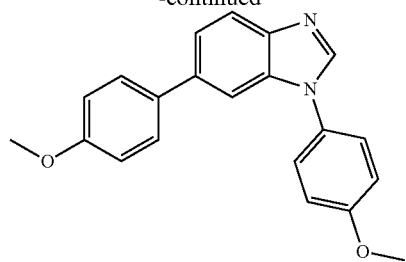
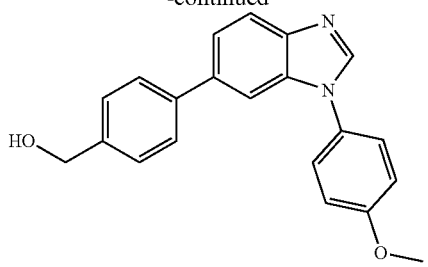
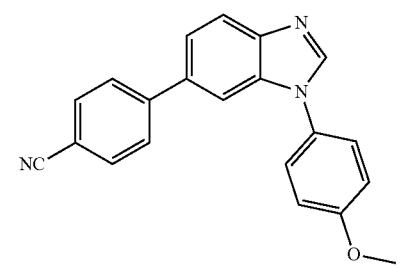
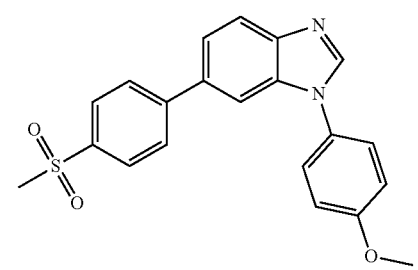
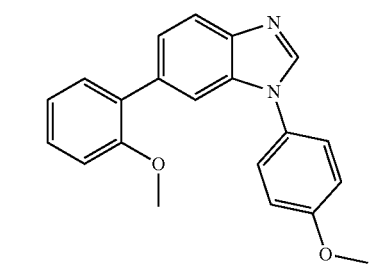
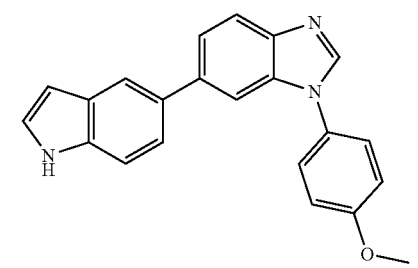
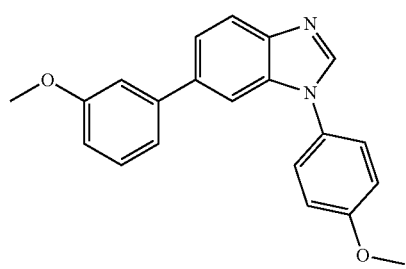
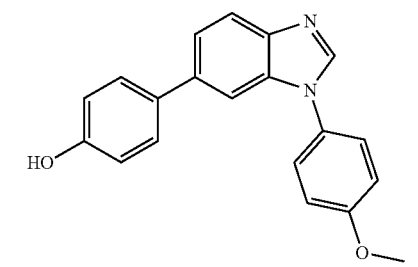
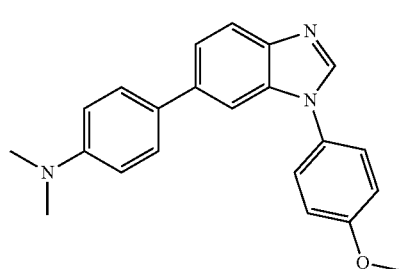
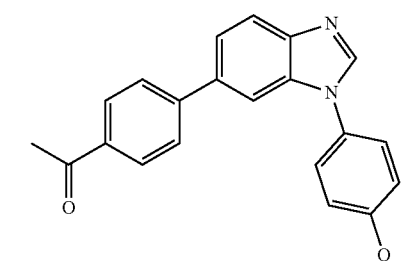
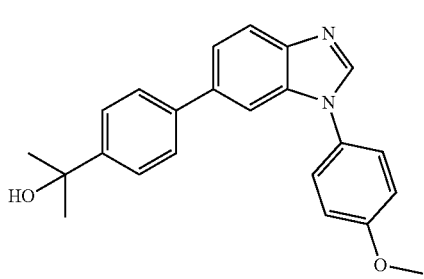
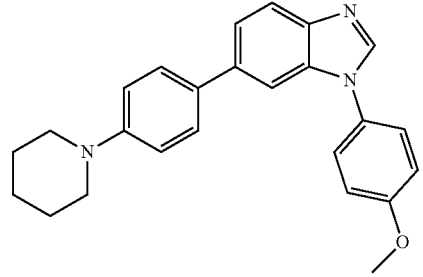

179
-continued
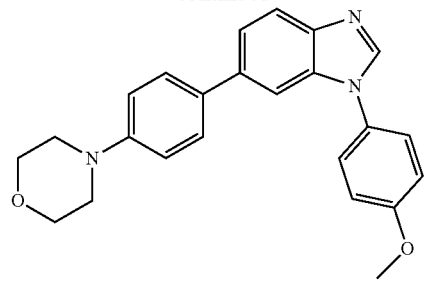
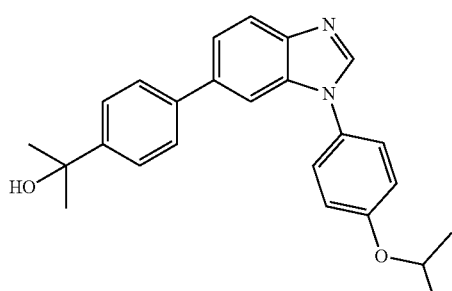
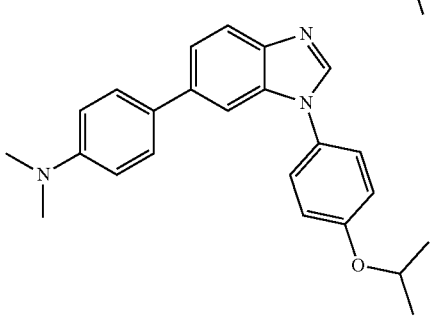
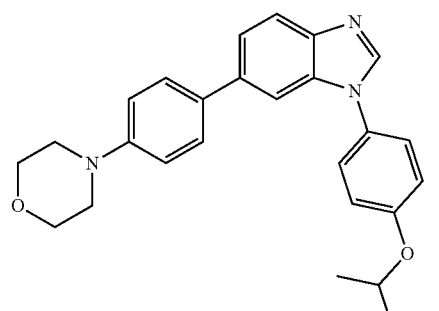
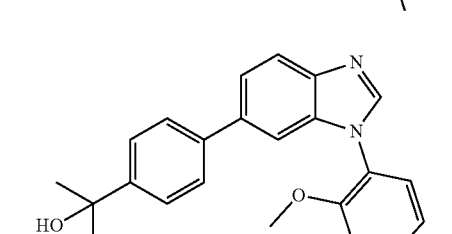
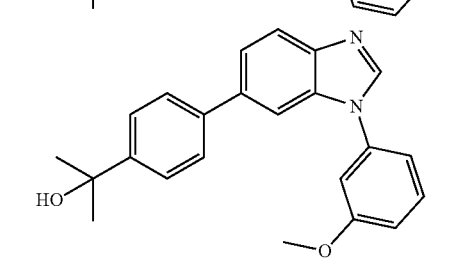
180
-continued
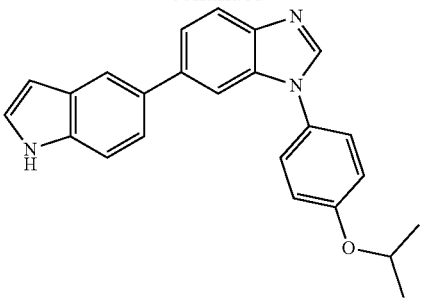
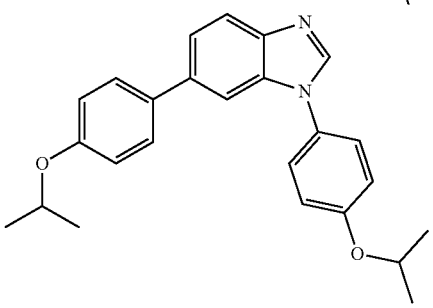
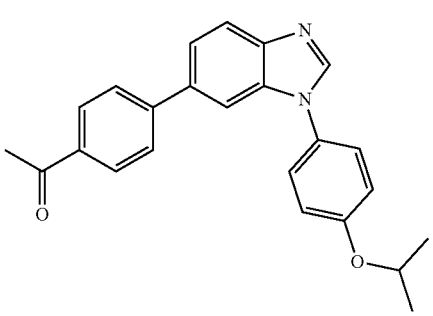
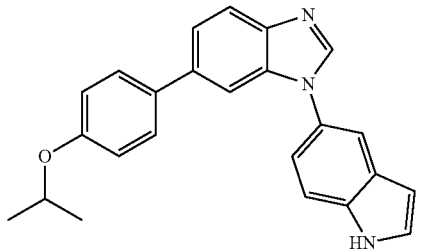
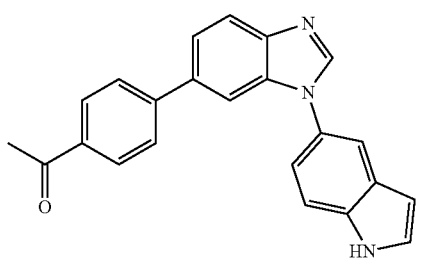
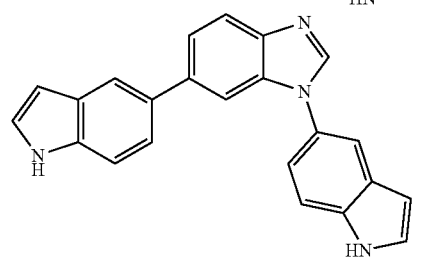

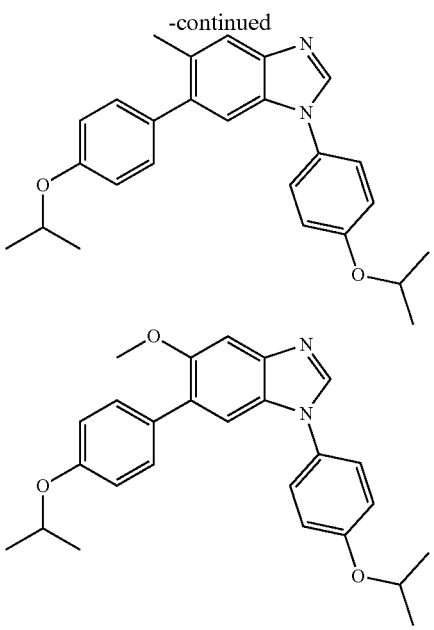

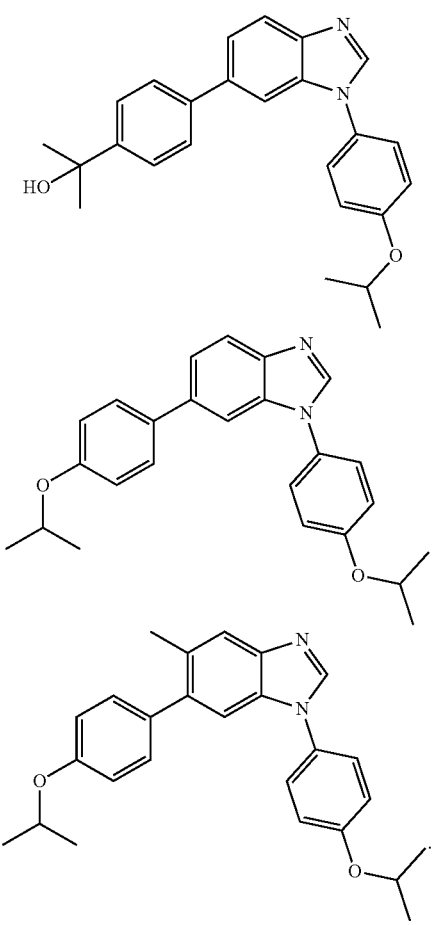

and a pharmaceutically acceptable carrier, diluent, or vehicle.

10. The pharmaceutical composition of claim 9 comprising a therapeutically effective amount of a compound, selected from:

and a pharmaceutically acceptable carrier, diluent, or vehicle.

11. The pharmaceutical composition of claim 10 comprising a therapeutically effective amount of a compound of claim 10 with a therapeutic agent selected from the group consisting of Ribavirin, polymerase inhibitors, T-705 (favipiravir), Triazavirin, small interfering RNAs (siRNAs), vaccines, and immunomodulators.

12. A method of relieving arenavirus infection comprising administration of a therapeutically effective amount of a compound of Structural Formula 1

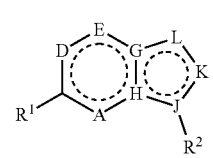

I wherein:
G and H are C;
J and L are N;
K is C—H;
A, D, and E are independently C—$R^3$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is substituted with at least one $R^{4a}$ group, and wherein said ($C_2$ to $C_9$) heteroaryl is C-attached;
with the proviso that $R^1$ is not selected from the group consisting of substituted 3-carbamoyl-2-phenyl-1-benzofuran-5-yl, substituted 1,3,4-oxadiazolyl, substituted 1,3,4-triazolyl, substituted 1,3,4-thiadiazolyl, substituted oxazoyl, substituted thiazoyl, substituted 1H-pyrazol-4- yl, substituted 1H-pyrazol-5-yl, optionally substituted 1-phenyl-1H-imidazol-5-yl, 4-{[(2-aminoethyl) amino]methyl}phenyl, (2-amino-1,3-benzoxazol)-5-yl; (2-amino-1,3-benzoxazol)-4-yl, 2-chloropyridyl-3-yl, 2-methylpyridinyl-4-yl, 2-fluoropyridyl-4-yl, 6-aminopyridyl-3-yl, 6-methoxypyridyl-3-yl, pyridyl-4-yl-N-oxide, 3,4-difluorphenyl, and substituted 1H-pyrrol-3-yl;
$R^2$ is selected from the group consisting of

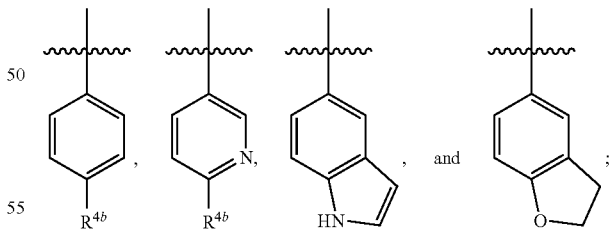

each of the $R^3$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)$NR^{6a}R^{6b}$, —$NR^{6a}R^{6b}$, —S(O)$_m R^5$, —S(O)$_m NR^{6a}R^{6b}$, —$NR^{6a}S(O)_m R^5$, —(CH$_2$)$_n$C(O)OR$^5$, —(CH$_2$)$_n$C(O)NR$^{6a}R^{6b}$, —OC(O)R$^5$, —NR$^{6a}$C(O)R$^5$, and —NR$^{6c}$C(O)NR$^{5a}R^{5b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4a}$ is independently selected from halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —$NR^{6a}R^{6b}$, —$NR^{6a}S(O)_mR^5$, —OC(O)$R^5$, —$NR^{6a}$C(O)$R^5$, and —$NR^{6c}$C(O)$NR^{6a}R^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4b}$ is selected from the group consisting of isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, acetyl, n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, propanoyl, isobutanoyl, sec-butanoyl, tert-butanoyl, cyclopropanoyl, cyclobutanoyl, and cyclopentanoyl;

each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, or $R^{6a}$ and $R^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)$NR^{9a}R^{9b}$, —$NR^{9a}R^{9b}$, —$NR^{9a}$S(O)$_mR^8$, —(CH$_2$)$_n$C(O)O$R^8$, —(CH$_2$)$_n$C(O)N($R^{9a}R^{9b}$), —OC(O)$R^8$, —$NR^{9a}$C(O)$R^8$, and —$NR^{9a}$C(O)N($R^{9a}R^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;

each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;

each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted;

m is 0, 1, or 2;

n is 1, 2, 3, 4, 5, or 6.

13. The method of claim 12, wherein $R^{4b}$ is isopropoxy.

14. The method of claim 12, wherein:

A, D, and E are independently C—$R^3$ and $R^3$ is H, $CH_3$, —CN, $CF_3$, —C(O)O$C_2H_5$, —$OCH_3$, —COOH, —C(O)$NH_2$, and halogen.

15. The method of claim 13, wherein:

A, D, and E are independently C—$R^3$ and $R^3$ is H, $CH_3$, —CN, $CF_3$, —C(O)O$C_2H_5$, —$OCH_3$, —COOH, —C(O)$NH_2$, arid halogen.

16. The method of claim 12, wherein:

D is C—$R^3$ and $R^3$ is $CH_3$.

17. A method of relieving arenavirus infection comprising administration of a therapeutically effective amount of a compound selected from the group consisting of

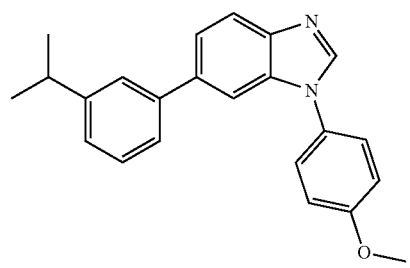

185
-continued
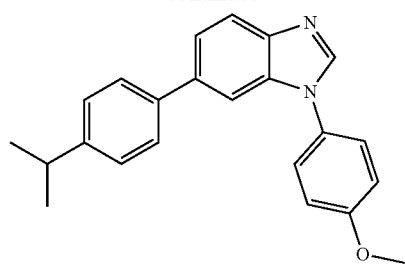
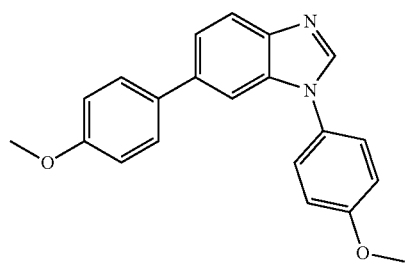
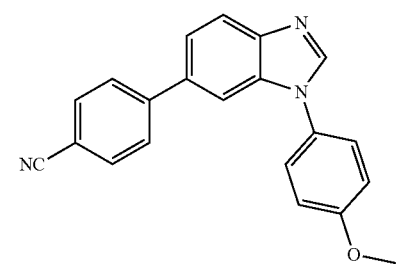
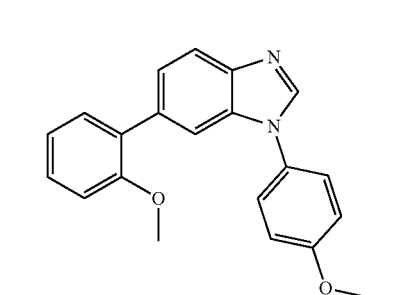
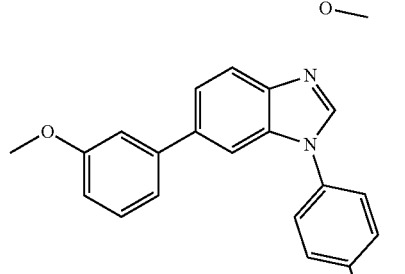
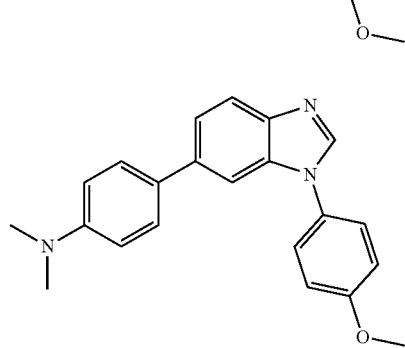
186
-continued
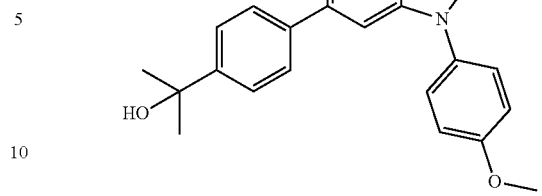
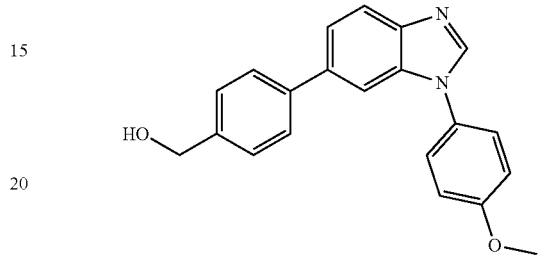
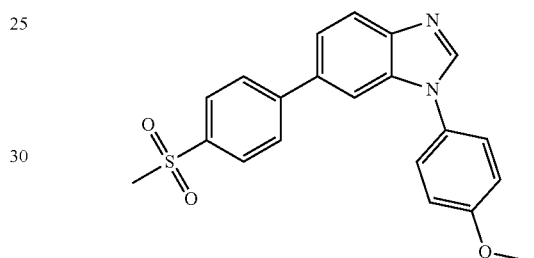
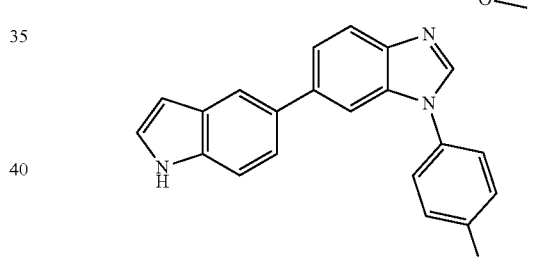
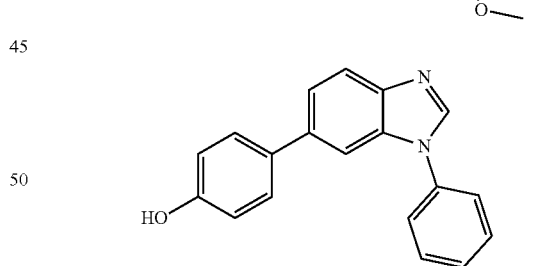
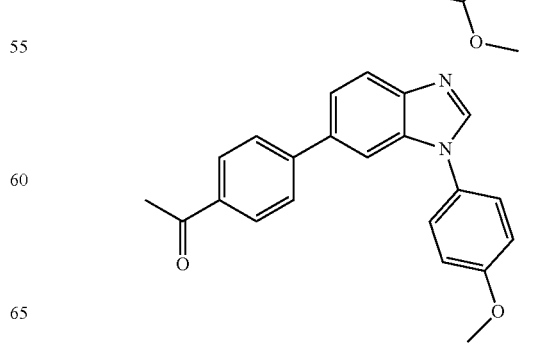

187
-continued
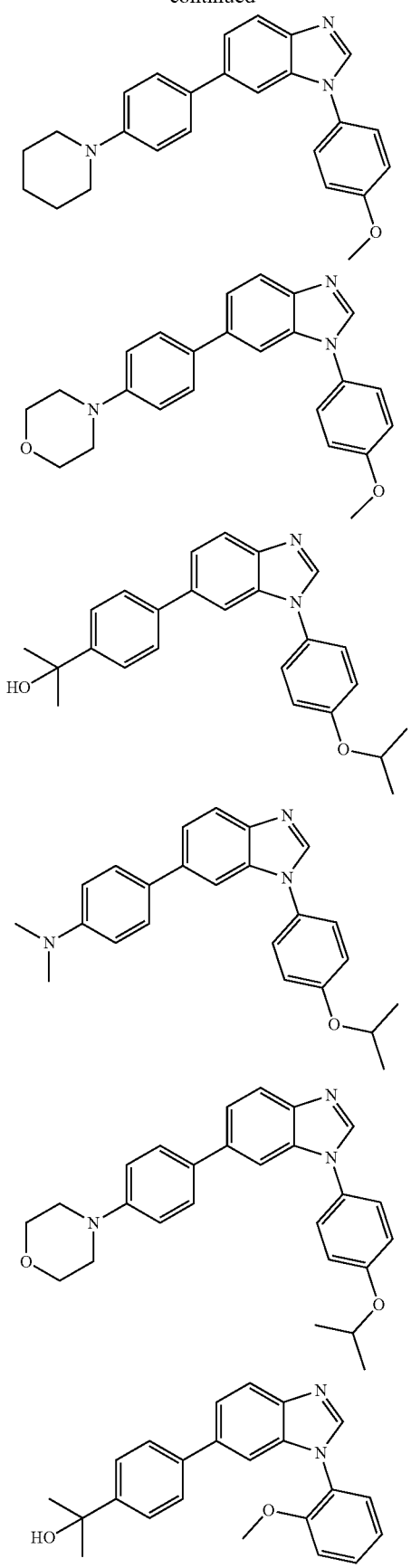
188
-continued
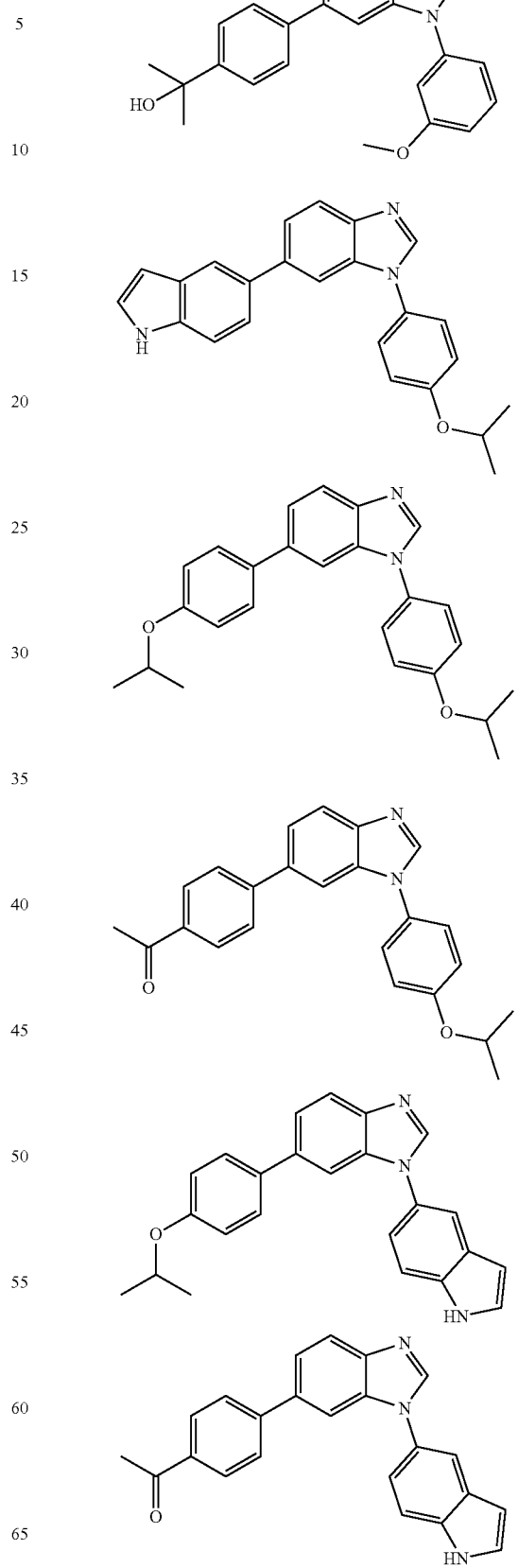

189

-continued

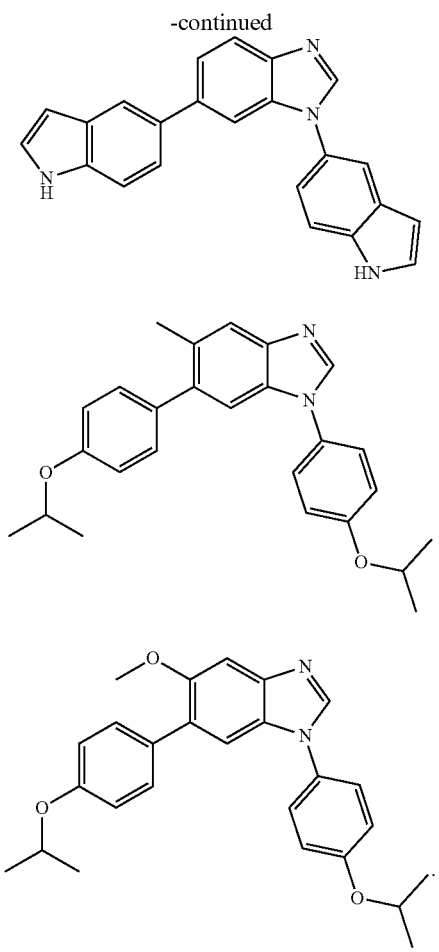

18. The method of claim 17, wherein the compound is selected from the group consisting of

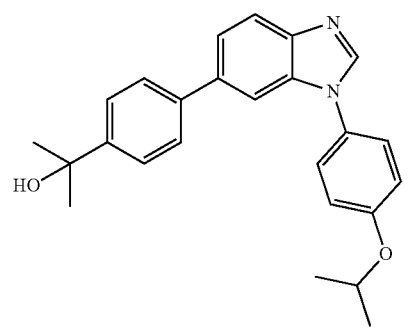

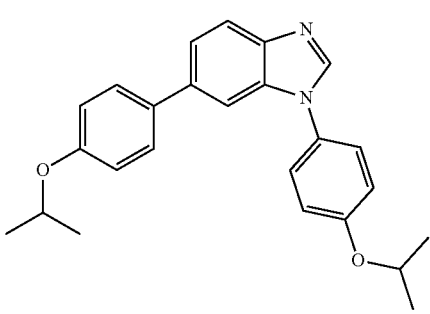

190

-continued

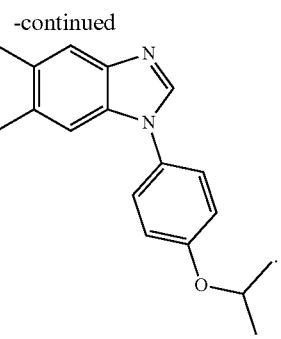

19. The method of claim 12 further comprising administering a therapeutic amount of a therapeutic agent selected from the group consisting of Ribavirin, viral RNA-dependent-RNA-polymerase inhibitors, Triazavirin, small interfering RNAs (siRNAs) and microRNAs, vaccines, and immunomodulators.

20. The method of claim 17 further comprising administering a therapeutic amount of a therapeutic agent selected from the group consisting of Ribavirin, viral RNA-dependent-RNA-polymerase inhibitors, Triazavirin, small interfering RNAs (siRNAs) and microRNAs, vaccines, and immunomodulators.

21. A method of alleviating arenavirus infection comprising administration of a therapeutically effective amount of a compound of Structural Formula I

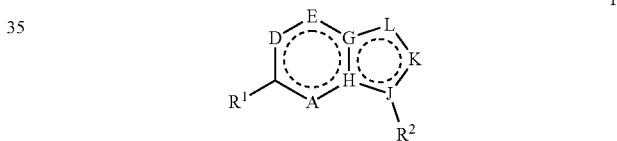

wherein:

G and H are C;

J and L are N;

K is C—H;

A, D, and E are independently C—R$^3$;

R$^1$ is selected from (C$_6$ to C$_{10}$) aryl and (C$_2$ to C$_9$) heteroaryl, wherein each of the said (C$_6$ to C$_{10}$) aryl and (C$_2$ to C$_9$) heteroaryl is substituted with at least one R$^{4a}$ group, and wherein said (C$_2$ to C$_9$) heteroaryl is C-attached;

with the proviso that R$^1$ is not selected from the group consisting of substituted 3-carbamoyl-2-phenyl-1-benzofuran-5-yl, substituted 1,3,4-oxadiazolyl, substituted 1,3,4-triazolyl, substituted 1,3,4-thiadiazolyl, substituted oxazoyl, substituted thiazoyl, substituted 1H-pyrazol-4- yl, substituted 1H-pyrazol-5-yl, optionally substituted 1-phenyl-1H-imidazol-5-yl, 4-{[(2-aminoethyl) amino]methyl}phenyl, (2-amino-1,3-benzoxazol)-5-yl; (2-amino-1,3-benzoxazol)-4-yl, 2-chloropyridyl-3-yl, 2-methylpyridinyl-4-yl, 2-fluoropyridyl-4-yl, 6-aminopyridyl-3-yl, 6-methoxypyridyl-3-yl, pyridyl-4-yl-N-oxide, 3,4-difluorphenyl, and substituted 1H-pyrrol-3-yl;

191

$R^2$ is selected from the group consisting of

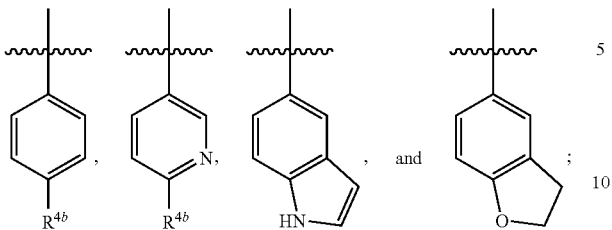

each of the $R^3$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —C(O)N$R^{6a}R^{6b}$, —N$R^{6a}R^{6b}$, —S(O)$_m R^5$, —S(O)$_m$N$R^{6a}R^{6b}$, —N$R^{6a}$S(O)$_m R^5$, —(CH$_2$)$_n$C(O)O$R^5$, —(CH$_2$)$_n$C(O)N$R^{6a}R^{6b}$, —OC(O)$R^5$, —N$R^{6a}$C(O)$R^5$, and —N$R^{6c}$C(O)N$R^{5a}R^{5b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4a}$ is independently selected from halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^5$, —N$R^{6a}R^{6b}$, —N$R^{6a}$S(O)$_m R^5$, —OC(O)$R^5$, —N$R^{6a}$C(O)$R^5$, and —N$R^{6c}$C(O)N$R^{6a}R^{6b}$, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

$R^{4b}$ is selected from the group consisting of
isopropoxy, cyclopropoxy, tert-butoxy, cyclopropylmethoxy, (2-hydroxypropan)-2-yl, (1-hydroxycyclopropan)-1-yl, (1-hydroxycyclobutan)-1-yl, difluoromethoxy, methoxyethoxy, difluoromethyl, cyclopropyl, acetyl, n-propyloxy, n-butyloxy, isobutyloxy, sec-butyloxy, cyclobutyloxy, cyclopentyloxy, (1-hydroxycyclopentan)-1-yl, hydroxyethoxy, ethoxyethoxy, isopropoxyethoxy, isopropyl, n-propyl, n-butyl, isobutyl, sec-butyl, cyclobutyl, cyclopentyl, propanoyl, isobutanoyl, sec-butanoyl, tert-butanoyl, cyclopropanoyl, cyclobutanoyl, and cyclopentanoyl;

each of the $R^5$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^7$ group;

each of the $R^{6a}$, $R^{6b}$, and $R^{6c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl,

192 or $R^{6a}$ and $R^{6b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted with at least one $R^7$ group;

$R^7$ is independently selected from hydrogen, halogen, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —C(O)$R^8$, —C(O)N$R^{9a}R^{9b}$, —N$R^{9a}R^{9b}$, —N$R^{9a}$S(O)$_m R^8$, —(CH$_2$)$_n$C(O)O$R^8$, —(CH$_2$)$_n$C(O)N($R^{9a}R^{9b}$), —OC(O)$R^8$, —N$R^{9a}$C(O)$R^8$, and —N$R^{9a}$C(O)N($R^{9a}R^{9b}$), wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, is optionally substituted with at least one $R^{10}$ group;

each of the $R^8$ is independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{10}$ group;

each of the $R^{9a}$, $R^{9b}$, and $R^{9c}$ are independently selected from hydrogen, ($C_1$ to $C_6$) alkyl, ($C_1$ to $C_6$) alkenyl, ($C_1$ to $C_6$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, or $R^{9a}$ and $R^{9b}$ may be taken together with the nitrogen atom to which they are attached to form a 4 to 8 membered cycloheteroalkyl ring, wherein said 4 to 8 membered cycloheteroalkyl ring has 1 to 3 ring heteroatoms selected from the group consisting of N, O, and S, and wherein the said 4 to 8 membered cycloheteroalkyl ring is optionally substituted;

$R^{10}$ is independently selected from hydrogen, halogen, cyano, OH, $CF_3$, ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_6$) alkyl, ($C_1$ to $C_6$) alkenyl, ($C_1$ to $C_6$) alkynyl, ($C_1$ to $C_6$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted;

m is 0, 1, or 2;

n is 1, 2, 3, 4, 5, or 6.

22. The method of claim 21, wherein $R^{4b}$ is isopropoxy.

23. The method of claim 21, wherein:
A, D, and E are independently C—$R^3$ and $R^3$ is H, $CH_3$, —CN, $CF_3$, —C(O)O$C_2H_5$, —O$CH_3$, —COOH, —C(O)N$H_2$, and halogen.

24. The method of claim 22, wherein:
A, D, and E are independently C—$R^3$ and $R^3$ is H, $CH_3$, —CN, $CF_3$, —C(O)O$C_2H_5$, —O$CH_3$, —COON, —C(O)N$H_2$, and halogen.

25. The method of claim 21, wherein:
D is C—R$^3$ and R$^3$ is CH$_3$.
26. A method of alleviating arenavirus infection comprising administration of a therapeutically effective amount of a compound selected from the group consisting of
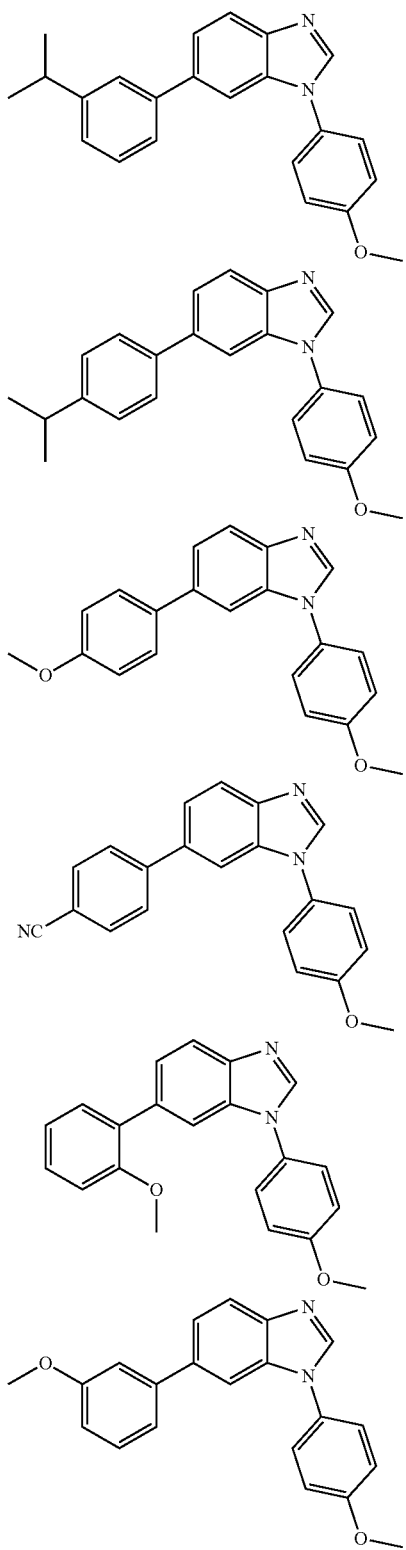
-continued
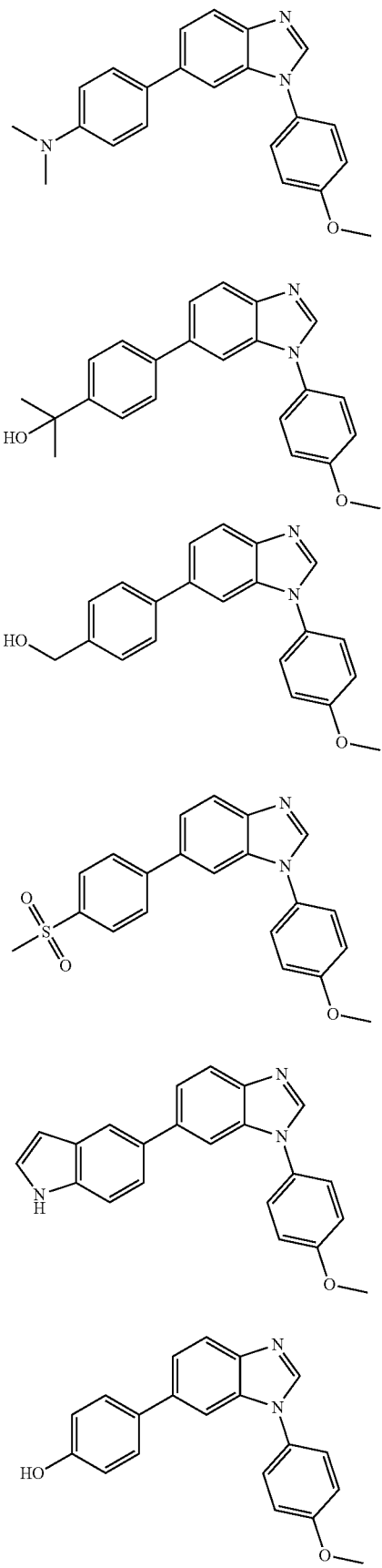

195
-continued
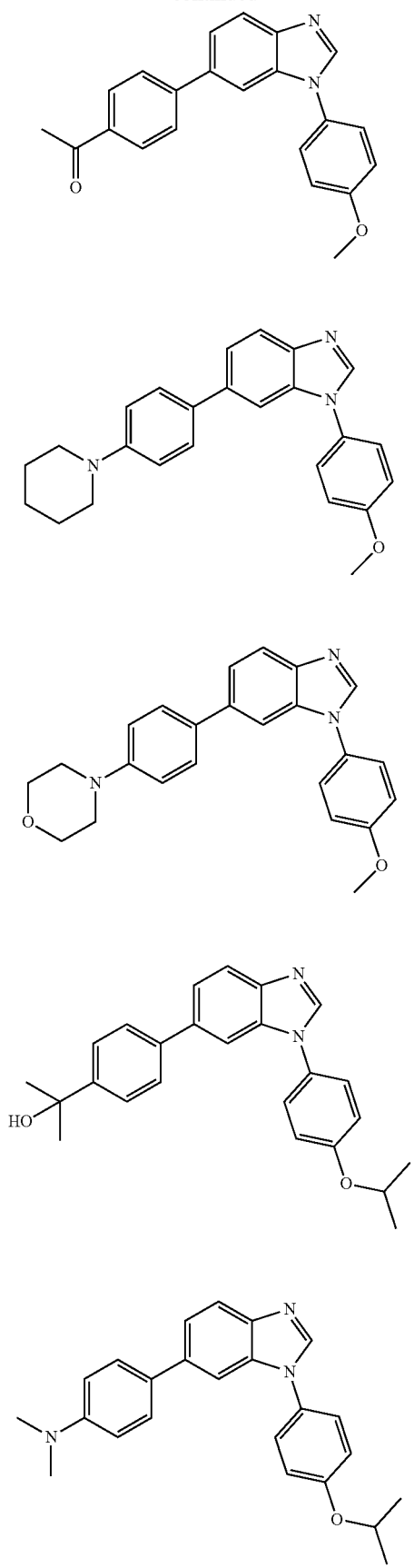
196
-continued
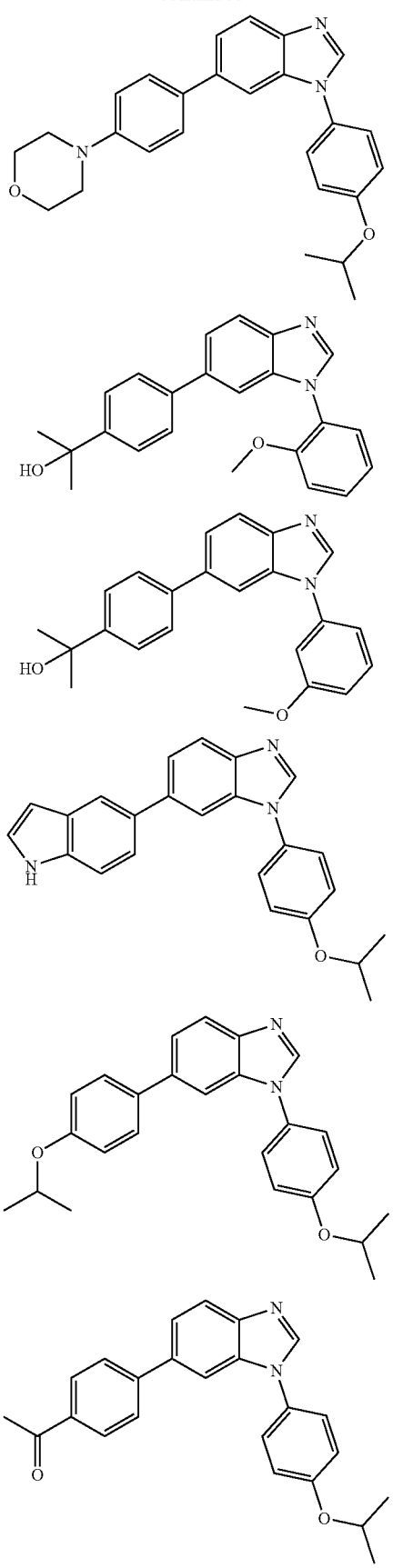

-continued

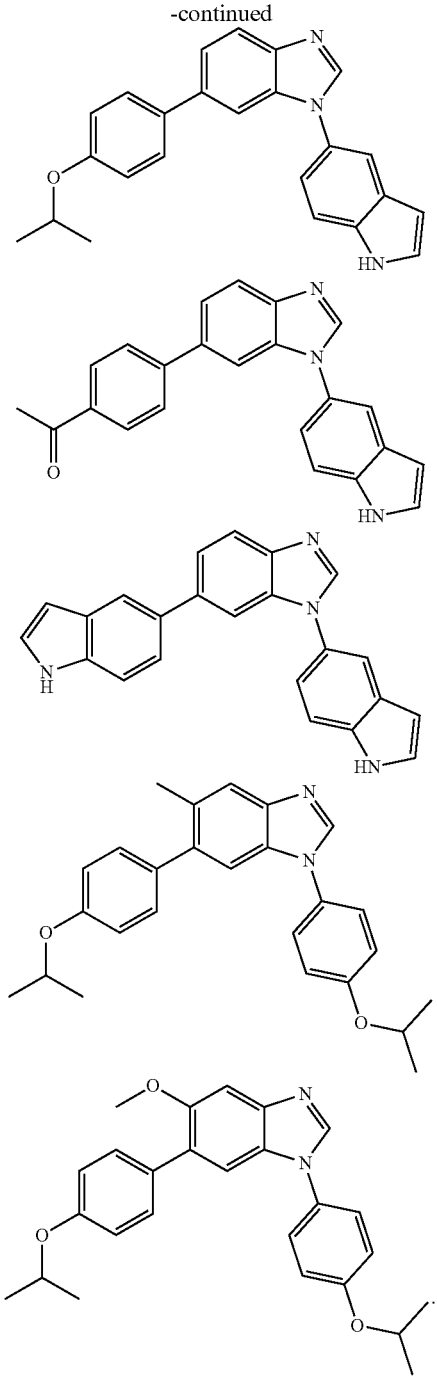

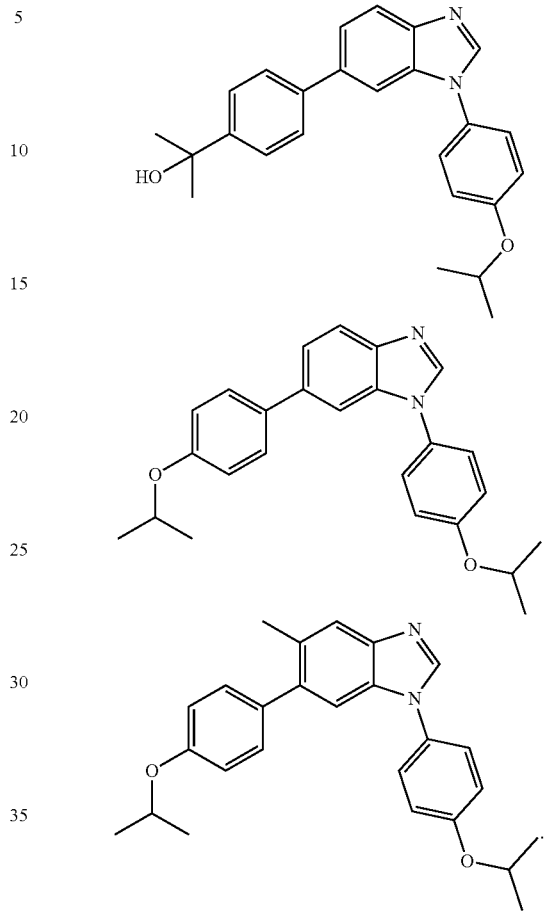

27. The method of claim 26, wherein the compound is selected from the group consisting of 28. The method of claim 21 further comprising administering a therapeutic amount of a therapeutic agent selected from the group consisting of Ribavirin, viral RNA-dependent-RNA-polymerase inhibitors, Triazavirin, small interfering RNAs (siRNAs) and microRNAs, vaccines, and immunomodulators.

29. The method of claim 26 further comprising administering a therapeutic amount of a therapeutic agent selected from the group consisting of Ribavirin, viral RNA-dependent-RNA-polymerase inhibitors, Triazavirin, small interfering RNAs (siRNAs) and microRNAs, vaccines, and immunomodulators.

* * * * *

UNITED STATES PATENT AND TRADEMARK OFFICE
CERTIFICATE OF CORRECTION

| | | |
|---|---|---|
| PATENT NO. | : 11,352,328 B2 | Page 1 of 5 |
| APPLICATION NO. | : 16/309858 | |
| DATED | : June 7, 2022 | |
| INVENTOR(S) | : Kenneth McCormack et al. | |

It is certified that error appears in the above-identified patent and that said Letters Patent is hereby corrected as shown below:

On the Title Page

Item (72), order of the Inventors should be: Kenneth McCormack, Michael Plewe, Nadezda V. Sokolova, Gregory Henkel, Eric Brown, Vidyasagar Gantla, Young-Jun Shin;

Item (72), Line 6, Inventor's name reads as Nadzeda; it should read as Nadezda;

In the Specification

Column 49, Line 8, replace "from 5 to 9 carbon atoms" with -- from 2 to 9 carbon atoms --;

Column 49, Line 35, replace "4H pyranyl" with -- 4H-pyranyl --;

Column 49, Line 39, replace "3H-indolyl quinolizinyl" with -- 3H-indolyl, quinolizinyl --;

Column 49, Lines 40-41, replace "1-oxo-2,8,diazaspiro[4.5]dec-8-yl" with
-- 1-oxo-2,8-diazaspiro[4.5]dec-8-yl --;

Column 51, Lines 18-19, replace "in combination water" with -- in combination with water --;

Column 53, Line 18, replace "The carbon carbon bonds" with -- The carbon-carbon bonds --;

Column 63, Line 39, replace "methods know to whose" with -- methods known to those --;

Column 161, Line 46, replace "$CC_{SO}$" with -- $CC_{50}$ --;

In the Claims

Column 168, Lines 62-63, Claim 1, replace "(2-amino-1,3-benzoxazol)-5-yl;" with
-- (2-amino-1,3-benzoxazol)-5-yl, --;

Signed and Sealed this
Ninth Day of August, 2022

Katherine Kelly Vidal
*Director of the United States Patent and Trademark Office*

Column 168, Line 66, Claim 1, replace "3,4-difluorphenyl" with -- 3,4-difluorophenyl --;

Column 169, Lines 15-16, Claim 1, replace "($C_1$ to $C_6$) alkenyl" with -- ($C_2$ to $C_6$) alkenyl --;

Column 169, Line 16, Claim 1, replace "($C_1$ to $C_6$) alkynyl" with -- ($C_2$ to $C_6$) alkynyl --;

Column 169, Line 24, Claim 1, replace "($C_1$ to $C_6$) alkenyl" with -- ($C_2$ to $C_6$) alkenyl --;

Column 169, Lines 24-25, Claim 1, replace "($C_1$ to $C_6$) alkynyl" with -- ($C_2$ to $C_6$) alkynyl --;

Column 169, Line 30, Claim 1, replace "($C_1$ to $C_6$) alkenyl" with -- ($C_2$ to $C_6$) alkenyl --;

Column 169, Lines 30-31, Claim 1, replace "($C_1$ to $C_6$) alkynyl" with -- ($C_2$ to $C_6$) alkynyl --;

Column 169, Line 37, Claim 1, replace "($C_1$ to $C_6$) alkenyl" with -- ($C_2$ to $C_6$) alkenyl --;

Column 169, Lines 37-38, Claim 1, replace "($C_1$ to $C_6$) alkynyl" with -- ($C_2$ to $C_6$) alkynyl --;

Column 169, Line 55, Claim 1, replace "($C_1$ to $C_6$) alkenyl" with -- ($C_2$ to $C_6$) alkenyl --;

Column 169, Line 55, Claim 1, replace "($C_1$ to $C_6$) alkynyl" with -- ($C_2$ to $C_6$) alkynyl --;

Column 169, Line 58, Claim 1, replace "($C_1$ to $C_6$) alkenyl" with -- ($C_2$ to $C_6$) alkenyl --;

Column 169, Lines 58-59, Claim 1, replace "($C_1$ to $C_6$) alkynyl" with -- ($C_2$ to $C_6$) alkynyl --;

Column 169, Line 64, Claim 1, replace "($C_1$ to $C_6$) alkenyl" with -- ($C_2$ to $C_6$) alkenyl --;

Column 169, Lines 64-65, Claim 1, replace "($C_1$ to $C_6$) alkynyl" with -- ($C_2$ to $C_6$) alkynyl --;

Column 170, Line 10, Claim 1, replace "($C_1$ to $C_6$) alkenyl" with -- ($C_2$ to $C_6$) alkenyl --;

Column 170, Lines 10-11, Claim 1, replace "($C_1$ to $C_6$) alkynyl" with -- ($C_2$ to $C_6$) alkynyl --;

Column 170, Line 18, Claim 1, replace "($C_1$ to $C_6$) alkenyl" with -- ($C_2$ to $C_6$) alkenyl --;

Column 170, Lines 18-19, Claim 1, replace "($C_1$ to $C_6$) alkynyl" with -- ($C_2$ to $C_6$) alkynyl --;

Column 170, Line 24, Claim 1, replace "($C_1$ to $C_6$) alkenyl" with -- ($C_2$ to $C_6$) alkenyl --;

Column 170, Line 24, Claim 1, replace "($C_1$ to $C_6$) alkynyl" with -- ($C_2$ to $C_6$) alkynyl --;

Column 170, Line 28, Claim 1, replace "($C_1$ to $C_6$) alkenyl" with -- ($C_2$ to $C_6$) alkenyl --;

Column 170, Lines 28-29, Claim 1, replace "($C_1$ to $C_6$) alkynyl" with -- ($C_2$ to $C_6$) alkynyl --;

Column 170, Line 34, Claim 1, replace "($C_1$ to $C_6$) alkenyl" with -- ($C_2$ to $C_6$) alkenyl --;

Column 170, Lines 34-35, Claim 1, replace "($C_1$ to $C_6$) alkynyl" with -- ($C_2$ to $C_6$) alkynyl --;

Column 170, Line 47, Claim 1, replace "($C_1$ to $C_6$) alkenyl" with -- ($C_2$ to $C_6$) alkenyl --;

Column 170, Line 48, Claim 1, replace "($C_1$ to $C_6$) alkynyl" with -- ($C_2$ to $C_6$) alkynyl --;

Column 170, Line 52, Claim 1, replace "($C_1$ to $C_6$) alkenyl" with -- ($C_2$ to $C_6$) alkenyl --;

Column 170, Lines 52-53, Claim 1, replace "($C_1$ to $C_6$) alkynyl" with -- ($C_2$ to $C_6$) alkynyl --;

Column 171, Line 4, Claim 1, replace "C $CH_3$" with -- C–$CH_3$ --;

Column 182, Lines 39-40, Claim 12, replace "(2-amino-1,3-benzoxazol)-5-yl;" with -- (2-amino-1,3-benzoxazol)-5-yl, --;

Column 182, Line 43, Claim 12, replace "3,4-difluorphenyl" with -- 3,4-difluorophenyl --;

Column 182, Lines 59-60, Claim 12, replace "($C_1$ to $C_6$) alkenyl" with -- ($C_2$ to $C_6$) alkenyl --;

Column 182, Line 60, Claim 12, replace "($C_1$ to $C_6$) alkynyl" with -- ($C_2$ to $C_6$) alkynyl --;

Column 183, Line 1, Claim 12, replace "($C_1$ to $C_6$) alkenyl" with -- ($C_2$ to $C_6$) alkenyl --;

Column 183, Lines 1-2, Claim 12, replace "($C_1$ to $C_6$) alkynyl" with -- ($C_2$ to $C_6$) alkynyl --;

Column 183, Line 7, Claim 12, replace "($C_1$ to $C_6$) alkenyl" with -- ($C_2$ to $C_6$) alkenyl --;

Column 183, Lines 7-8, Claim 12, replace "($C_1$ to $C_6$) alkynyl" with -- ($C_2$ to $C_6$) alkynyl --;

Column 183, Line 13, Claim 12, replace "($C_1$ to $C_6$) alkenyl" with -- ($C_2$ to $C_6$) alkenyl --;

Column 183, Lines 13-14, Claim 12, replace "($C_1$ to $C_6$) alkynyl" with -- ($C_2$ to $C_6$) alkynyl --;

Column 183, Line 31, Claim 12, replace "($C_1$ to $C_6$) alkenyl" with -- ($C_2$ to $C_6$) alkenyl --;

Column 183, Line 31, Claim 12, replace "($C_1$ to $C_6$) alkynyl" with -- ($C_2$ to $C_6$) alkynyl --;

Column 183, Line 34, Claim 12, replace "($C_1$ to $C_6$) alkenyl" with -- ($C_2$ to $C_6$) alkenyl --;

Column 183, Lines 34-35, Claim 12, replace "($C_1$ to $C_6$) alkynyl" with -- ($C_2$ to $C_6$) alkynyl --;

Column 183, Line 40, Claim 12, replace "($C_1$ to $C_6$) alkenyl" with -- ($C_2$ to $C_6$) alkenyl --;

Column 183, Lines 40-41, Claim 12, replace "($C_1$ to $C_6$) alkynyl" with -- ($C_2$ to $C_6$) alkynyl --;

Column 183, Lines 53, Claim 12, replace "($C_1$ to $C_6$) alkenyl" with -- ($C_2$ to $C_6$) alkenyl --;

Column 183, Lines 53-54, Claim 12, replace "($C_1$ to $C_6$) alkynyl" with -- ($C_2$ to $C_6$) alkynyl --;

Column 183, Line 61, Claim 12, replace "($C_1$ to $C_6$) alkenyl" with -- ($C_2$ to $C_6$) alkenyl --;

Column 183, Lines 61-62, Claim 12, replace "($C_1$ to $C_6$) alkynyl" with -- ($C_2$ to $C_6$) alkynyl --;

Column 183, Line 67, Claim 12, replace "($C_1$ to $C_6$) alkenyl" with -- ($C_2$ to $C_6$) alkenyl --;

Column 183, Lines 67, Claim 12, replace "($C_1$ to $C_6$) alkynyl" with -- ($C_2$ to $C_6$) alkynyl --;

Column 184, Line 4, Claim 12, replace "($C_1$ to $C_6$) alkenyl" with -- ($C_2$ to $C_6$) alkenyl --;

Column 184, Lines 4-5, Claim 12, replace "($C_1$ to $C_6$) alkynyl" with -- ($C_2$ to $C_6$) alkynyl --;

Column 184, Line 10, Claim 12, replace "($C_1$ to $C_6$) alkenyl" with -- ($C_2$ to $C_6$) alkenyl --;

Column 184, Lines 10-11, Claim 12, replace "($C_1$ to $C_6$) alkynyl" with -- ($C_2$ to $C_6$) alkynyl --;

Column 184, Line 26, Claim 12, replace "($C_1$ to $C_6$) alkenyl" with -- ($C_2$ to $C_6$) alkenyl --;

Column 184, Line 27, Claim 12, replace "($C_1$ to $C_6$) alkynyl" with -- ($C_2$ to $C_6$) alkynyl --;

Column 184, Line 31, Claim 12, replace "($C_1$ to $C_6$) alkenyl" with -- ($C_2$ to $C_6$) alkenyl --;

Column 184, Lines 31-32, Claim 12, replace "($C_1$ to $C_6$) alkynyl" with -- ($C_2$ to $C_6$) alkynyl --;

Column 184, Line 48, Claim 12, replace "arid halogen" with -- and halogen --;

Column 190, Lines 62-63, Claim 21, replace "(2-amino-1,3-benzoxazol)-5-yl;" with
-- (2-amino-1,3-benzoxazol)-5-yl, --;

Column 190, Line 66, Claim 21, replace "3,4-difluorphenyl" with -- 3,4-difluorophenyl --;

Column 191, Lines 15-16, Claim 21, replace "($C_1$ to $C_6$) alkenyl" with -- ($C_2$ to $C_6$) alkenyl --;

Column 191, Line 16, Claim 21, replace "($C_1$ to $C_6$) alkynyl" with -- ($C_2$ to $C_6$) alkynyl --;

Column 191, Line 24, Claim 21, replace "($C_1$ to $C_6$) alkenyl" with -- ($C_2$ to $C_6$) alkenyl --;

Column 191, Lines 24-25, Claim 21, replace "($C_1$ to $C_6$) alkynyl" with -- ($C_2$ to $C_6$) alkynyl --;

CERTIFICATE OF CORRECTION (continued)
U.S. Pat. No. 11,352,328 B2

Column 191, Line 30, Claim 21, replace "($C_1$ to $C_6$) alkenyl" with -- ($C_2$ to $C_6$) alkenyl --;

Column 191, Lines 30-31, Claim 21, replace "($C_1$ to $C_6$) alkynyl" with -- ($C_2$ to $C_6$) alkynyl --;

Column 191, Line 37, Claim 21, replace "($C_1$ to $C_6$) alkenyl" with -- ($C_2$ to $C_6$) alkenyl --;

Column 191, Lines 37-38, Claim 21, replace "($C_1$ to $C_6$) alkynyl" with -- ($C_2$ to $C_6$) alkynyl --;

Column 191, Line 55, Claim 21, replace "($C_1$ to $C_6$) alkenyl" with -- ($C_2$ to $C_6$) alkenyl --;

Column 191, Line 55, Claim 21, replace "($C_1$ to $C_6$) alkynyl" with -- ($C_2$ to $C_6$) alkynyl --;

Column 191, Line 58, Claim 21, replace "($C_1$ to $C_6$) alkenyl" with -- ($C_2$ to $C_6$) alkenyl --;

Column 191, Lines 58-59, Claim 21, replace "($C_1$ to $C_6$) alkynyl" with -- ($C_2$ to $C_6$) alkynyl --;

Column 191, Line 64, Claim 21, replace "($C_1$ to $C_6$) alkenyl" with -- ($C_2$ to $C_6$) alkenyl --;

Column 191, Lines 64-65, Claim 21, replace "($C_1$ to $C_6$) alkynyl" with -- ($C_2$ to $C_6$) alkynyl --;

Column 192, Line 10, Claim 21, replace "($C_1$ to $C_6$) alkenyl" with -- ($C_2$ to $C_6$) alkenyl --;

Column 192, Lines 10-11, Claim 21, replace "($C_1$ to $C_6$) alkynyl" with -- ($C_2$ to $C_6$) alkynyl --;

Column 192, Line 18, Claim 21, replace "($C_1$ to $C_6$) alkenyl" with -- ($C_2$ to $C_6$) alkenyl --;

Column 192, Lines 18-19, Claim 21, replace to "($C_1$ to $C_6$) alkynyl" with -- ($C_2$ to $C_6$) alkynyl --;

Column 192, Line 28, Claim 21, replace "($C_1$ to $C_6$) alkenyl" with -- ($C_2$ to $C_6$) alkenyl --;

Column 192, Lines 28-29, Claim 21, replace "($C_1$ to $C_6$) alkynyl" with -- ($C_2$ to $C_6$) alkynyl --;

Column 192, Line 34, Claim 21, replace "($C_1$ to $C_6$) alkenyl" with -- ($C_2$ to $C_6$) alkenyl --;

Column 192, Lines 34-35, Claim 21, replace "($C_1$ to $C_6$) alkynyl" with -- ($C_2$ to $C_6$) alkynyl --;

Column 192, Line 47, Claim 21, replace "($C_1$ to $C_6$) alkenyl" with -- ($C_2$ to $C_6$) alkenyl --;

Column 192, Line 48, Claim 21, replace "($C_1$ to $C_6$) alkynyl" with -- ($C_2$ to $C_6$) alkynyl --;

Column 192, Line 52, Claim 21, replace "($C_1$ to $C_6$) alkenyl" with -- ($C_2$ to $C_6$) alkenyl --;

Column 192, Lines 52-53, Claim 21, replace "($C_1$ to $C_6$) alkynyl" with -- ($C_2$ to $C_6$) alkynyl --.